(12) United States Patent
Sauer

(10) Patent No.: US 12,178,428 B2
(45) Date of Patent: *Dec. 31, 2024

(54) SURGICAL SUTURING DEVICE FOR REPAIR OF TRICUSPID REGURGITATION AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 407 days.

This patent is subject to a terminal disclaimer.

(21) Appl. No.: 17/739,770

(22) Filed: May 9, 2022

(65) Prior Publication Data

US 2022/0257239 A1    Aug. 18, 2022

Related U.S. Application Data

(63) Continuation of application No. 16/568,465, filed on Sep. 12, 2019, now Pat. No. 11,357,500.
(Continued)

(51) Int. Cl.
*A61B 17/06* (2006.01)
*A61B 17/00* (2006.01)
*A61B 17/04* (2006.01)

(52) U.S. Cl.
CPC .......... *A61B 17/06* (2013.01); *A61B 17/0482* (2013.01); *A61B 17/0483* (2013.01);
(Continued)

(58) Field of Classification Search
CPC ............ A61B 17/0469; A61B 17/0482; A61B 17/0483; A61B 17/06; A61B 17/062;
(Continued)

(56) References Cited

U.S. PATENT DOCUMENTS 8,926,640 B2   1/2015  Sauer et al.
2002/0045908 A1  4/2002  Nobles et al.
(Continued)

FOREIGN PATENT DOCUMENTS

EP    2298180    3/2011

OTHER PUBLICATIONS

Supplementary EP Search Report dated Aug. 4, 2022 for European Application No. 19859509 filed Sep. 12, 2019.
(Continued)

*Primary Examiner* — Majid Jamialahmadi
(74) *Attorney, Agent, or Firm* — Michael E. Coyne

(57) ABSTRACT

A surgical suturing device is disclosed. The surgical suturing device may include a first or a second tissue gap, a first pair of needles configured to be movable across the first tissue gap, a second pair of needles configured to be movable across the second tissue gap, and a first suture having first and second ends. The surgical suturing device also includes a second suture having first and second ends and a needle actuator which selectively engages either: the first pair of needles to drive them through the first tissue gap and into communication with the first end of the first suture and the first end of the second suture, respectively; or the second pair of needles to drive them through the second tissue gap and into communication with the second end of the first suture and the second end of the second suture.

3 Claims, 152 Drawing Sheets

Related U.S. Application Data

(60) Provisional application No. 62/827,387, filed on Apr. 1, 2019, provisional application No. 62/811,527, filed on Feb. 27, 2019, provisional application No. 62/791,583, filed on Jan. 11, 2019, provisional application No. 62/746,353, filed on Oct. 16, 2018, provisional application No. 62/730,521, filed on Sep. 12, 2018.

(52) U.S. Cl.
CPC ............ *A61B 2017/00243* (2013.01); *A61B 2017/0496* (2013.01); *A61B 2017/06009* (2013.01)

(58) Field of Classification Search
CPC .......... A61B 17/0472; A61B 17/06061; A61B 17/06004; A61B 17/0625; A61B 17/0485
See application file for complete search history.

(56) References Cited

U.S. PATENT DOCUMENTS

| | | |
|---|---|---|
| 2007/0005079 A1 | 4/2007 | Zarbatany et al. |
| 2009/0312773 A1 | 12/2009 | Cabrera et al. |
| 2012/0016383 A1* | 1/2012 | Sauer ................. A61B 17/0483 606/144 |

OTHER PUBLICATIONS

International Search Report for PCT/US2019/50735 filed Sep. 12, 2019 mailed Jan. 27, 2020.
Supplementary Partial EP Search Report dated Mar. 21, 2022 for European Application No. 19859509 filed Sep. 12, 2019.

* cited by examiner

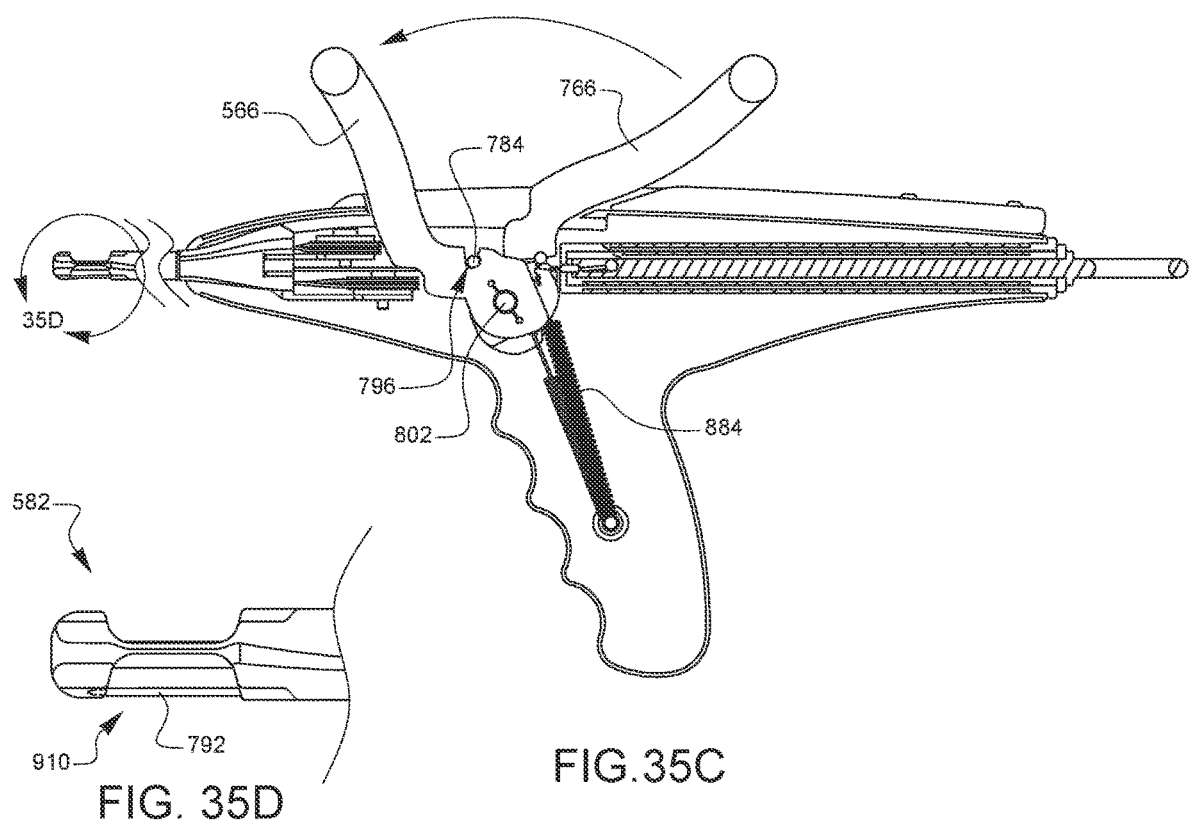

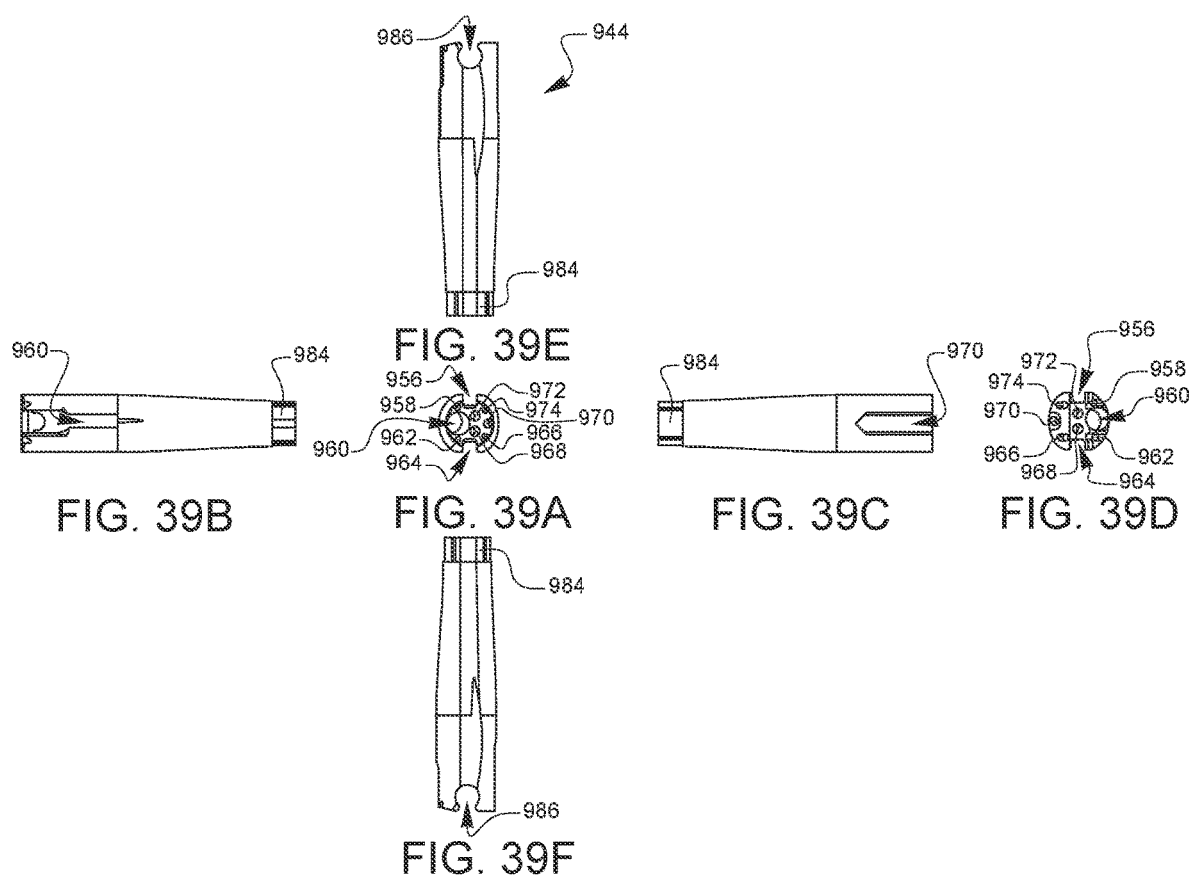

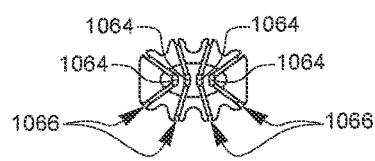
FIG. 52E
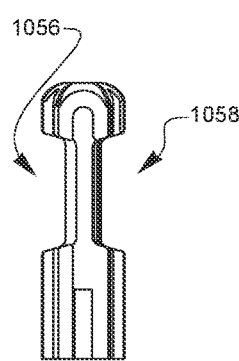
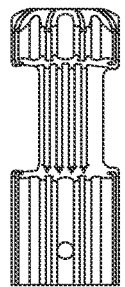
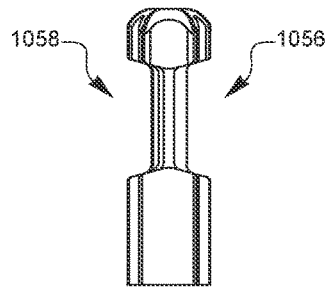
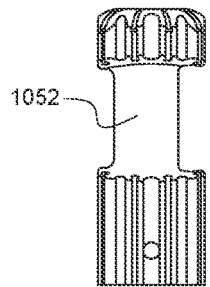
FIG. 52B          FIG. 52A          FIG. 52C          FIG. 52D
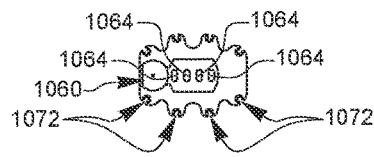
FIG. 52F

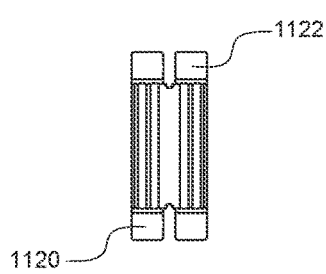
FIG. 61E
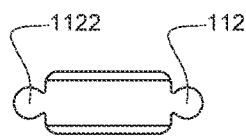
FIG. 61B
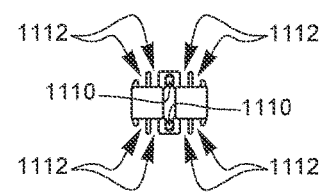
FIG. 61A
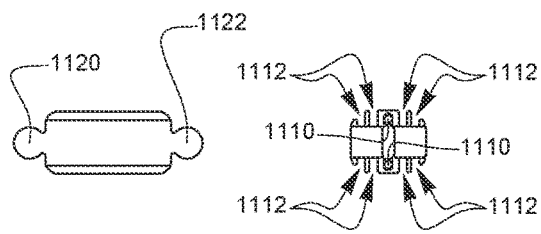
FIG. 61C
FIG. 61D
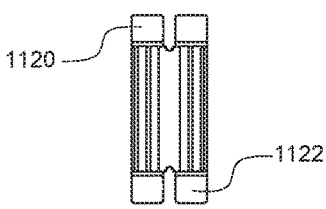
FIG. 61F

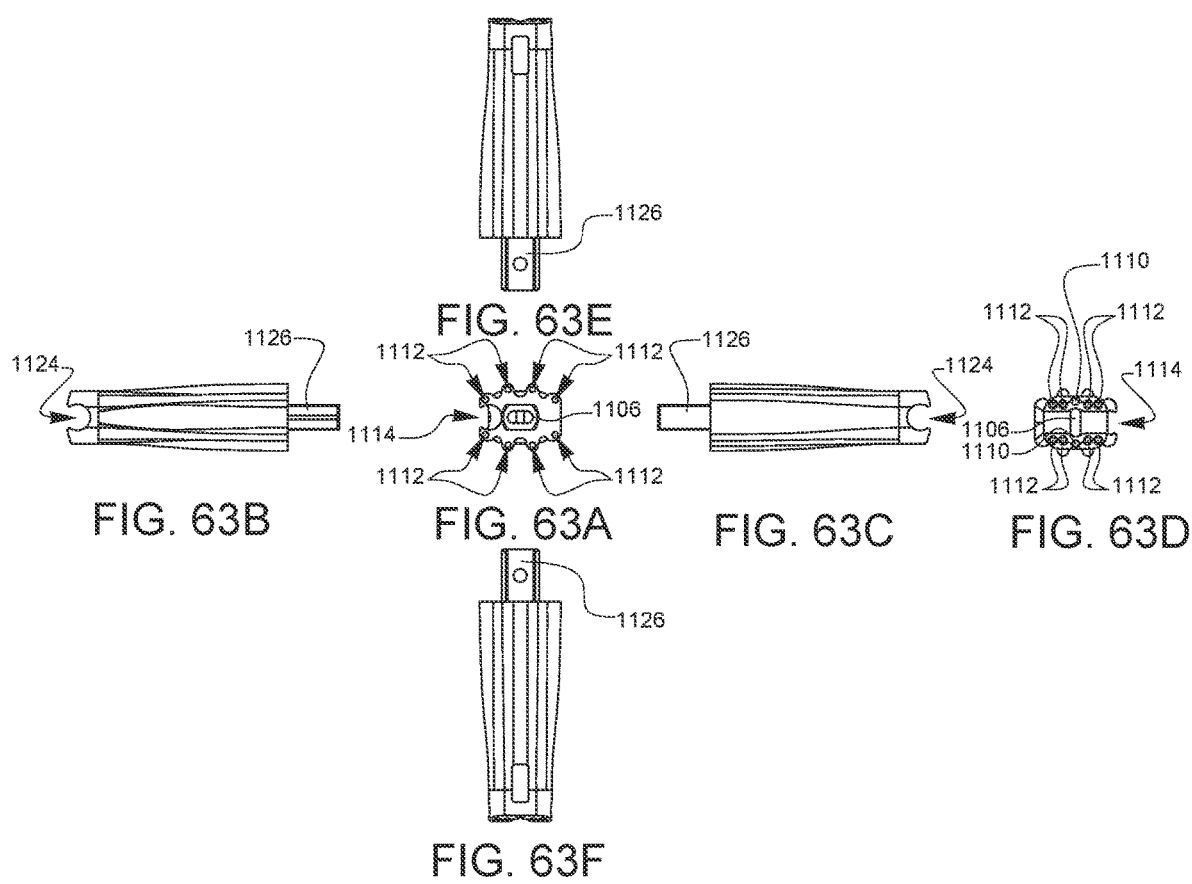

SURGICAL SUTURING DEVICE FOR REPAIR OF TRICUSPID REGURGITATION AND METHODS THEREOF

REFERENCE TO RELATED APPLICATIONS

This patent application claims priority to U.S. patent application Ser. No. 16/568,465, filed Sep. 12, 2019, which claims priority to each of U.S. Provisional Patent Application No. 62/827,387, filed Apr. 1, 2019, U.S. Provisional Patent Application No. 62/811,527, filed Feb. 27, 2019, U.S. Provisional Patent Application No. 62/791,583, filed Jan. 11, 2019, U.S. Provisional Patent Application No. 62/746,353 filed Oct. 16, 2018, U.S. Provisional Patent Application No. 62/730,521, filed Sep. 12, 2018, each of which is hereby incorporated by reference in its entirety.

FIELD

The claimed invention relates to surgical devices, and more specifically to a surgical suturing device useful in the correction of tricuspid regurgitation and methods thereof.

BACKGROUND

The availability of safe and effective therapy for tricuspid valve (TV) disease remains an area of significant unmet clinical need. Tricuspid regurgitation (TR) or the pathologic leakage of blood back into the right atrium during systole, quite common in cardiac patients with left-sided valvular or myocardial disease, is estimated to affect >1.5 million people in the United States, with a yearly incidence of about 200,000 and >300,000 patients in the United States and Europe, respectively. Specific anatomic features from the TV complex might vary according to the causing mechanism (primary vs. secondary) and throughout the progressive stages of ventricular remodeling in patients with functional TR. TR is most often functional, primarily due to annular dilatation and leaflet tethering from right ventricular remodeling caused by left-sided heart disease, atrial fibrillation, or pulmonary hypertension. Primary TR accounts for ~10% of cases of TR and can be due to congenital (Ebstein's anomaly, prolapse) or acquired diseases (rheumatic, endocarditis, carcinoid, endomyocardial fibrosis, intracardiac leads, or bioptome-related iatrogenic trauma). Today, TV disease is often considered a marker for late-stage chronic heart failure. TV is associated with a grim prognosis with most patients receiving lifetime medical therapy until intractable right heart failure and end-organ dysfunction appear.

Secondary TR has been divided into 3 stages for therapeutic purposes. In the early stage, initial dilation of the right ventricle leads to tricuspid annular dilation without significant leaflet tethering. Annular-based systems should easily repair TR in these first stages. In the absence of long-term durability data for transcatheter TV therapy and on the basis of a surgical predicate, ring may be preferred over suture annuloplasty when possible in order to reduce TR recurrence. In the second stage, progressive right ventricular and tricuspid annular dilation develop, impairing leaflet coaptation. The likelihood for successful Transcatheter Tricuspid Valve Repair (TTVr) using annuloplasty alone is less suitable in cases with progressive tethering and tricuspid annular dilation. Finally, as the right ventricle continues to remodel, further leaflet tethering worsens, resulting in a lack of coaptation and massive or torrential TR. When severe tethering occurs, any repair attempt could be considered futile.

FIG. 1A is a side cross-sectional view of a heart. The heart 10 is shown schematically with some of the relevant anatomical features in view. The tricuspid valve 16 (TV) is a complex structure, with several anatomic peculiarities rendering it unique. The TV apparatus, shown in FIG. 1A, normally has three leaflets, the septal leaflet 22, the posterior leaflet 24, and the anterior leaflet 20, chordae tendineae 26, and usually three papillary muscles 28. Also shown are the general locations of a superior vena cava 12 and an inferior vena cava 14.

As shown in FIG. 1B, the tricuspid annulus valve 16 is the largest of four heart valves, with very thin, fragile leaflets composing a potentially large regurgitant orifice area. The tricuspid valve 16 is surrounded by the tricuspid valve annulus 18 a saddle-shaped ellipsoid that becomes planar and circular as it dilates primarily in the anterolateral free wall in patients with left-sided heart disease with sinus rhythm verses expanding mostly along the posterior border with less prominent leaflet tethering in patients with functional TR secondary to chronic atrial fibrillation. Three leaflets, an anterior leaflet 20, septal leaflet 22, and posterior leaflet 24 are also shown in FIG. 1B. The relative locations of a mitral valve 34 and mitral annulus 36, as well as an aortic valve 30 and aortic annulus 32, and a pulmonary valve 38 and pulmonary annulus 40 are also indicated for reference. Four chief anatomic structures surround the TV and are therefore at risk for interventions addressing TV disease: the conduction system (atrioventricular node and the right bundle of His) coursing the membranous septum at 3 to 5 mm from the anteroseptal commissure, the right coronary artery (encircling the right atrioventricular groove ~5.5 mm from the septal and posterior portions, 7 mm from the anterior portion), the non-coronary sinus of Valsalva, and the coronary sinus ostium being an important landmark of the posteroseptal commissure. The TV apparatus poses additional challenging issues to overcome: lack of calcium, angulation in relation to the superior vena cava (SVC) and inferior vena cava (IVC), a trabeculated and thin right ventricle hindering a transapical approach, or the presence of pre-existing cardiac implantable electronic devices.

Traditional isolated TV surgery typically requires highly invasive surgical access and cardio-pulmonary by-pass. Since this current approach continues to be associated with one of the highest risks of mortality among all cardiac valve procedures in contemporary practice (operative mortality rates of 8.8% to 9.7%), it is rarely utilized relative to the large number of untreated TR patients (only 5,005 isolated tricuspid procedures were performed in a large contemporary U.S. nationwide registry over a 10-year period). Durability remains the Achilles heel of most surgical interventions addressing the TV. Many factors, such as right ventricular remodeling and dysfunction, tricuspid annular size progression, and pulmonary hypertension, may contribute to the high rates of TR recurrence observed following surgical TR correction. Surgical experience has shown more sustained durability of ring annuloplasty compared with suture annuloplasty, as well as for TV replacement over repair. However, concerns about increased perioperative mortality for TV replacement compared with repair in contemporary series—somewhat linked to selection bias of patients with larger tricuspid annular dilation and more severe right ventricular dysfunction—have led to a trend over time toward TV repair rather than replacement.

Therefore, it would be desirable to have a reliable surgical suturing device for repair of tricuspid regurgitation as well as associated methods thereof. Ideally, such a device and method would be minimally invasive and not require aortic cross-clamp or cardio-pulmonary bypass (CPB) machine, thereby reducing the likelihood of CPB-related side effects. Faster and more reliable cardiac operations offer additional benefits, such as reduced surgical team fatigue and more efficient use of critical resources. Expediting cardiac surgery can also improve patient outcomes.

SUMMARY

A surgical suturing device is disclosed. The surgical suturing device includes a first tissue gap, a second tissue gap, a first pair of needles configured to be movable across the first tissue gap, a second pair of needles configured to be movable across the second tissue gap, and a first suture having first and second ends. The surgical suturing device also includes a second suture having first and second ends and a needle actuator which selectively engages either: the first pair of needles to drive them through the first tissue gap and into communication with the first end of the first suture and the first end of the second suture, respectively; or the second pair of needles to drive them through the second tissue gap and into communication with the second end of the first suture and the second end of the second suture.

Another surgical suturing device is disclosed. The surgical suturing device includes a first tissue gap, a second tissue gap, a first pair of needles configured to be movable across the first tissue gap, a second pair of needles configured to be movable across the second tissue gap, a first suture having first and second ends, a second suture having first and second ends, a first needle actuator which engages the first pair of needles to drive them through the first tissue gap and into communication with the first end of the first suture and the first end of the second suture, respectively, and a second needle actuator which engages the second pair of needles to drive them through the second tissue gap and into communication with the second end of the first suture and the second end of the second suture.

A loading and retrieval apparatus is also disclosed. The loading and retrieval apparatus includes a pledget, a mechanical fastener, a snare passing through the mechanical fastener and a proximal side of the pledget, forming at least one snare loop on a distal side of the pledget, and a tether loop passing through the pledget.

BRIEF DESCRIPTION OF THE DRAWINGS

FIGS. 35A-35G are side partial cross-sectional views of the surgical suturing device of FIG. 29 illustrating the operation principles of the needle drivers and retracting telescope.

FIGS. 39A, 39B, 39C, 39D, 39E, and 39F are front, left side, right side, rear, top, and bottom elevational views, respectively of the unique vertebra segment of FIGS. 38A-38B.

FIGS. 52A, 52B, 52C, 52D, 52E, and 52F are front, left side, right side, rear, top, and bottom elevational views, respectively, of the distal tip of FIGS. 51A-51B.

FIGS. 61A, 61B, 61C, 61D, 61E, and 61F are front, left side, right side, rear, top, and bottom elevational views, respectively of the unique vertebra segment of FIGS. 60A and 60B.

FIGS. 63A, 63B, 63C, 63D, 63E, and 63F are front, left side, right side, rear, top, and bottom elevational views, respectively of the unique vertebra segment of FIGS. 62A and 62B.

Figure 1A:
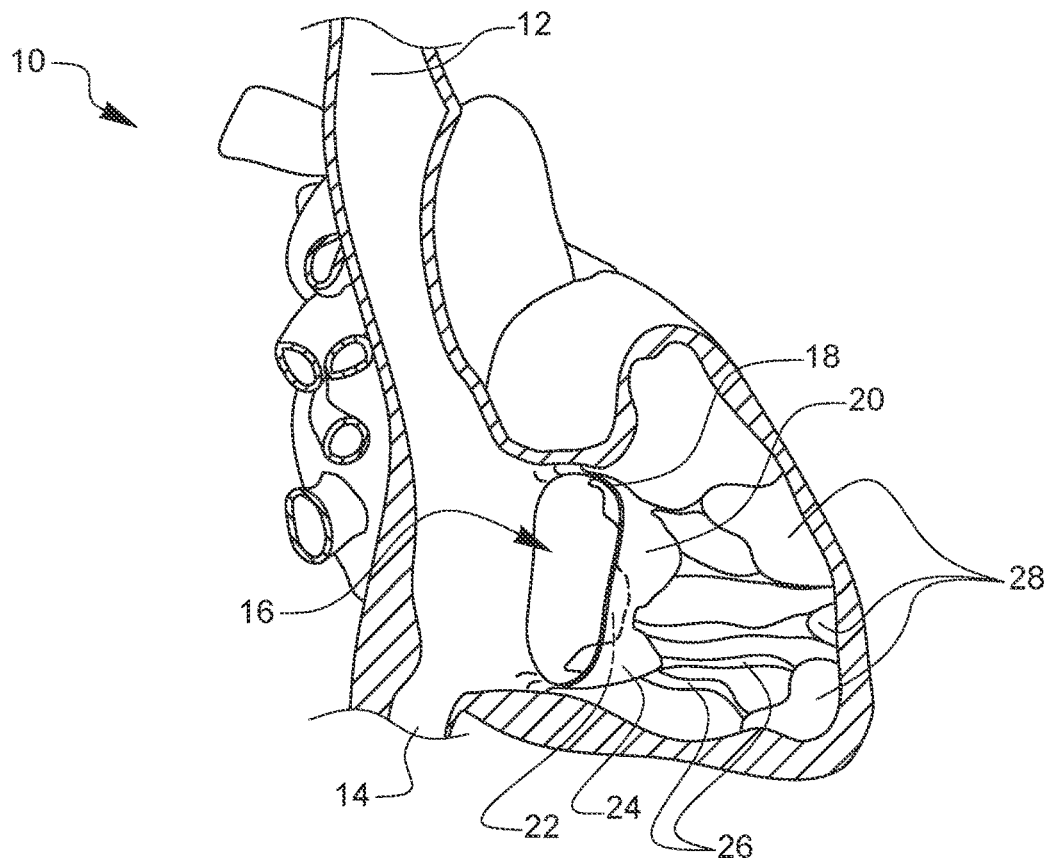
FIGS. 1A-1B are cross-sectional views of a human heart.
Figure 1B:
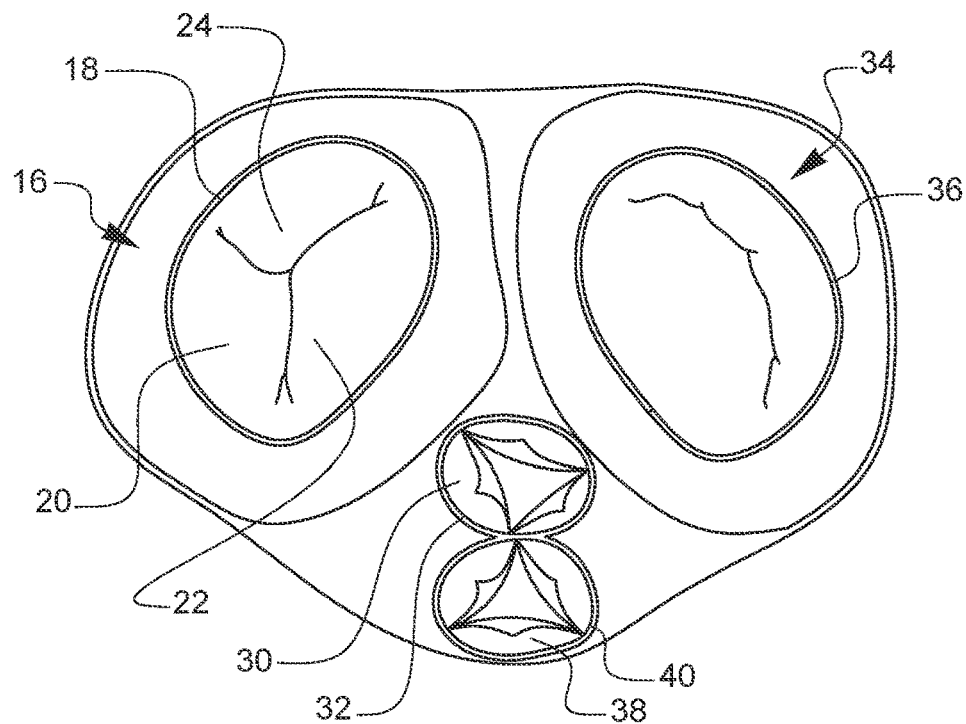

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 2:
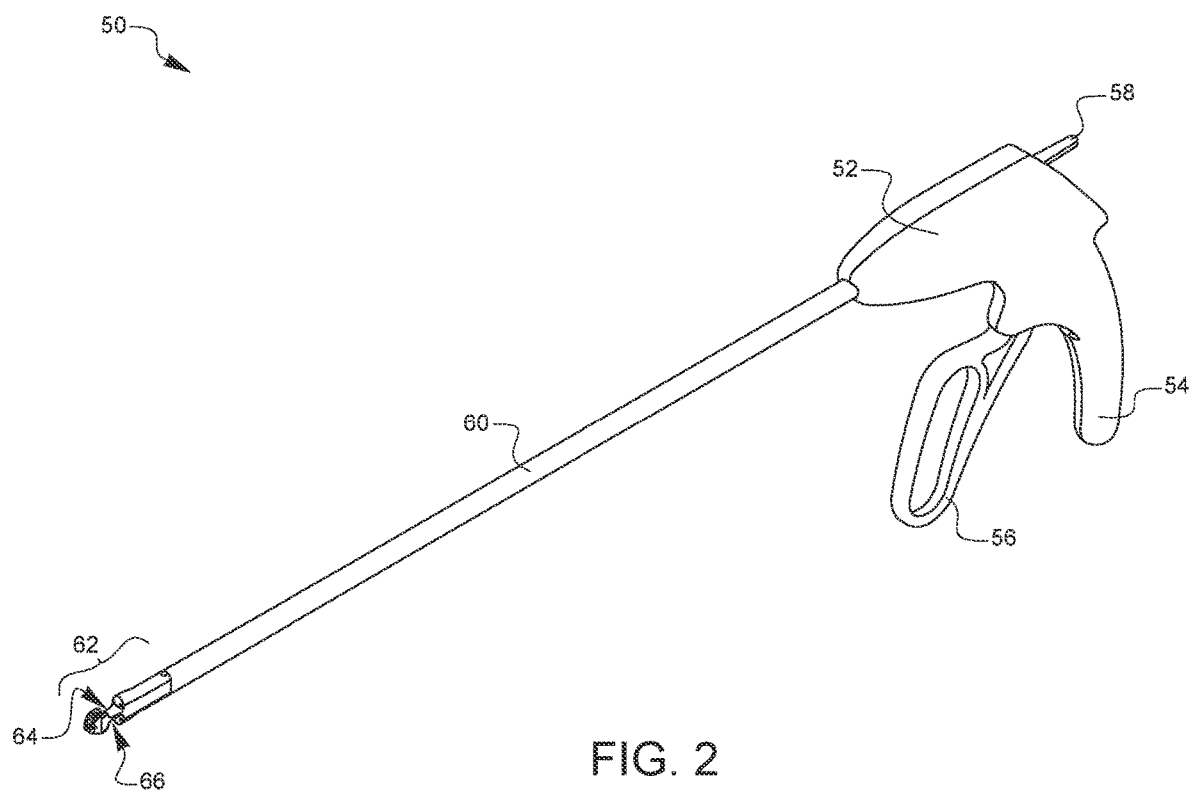
FIG. 2 is a top-left-front perspective view of one embodiment of a surgical suturing device.

FIG. 2 illustrates one embodiment of a surgical suturing device 50. The surgical suturing device 50 has a handle 54 and a lever 56 which is pivotable with respect to the handle 54. The device also has a selection switch 58. Extending from the handle housing 52 is a flexible shaft 60 which terminates in a distal tip 62. The distal tip 62 defines a first tissue gap 64 and a second tissue gap 66, which in this embodiment are symmetrical and facing opposite directions.

Figure 3A:
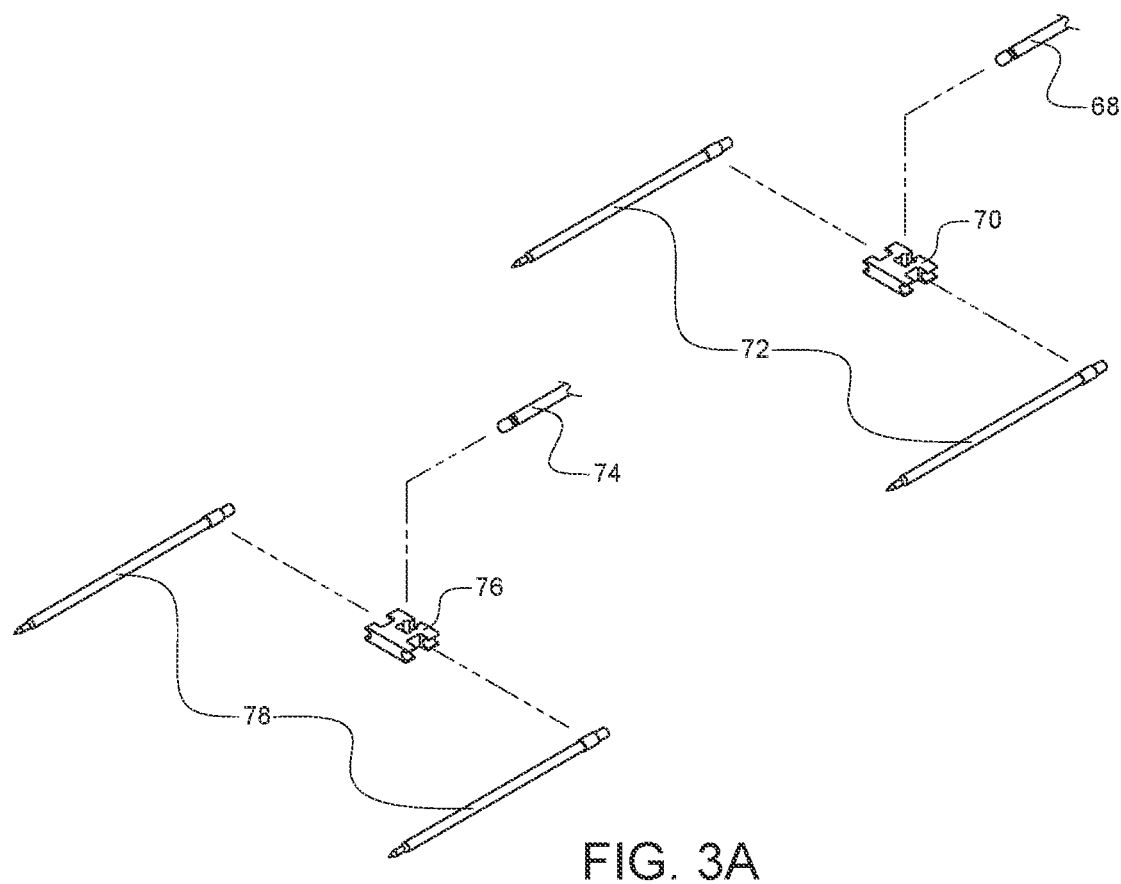
FIGS. 3A-3E are exploded views illustrating the assembly of a distal end of the surgical suturing device of FIG. 2.

FIGS. 3A-3E are exploded views illustrating assembly of the distal end of the device. As shown in FIG. 3A, a first pair of needles 72 are coupled to a first needle holder 70. A first needle drive wire 68 is also coupled to the first needle holder 70. A second pair of needles 78 are coupled to a second needle holder 76. A second needle drive wire 74 is also coupled to the second needle holder 76. Although not shown in these views, the first and second needle drive wires 68, 74 will pass through the flexible shaft 60 and will be coupled to the selection switch 58. Those skilled in the art are familiar with mechanisms which will enable a squeezing of the device lever 56 to move the first pair of needles 72 when it is in a first selection position, while also enabling a squeezing of the device lever 56 to move the second pair of needles 74 when the selection switch 58 is in a second position. Having only two needle drive wires leaves open the possibility of locating the needle drive wires along a single line on which the flexible shaft 60 may more easily bend. In other embodiments, the two needles which make up the first pair of needles 72 and the two needles which make up the second pair of needles 78 may be long enough to pass all the way back through the flexible shaft 60 to the handle housing 52 where they can be coupled to the selection switch 58 more proximal to the user.

Figure 3B:
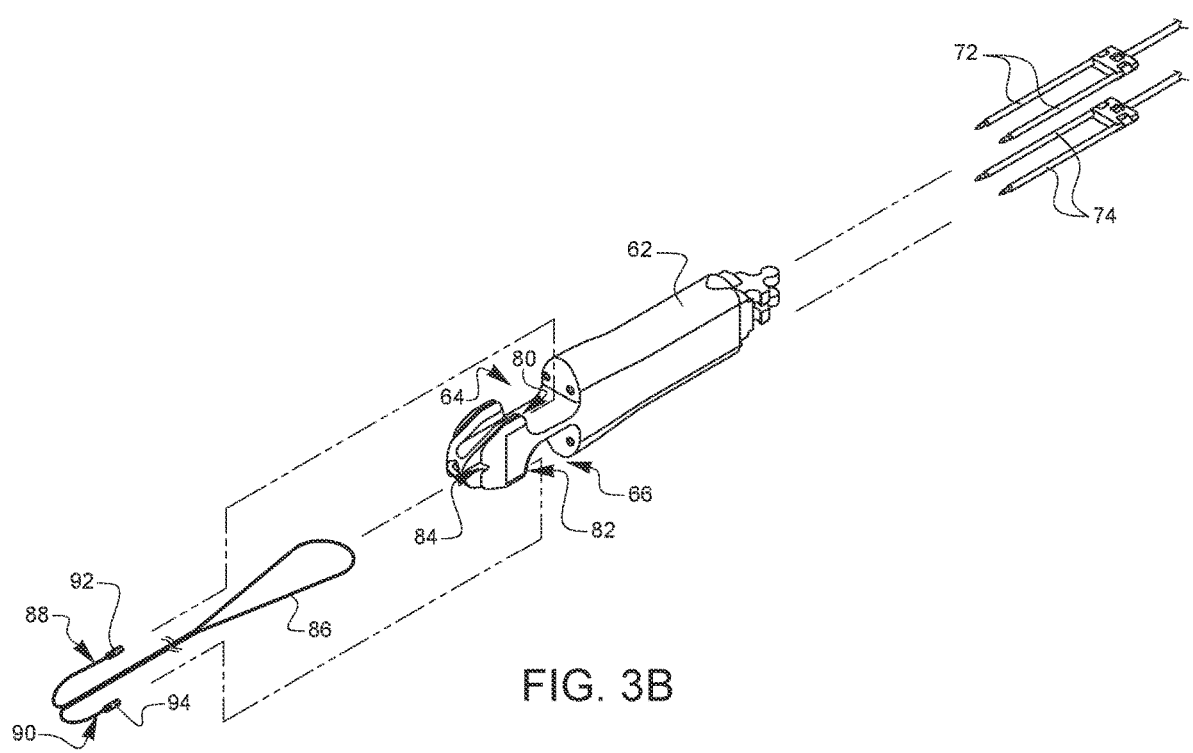
Figure 3C:
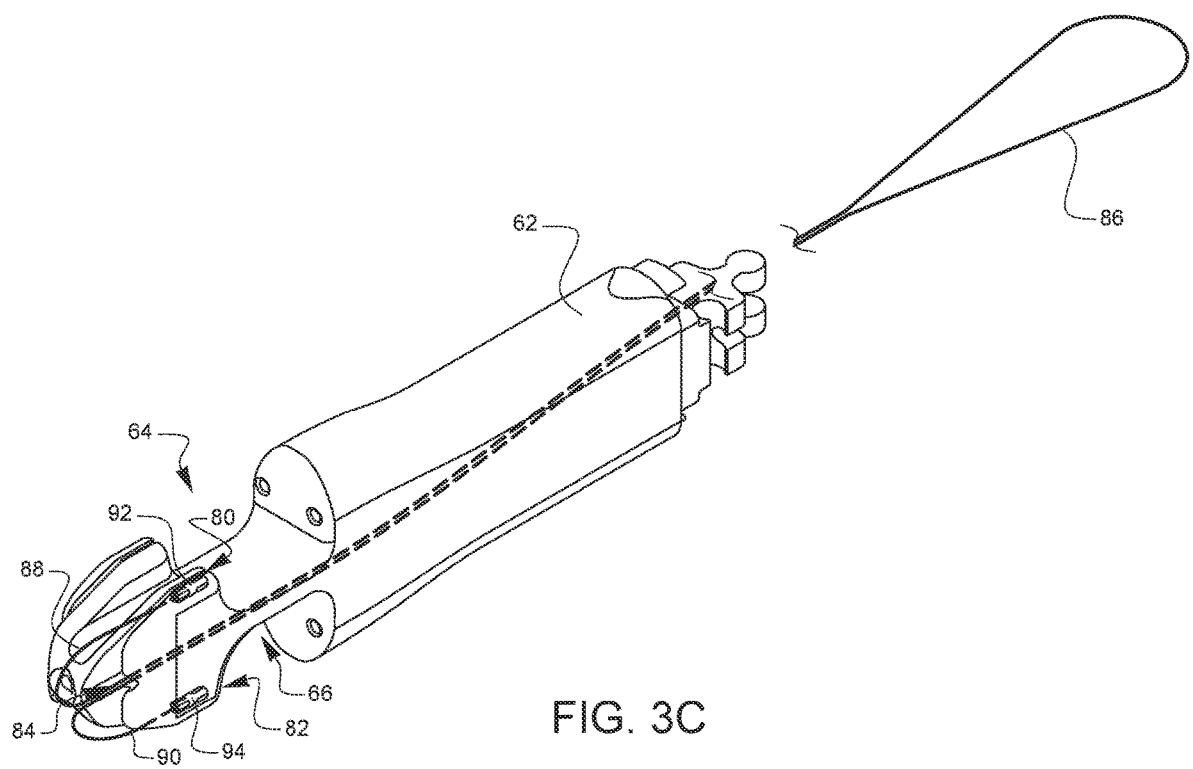

As shown in FIG. 3B, the device has a first suture 86 which has its own first and second ends 88, 90. A first ferrule 92 is coupled to the first end of the first suture 86, while a second ferrule 94 is coupled to the second end of the first suture 86. The distal tip 62 defines a first ferrule holder 80 adjacent to the first tissue gap 64. The distal tip 62 also defines a second ferrule holder 82 adjacent to the second tissue gap 66. The first ferrule 92 is placed within the first ferrule holder 80, while the second ferrule 94 is placed within the second ferrule holder 82. At least a portion of the middle of the first suture 86 is placed into a first suture passage 84 of the distal tip 62. The first suture 86 will be long enough so that the suture middle or approximate middle can reach all the way to the housing handle 52, or at least beyond the flexible shaft 60. FIG. 3C shows the first suture 86 and its ferrules 92, 94 installed in the distal tip 62.

Figure 3D:
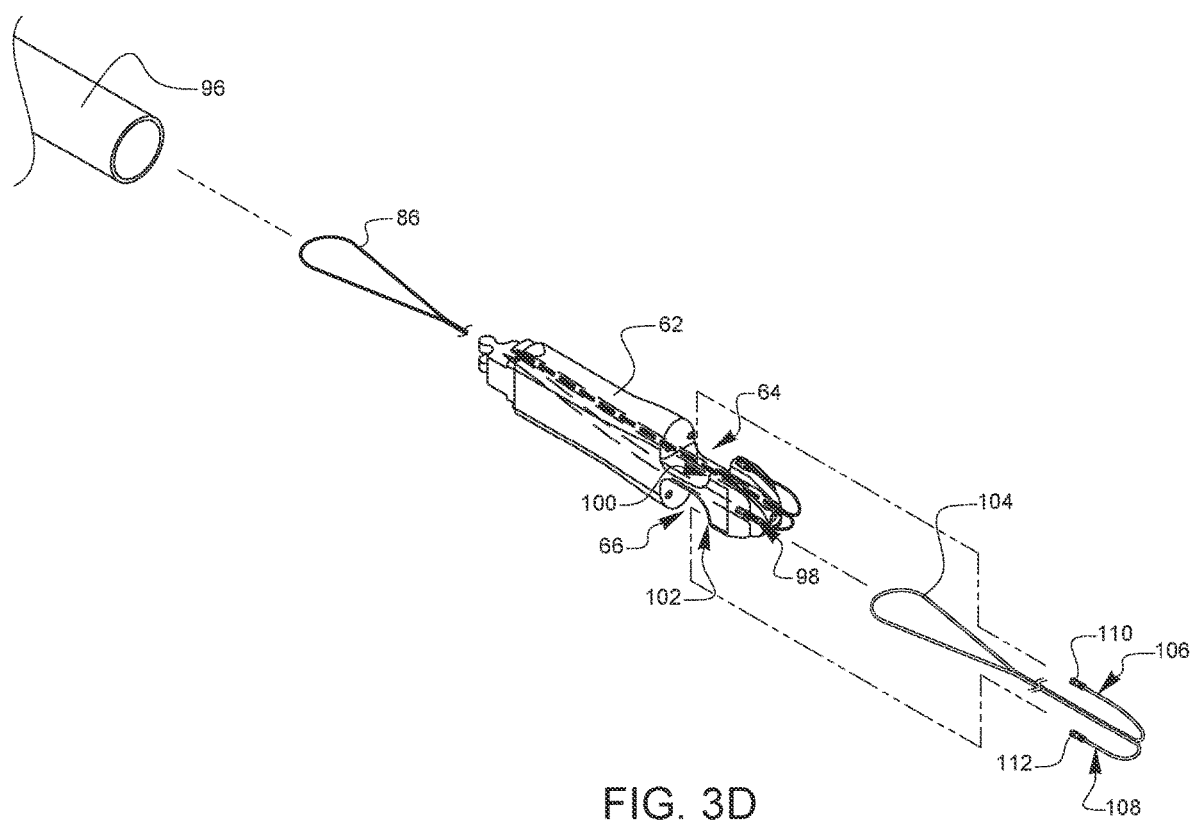
Figure 3E:
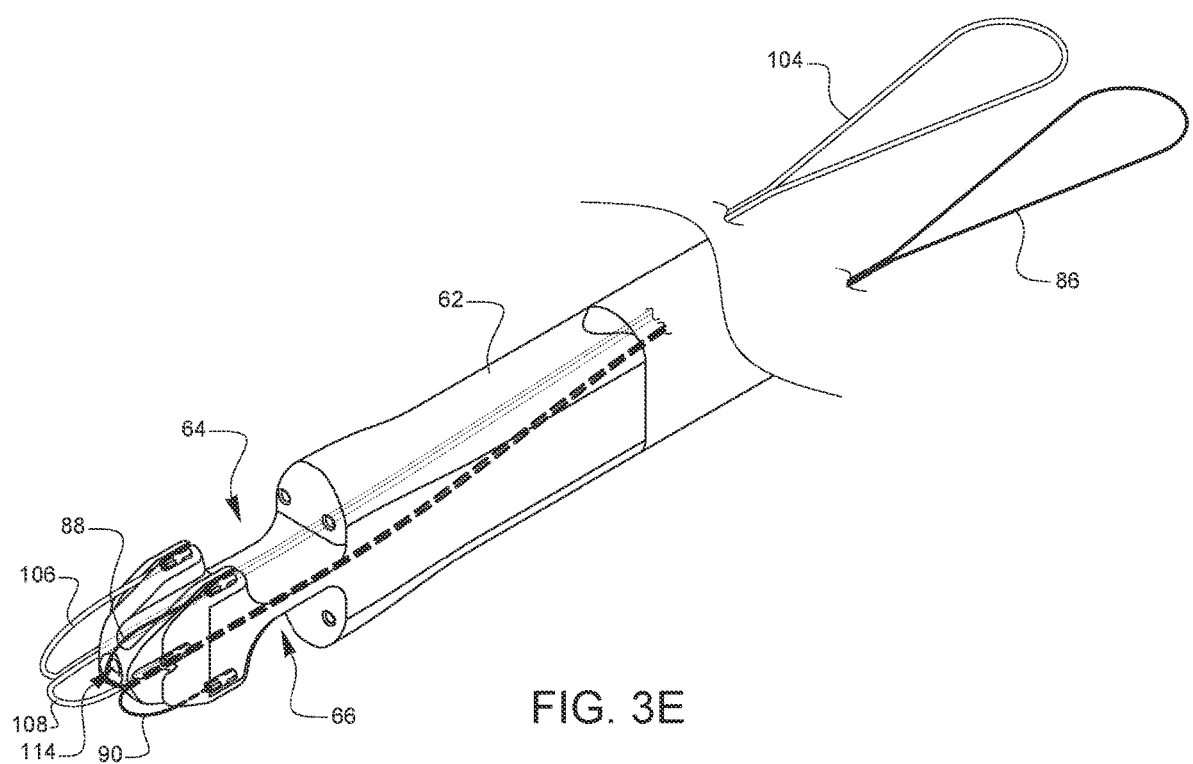

As shown in FIG. 3D, the device has a second suture 104 which has its own first and second ends 106, 108. A third ferrule 110 is coupled to the first end of the second suture 106, while a fourth ferrule 112 is coupled to the second end of the second suture 108. The distal tip 62 defines a third ferrule holder 100 adjacent to the first tissue gap 64. The distal tip 62 also defines a fourth ferrule holder 102 adjacent to the second tissue gap 66. The third ferrule 110 is placed within the third ferrule holder 100, while the fourth ferrule 112 is placed within the fourth ferrule holder 102. At least a portion of the middle of the second suture 104 is placed into a second suture passage 98 of the distal tip 62. The second suture 104 will be long enough so that the suture middle or approximate middle can reach all the way to the housing handle 54, or at least beyond the flexible shaft 60. FIG. 3E shows the first and second sutures 86, 104 and their ferrules installed in the distal tip 62. FIG. 3E also shows a guidewire channel 114 which is formed through the distal tip 62. The guidewire channel 114 continues through the end of the flexible shaft 60, and it allows a guidewire to be inserted therein so that the device can be passed over a guidewire to a surgical location.

Referring to FIG. 3B again, the first and second pairs of needles are inserted into the distal tip 62 in alignment with the ferrules. The first ferrule holder 80 and third ferrule holder 100 are configured to align the first ferrule 92 and the third ferrule 110 in alignment with a travel path of the first pair of needles 72 when traversing the first tissue gap 64, respectively. The second ferrule holder 82 and fourth ferrule holder 102 are configured to align the second ferrule 94 and the fourth ferrule 112 in alignment with a travel path of the second pair of needles 74 when traversing the second tissue gap 66, respectively.

Figure 4A:
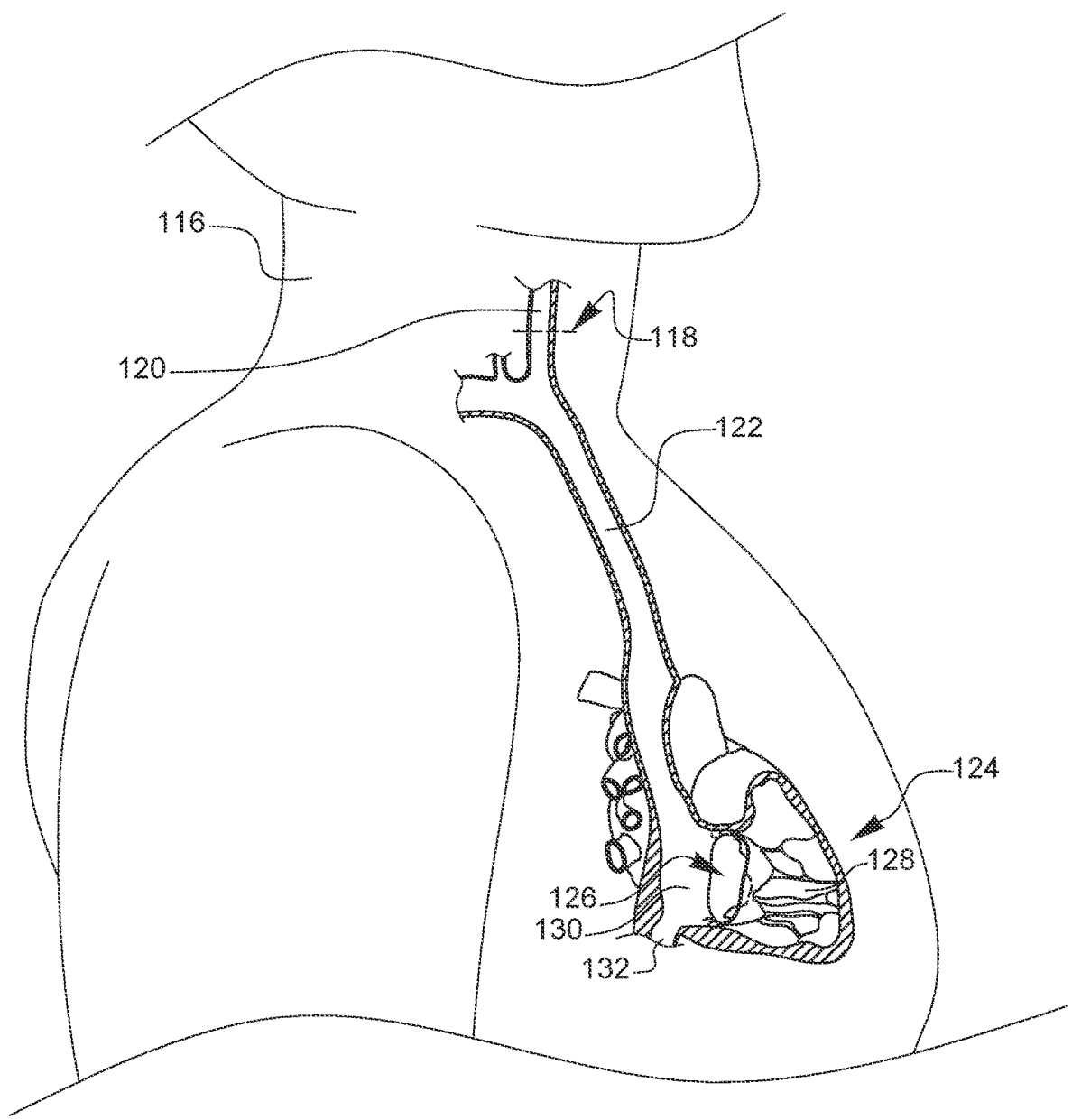
FIGS. 4A-4H, 4J-4N, and 4P-4R are schematic illustrations of a surgical method for repair of tricuspid regurgitation using the surgical suturing device of FIG. 2.

FIGS. 4A-4H, 4J-4N, and 4P-4R schematically illustrate a surgical method for repair of tricuspid regurgitation using the surgical suturing device of FIG. 2. FIG. 4A illustrates an example starting surgical situation, where the surgeon locates an incision site 118 on a patient's neck 116 in a location which will allow access to the inner jugular vein 120. The inner jugular vein 120 joins the superior vena cava 122 which then leads to the right atrium 130 of the heart 124. The inferior vena cava 122 also leads to the right atrium 130 of the heart 124 from the patient's lower body. The tricuspid valve 126 is located between the right atrium 130 and the right ventricle 128.

Figure 4B:
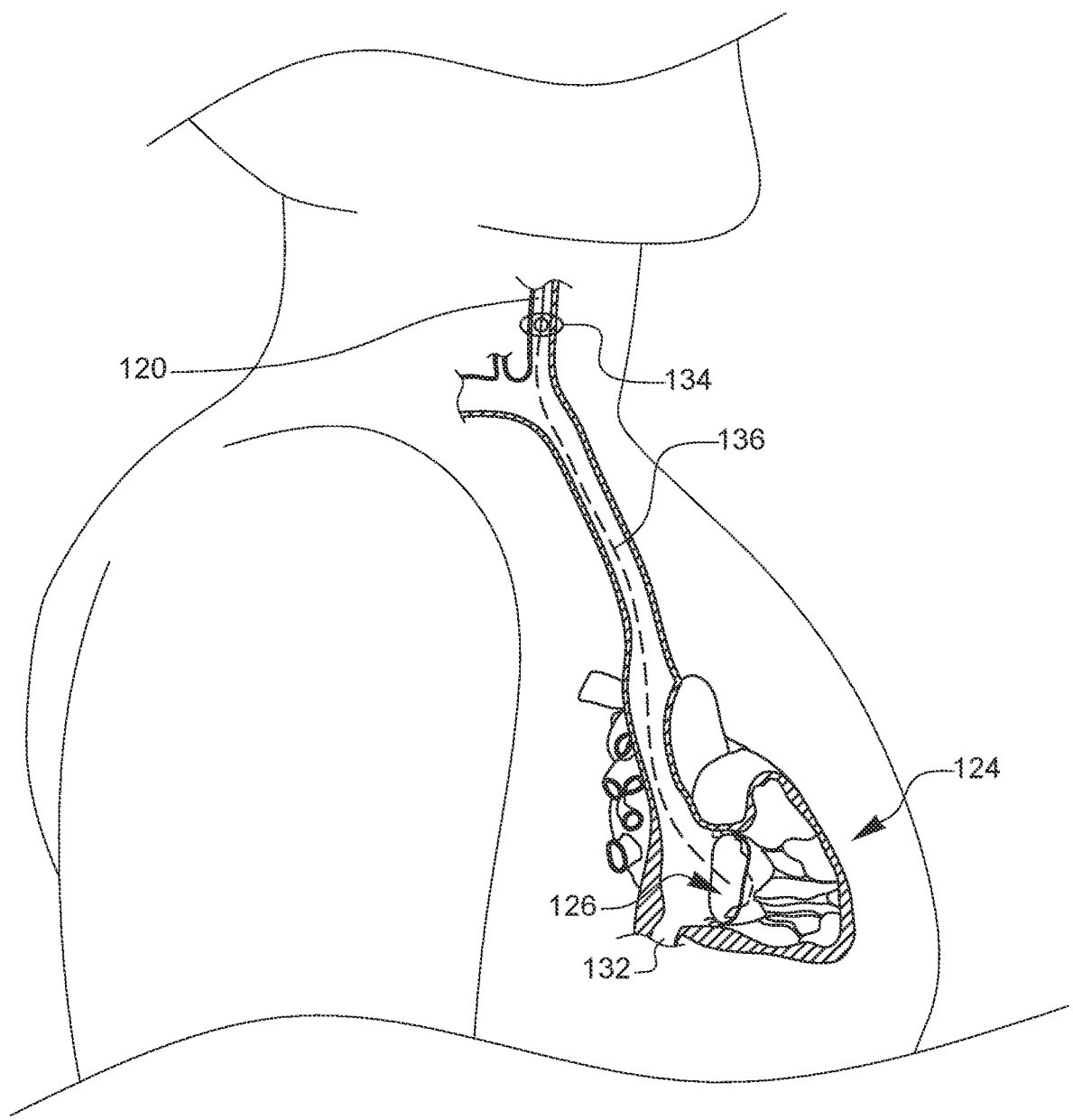

As schematically illustrated in FIG. 4B, a cannula 134 is placed into the inner jugular vein 120, and a guidewire 136 is advanced down the inner jugular vein 120, through the superior vena cava 122, and into the right atrium 130 until it is positioned within the tricuspid valve 126. These steps, like all the steps of this procedure, may be performed while the patient is under conscious sedation and while the heart is still beating. This is advantageous because it avoids aortic cross clamping, cardiopulmonary bypass, and the complications associated therewith.

Figure 4C:
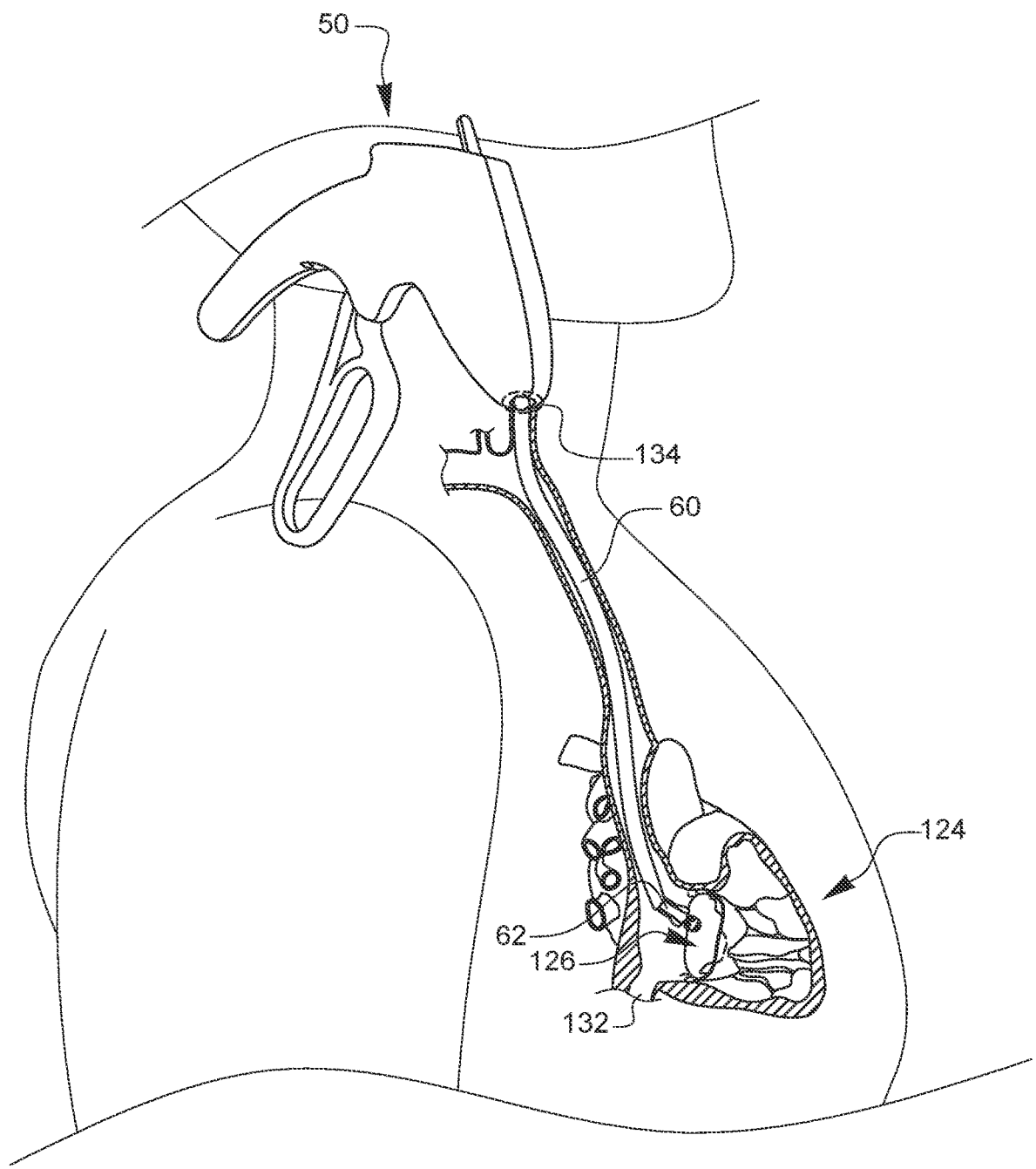
Figure 4D:
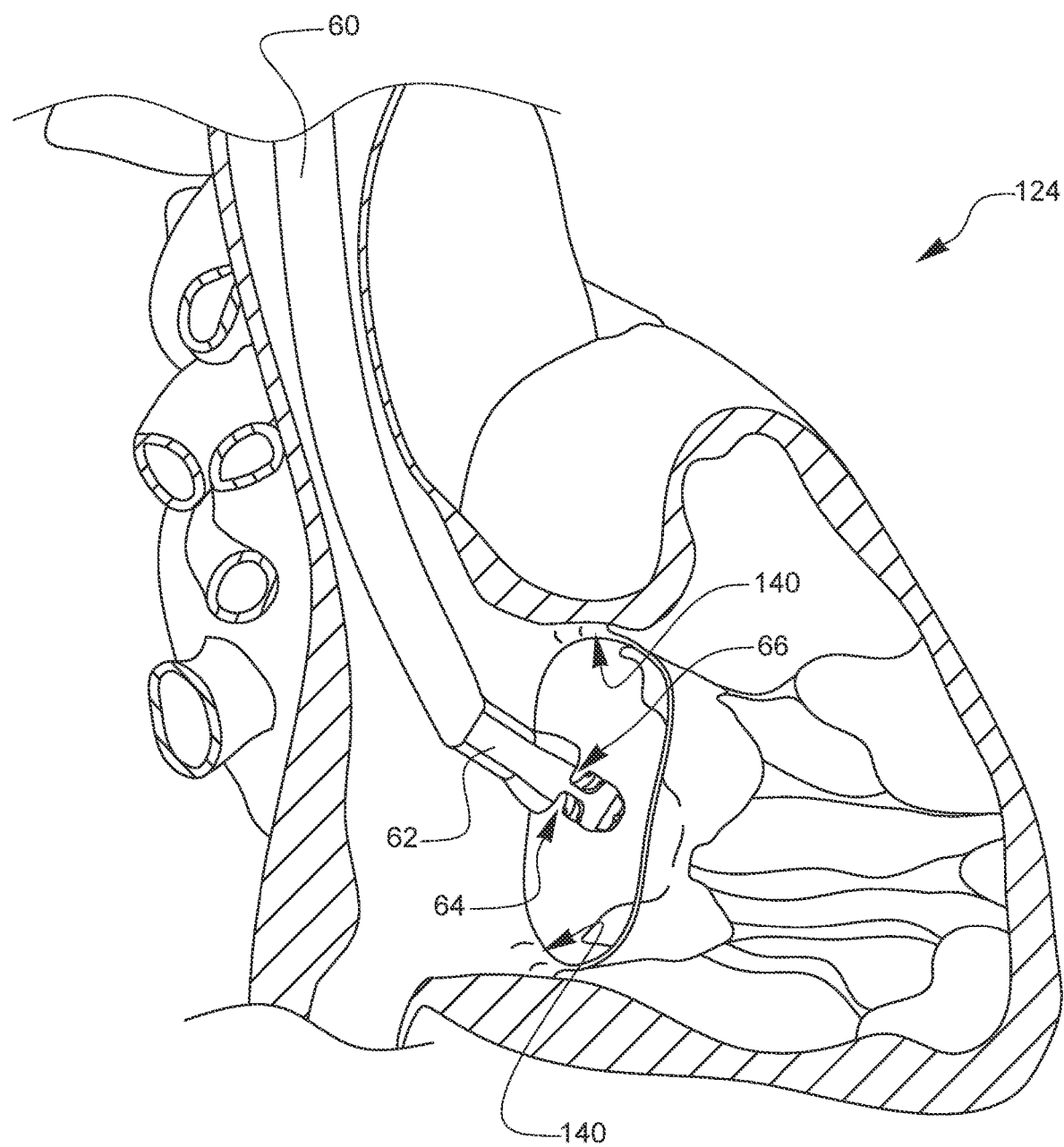

As shown in FIG. 4C, the surgical suturing device 50 has been advanced through the cannula 134 and over the guidewire 136 so that the distal tip 62 is located within the tricuspid valve 126. The surgical suturing device 50 may have steering controls to help guide the flexible shaft 60. The flexible shaft 60 may include a series of linked vertebrae as well as one or more articulating links which can be angled as desired. FIG. 4D is an enlarged view of the heart 124 from FIG. 4C. It can be seen that the tissue gaps 64, 66 in the distal tip 62 are generally aligned with the tricuspid annulus 140.

Figure 4E:
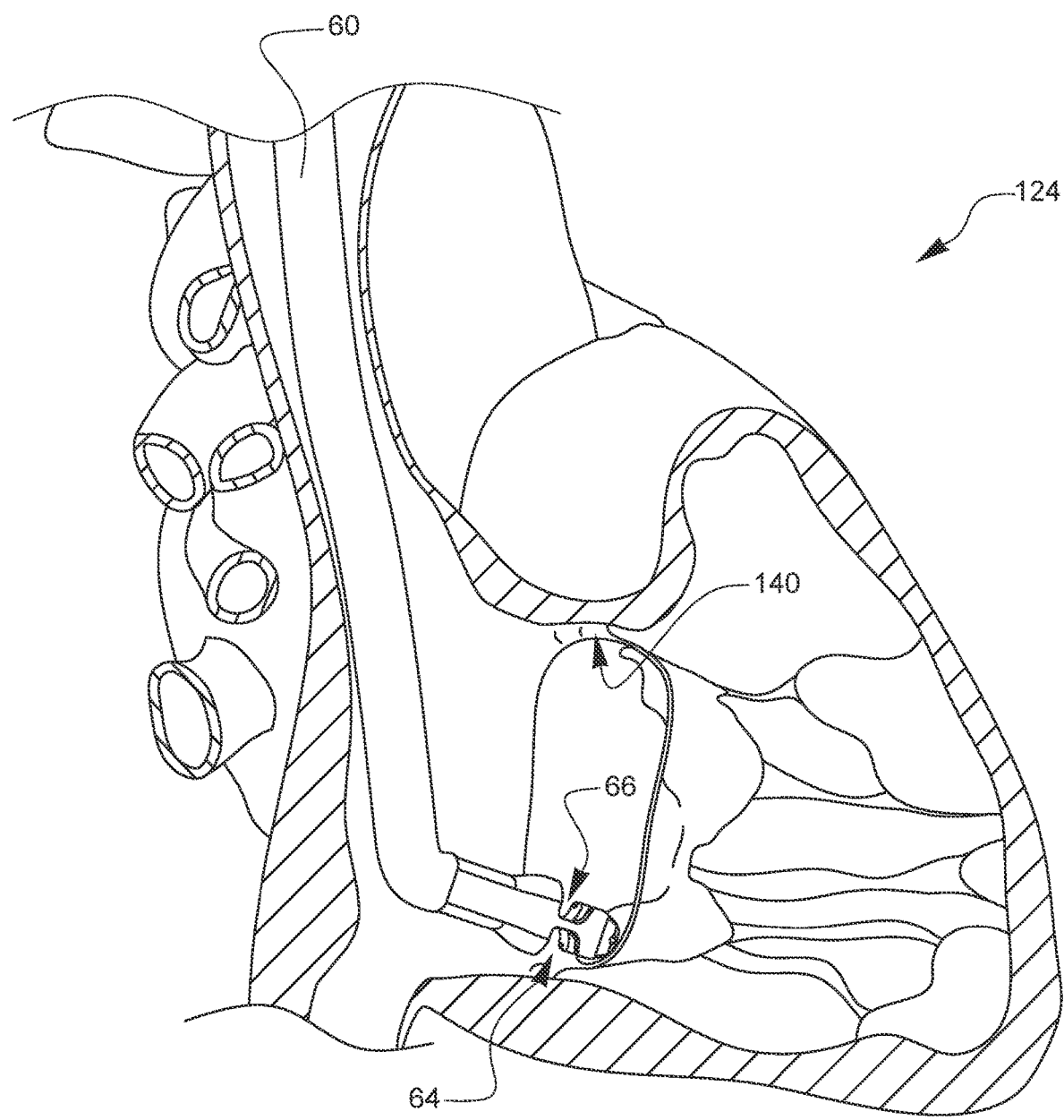
Figure 4F:
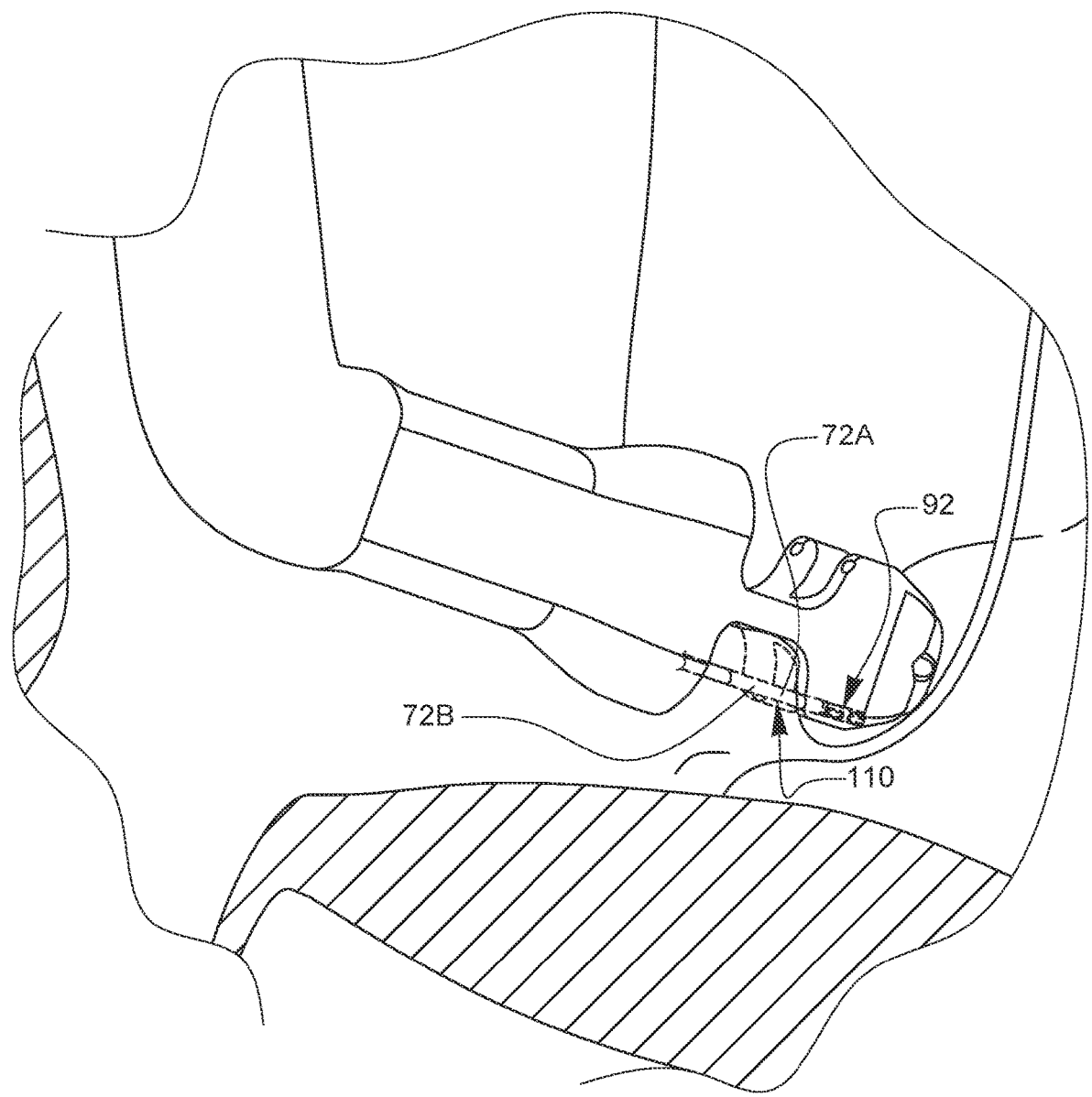
Figure 4G:
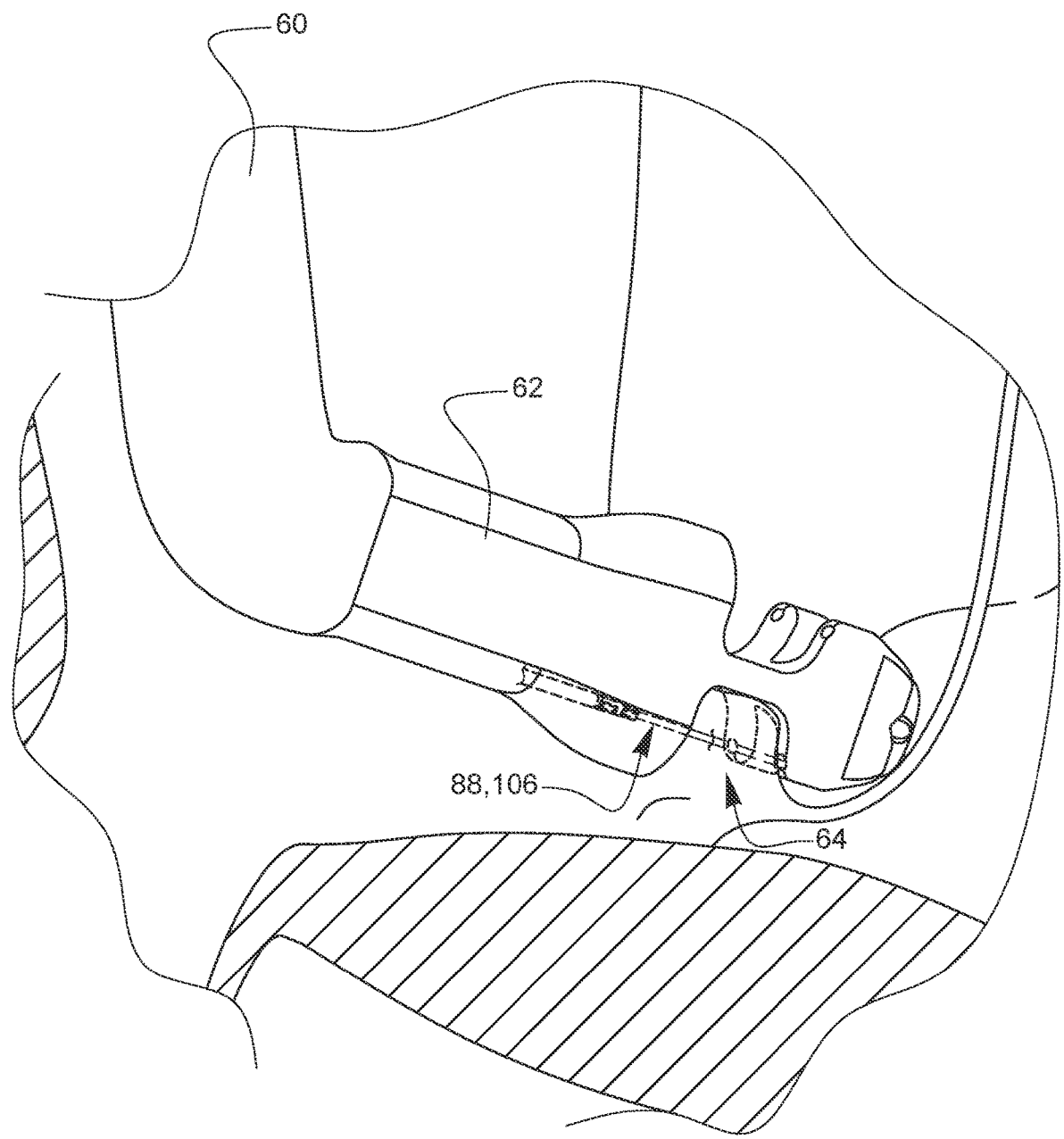

As shown in FIG. 4E, the distal tip 62 is further positioned against one side of the tricuspid valve 126 so that one side of the annulus is within the first tissue gap 64. As shown in the enlarged view of FIG. 4F, the first pair of needles 72 are advanced (by squeezing the lever which is not shown) through the tissue in the tissue gap 64 and into contact with the first and third ferrules 92, 110. For simplicity, the sutures are not shown in this view. The needles couple with their respective ferrules, and then the needles are retracted (by releasing the lever which is not shown) back through the tissue in the tissue gap, as shown in FIG. 4G, pulling the first end of the first suture 86 and the first end of the second suture 106 back through the tissue as well.

Figure 4H:
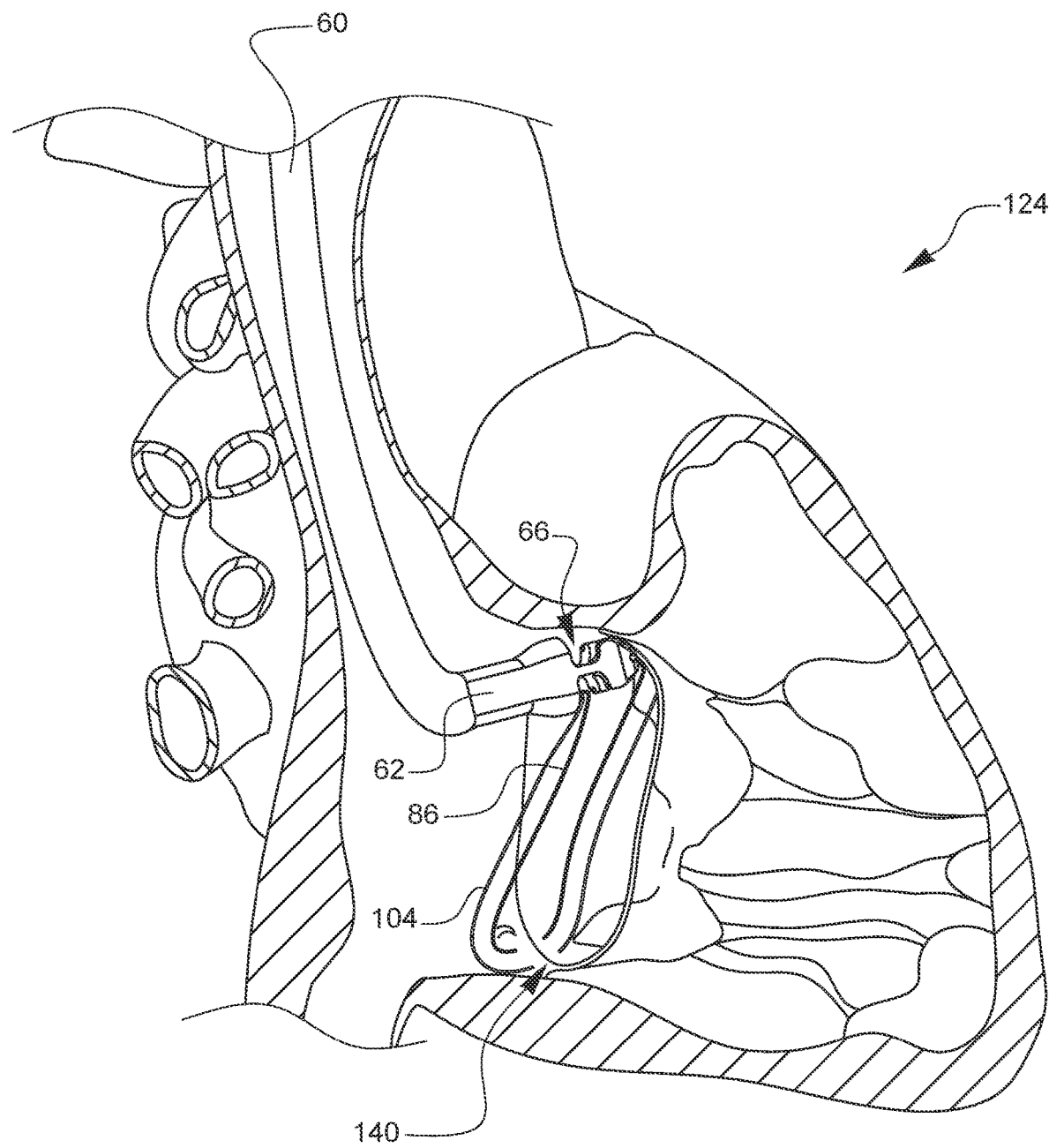
Figure 4J:
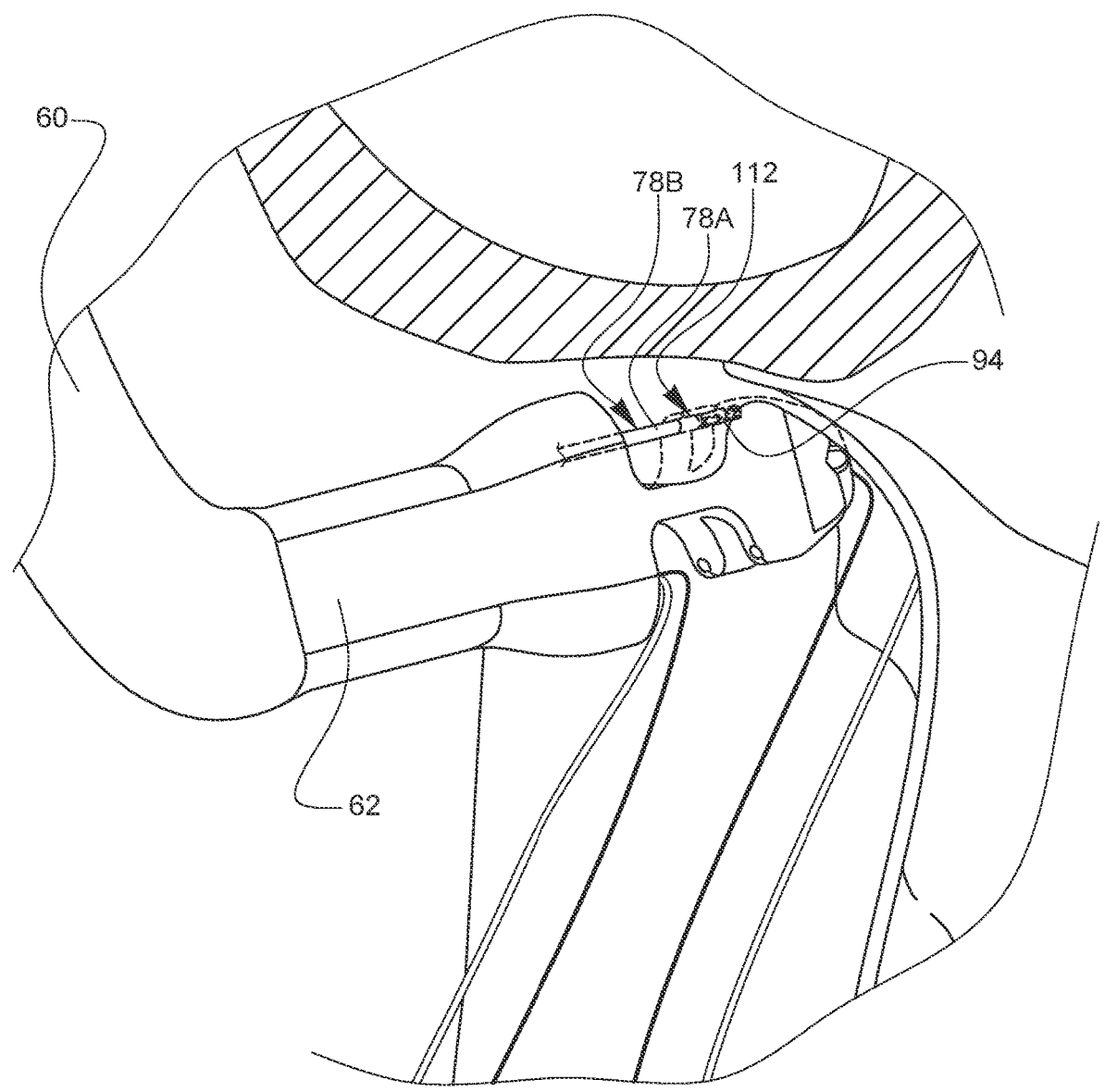
Figure 4K:
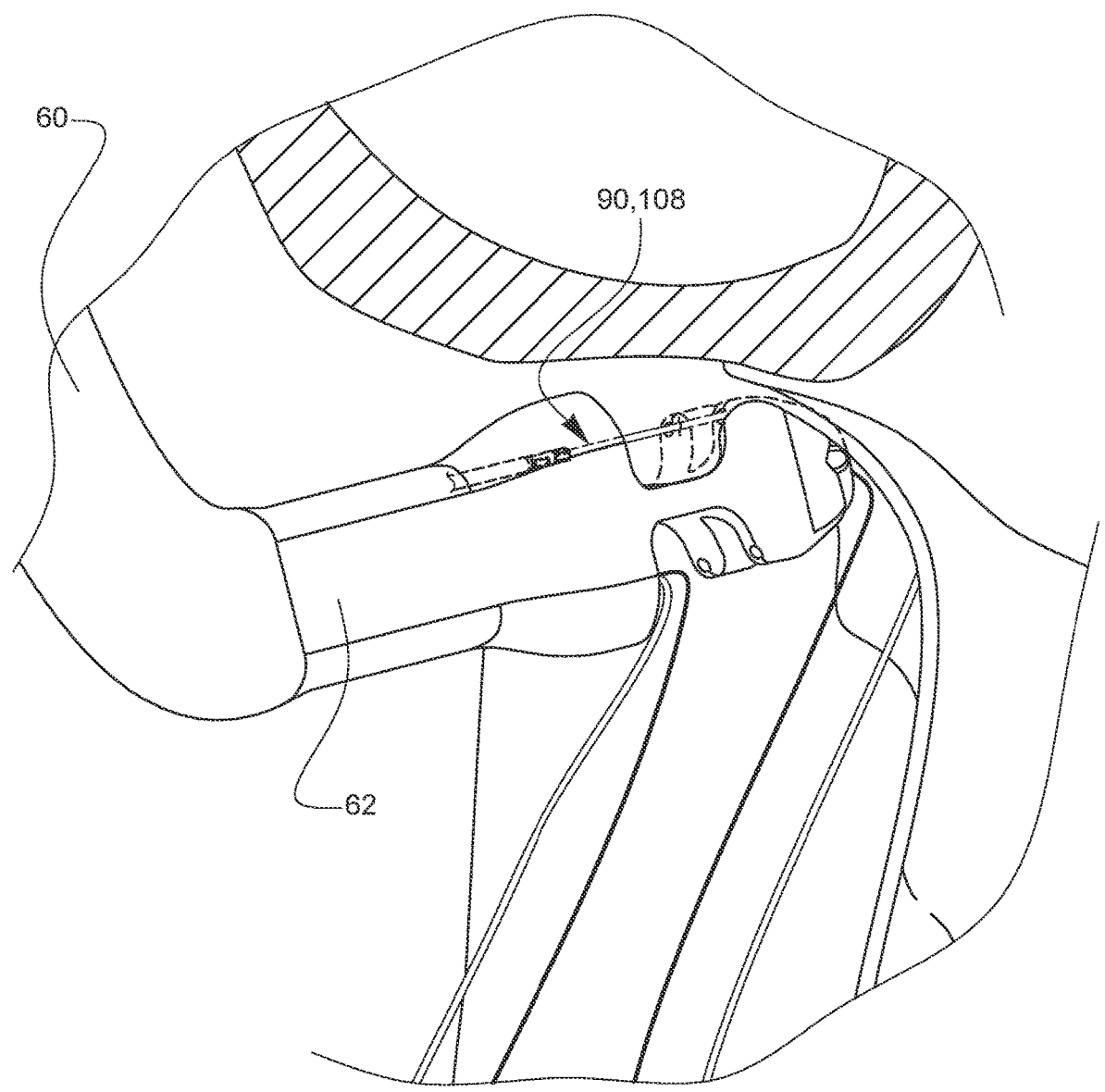

As shown in FIG. 4H, the distal tip 62 is now positioned against the opposite side of the annulus so that a second annulus location is placed within the second tissue gap 66. The stitches made from the first end of the first suture 86 and the first end of the second suture 106 at the first annulus location can clearly be seen in this view. Note that there is no FIG. 4I, as this looks confusingly like the number 41. The user switches the selector switch 58 so that the second pair of needles 78 may be actuated, and as shown in the enlarged view of FIG. 4J, the second pair of needles 78 are advanced (by squeezing the lever which is not shown) through the tissue in the second tissue gap 66 and into contact with the second and fourth ferrules 94, 112. The needles couple with their respective ferrules, and then the needles are retracted (by releasing the lever which is not shown) back through the tissue in the second tissue gap 66, as shown in FIG. 4K, pulling the second end of the first suture 86 and the second end of the second suture 108 back through the tissue as well.

Thus, the selector switch 58 can be switched to selectively couple either the first pair of needles 72 or the second pair of needles 78.

Figure 4L:
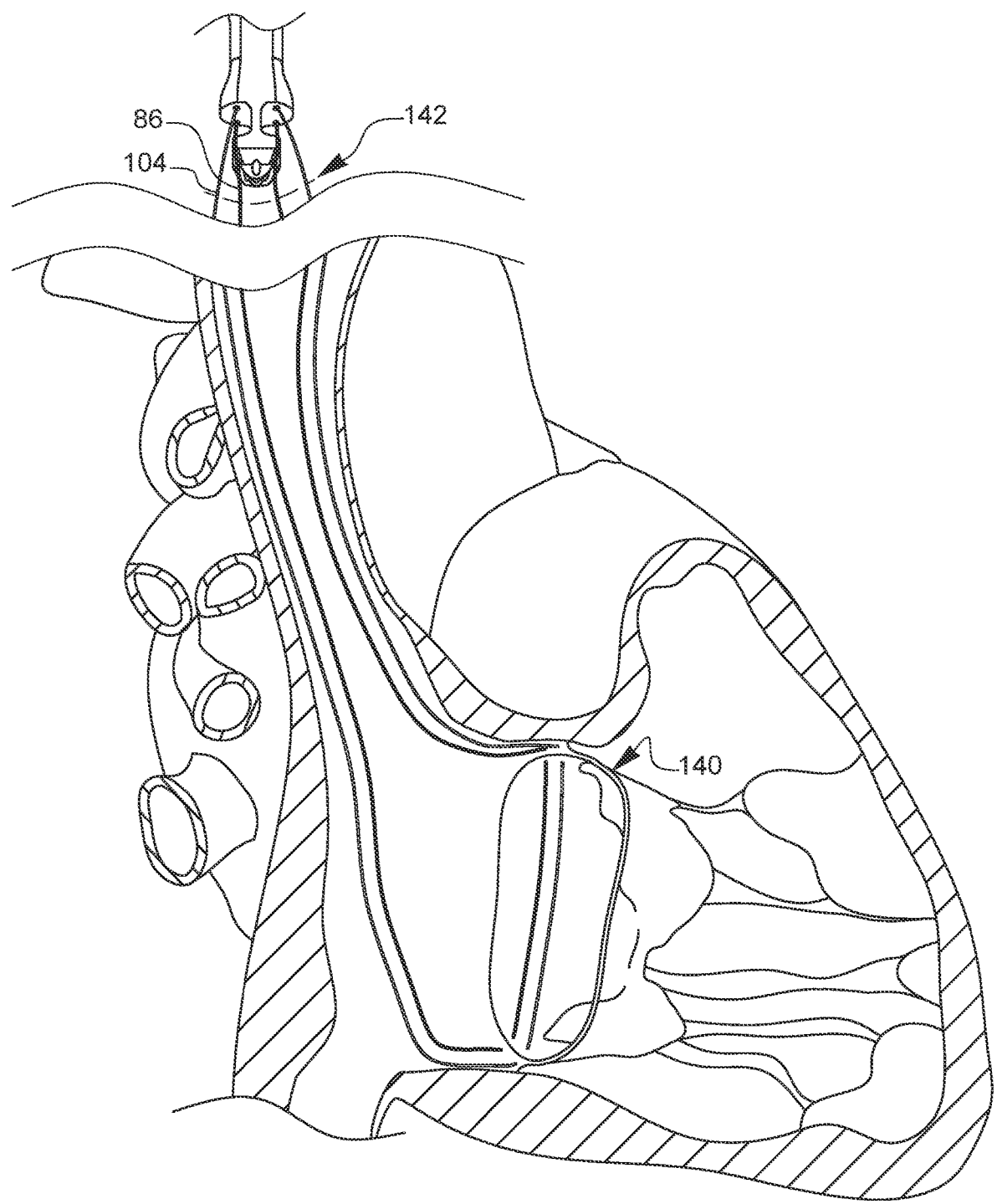
Figure 4M:
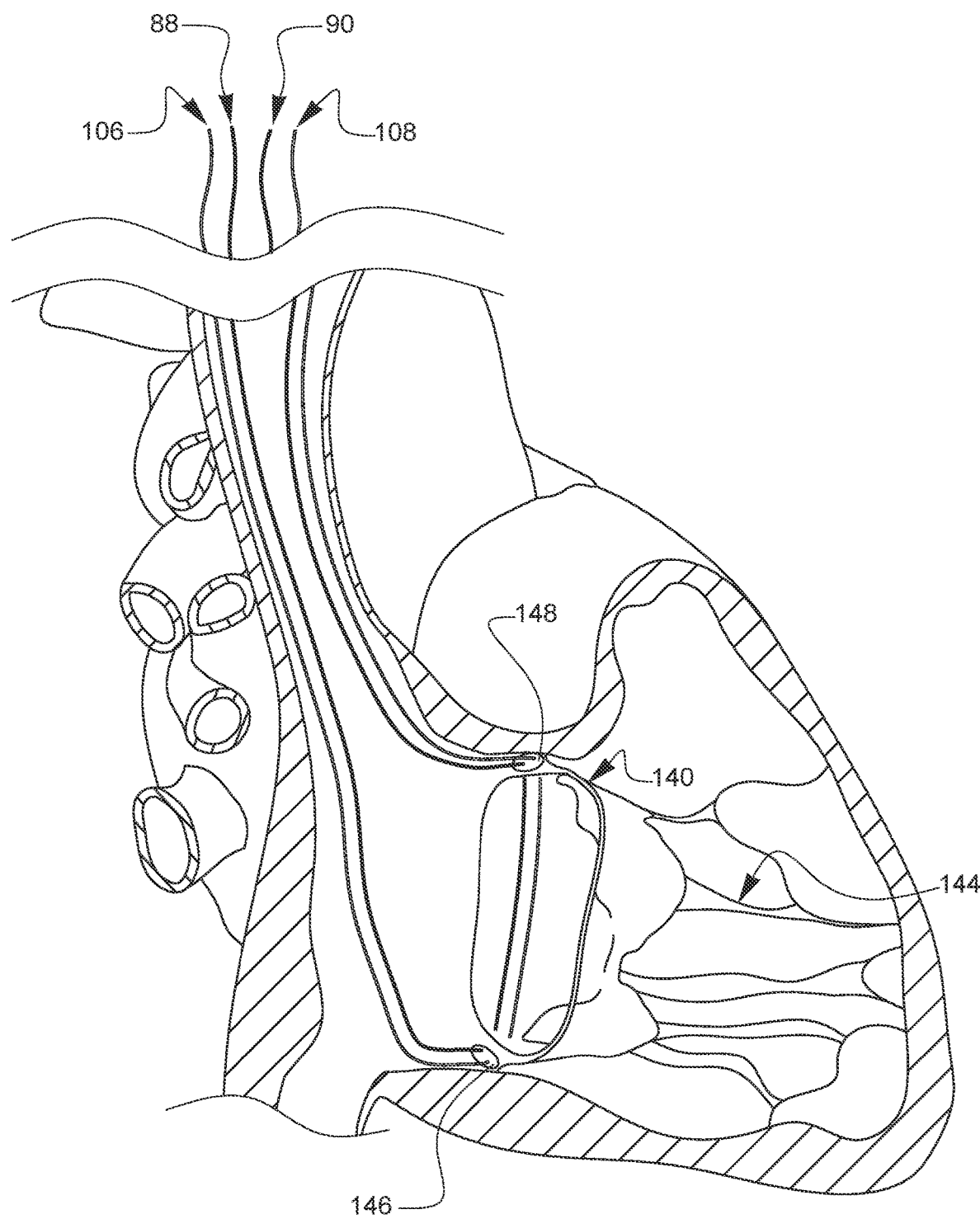

As shown in FIG. 4L, the device is carefully removed from the patient as the sutures are allowed to payout from the device. Once the device is outside of the patient, the ends of the first and second sutures may be cut from the device, leaving the ferrules behind in the suturing device, and the suturing device may be set aside. As illustrated in FIG. 4M, a first pledget 146 may be placed over the first end of the first suture 86 and the first end of the second suture 106 and advanced down to the first location on the tricuspid annulus 140. Similarly, as second pledget 148 may be placed over the second end of the first suture 86 and the second end of the second suture 106 and advanced down to the second location on the tricuspid annulus 140.

Figure 4N:
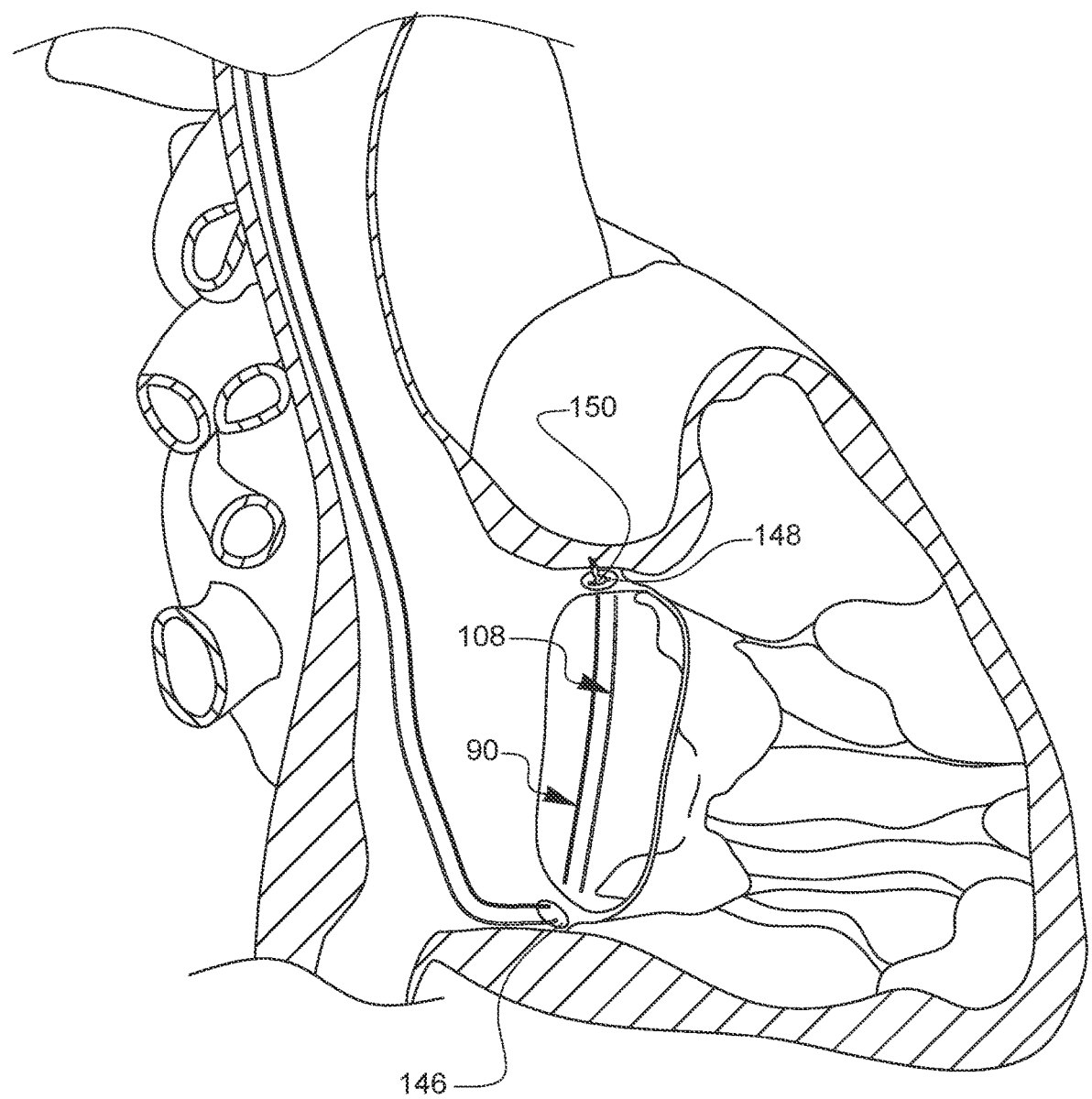

As illustrated in FIG. 4N, a mechanical fastener 150, such as the COR-KNOT® titanium fastener available from LSI Solutions, Inc., Victor, NY (www.lsisolutions.com) may be used to secure the first and second sutures 86, 104 against the first and second pledgets 146, 148 at the second annulus location. The excess second end of the first suture 86 and excess second end of the second suture 106 are also trimmed away. Note that there is not a FIG. 4O, since this looks confusingly like the number 40.

Figure 4P:
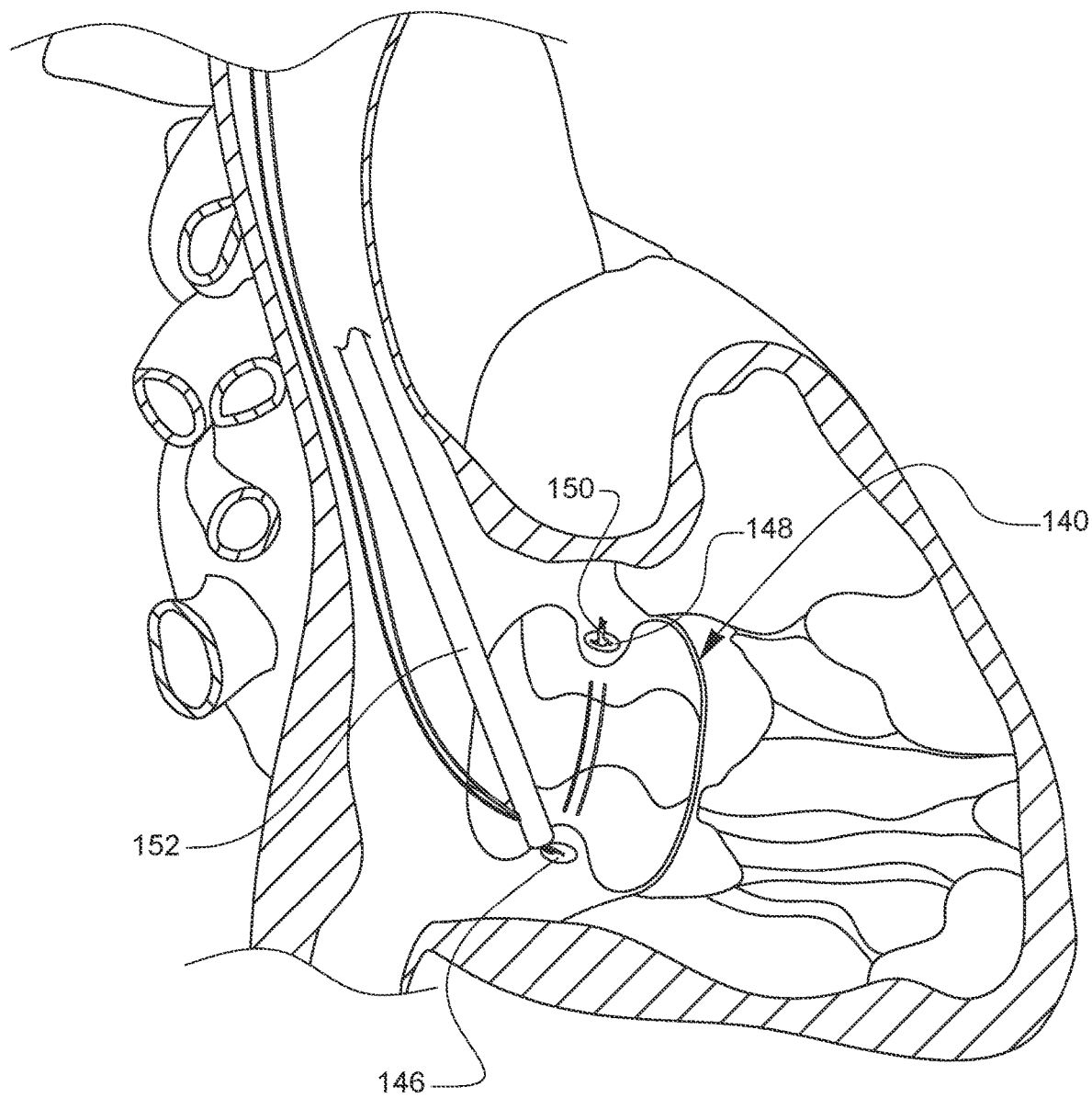
Figure 4Q:
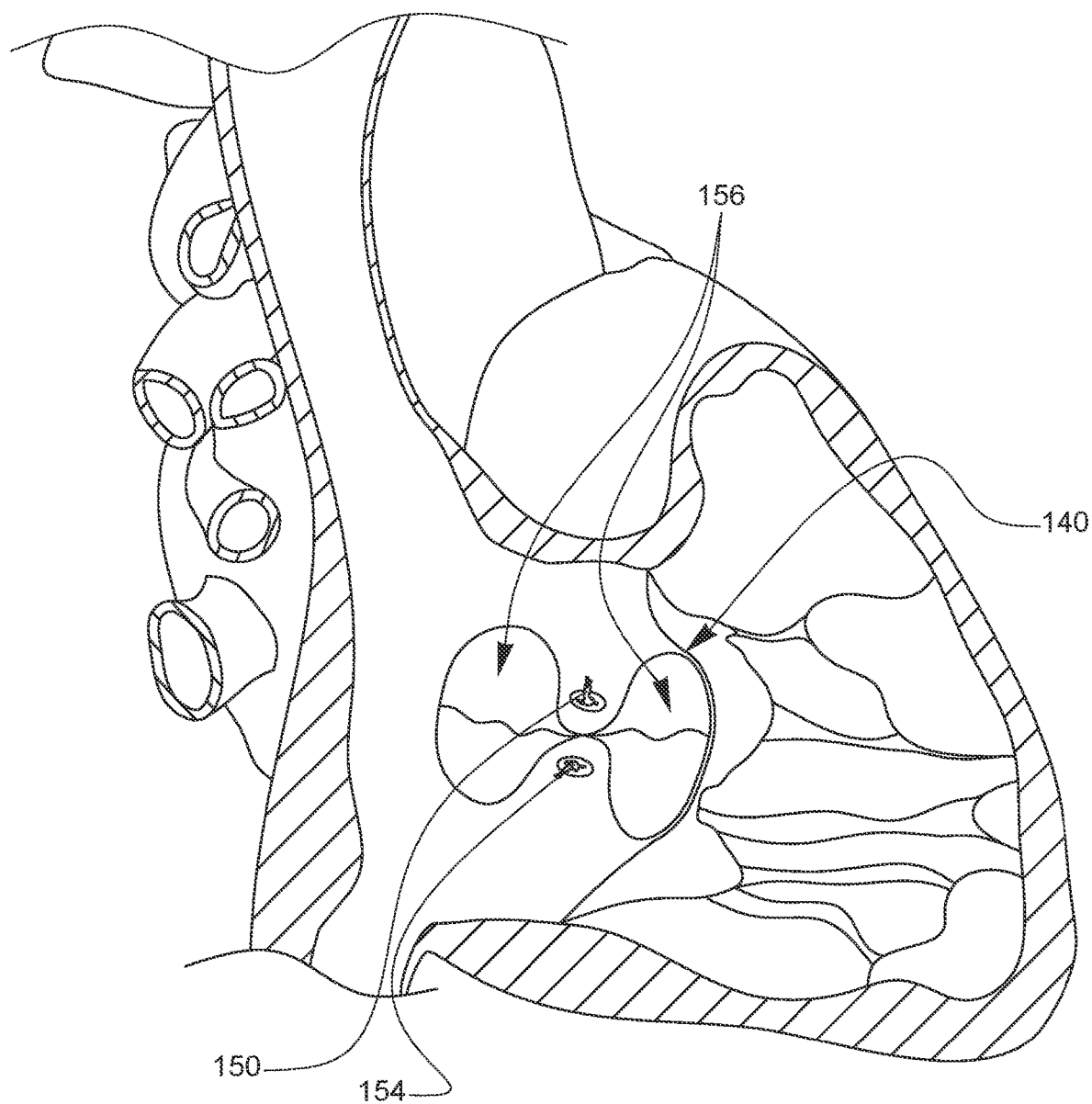
Figure 4R:
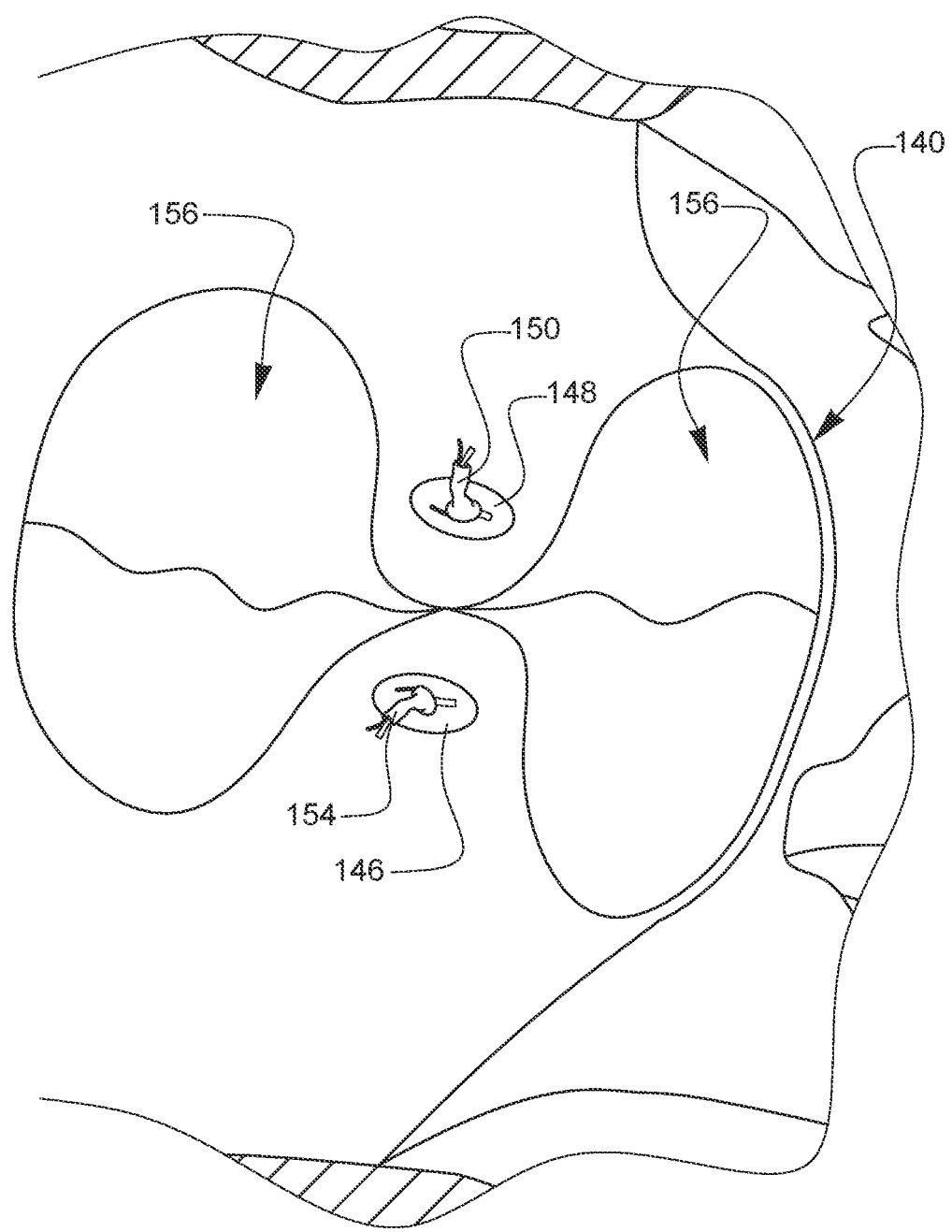

As illustrated in FIG. 4P, the first ends of the first and second sutures 88, 106 may be threaded through a mechanical fastening device 152, like a COR-KNOT® Device. The mechanical fastening device 152 holds a mechanical fastener 150, such as a titanium fastener, which can be placed against the first pledget 146 at the first annulus location. Before the mechanical fastener 150 is applied, however, the first and second sutures 86, 104 are tensioned, drawing the opposite ends of the tricuspid annulus 140 together. When the opposite sides of the tricuspid annulus 140 are touching each other, the second mechanical fastener 154 is applied, the excess suture ends are trimmed, and the result is the creation of a double orifice 156 in the tricuspid valve 126 as shown in FIG. 4Q and the enlarged view of FIG. 4R. The double orifice 156 has the advantage of enabling the tricuspid leaflets to coapt properly, thereby repairing the tricuspid valve to prevent tricuspid regurgitation.

Figure 5:
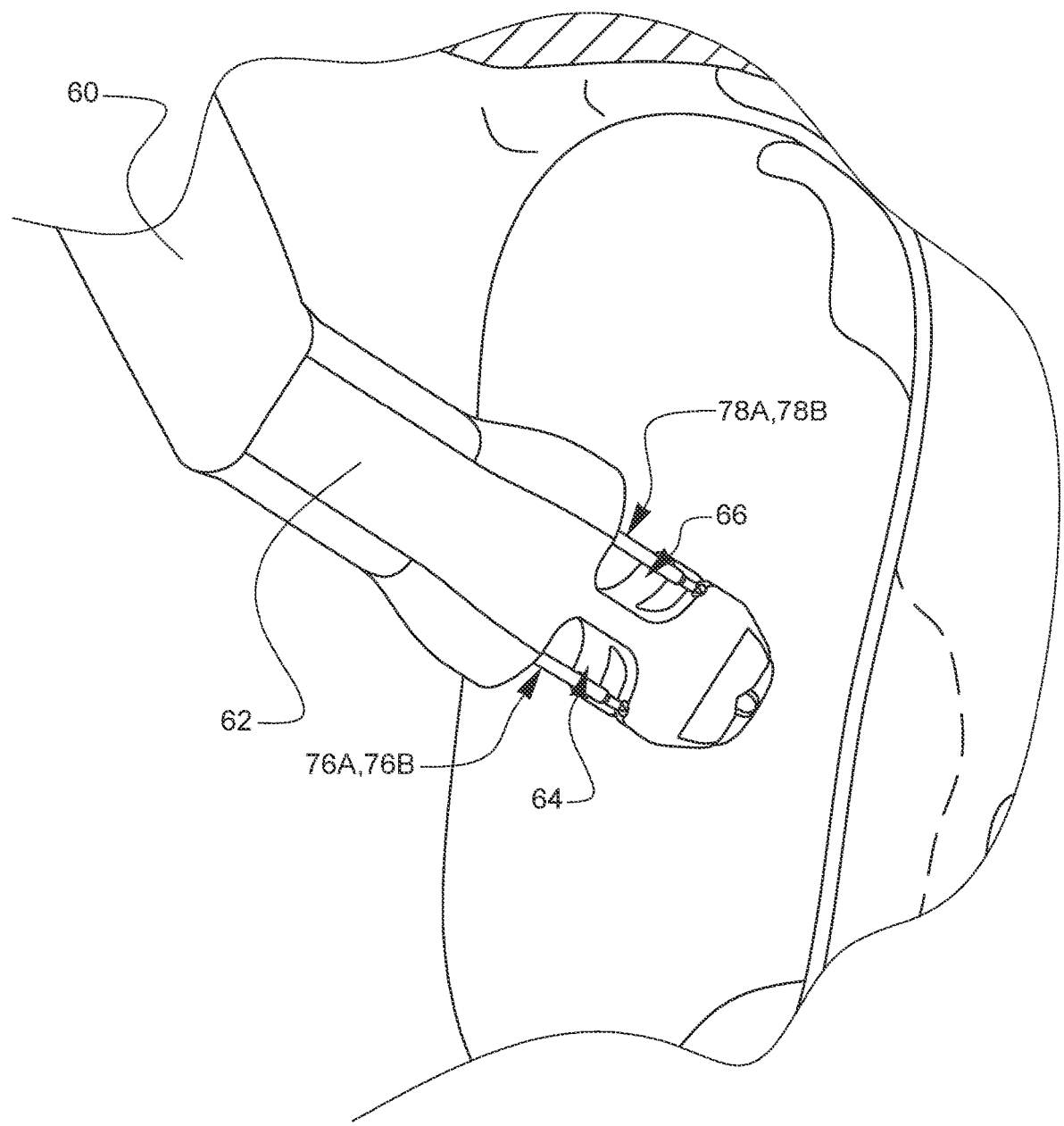
FIG. 5 is a schematic illustration of the surgical method for repair of tricuspid regurgitation showing an alternate embodiment of a surgical suturing device allowing for partial advancement of needles across the first and second tissue gaps.

Looking back at FIG. 4M, the tricuspid chordae 144, which tether the tricuspid valve leaflets to the right ventricle, can be seen. When the surgical suturing device 50 is first being positioned on the guidewire 136 within the tricuspid valve 126, some embodiments may allow for the needles to be partially advanced across the first and second tissue gaps 64, 66 as shown in FIG. 5. In this position, the needles are not far enough forward to engage the ferrules, however, the needles may help to block chordae from entering and being snagged by the first and second tissue gaps 64, 66 of the distal tip 62. The needles in this position can be said to be in a guard position. When the user is ready to place tissue within one of the gaps, the corresponding needles can be withdrawn to a retracted position and the procedure may go ahead as detailed in the above embodiment.

Figure 6A:
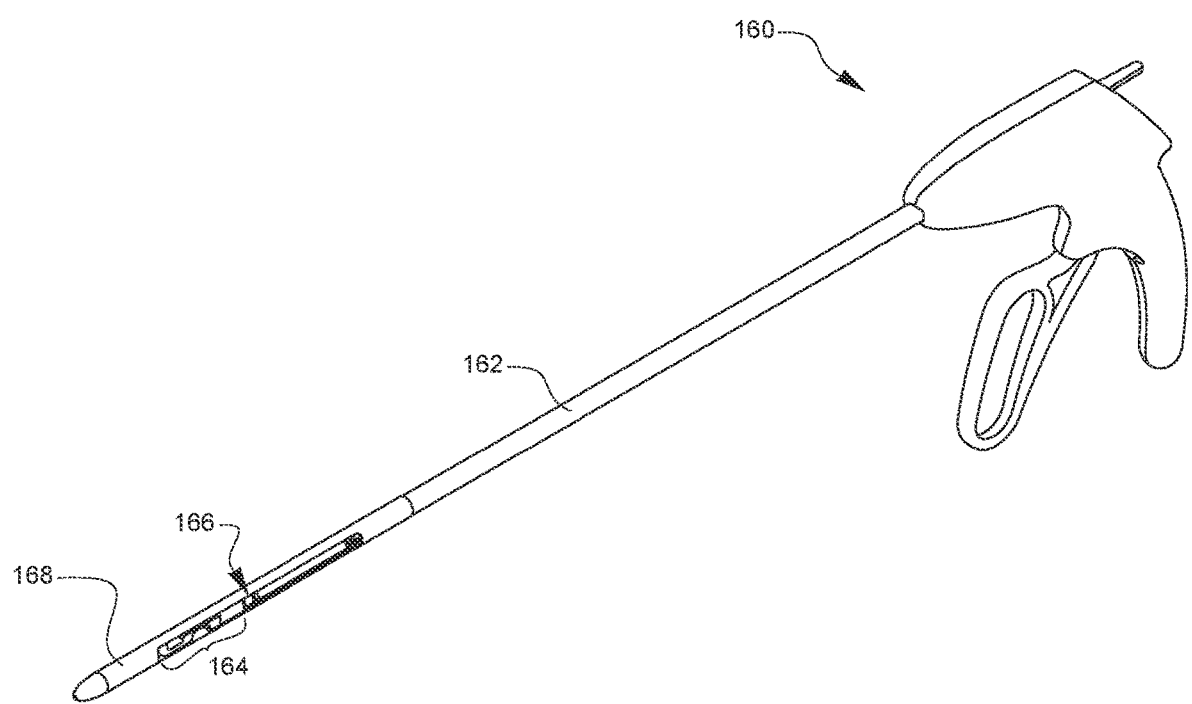
FIGS. 6A-6C are top-left-front perspective views of another embodiment of a surgical suturing device.
Figure 6B:
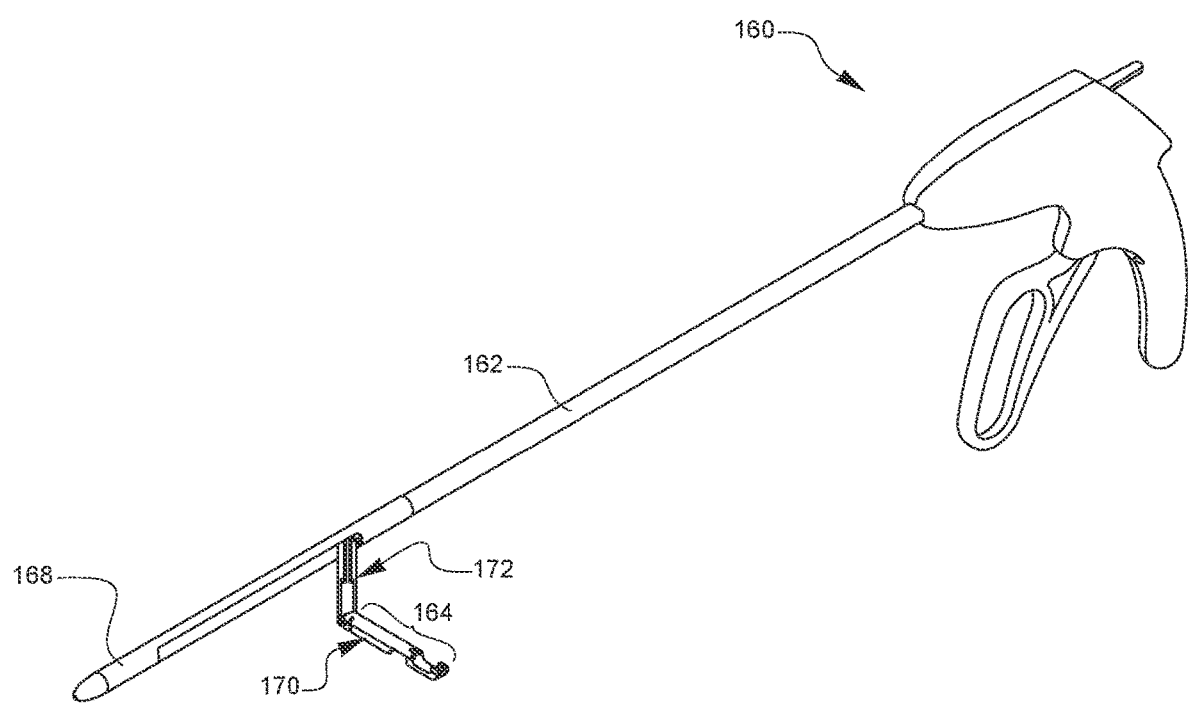

FIG. 6A illustrates another embodiment of a surgical suturing device. This embodiment is similar to the previous embodiment but has some differences. For example, the device of FIG. 6A includes a guidewire tip 168 over the distal tip 164 at the end of the shaft 162. The guidewire tip 168 has an opening in its side. The distal tip 164 can be seen through this opening. In the view of FIG. 6A, the distal tip 164 is in a retracted position. As shown in FIG. 6B, however, the distal tip articulating link 170 and an adjacent articulation link 172 may be moved to an advanced position outside of the guidewire tip 168. Other vertebrae, not shown here, may continue through the shaft 162, allowing the articulation links to remain coupled to the shaft 162, but allowing for the shaft 162 to be flexible.

Figure 6C:
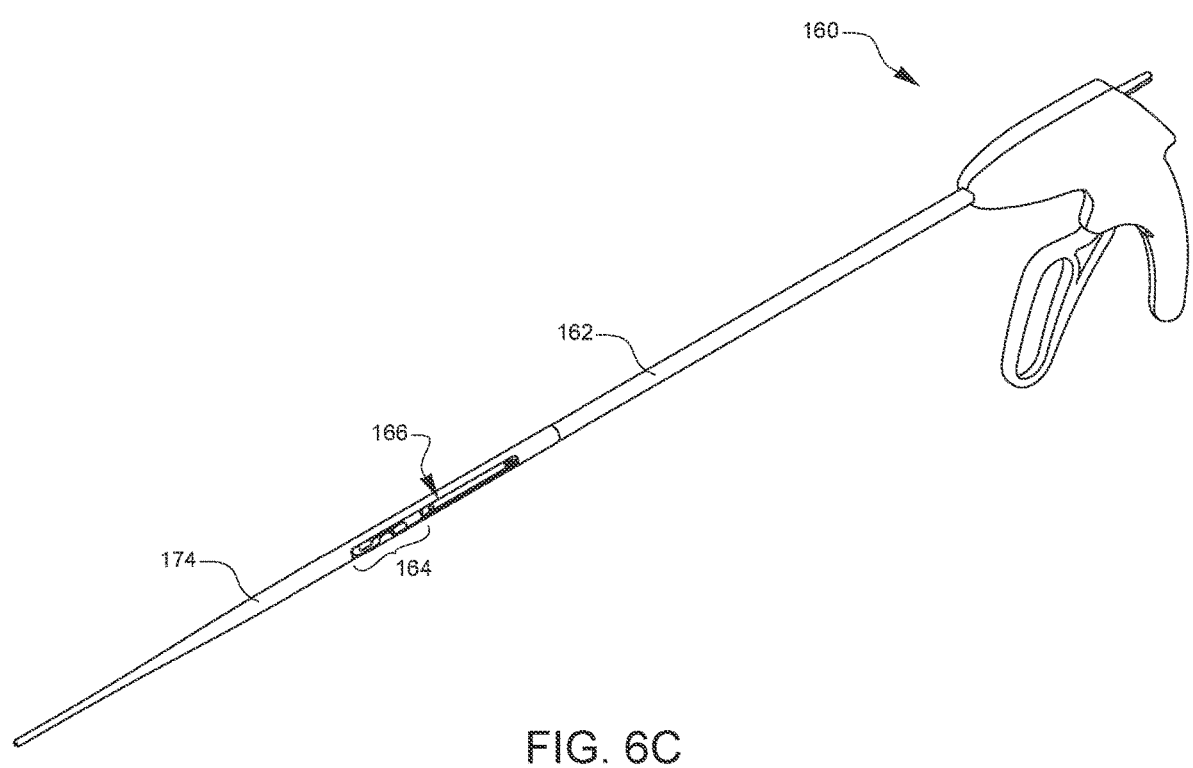

The device of FIGS. 6A and 6B will allow the guidewire tip 168 to pass over a guidewire 136. The guidewire 136 would not pass through the distal articulating tip, but it would still pass through the device shaft 162. This would allow the guidewire 136 to be kept out of the heart 124. Instead, the guidewire 136 could be advanced past the right atrium 130 and down into the inferior vena cava 132. The guidewire tip 168 would also stay out of the right atrium 130, however, the distal tip 164 link and the articulating link 172 would be able to reach into the right atrium 130 to the tricuspid valve 126 to place the suture stitches similarly to what has been described above. FIG. 6C illustrates the surgical suturing device of FIG. 6A, having an additional IVC guide tip 174, which is a soft, flexible proboscis or monorail over the distal tip 164 of the surgical suturing device 160, which is configured to assist in insertion and positioning of the distal tip 164 of the surgical suturing device 160 within the patient. The proboscis is configured to reduce trauma during this procedural step.

Figure 7:
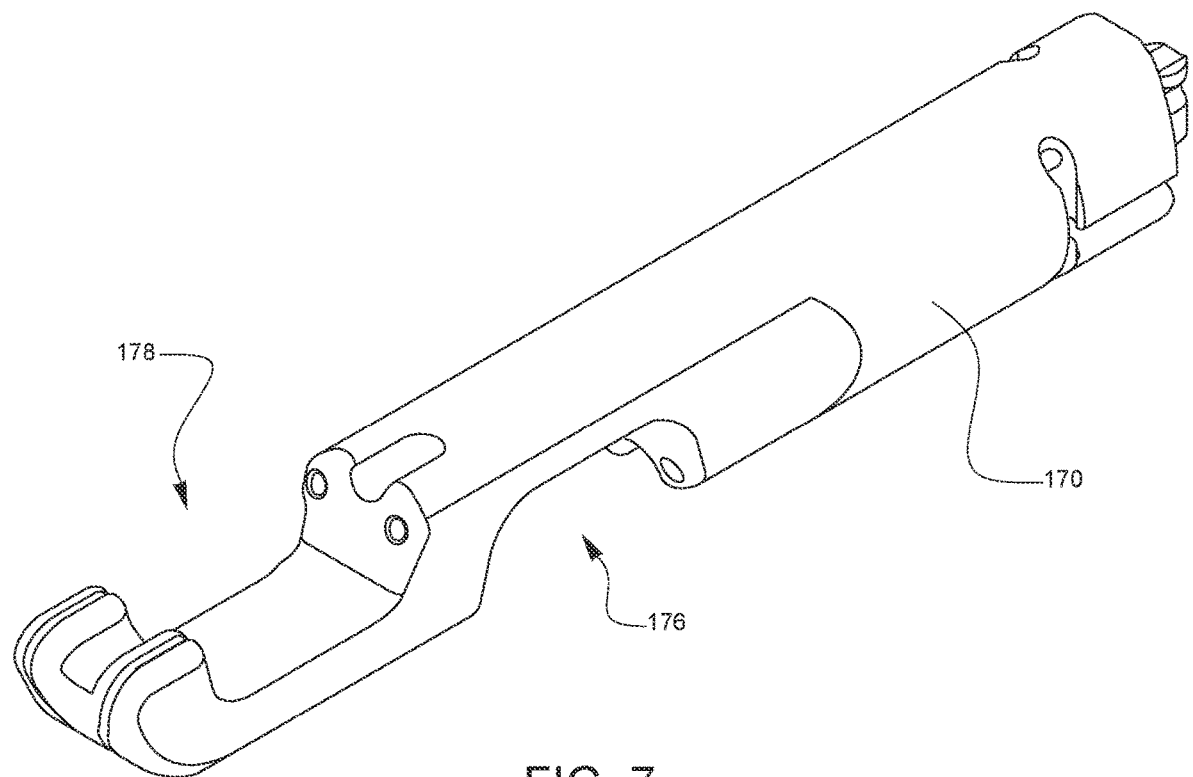
FIG. 7 is an enlarged top-left-front perspective view of the distal tip link of FIG. 6B.

FIG. 7 is an enlarged top-left-front perspective view of the distal tip 164 link from FIG. 6B. In this embodiment, the first and second tissue gaps 176,178 face in opposite directions, but they are staggered instead of symmetrical. This type of embodiment allows for a smaller diameter of the distal tip link 170.

Figure 8A:
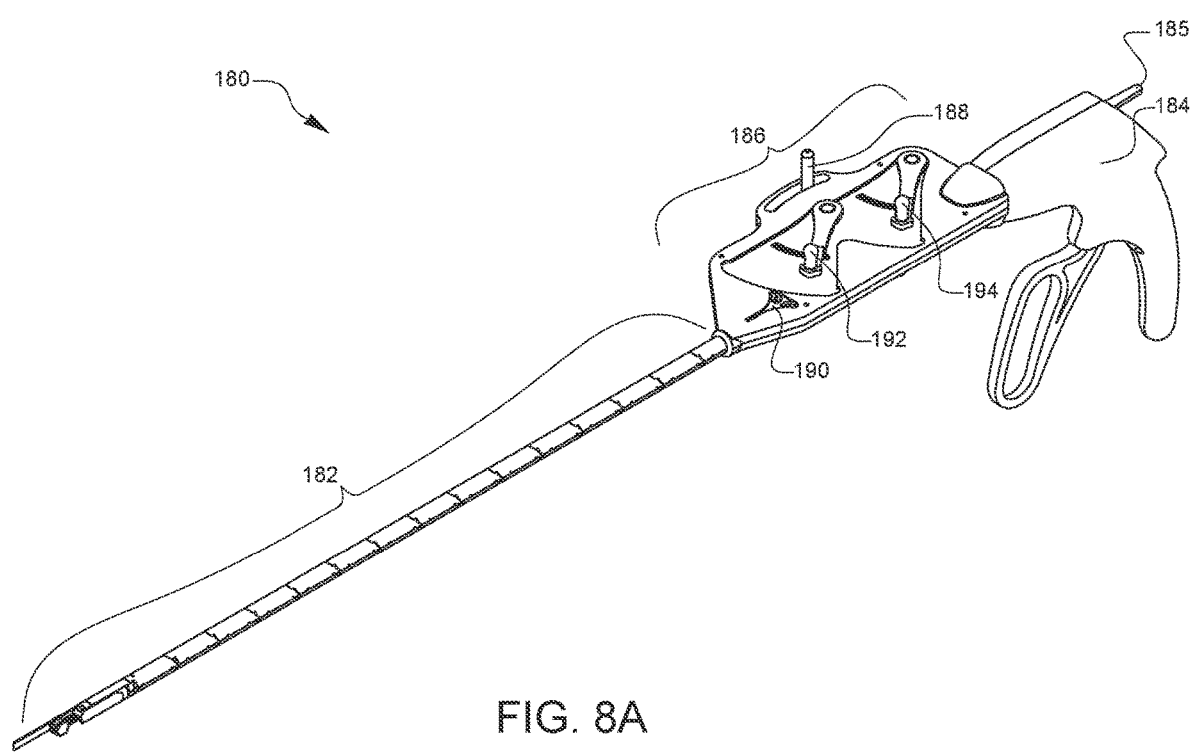
FIGS. 8A-8C are top-left-front perspective views of another embodiment of a surgical suturing device.

FIG. 8A illustrates another embodiment of a surgical suturing device 180. In this embodiment, a control panel is located between the shaft 182 and the handle housing 184. Two articulation control levers 192 are coupled to the two articulation links 192 at the distal end. In the position shown, the distal tip 164 is in a retracted position. Steering cables (not visible in this view) connect the control levers to the distal links so that the links may be moved. A tension cable may be provided within the device shaft 182 and coupled to a locking control 188. To enable movement, the tension cable is untensioned by releasing the locking control 188. Once a desired position for the distal tip 164 is established, the tension cable may be tensioned by locking the locking control 188.

A suture viewing window 190 may also be provided in the control panel 186. As described above, the middles of the first and second sutures 86, 104 are fed up through the device shaft 182 when the device is assembled. A portion of this middle suture may be placed to be visible within the suture viewing window 190 so that successful stitching may be verified through movement of the suture middle portions after squeezing and releasing the device lever 56. When needles successfully pass through tissue, engage a ferrule, and pull the ferrule back through the tissue, the attached suture is also pulled through the tissue. As the suture moves through the tissue, its middle will also move within the suture viewing window 190, providing valuable feedback to the surgeon. Suture viewing windows 190 such as this may be continuous or alternatively in separate locations on the control panel 186 or housing depending on the number of sutures required to be loaded in the device or instrument.

Figure 8B:
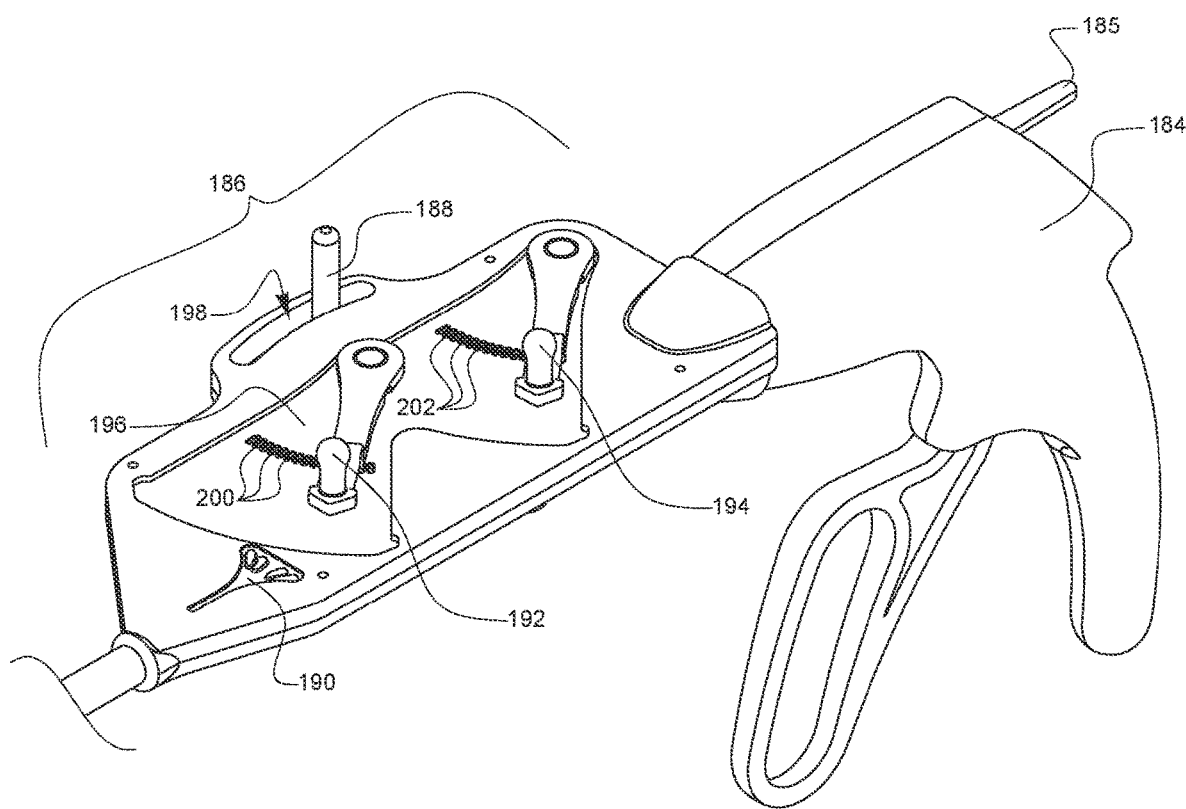

FIG. 8B is an enlarged perspective view of an embodiment of a proximal end of a surgical suturing device 180, focusing on the control panel 186. In this view, a proximal articulation control lever 194 and a distal articulation control lever 192 positioned atop the control panel surface 196, are both shown in an articulated position. The proximal articulation control lever 194 is configured to flex or articulate two articulation joints 208, 214 in the flexible shaft 182, and the distal articulation control lever 192 is configured to articulate a second articulation joint 214 in the flexible shaft 182. These articulation joints 208, 214 are further discussed in regard to FIG. 8C. Each of the articulation control levers 192, 194 are paired with several positional keyways, located on the control panel surface 196, which are configured to receive a key (not visible here) attached to the underside of the articulation control lever 192, 194. The keys will hold each articulation control lever 192, 194 in a specific keyway position until moved by the operator. This is not shown in this view but discussed later in regard to FIGS. 23A and 23B. The control panel 186 also has a locking control 188, which is shown in a fully articulated position and is configured to travel within a locking channel 198. This function is not fully shown in this view but is discussed later in regard to an alternate embodiment described in regard to FIG. 22.

Figure 8C:
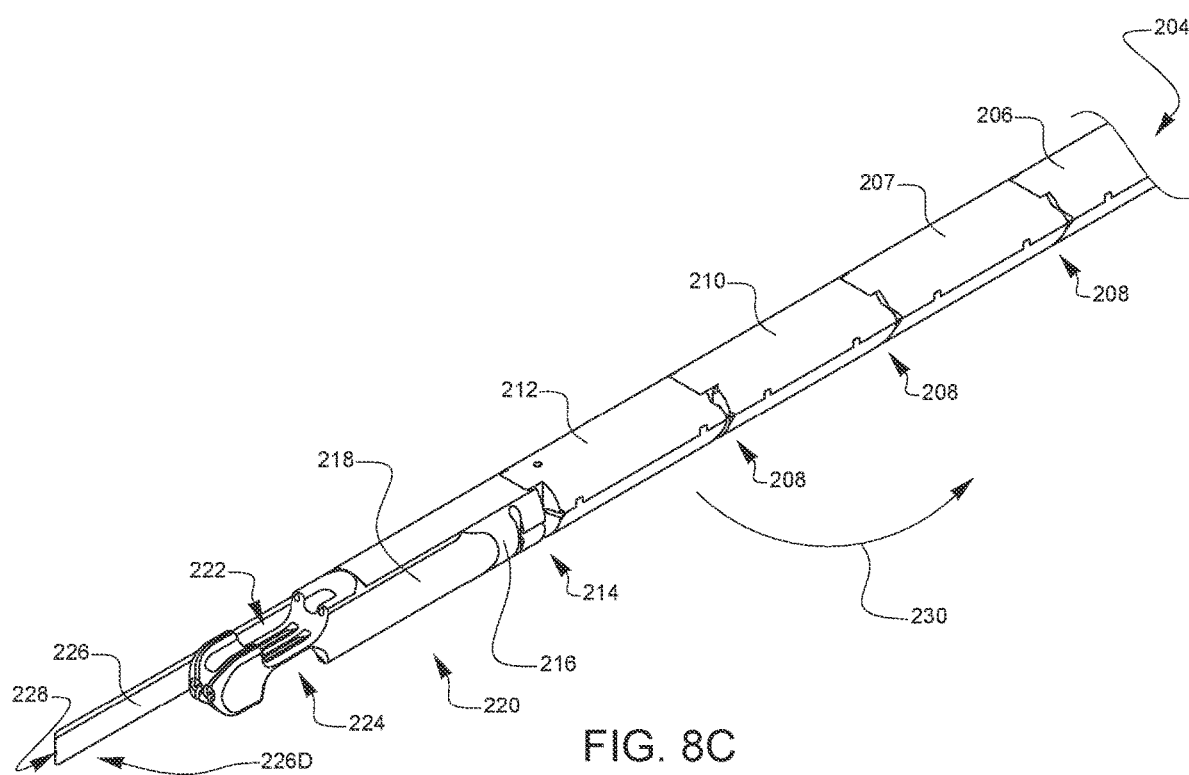

FIG. 8C is an enlarged perspective view of the distal end of an embodiment of a surgical suturing device 180, focusing on the distal tip 220 and distal articulation joints 208, 214. This illustrates two vertebrae 206, 207 segments or links at the proximal end of the flexible shaft 204, connected sequentially to a first middle link, a second middle link 212, a distal jaw link 216, and a distal tip 220 having a first tissue gap 222 and a second tissue gap 224. An IVC (inferior vena cava) guide tip 226 is also attached to the distal jaw link 216 and is located at the distal end of the flexible shaft 182 of the surgical suturing device 180. The IVC guide tip 226 has a guide wire channel 228 at its distal end. In other embodiments, there may be a soft, flexible proboscis or monorail on the end of the IVC guide tip 226 configured to assist in insertion and positioning of the distal tip 220 of the surgical suturing device 180 within the patient. The proboscis is configured to reduce trauma during this procedural step. Referring back to FIG. 8B, the proximal articulation control lever 194, when articulated, will flex or articulate the first two articulation joints 208, 214 in the flexible shaft 182 which are located between the last vertebrae 207 and the first middle link, and between the first middle link and the second middle link 212. The distal articulation control lever 192 will flex or articulate the second articulation joint 214 located between the second middle link 212 and the distal jaw link 216. As described previously, the amount of flex or articulation selected with each of the articulation control levers 192, 194 will be fixed in place by the engagement of the positional keyways 200, 202 located on the control panel surface 196 and the keys located on the proximal articulation control lever 194 and the distal articulation control lever 192. As the first two articulation joints 208, 214 and the second articulation joints 214 are flexed or articulated in order to make the required tissue bites as previously described, the IVC guide tip 226 remains parallel and aligned with the original axis of the flexible shaft 182.

Figure 9:
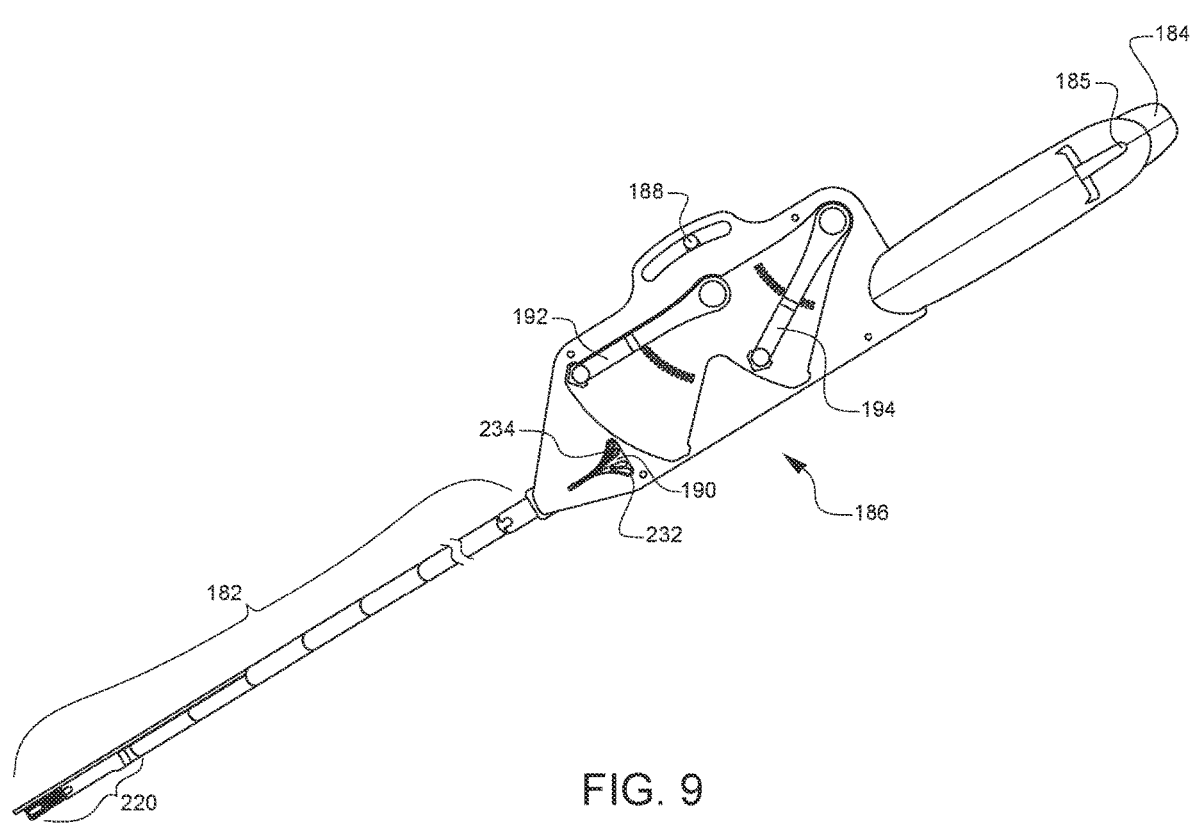
FIG. 9 is a top view of the embodiment of the surgical suturing device of FIG. 8A.

FIG. 9 is a top view of the embodiment of the surgical suturing device 180 of FIG. 8A. The distal tip 220, flexible shaft 182, control panel 186, housing handle 184 as previously described are shown in this view. On the control panel 186 are the suture viewing window 190 with two visible sutures 232, 234, the distal articulation control lever 192 in a non-actuated position, the proximal articulation control lever 194 in a partially articulated position, and the locking control 188 in a partially locked position.

Figure 10:
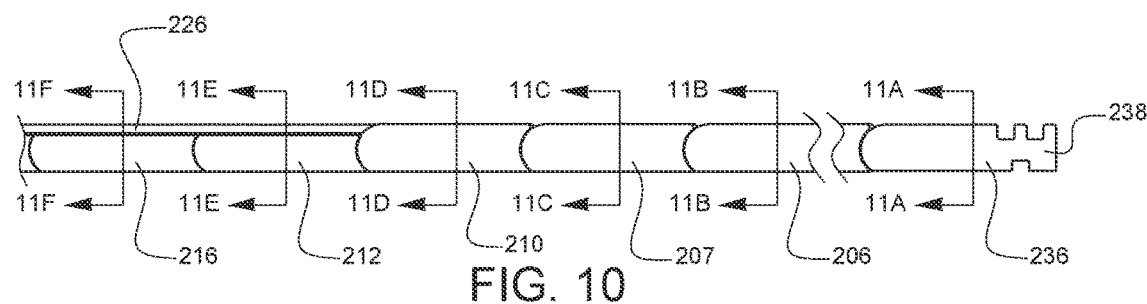
FIG. 10 is a top view of the flexible shaft of the surgical suturing device of FIG. 8A.

FIG. 10 is a top view of the flexible shaft of the surgical suturing device 180 of FIG. 8A, detailing a number of unique vertebrae segments or links, the cross-sections of which are shown in greater detail in FIGS. 11A-F. These vertebrae segments 206, 207, 210, 212, 216, when connected, comprise the flexible shaft 182 of the surgical suturing device 180 of the present disclosure. Illustrated in FIG. 10 is a first vertebrae 236 indicated by cross-sectional marker 11A, several vertebrae segments 206, 207, 210, 212, 216 indicated by cross-sectional markers 111B, 11C, and 11D, 11E, and 11F. The first vertebrae 236, indicated by cross-sectional marker 11A, includes a linking end 238 to fixedly attach the flexible shaft 182 to the control panel 186 section of the surgical suturing device 180. The cross-sectional features of these vertebrae are further discussed in regard to FIGS. 11A, 11B, 11C, 11D, 11E, and 11F. The cross-sectional features shown in this embodiment of the surgical suturing device 180 are one arrangement, and it should be noted that other arrangements or configurations may be useful or effective in maintaining and articulating the various control and locking cables, sutures, guide wire, and needle pairs along the internal path of a flexible shaft 182 may be known to those skilled in the art.

Figure 11A:
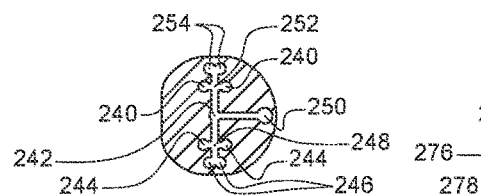
FIGS. 11A-11F are cross-sectional views of flexible shaft vertebra segments of FIG. 10.

FIG. 11A is a cross section of the vertebra segment of FIG. 10. The inner structure of the first vertebra 236 possesses several features related to cable pathway management throughout the length of the flexible shaft 182. The vertebra segment 236 defines two first needle channels 254 which are configured to guide the first needle pair along the flexible shaft 182. The vertebra segment 236 also defines a first suture pair path 252, surrounded by two distal articulation cable channels 240, which are configured to guide the first suture pair and the distal articulation cables from the distal articulation lever 192 along the flexible shaft 182 to the distal jaw articulation joint. The distal articulation cables, not shown in this view, include a pulling articulation cable and a return articulation cable. The vertebra segment 236 further defines a central locking cable channel 242 configured to guide the locking cable from the locking control mechanism throughout the flexible shaft 182. The vertebra segment 236 further defines a guidewire channel 250 which carries the guidewire along the flexible shaft 182, and finally a second suture pair path 248, proximal articulation cable channels 244, and second needle channels 246. These channels are configured to guide the second suture pair, the proximal articulation cables, and the second needle pair along the flexible shaft 182.

Figure 11C:
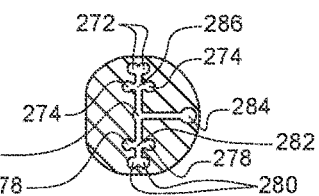
Figure 11E:
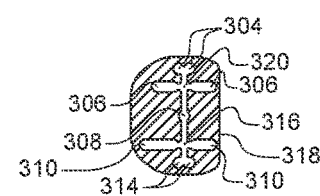
Figure 11B:
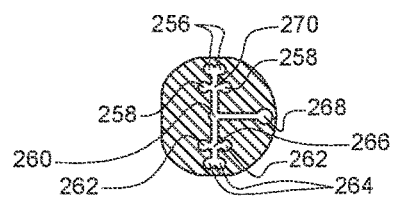

FIG. 11B is a cross section of the vertebra segment 206 of FIG. 10. The inner structure of this vertebra possesses several features related to cable pathway management throughout the length of the flexible shaft 182. The inner structure is identical to the vertebra 236 illustrated in FIG. 11A, however, the vertebra segment 206 of FIG. 11B does not have a linking end as in the vertebra segment 236 of FIG. 11A.

FIG. 11C is a cross section of the vertebra segment 207 of FIG. 10. The inner structure of this vertebra possesses several features related to cable pathway management throughout the length of the flexible shaft 182. The inner structure is similar to the vertebrae illustrated in FIGS. 11A-11B, except that the guidewire channel 284 terminates at this vertebra segment 207 in the flexible shaft 182, where the guidewire passes through to the guidewire channel 250 in the IVC guide.

Figure 11D:
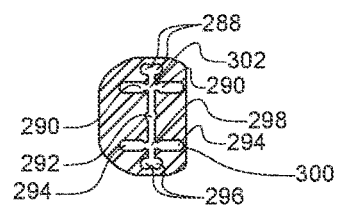

FIG. 11D is a cross section of the vertebra segment 210 of FIG. 10. The outer structure of this vertebra segment 210 is flat on one side to accommodate the IVC guide shown in FIG. 10. The inner structure of this vertebra possesses several features related to cable pathway management throughout the length of the flexible shaft 182. The inner structure is similar to the vertebrae illustrated in FIGS. 11A-11C, but the vertebra segment 210 illustrated in FIG.

11D has no guidewire channel 284, as the guidewire passes through to the guidewire channel 284 in the IVC guide after passing through the vertebra segment 207 illustrated in FIG. 11C. Another difference in the inner structure of the vertebra segment 210 of FIG. 11D as compared to those previously described is a pair of wider proximal articulation cable channels 294. Since previous sequential vertebrae segments constrain the proximal articulation cables, the joint at the intersections will not flex or bend. As the proximal articulation cable channels 294 in the vertebra segment 210 of FIG. 11D are wider, they allow for the movement of the joint at the intersection of the vertebra segment 210 of FIG. 11D and the first middle link illustrated in FIG. 11E when the proximal articulation cables are pulled or released.

FIG. 11E is a cross section of the vertebra segment of FIG. 10. The outer structure of this vertebra segment 212 is flat on one side to accommodate the IVC guide shown in FIG. 10. The inner structure of this vertebra possesses several features related to cable pathway management throughout the length of the flexible shaft 182. The inner structure is similar to the vertebra segment 210 of FIG. 11D, but the vertebra segment 212 illustrated in FIG. 11E, the first middle link, has a pair of still wider proximal articulation cable channels 310 to accommodate the flex or bend of the proximal articulation cables. The first middle link also defines two proximal articulation cable recesses 312, which are configured to accommodate the termination of the proximal articulation cables at the joint between the first middle link of FIG. 11E, and the second middle link of FIG. 11F. Another difference in the inner structure of the vertebra segment 212 of FIG. 11E as compared to the vertebra segment 210 previously described in FIG. 11D is a pair of wider distal articulation cable channels 306. Since previous sequential vertebrae segments 210, 207, 206 constrain the distal articulation cables 306, the joint at those intersections will not flex or bend. Since the distal articulation cable channels 306 in the vertebra segment 212 of FIG. 11E are wider, they allow for the movement of the joint at the intersection of the second middle link illustrated in FIG. 11F and the distal tip 220 of the instrument when the distal articulation cables are pulled or released.

Figure 11F:
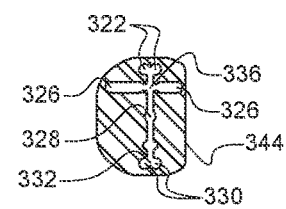

FIG. 11F is a cross section of the vertebra segment 216 of FIG. 10. The outer structure of this vertebra segment 216 is flat on one side to accommodate the IVC guide shown in FIG. 10. The inner structure is similar to the vertebra segment 216 of FIG. 11E, but the vertebra segment 216 illustrated in FIG. 11F, does not have proximal articulation cable channels 310, since the proximal articulation cables terminated in the vertebra segment 212 of FIG. 11E. Another difference in the inner structure of the vertebra segment 216 of FIG. 11F as compared to the vertebra segment 212 previously described in FIG. 11E is a pair of still wider distal articulation cable channels 326 to allow for the movement of the joint at the distal tip 220 of the instrument when the distal articulation cables are pulled or released. The second middle link 212 also defines two distal articulation cable recesses 324, which are configured to accommodate the termination of the distal articulation cables within the vertebra segment of FIG. 11F.

Figure 12A:
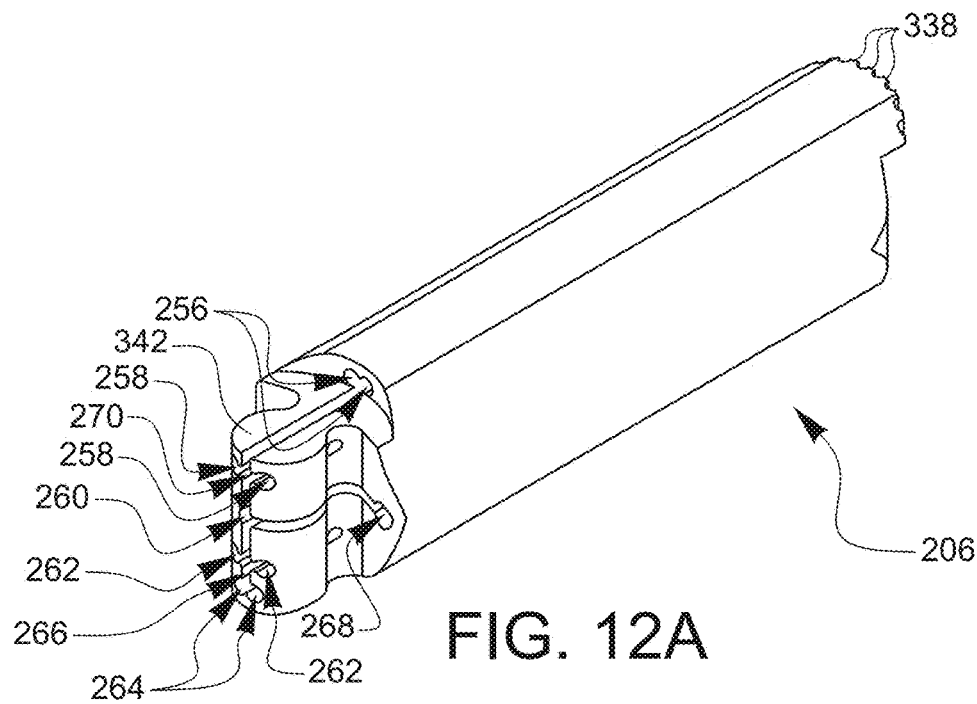
FIGS. 12A-12B are perspective views of the unique vertebra segment of FIG. 11B.
Figure 12B:
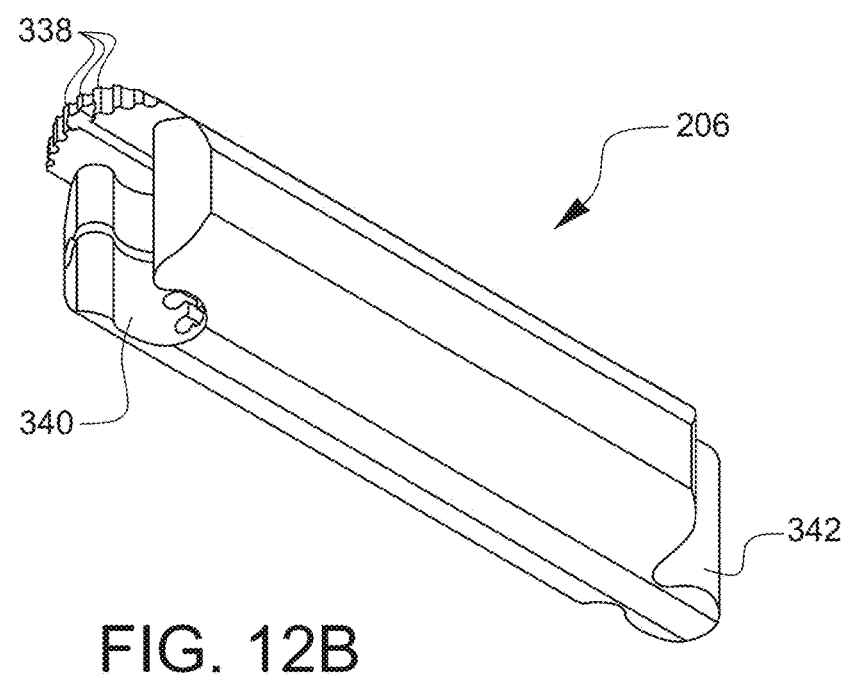
Figure 13E:
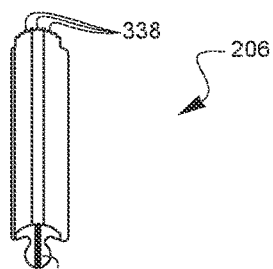
FIGS. 13A, 13B, 13C, 13D, 13E, and 13F are front, left side, right side, rear, top, and bottom elevational views, respectively of the unique vertebra segment of FIGS. 12A-B.
Figure 13B:
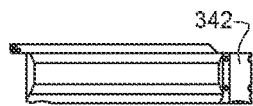
Figure 13A:
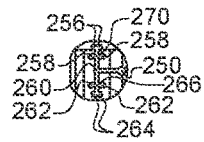
Figure 13C:
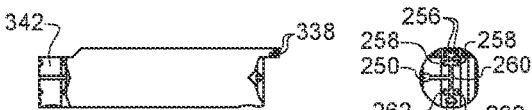
Figure 13D:
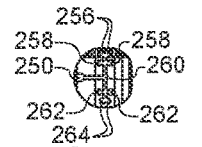
Figure 13F:
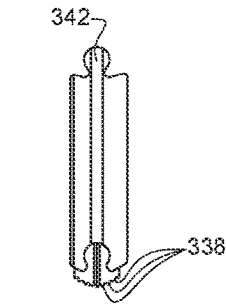

FIG. 12A-12B are perspective views of the unique vertebra segment of FIG. 11B. The vertebra segment 206 illustrated in FIGS. 12A and 12B defines two first needle channels 256, a first suture pair path 270, surrounded by two distal articulation cable channels 258, a central locking cable channel 260, a guidewire channel 268, a second suture pair path 266 surrounded by two proximal articulation cable channels 262, and second needle channels 264. These have been described in detail with regard to FIG. 11B. The vertebra segment 206 illustrated in FIGS. 12A and 12B further defines a vertebra link 342 and a vertebra recess 340 configured to link similar or distinct vertebra segments as described herein, depending the desired length of chain or inner channel configuration of a particular embodiment. The vertebra segment 206 also defines a groove 338 or grooved end that is configured to provide a friction fit when the flexible shaft 182 vertebra segments 206 are locked using the locking mechanism. The grooves 338 will enable improved fit or immobilization of the various vertebrae comprising a flexible shaft 182 in this embodiment of the surgical suturing device 180 as described herein. FIGS. 13A-13F are front, left side, right side, rear, top, and bottom elevational views, respectively of the unique vertebra segment of FIGS. 12A-B.

Figure 14A:
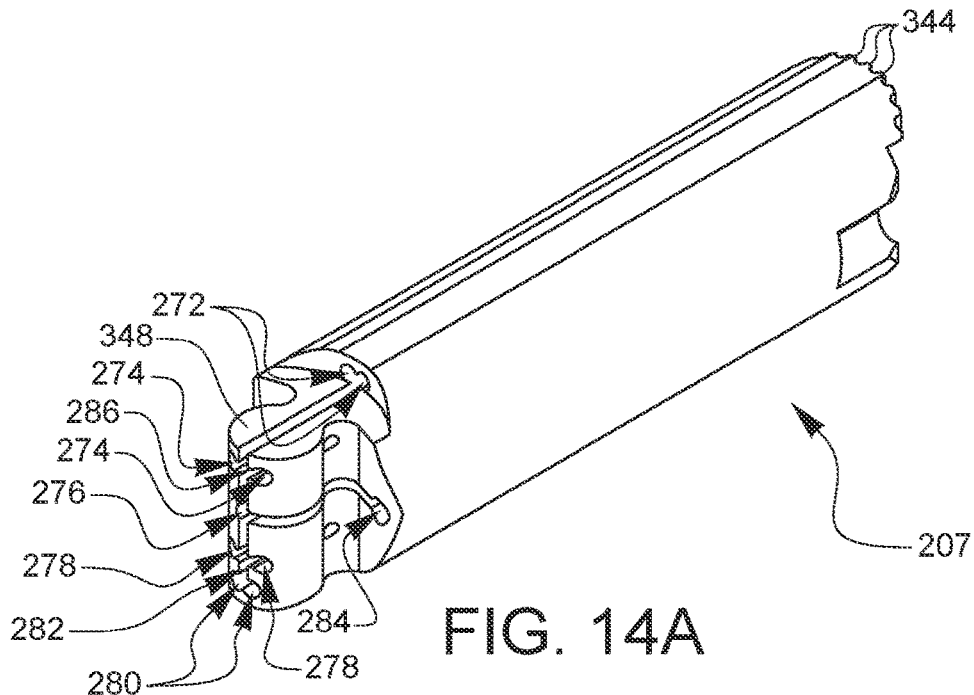
FIGS. 14A-14B are perspective views of the unique vertebra segment of FIG. 11C.
Figure 14B:
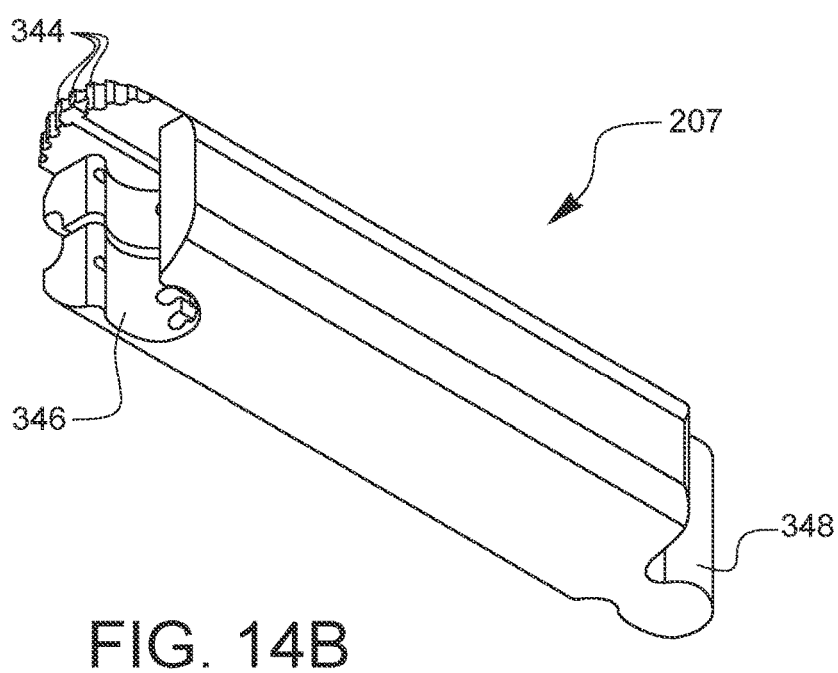
Figure 15E:
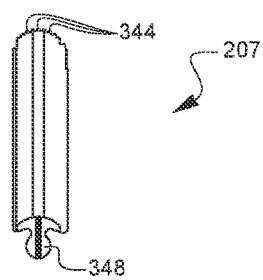
FIGS. 15A, 15B, 15C, 15D, 15E, and 15F are front, left side, right side, rear, top, and bottom elevational views, respectively of the unique vertebra segment of FIGS. 14A-14B.
Figure 15B:
Figure 15A:
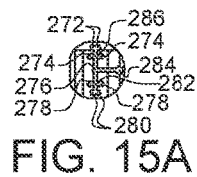
Figure 15C:
Figure 15D:
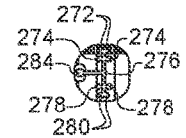
Figure 15F:
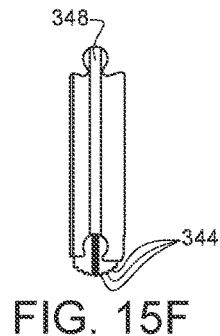

FIG. 14A-14B are perspective views of the unique vertebra segment of FIG. 11C 207. The vertebra segment illustrated in FIGS. 14A and 14B 207 defines two first needle channels 272, a first suture pair path 286, surrounded by two distal articulation cable channels 274, a central locking cable channel 276, a guidewire channel 284, a second suture pair path 282 surrounded by two proximal articulation cable channels 278, and second needle channels 280. These have been described in detail with regard to FIG. 11C. The vertebra segment 207 illustrated in FIGS. 14A and 14B further defines a vertebra link 348 and a vertebra recess 346 configured to link similar or distinct vertebra segments 207 as described herein, depending the desired length of chain or inner channel configuration of a particular embodiment. The vertebra segment 207 also defines a groove 344 or grooved end that is configured to provide a friction fit when the flexible shaft 182 vertebra segments 207 are locked using the locking mechanism. The grooves 344 will enable improved fit or immobilization of the various vertebrae comprising a flexible shaft 182 in this embodiment of the surgical suturing device 180 as described herein. FIGS. 15A-15F are front, left side, right side, rear, top, and bottom elevational views, respectively of the unique vertebra segment of FIGS. 14A-14B.

Figure 16A:
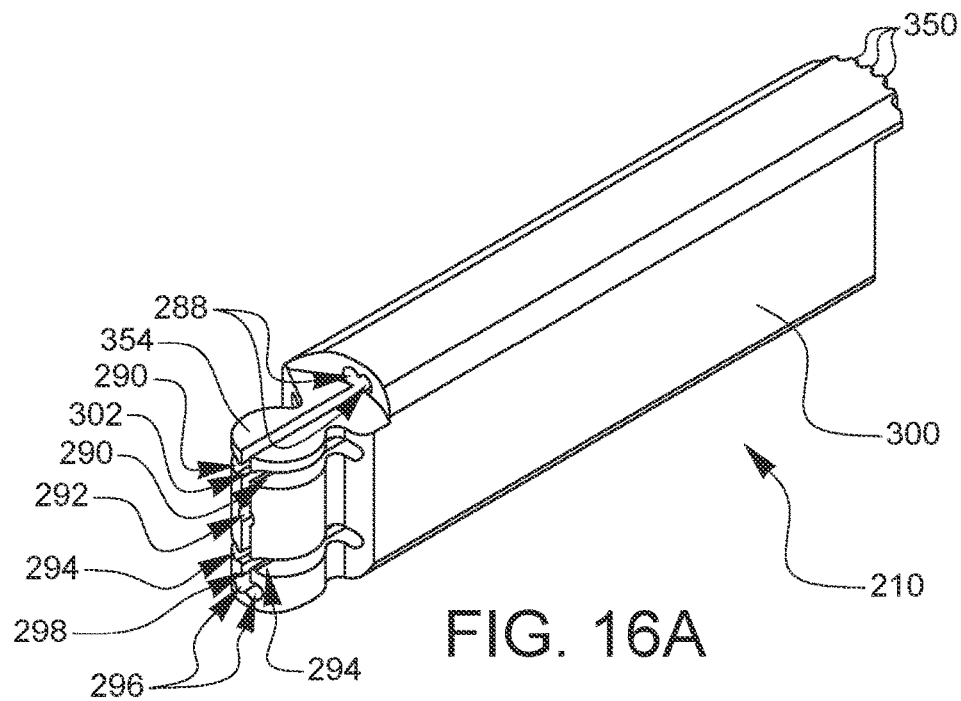
FIGS. 16A-16B are perspective views of the unique vertebra segment of FIG. 11D.
Figure 16B:
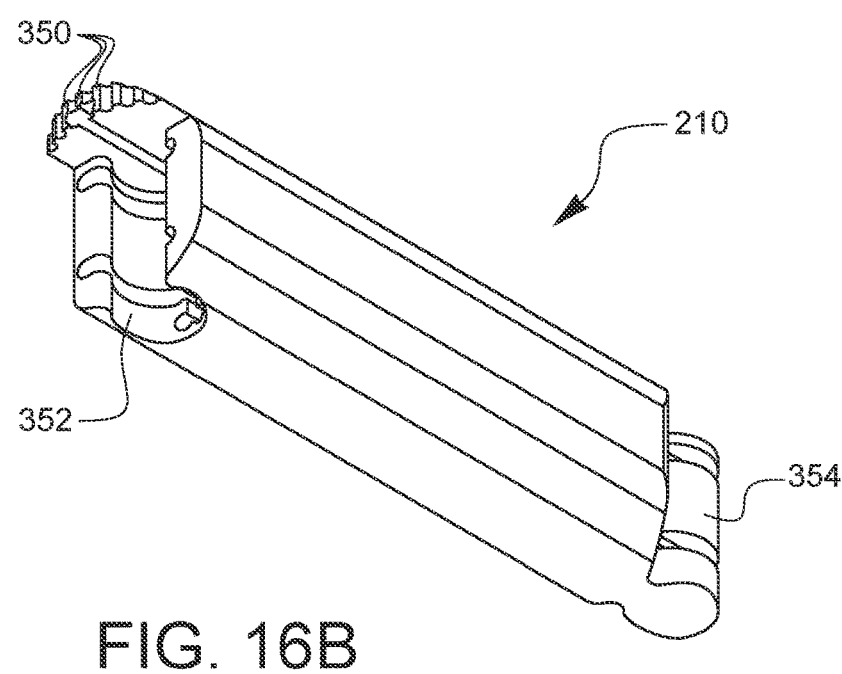
Figure 17E:
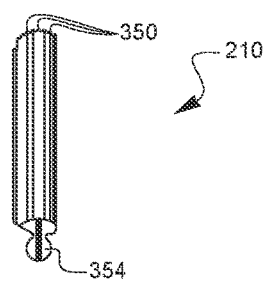
FIGS. 17A, 17B, 17C, 17D, 17E, and 17F are front, left side, right side, rear, top, and bottom elevational views, respectively of the unique vertebra segment of FIGS. 16A-16B.
Figure 17B:
Figure 17A:
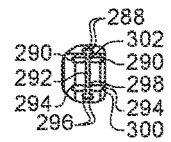
Figure 17C:
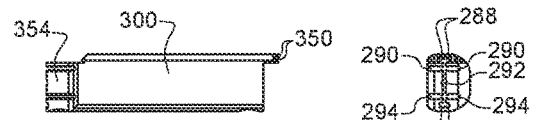
Figure 17D:
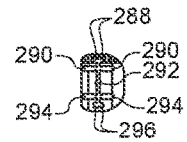
Figure 17F:
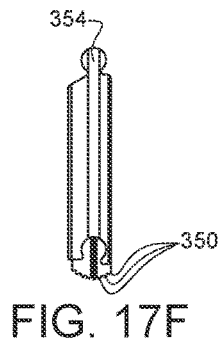

FIGS. 16A-16B are perspective views of the unique vertebra segment of FIG. 11D 210. The vertebra segment 210 illustrated in FIGS. 16A and 16B has a flat side and defines two first needle channels 288, a first suture pair path 302, surrounded by two distal articulation cable channels 290, a central locking cable channel 276, a second suture pair path 298 surrounded by two proximal articulation cable channels 294, and second needle channels 296. These have been described in detail with regard to FIG. 11D. The vertebra segment 212 illustrated in FIGS. 16A and 16B further defines a vertebra link 354 and a vertebra recess 352 configured to link similar or distinct vertebra segments 206, 207, 210, 212 as described herein, depending the desired length of chain or inner channel configuration of a particular embodiment. The vertebra segment 212 also defines a groove 350 or grooved end that is configured to provide a friction fit when the flexible shaft 182 vertebra segments 206, 207, 210, 212 are locked using the locking mechanism. The grooves 350 will enable improved fit or immobilization of the various vertebrae 206, 207, 210, 212 comprising a flexible shaft 182 in this embodiment of the surgical suturing device 180 as described herein. FIGS. 17A-17F are front, left side, right side, rear, top, and bottom elevational views, respectively of the unique vertebra segment of FIGS. 16A-16B.

Figure 18A:
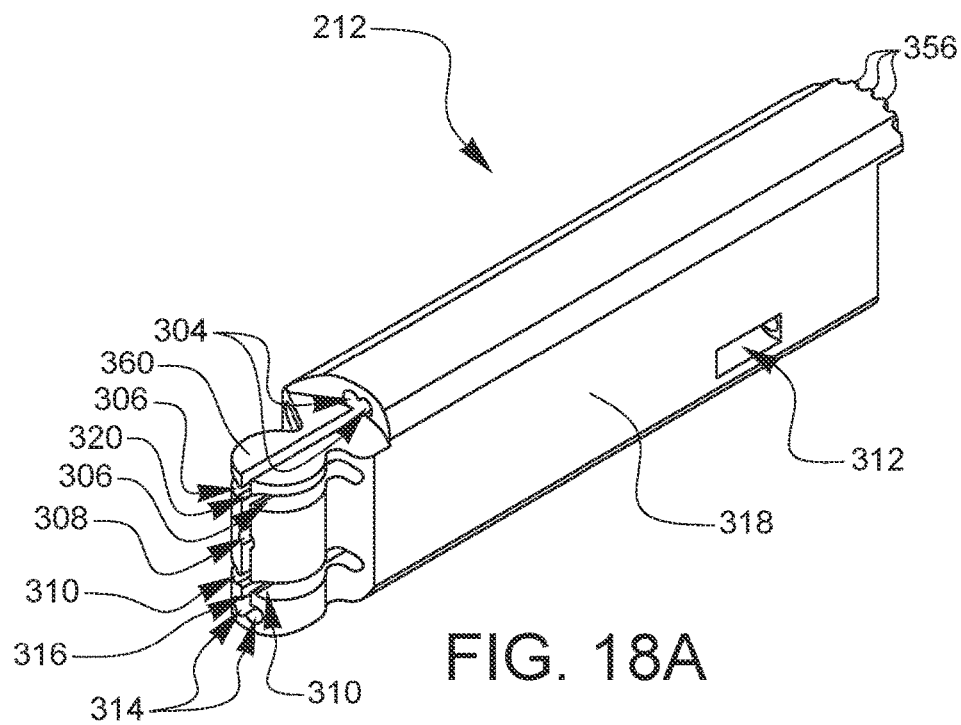
FIGS. 18A-18B are perspective views of the unique vertebra segment of FIG. 11E.
Figure 18B:
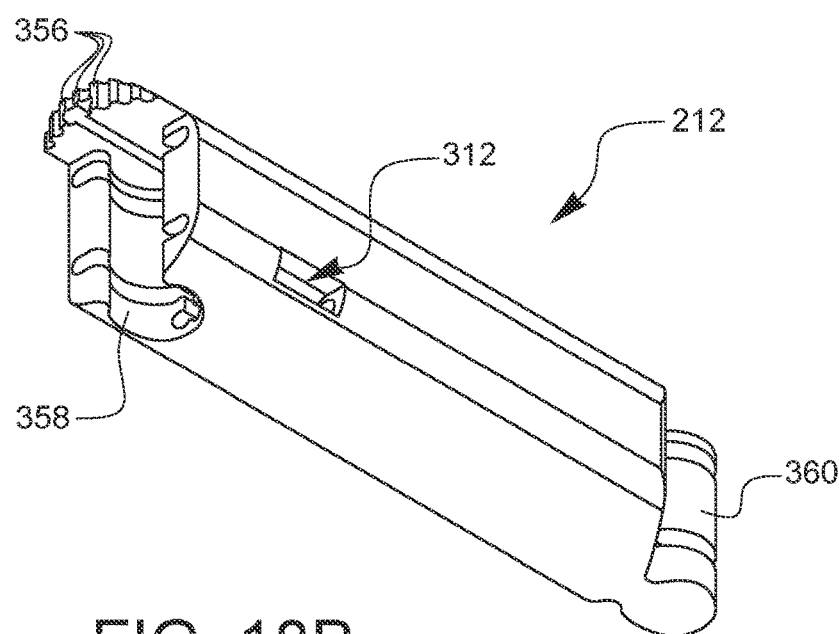
Figure 19E:
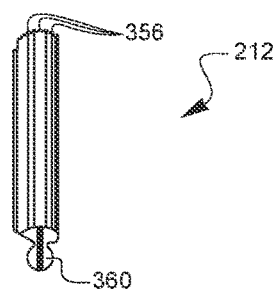
FIGS. 19A, 19B, 19C, 19D, 19E, and 19F are front, left side, right side, rear, top, and bottom elevational views, respectively of the unique vertebra segment of FIGS. 18A-18B.
Figure 19B:
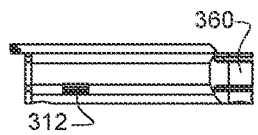
Figure 19A:
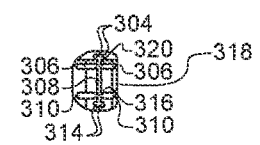
Figure 19C:
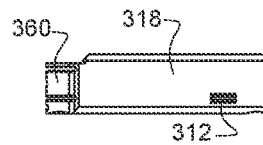
Figure 19D:
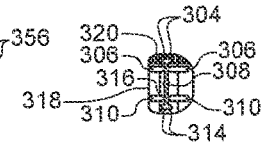
Figure 19F:
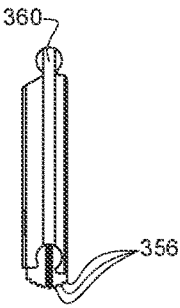

FIGS. 18A-18B are perspective views of the unique vertebra segment of FIG. 11E. The vertebra segment 212 illustrated in FIGS. 18A and 18B has a flat side and defines two first needle channels 304, a first suture pair path 320, surrounded by two distal articulation cable channels 306, a central locking cable channel, a second suture pair path 316 surrounded by two proximal articulation cable channels 310, and second needle channels 314. The vertebra segment 212 also defines two proximal articulation cable recesses 310. These features have been described in detail with regard to FIG. 11E. The vertebra segment 212 illustrated in FIGS. 18A and 18B further defines a vertebra link 360 and a vertebra recess 358 configured to link similar or distinct vertebra segments 206, 207, 210, 212 as described herein, depending the desired length of chain or inner channel configuration of a particular embodiment. The vertebra segment 212 also defines a groove 356 or grooved end that is configured to provide a friction fit when the flexible shaft 182 vertebra segments 206, 207, 210, 212 are locked using the locking mechanism. The grooves 356 will enable improved fit or immobilization of the various vertebrae comprising a flexible shaft 182 in this embodiment of the surgical suturing device as described herein. FIGS. 19A-19F are front, left side, right side, rear, top, and bottom elevational views, respectively of the unique vertebra segment of FIGS. 18A-18B.

Figure 20A:
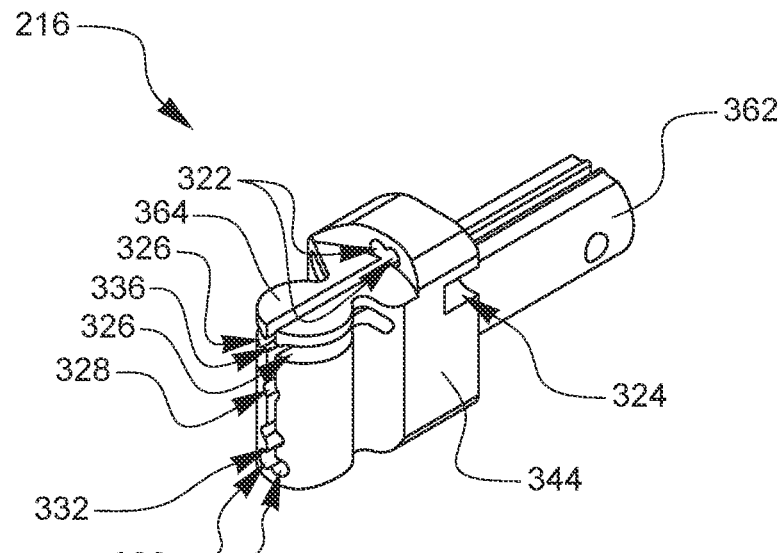
FIGS. 20A-20B are perspective views of the unique vertebra segment of FIG. 11F.
Figure 20B:
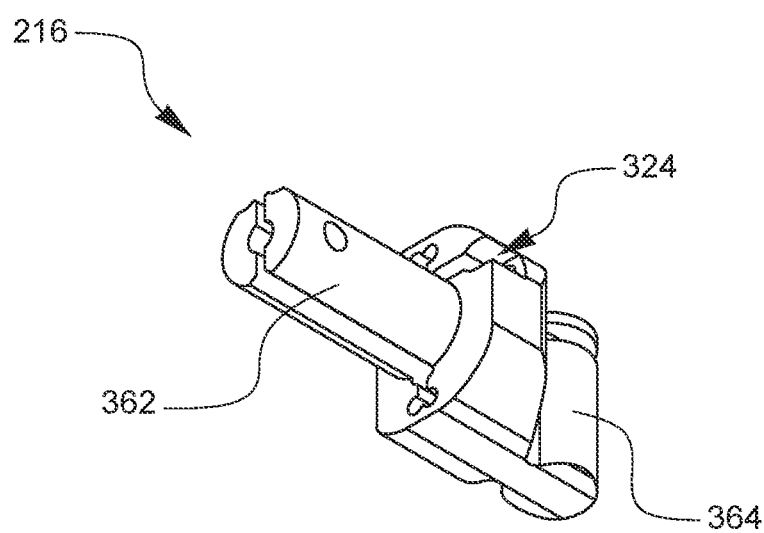
Figure 21E:
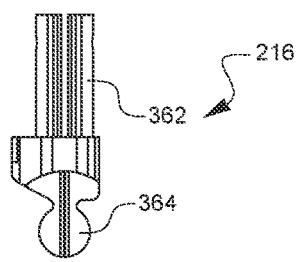
FIGS. 21A, 21B, 21C, 21D, 21E, and 21F are front, left side, right side, rear, top, and bottom elevational views, respectively of the unique vertebra segment of FIGS. 20A-20B.
Figure 21B:
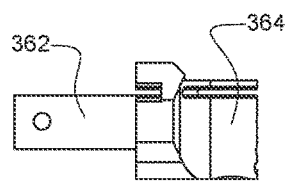
Figure 21A:
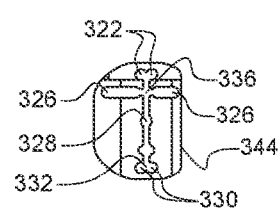
Figure 21C:
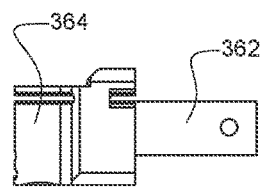
Figure 21D:
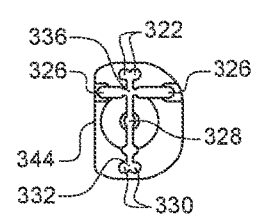
Figure 21F:
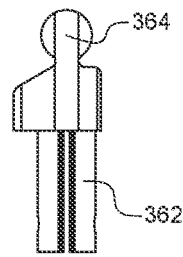

FIG. 20A-20B are perspective views of the unique vertebra segment of FIG. 11F. The vertebra segment 216 illustrated in FIGS. 20A and 20B has a flat side and defines two first needle channels 322, a first suture pair path 336, surrounded by two distal articulation cable channels 326, a central locking cable channel, a second suture pair path 332, and second needle channels 330. The vertebra segment 216 also defines two distal articulation cable recesses 324. These features have been described in detail with regard to FIG. 11E. The vertebra segment 216 illustrated in FIGS. 20A and 20B further defines a connection end 362 for attaching a distal tip 220 to the end of the flexible shaft 182, and a connection for terminating the locking cable, not shown in this view. FIG. 21A-21F are front, left side, right side, rear, top, and bottom elevational views, respectively of the unique vertebra segment 212 of FIGS. 20A-20B.

Figure 22:
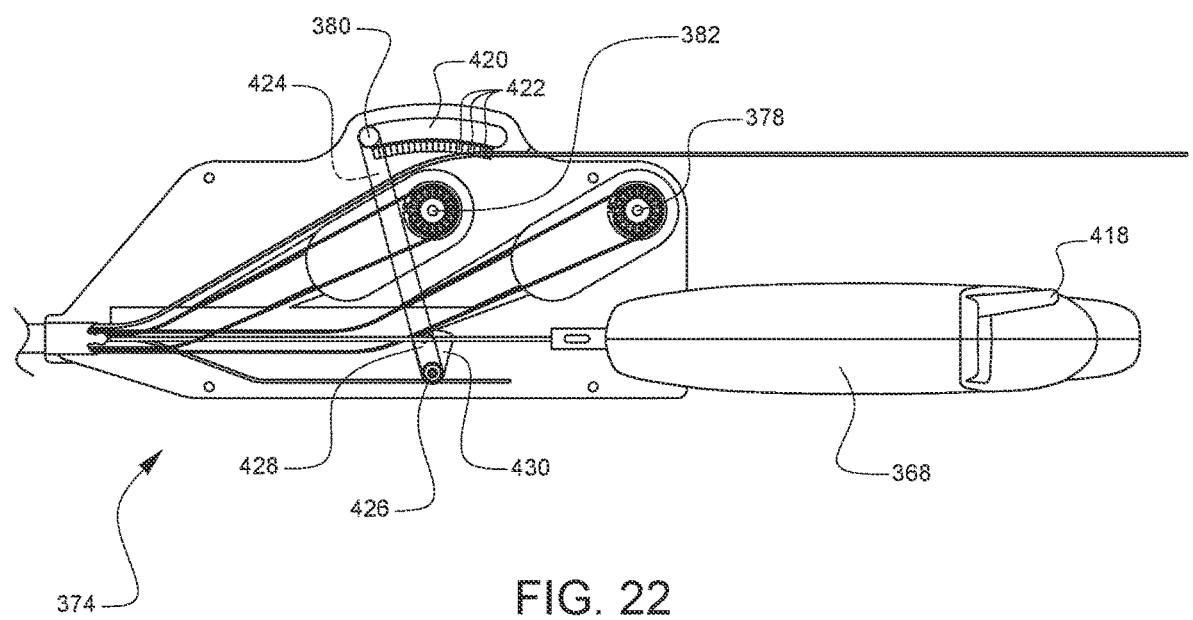
FIG. 22 is an enlarged top view of another embodiment of a proximal end of a surgical suturing device.

FIG. 22 is an enlarged top view of the embodiment of a proximal end of a surgical suturing device, focusing on the control panel 374 with the cover removed. A locking control 380, shown in FIG. 22 in an unlocked position, is connected to a locking control arm 424 attached to a pivot on the opposite side of a control panel of a surgical suturing device 366. There is a catch, not shown in this view, on the underside of the locking control 380, configured to engage in the steps of a stepped positioning ratchet as the locking control 380 is moved through the locking control channel 420. A locking cable, not visible in this view, as it is obscured by the first needle pair wire, having a locking cable connection end 428 is attached to the locking control arm 424 by engaging the locking cable connection end 428 into a locking control arm recess 430, also not shown in this view. As the locking control arm 424 is moved to a locking position around a pivot 426, the locking cable is pulled and therefore tensioned. This tensioning of the locking cable tensions the entire flexible shaft 182, not shown here, but previously described, locks the flexible shaft and its vertebrae into its position when the locking control 380 is engaged.

Figure 23A:
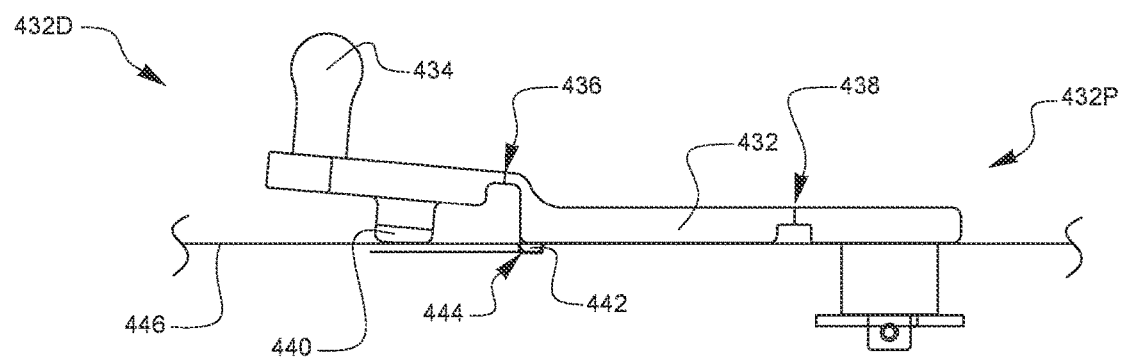
FIG. 23A-23B are side views of an embodiment of an articulation control lever of the surgical suturing device of FIG. 22 shown in an engaged position and disengaged position, respectively.
Figure 23B:
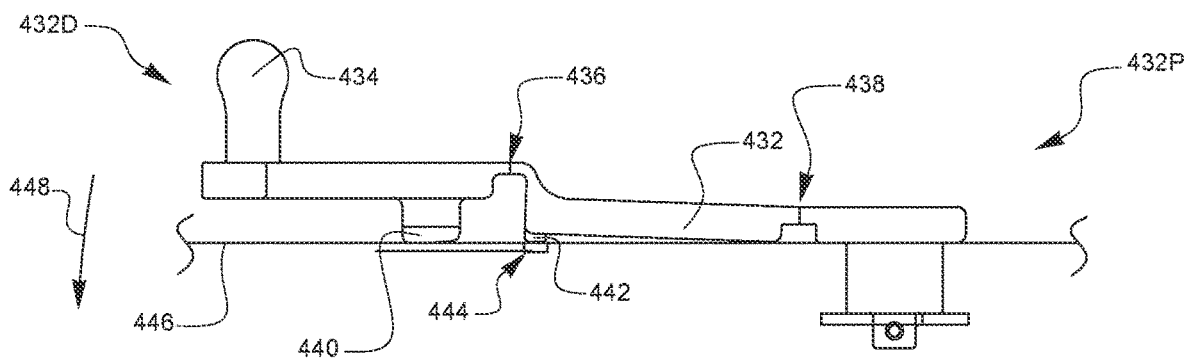

FIG. 23A-23B are side views of an embodiment of an articulation control lever of the surgical suturing device of FIG. 22 shown in an engaged position and disengaged position, respectively. FIG. 23A is a side view of an embodiment of an articulation control lever 432 in an engaged position. The articulation control lever 432 has a knob connected to an end of the lever 372. The lever 372 is made of a single structure as shown, having a first flexure point 436, and a second flexure point 438. A tab 440 on the underside of the lever 372 near the distal end provides leverage against a first flexure point 436 and a second flexure point to hold a key on the underside of the lever 372 adjacent to the first flexure point 436 engaged in a keyway, in the control panel surface 446. To disengage the key 442 from the keyway 444 and subsequently move the articulation control lever 432 to a different position, the knob 434 is pushed in a direction towards the control panel surface 446, which utilizes the tab 440 as a pivot point to flex the first flexure point 436 and the second flexure point 438 sufficiently to lift the key 442 out of the keyway 444. The articulation control lever 432 is now disengaged and can be moved to a different position. FIG. 23B is a side view of an embodiment of an articulation control lever 432 in a disengaged position.

Figure 24A:
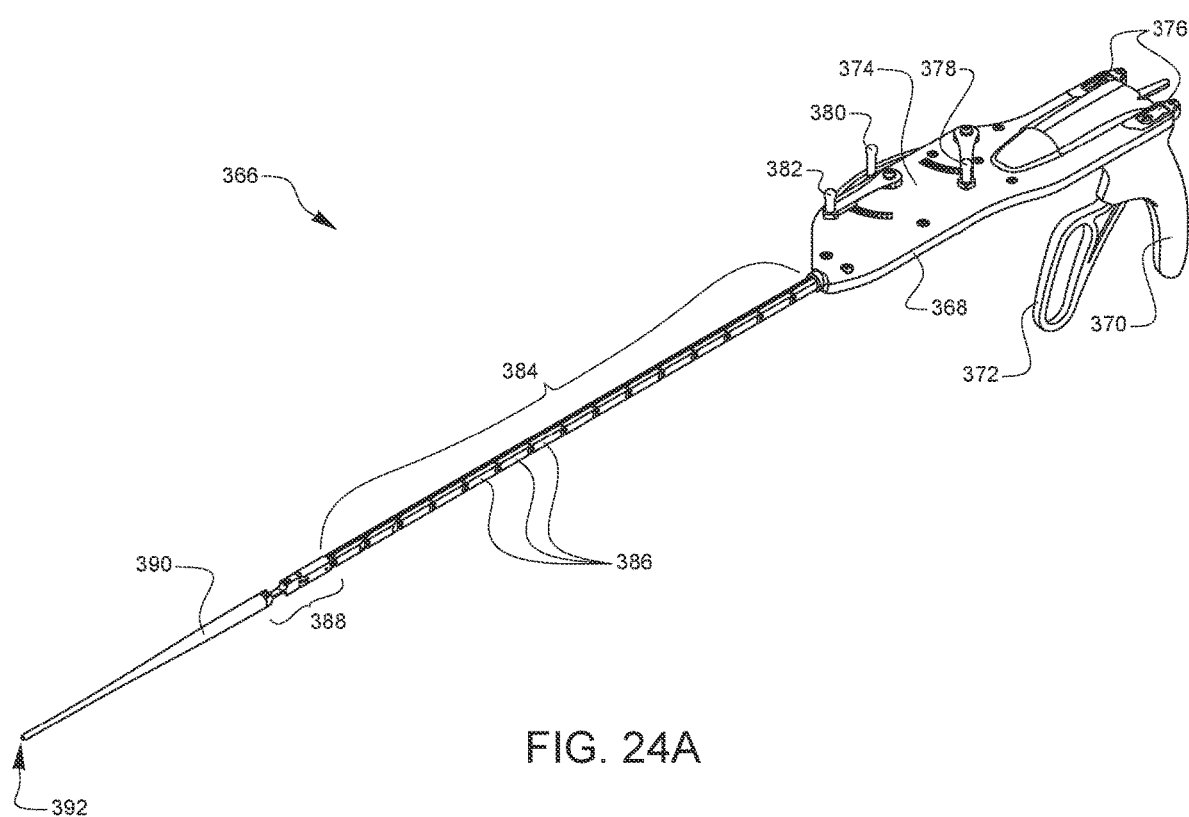
FIG. 24A is a top-left-front perspective view of another embodiment of a surgical suturing device.

FIG. 24A is a perspective view of another embodiment of a surgical suturing device, as described herein. The surgical suturing device 366 has a housing 368 that has a handle 370, a needle selection switch, a lever 372, and a suture viewing window 376. The upper portion of the housing 368 defines a control panel 374 having a locking control 380, a distal articulation control lever 382, and a proximal articulation control lever 378. Attached to the housing 368 is a flexible shaft 384 composed of several vertebrae 386 and terminating in a distal tip 388 and an IVC guide 390. The vertebrae are characterized by several channels similar to previously described embodiments, the channels configured to accommodate steering wires, sutures, needles, and other components for the assembly and operation of the surgical suturing device. The IVC guide 390 defines a guide wire channel 392.

Figure 24B:
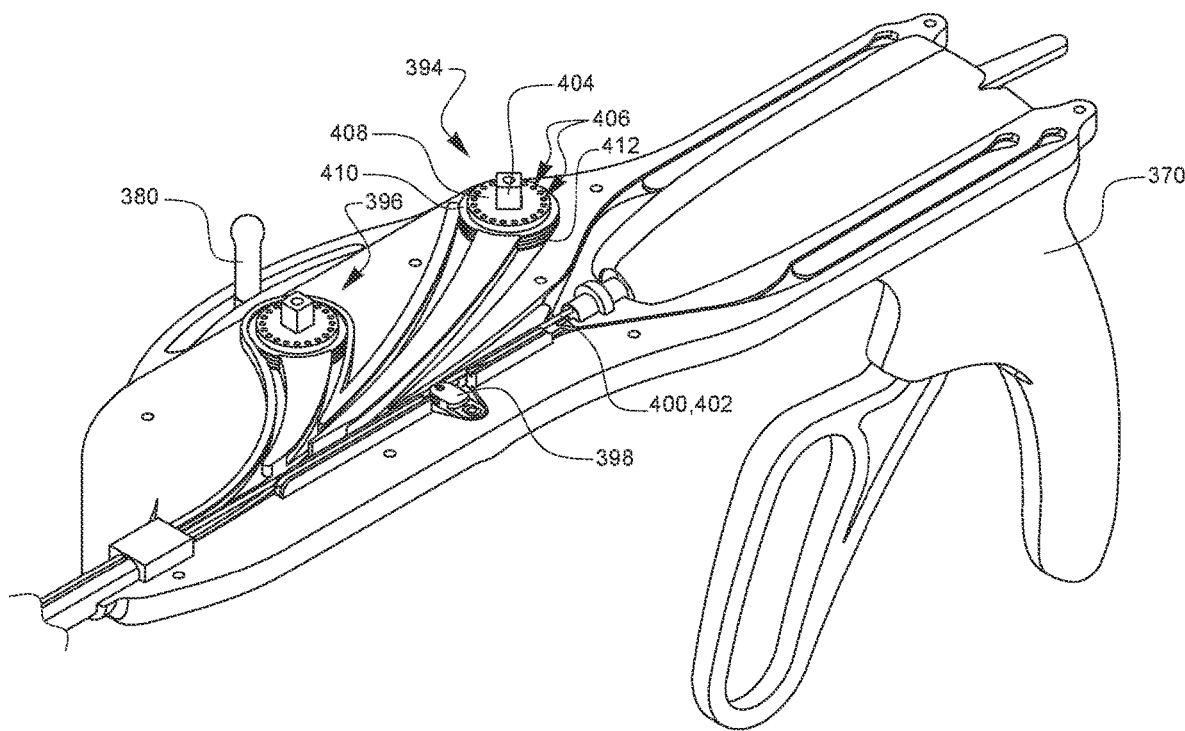
FIGS. 24B-24C are enlarged top-left-front and top-left-rear perspective views, respectively, of portions of the surgical suturing device of FIG. 24A.
Figure 24C:
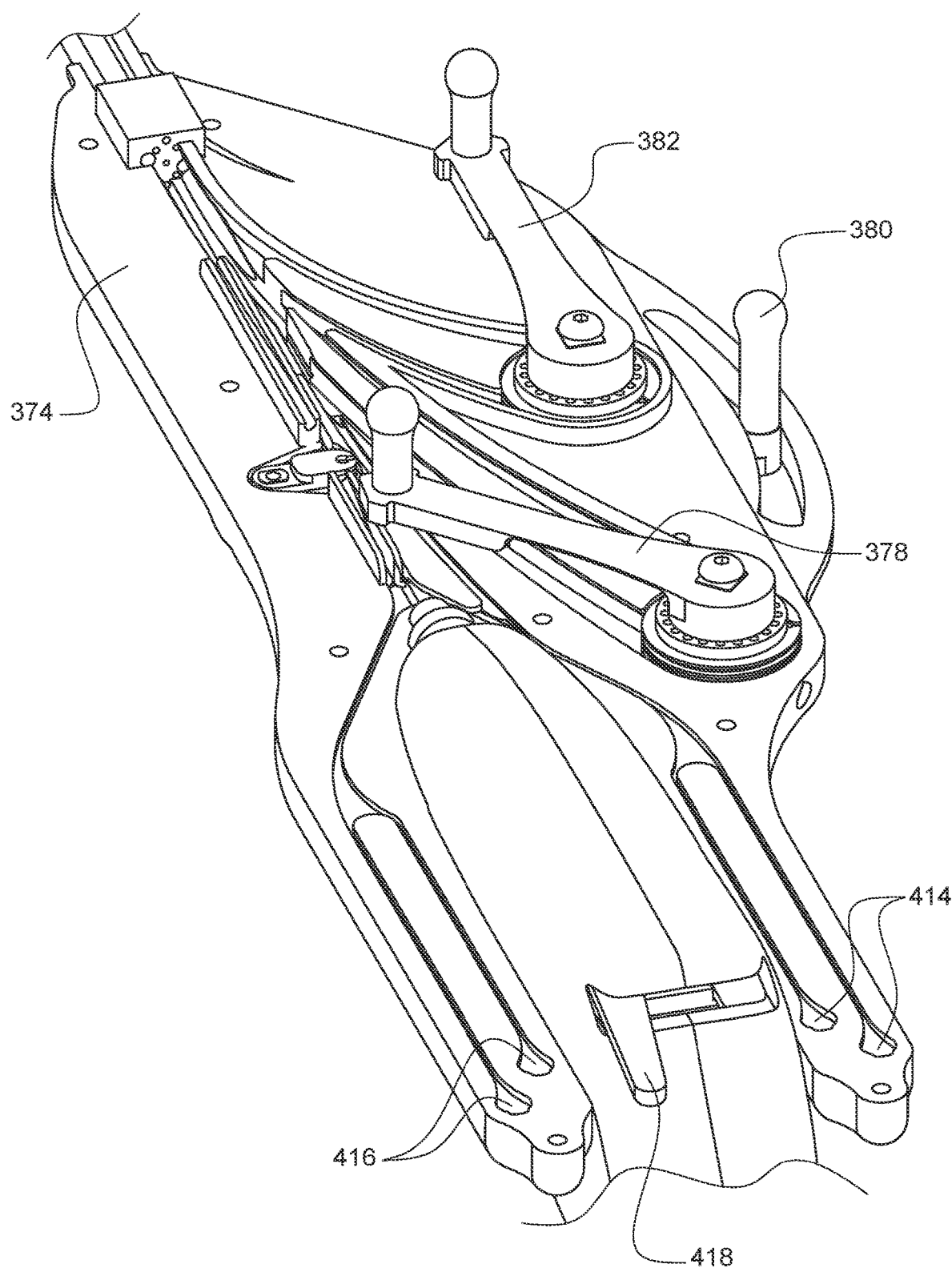

FIG. 24B is an enlarged top-left-front top perspective view of an embodiment of a proximal end of the surgical suturing device of FIG. 24A, focusing on the control panel 374 with the cover removed. The control panel 374 of the surgical suturing device 366 is shown with the distal articulation control lever 382 and the proximal articulation control lever 378 removed. The distal articulation control mechanism 396 and the proximal articulation control mechanism 394 are illustrated. The proximal articulation control mechanism 394 has an axle 404, which is rectangular in shape, and to which the proximal articulation control lever 378 is attached. The proximal articulation control mechanism 394 also has a pulley and capture stack consisting of a lower pulley 412, an upper pulley 410, and a capture element 408. Each of the lower pulley 412, upper pulley 410, and capture element 408 have several alignment holes 406. The lower pulley 412, upper pulley 410, and capture element 408 have fifteen alignment holes 406, sixteen alignment holes 406, and fifteen alignment holes 406, respectively. The lower pulley 412 and upper pulley 410 each define a slot to attach the ends of the two proximal articulation control cables. One proximal articulation control cable is wound around either the upper or lower pulley 410, 412 clockwise, and the other proximal articulation control cable is wound around the other of the upper or lower pulley 410, 412 counterclockwise. The alignment holes 406 are configured for fine adjustment of the two proximal articulation control cables during assembly and adjustment. The cables and associated fine adjustment details of the pulley and capture stack are not shown in this view. The distal articulation control mechanism 396 is similarly constructed and is not described in detail herein. While this embodiment of a surgical suturing device 366 shows a pulley and capture stack system of cable articulation, other means of cable articulation known to those skilled in the art may also be used, such as a rocker arm assembly and the like. FIG. 24C is an enlarged top-left-rear perspective of the proximal end of the surgical suturing device 366 of FIG. 24A, focusing on the control panel 374 with the cover removed. It is an alternate view of the details shown in FIG. 24B.

Loading and Retrieval Apparatus

Looking back at the surgical situation illustrated in FIG. 4M, the first end of the first suture 86 and the first end of the second suture 108 were each placed through a first pledget 146 on one side of the tricuspid valve 126. Similarly, the second end of the first suture 86 and the second end of the second suture 108 were each placed through a second pledget 148 on the opposite side of the tricuspid valve 126. For the sake of explanation, picture a similar surgical situation, but one where pledgets 146 have not been installed onto the suture ends yet. This surgical situation will be discussed with respect to the apparatus of FIG. 25, by way of example.

Figure 25:
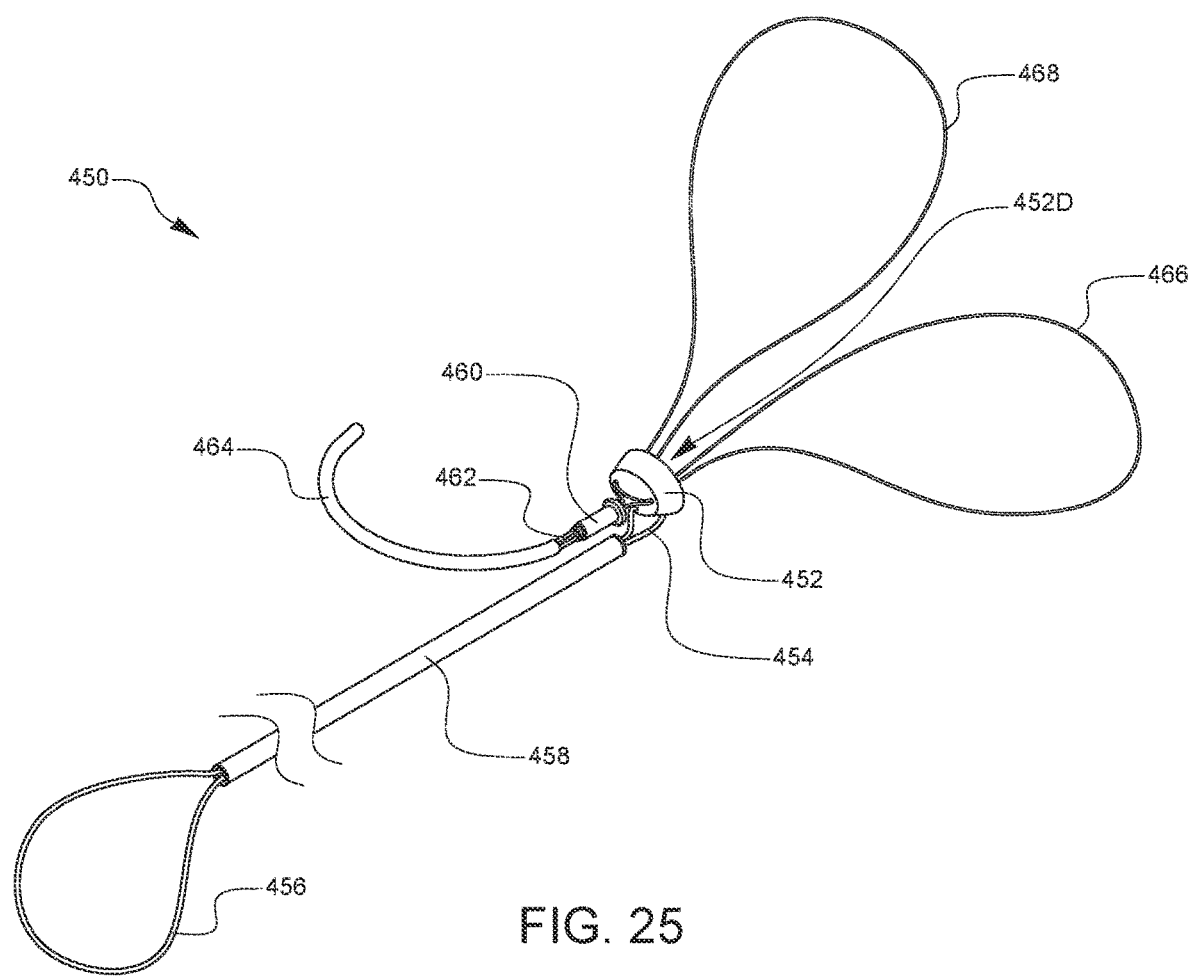
FIG. 25 is a top-left front perspective view of an embodiment of a loading and retrieval apparatus.

FIG. 25 illustrates one embodiment of a loading and retrieval apparatus 450 for use in installing a pledget 452 over two suture ends while also threading those suture ends through a mechanical fastener 460 which has been loaded into a fastening device. In this embodiment, the apparatus has a curved handle 464 which is coupled to a snare 462 which passes through the mechanical fastener 460 and then through different portions of a pledget 452, forming first and second snare loops 466, 468 on a distal side of the pledget 452D. In other embodiments, the snare 462 may have fewer or more snare loops 466, 468 coupled to the handle 476. The curved handle 464 may be passed into a mechanical fastening device, such as, but not limited to, the COR-KNOT® fastening device from LSI Solutions, Inc. (Victor, NY, www.lsisolutions.com) in order to load the mechanical fastener 460 into the device.

Thinking of the surgical scenario outlined in regard to FIG. 4M, one suture end, such as the first end of the first suture from our explanatory surgical situation may be placed through the first snare loop 468. Another suture end, such as the first end of the second suture from our explanatory surgical situation may be placed through the second snare loop 466. The curved handle 464 may then be pulled, causing the snare loops 468, 466 to pull the suture ends back through the pledget 452 and back through the mechanical fastener 460. The loading and retrieval apparatus 450 also has a tether loop 456 which passes through the pledget 452 and extends a distance away from the pledget 452. In this embodiment, the tether loop 456 also passes through a tube 458, exiting the tube 458 on a proximal end of the apparatus. Although not shown in this view so that the tether loop 456 may be seen more clearly, a tether holder 484 may be placed within the proximal end of the tether loop 456 to prevent it from passing back into the tube 458. The tether loop 456 and tube 458 are preferably selected to be a length which will always ensure a portion of the tube 458 and the proximal end of the tether loop 456 are accessible from outside of the patient, even when first the pledget 452 and mechanical fastener 460 and second the distal portion of a mechanical fastening device 366 holding the mechanical fastener 460 are parachuted down the first and second sutures against the tricuspid valve 126.

If we consider a situation where the pledget 452 and mechanical fastener 460 and the distal portion of a mechanical fastening device holding the mechanical fastener 460 are parachuted down the first and second sutures against the tricuspid valve 126: When the pledget 452 is positioned against the valve annulus or other tissue and the mechanical fastener 460 is crimped, the mechanical fastening device may be withdrawn, leaving a crimped mechanical fastener 460 behind, along with its corresponding pledget 452. The resultant situation would be like that shown in FIG. 4N, but with the addition of a tether loop 454 which is still passing through the pledget 452 (the pledget 452 that is held against the tissue by the mechanical fastener 460 crimped onto the suture) and then up and out of the tube 458, where the proximal end of the tube and the proximal end of the tether loop 456 are still accessible outside of the patient. It should be noted that the lower pledget 452 shown in the base scenario of FIG. 4N would not be present in this scenario. If, for any reason, the surgeon would wish to remove the crimped fastener and pledget 452 at this point, the surgeon could grasp the proximal end of the tether loop 456 (and the proximal end of the tube 458, if a tube 458 was present in the embodiment) and pull to remove the pledget 452 attached to the tether loop 454. This would also remove the mechanical fastener 460, since it is held against the pledget 452. This offers a big advantage for being able to reverse part of the procedure while percutaneously retrieving the fastener 460, pledget 452, and sutures.

If, however, the surgeon was satisfied with the placement of the mechanical fastener 460 and pledget 452, the surgeon could remove the tether holder (if one was present) from the proximal end of the tether loop 456, cut the proximal end of the tether loop 456, and then pull one end of the tether loop 456 to release the pledget 452 from the tether 456. Then, the remaining length of tether 456 and tube 458 may safely be removed from the patient, leaving the implanted pledget 452 and mechanical fastener 460 behind for the surgical repair being performed.

Figure 26A:
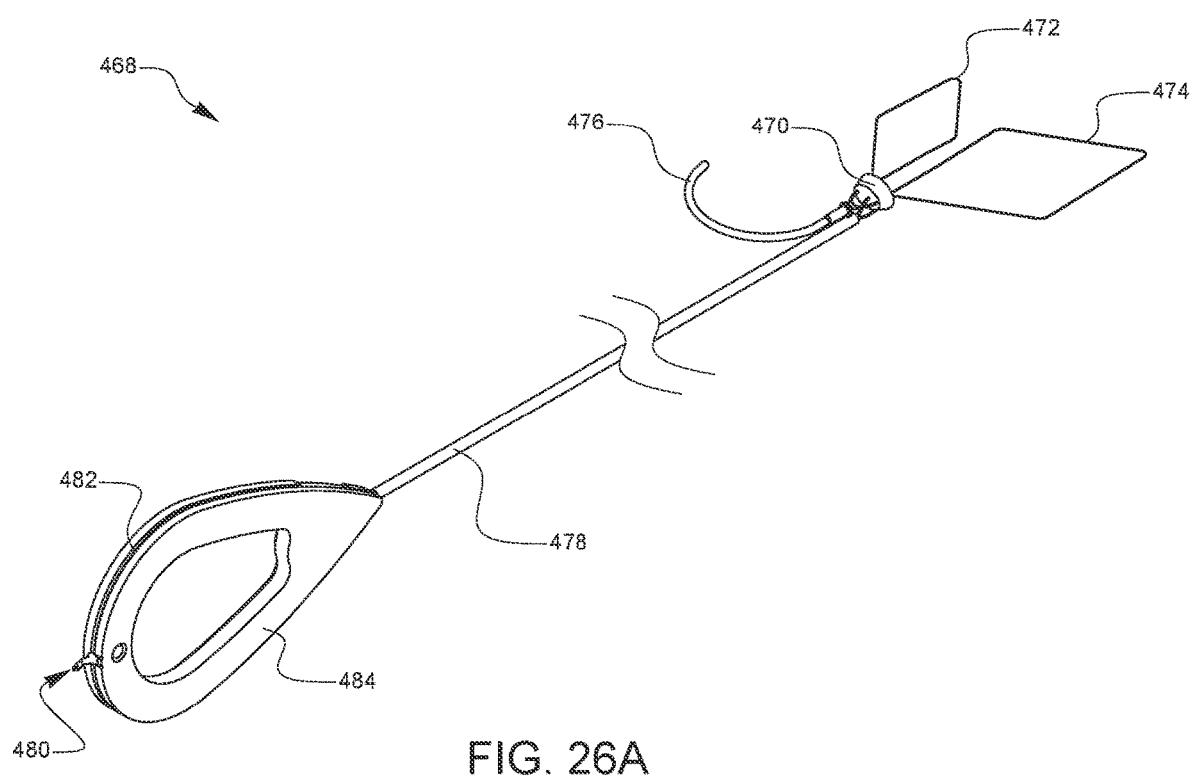
FIG. 26A-26D are top-left-front perspective views of various aspects of another embodiment of a loading and retrieval apparatus.

FIG. 26A shows another embodiment of a loading and retrieval apparatus like that of FIG. 25, but with a tether holder 484. It is also noteworthy that in this embodiment, the tether loop 482 is formed by a fastener holding two ends of the tether together 480. Instead of a fastener, other embodiments could have the tether loop 482 formed by a tied knot, an adhesive, a welding, or the like.

Figure 26B:
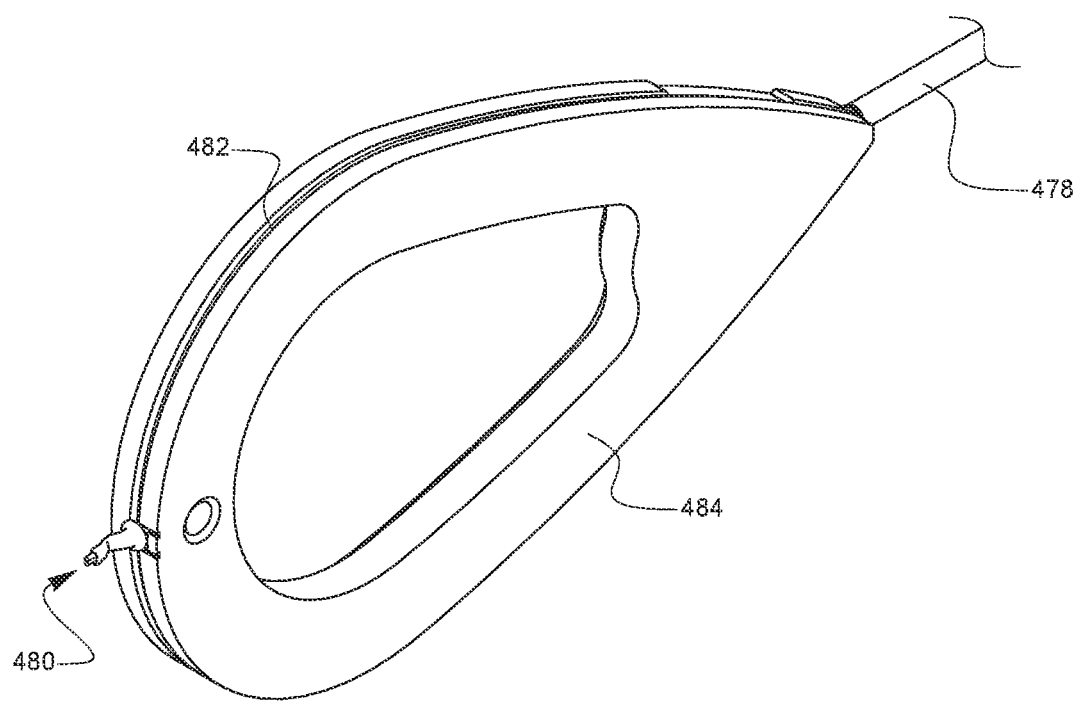
Figure 26C:
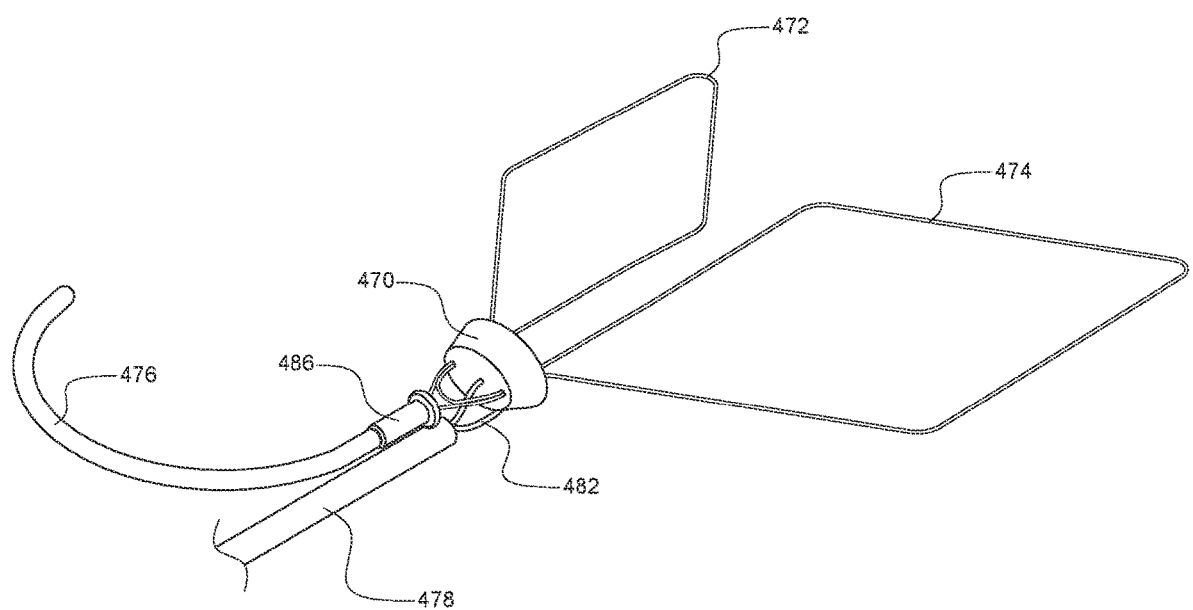
Figure 26D:
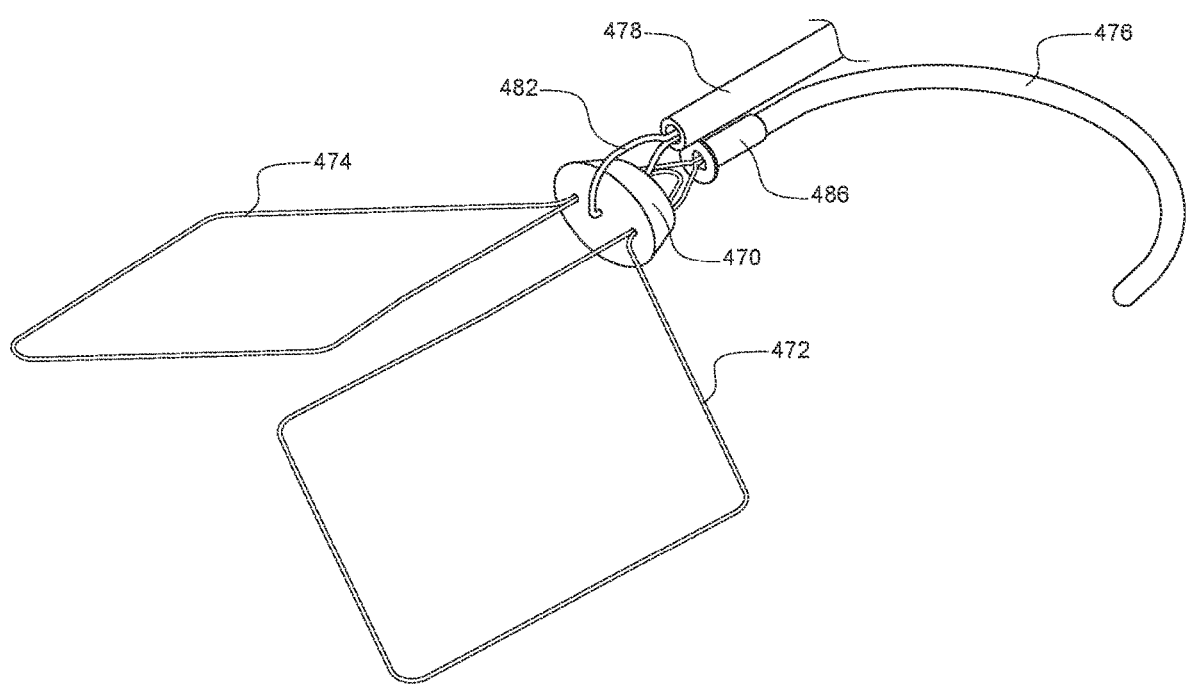

FIG. 26B is an enlarged view of the proximal end of the apparatus from FIG. 26A. FIG. 26C is an enlarged proximal view of the pledget end of the apparatus from FIG. 26A. It should be noted that although the handle 476 is curved in the illustrated embodiments, the handle 476 bin other embodiments may have other shapes. FIG. 26D is an enlarged distal view of the pledget end of the apparatus from FIG. 26A.

Figure 27:
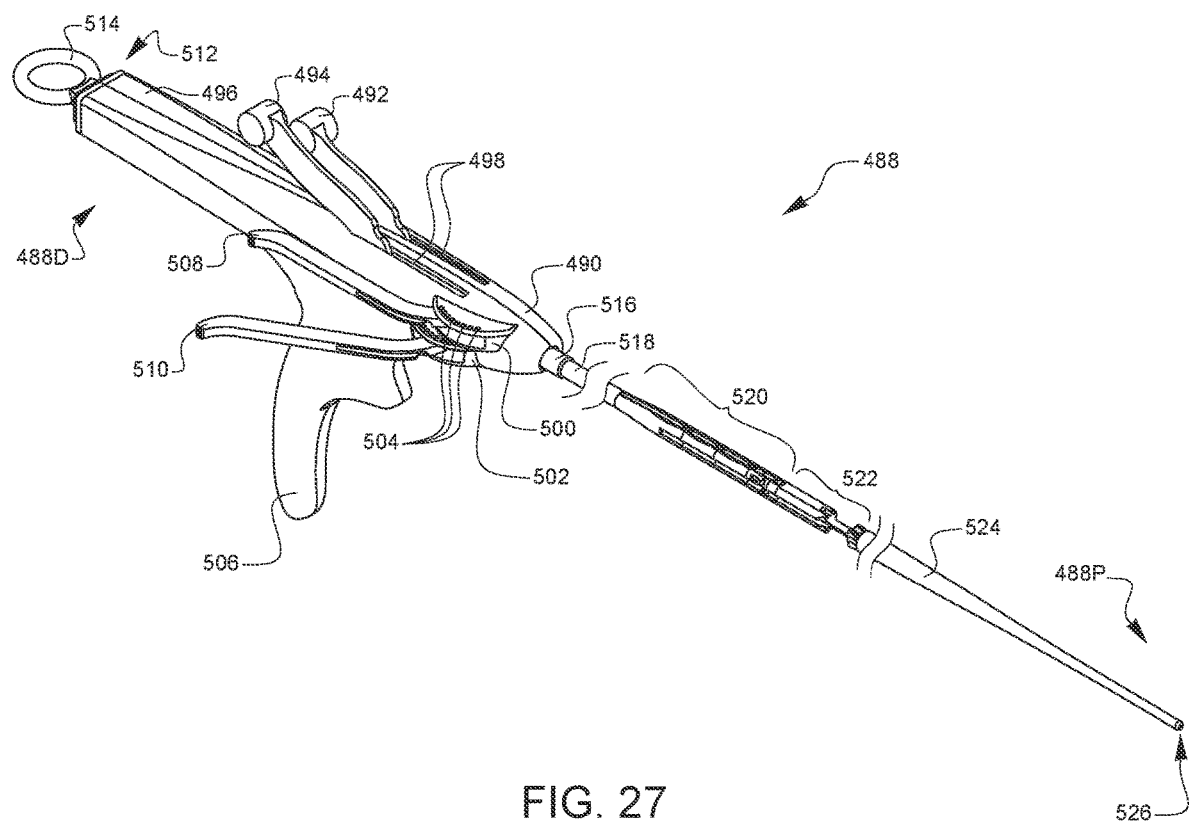
FIG. 27 is a top-right-front perspective view of another embodiment of a surgical suturing device.

FIG. 27 is a perspective view of an alternate embodiment of the surgical suturing device 488 described previously. This embodiment has a housing 490 which defines a handle 506, a top lever stop 500 and a bottom lever stop 502. Both the top lever stop 500 and the bottom lever stop 502 define several positional keyways 504. The housing 490 has several slots within the top lever stop 500 and the bottom lever stop 502 that allow movement of a first articulation lever 508 and a second articulation lever 510 towards either a distal end 488D or a proximal end 488P of the surgical suturing device 488. The first articulation lever 508 and the second articulation lever 510 define one or more keys, not shown here, that engage within the positional keyways 504 in order to hold or lock the position of the respective articulation levers 508, 510, similar in principle to the mechanism described in regard to FIGS. 23A and 23B. The first articulation lever 508 and second articulation lever 510 are configured such that they can flex in a direction away from the positional keyways 504 and can be moved to a desired position and released, where they are biased such that the key on the respective articulation lever 508, 510 engages with the appropriate positional keyway 504, preventing undesired movement of the articulation lever 508, 510. The levers are made of either plastic or metal that can flex or bend away from the keyway 504, and when released will be biased toward the stop mechanism or positional keyway 504 in its assembled configuration. This described stop or positional mechanism may also include teeth on the levers 508, 510 configured to move then rest within the desired locked position in gears located in the lever stops 500, 502. The top of the housing 490 further defines two slots that allow movement of the first needle driver 492 and the second needle driver 494 towards either the distal end 488D or the proximal end 488P of the surgical suturing device 488. Towards the proximal end of the housing 490, a rigid shaft 518 is attached to a mount 516 attachment connected to the housing 490. Further towards the proximal end of the surgical suturing device 488, a flexible shaft 520 portion is attached to the rigid shaft 518, terminating in a distal tip 522 to which an inferior vena cava (IVC) guide 524 or proboscis is attached. The IVC guide 524 defines a guide wire channel 526, which also continues throughout the entire surgical suturing device 488.

Figure 28A:
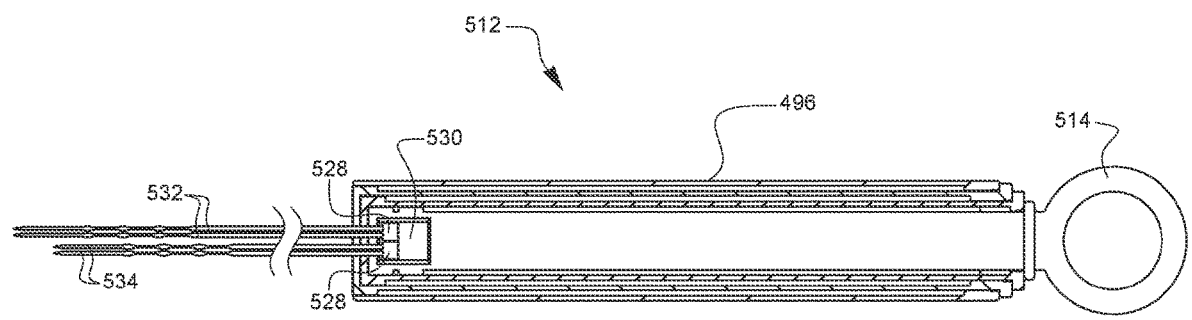
FIGS. 28A-28B are top partial cross-sectional schematic views of a retracting telescope of the surgical suturing device of FIG. 27.
Figure 28B:
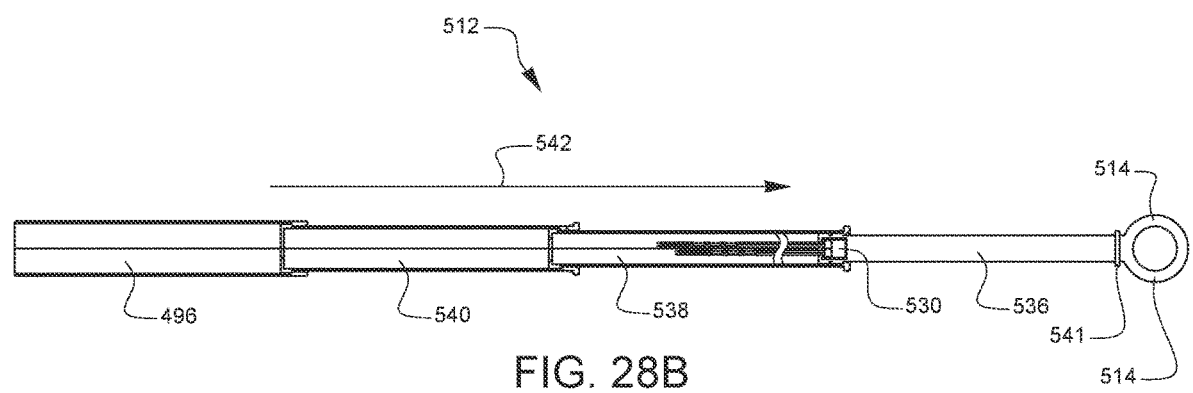

FIGS. 28A-28B are top partial cross-sectional schematic views of a retracting telescope of the surgical suturing device of FIG. 27. FIG. 28A is a top view showing the retracting telescope 512 portion of the surgical suturing device 488 of FIG. 27 in a closed position. FIG. 28A is a hidden view of the inner telescope segment 536, the middle telescope segment 538, and the outer telescope segment 540 closed or stacked or nested or collapsed coaxially within the telescope housing 496. The first needle 532 and second needle 534 are held captive in the inner telescope, the details of which will be discussed later. FIG. 28B is a top view showing the retracting telescope 512 portion of the surgical suturing device 488 of FIG. 27 in a retracted position. The operator grasps the telescope handle 514, which is defined by the inner telescope segment 536, and pulls the handle 514 in a proximal direction, thereby extending the inner telescope segment 536 out from the middle telescope segment 538, and in turn the outer telescope segment 540 out from the telescope housing 496. This action also brings the first needle 532 and the second needle 534 along with the inner telescope segment 536 as the needle barrels 528 are held captive in the barrel recess 530. Once the needles 532, 534 have ferrules attached during a surgical procedure are, this telescope provides a mechanism for retracting the needles, and therefore any attached ferrules or sutures from the surgical site. This can be advantageous as a method to remotely remove needles, sutures, or other instrumentation from a surgical site via a constrained space, such as a small incision site or cannula. The inner telescope segment 536 also defines a stop 541 which prevents the telescope handle 514 from nesting too far inside the middle telescope segment 538. The inner telescope 536 further defines a barrel recess 530 which releasably holds a barrel from one or more needles. This barrel recess 530 will be described in more detail later. While each of the inner telescope segment 536, middle telescope segment 538, and outer telescope segment 540 shown here are tubular, with right angle side walls, it should be noted that tubular members or structures with rounded, cylindrical, or circular side walls may be used in similar embodiments. It should also be noted that although three segments are used herein, embodiments with only two telescope segments or multiple telescope segments may also be used.

Figure 29:
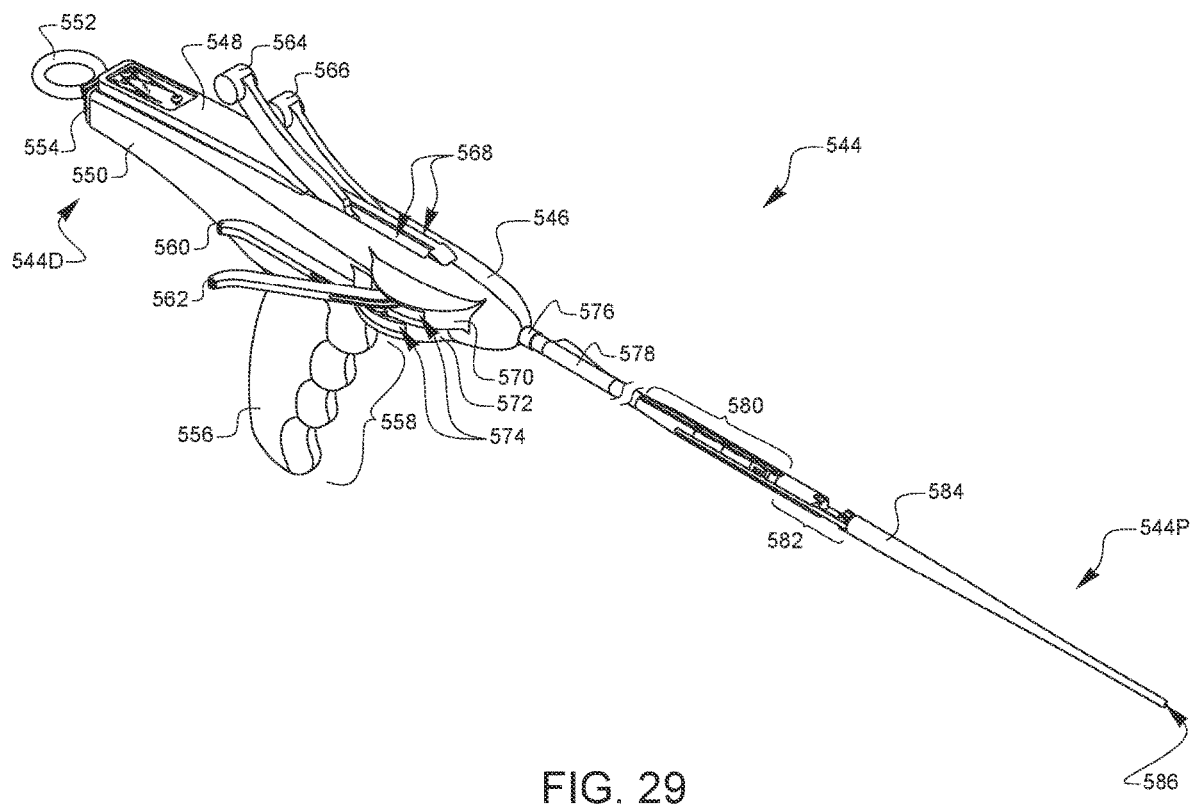
FIG. 29 is a top-right-front perspective view of another embodiment of a surgical suturing device.

FIG. 29 is a perspective view of another embodiment of a surgical suturing device 544 as described herein. This embodiment has a housing 546 which defines a handle 556, a top lever stop 570 and a bottom lever stop 572. Neither the top lever stop 570 nor the bottom lever stop 572 have positional keyways as in previous embodiments, but have internal gear stops, not shown in this view, to engage corresponding tabs on a first articulation lever 560 and a second articulation lever 562. The housing 546 has several slots within the top lever stop 570 and the bottom lever stop 572 that allow movement of the first articulation lever 560 and the second articulation lever 562 towards a distal end 544D or a proximal end 544P of the surgical suturing device 544. The first articulation lever 560 and the second articulation lever 562 define one or more tabs, not shown in this view, that engage within the internal gear stops to hold or lock the position of the respective articulation levers 560, 562. The first articulation lever 560 and second articulation lever 562 are configured such that they can flex in a direction away from the gear stops and can be moved to a desired position and released, where they are biased such that the key on the respective articulation lever engages with the appropriate gear stop, preventing undesired movement of the articulation lever. This described mechanism may also include positional keyways as described in regard to previous embodiments. The first or upper articulation lever 560, 562 adjusts the position of the flexible portion of the shaft 580 and the second or lower articulation lever 560, 562 adjusts the position of the distal tip 582, which will be described later in greater detail. The top of the housing 546 further defines two slots that allow movement of a first needle driver 566 and a second needle driver 564 towards either the distal end or the proximal end of the surgical suturing device 544. Towards the proximal end of the housing 546, a rigid shaft 578 is attached to a mount 576 held captive in the housing 546. Further towards the proximal end of the surgical suturing device 544, a flexible shaft 578 portion is attached to the rigid shaft 578, terminating in a distal tip 582 to which an inferior vena cava (IVC) monorail guide 584 or proboscis is also attached. The distal tip 582 defines a first tissue gap and a second tissue gap, which in this embodiment are symmetrical and facing opposite directions. The flexible IVC monorail guide 584 defines a guide wire channel 586, which also continues throughout the entire surgical suturing device 544.

Figure 30A:
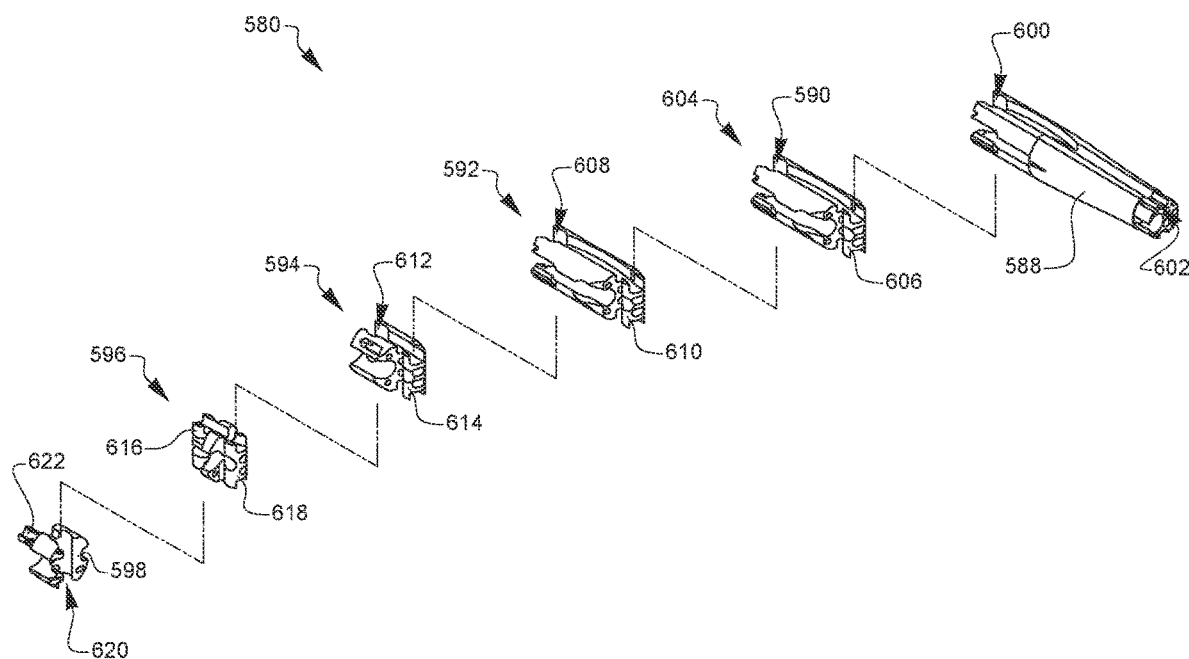
FIGS. 30A-30H, 30J-30N, 30P-30Z, 30AA-30AH, 30AJ-30AN, and 30AP are exploded views illustrating the assembly of the surgical suturing device of FIG. 29.
Figure 30B:
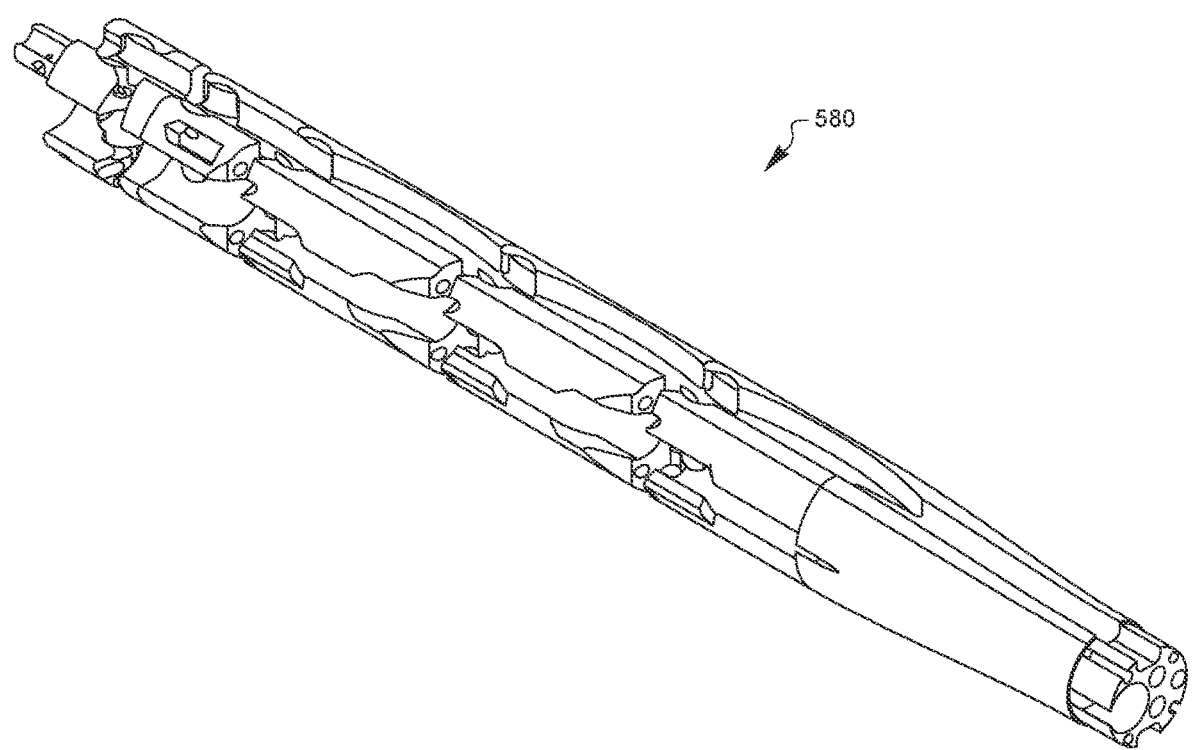

FIGS. 30A-30H, 30J-30N, 30P-30AH, 30AJ-30AN, and 30AP are exploded views illustrating an assembly sequence of the surgical suturing device 544 of FIG. 29. FIG. 30A is an exploded view illustrating an assembly step of the surgical suturing device 544 of FIG. 29, depicting the assembly of the flexible shaft portion 580. The flexible shaft 580 is constructed by attaching several vertebrae together by way of slidably connecting a vertebra link into a vertebra recess 600 on a subsequent vertebra segment. The proximal link 588 or last vertebra of the shaft 580 is slidably connected to the first middle link 590 and subsequently to the second middle link 592, the third middle link 594, the fourth middle link 596, and the distal jaw link 598 in the same manner. The proximal link 588 defines a recessed portion 602 configured to insert within the rigid shaft 628 portion. Each vertebra further defines channels therethrough to accommodate the sutures, needles, guide wire, instrumentation, and other features of the surgical suturing device 544 which will be described in more detail later in regard to FIGS. 44-57F. FIG. 30B is a perspective view of the assembled flexible shaft 580.

Figure 30C:
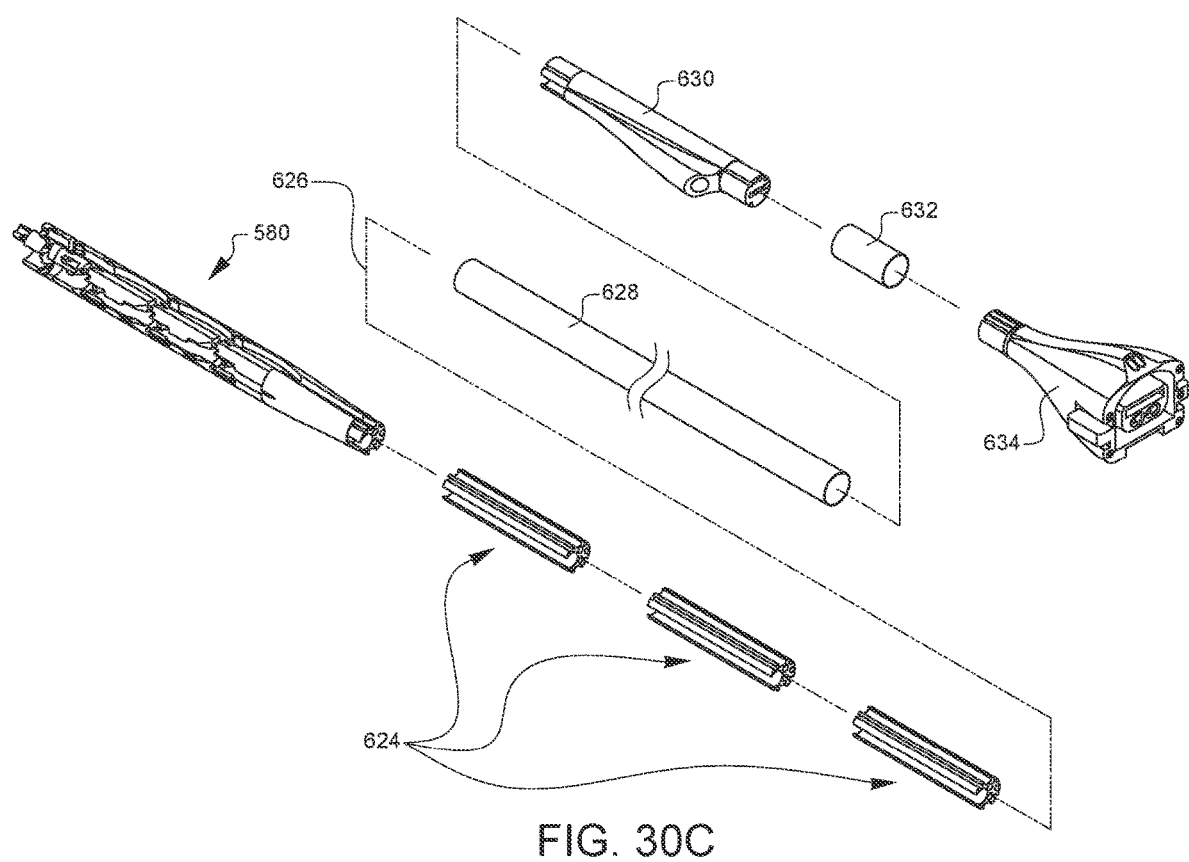
Figure 30D:
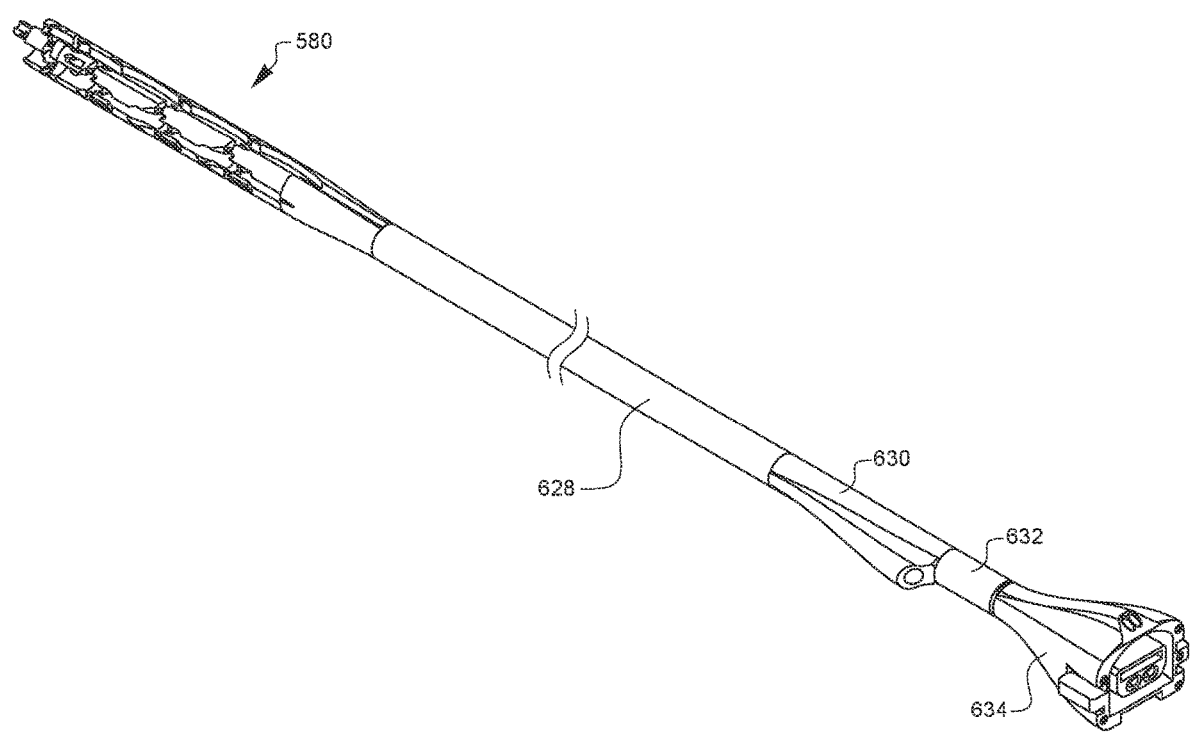

FIG. 30C is an exploded view illustrating an assembly step of the surgical suturing device 544 of FIG. 29, depicting the assembly of the shaft 580. First, several inner shaft segments 624, which make up the inner portions of the shaft are inserted into a rigid shaft 628. Then the flexible shaft portion 580 as assembled and shown in FIG. 30B is partially inserted into the rigid shaft 628 along an axis 626 as shown. At the opposite end of the rigid shaft 628, a rigid tube adapter 630 is inserted into the rigid shaft 628 along an assembly axis 626. The opposite end of the rigid tube adapter 630 is inserted into a tube bolster 632, into which a shaft mount 634 is inserted on the opposite end of the tube bolster 632. These segments and components are all fixedly attached by friction fit, welding or adhesion using a suitable adhesive or other assembly means known toiled in the art. It should be noted that each component shown defines channels corresponding to the arrangement of the needles, sutures, guide wire, and steering cables in the surgical suturing instrument 544 described herein. The inner shaft segment 624 may be composed of either one single inner shaft segment 624, or multiple inner shaft segments 624 of varying lengths as long as the inner shaft segments 624 are likewise configured with channels for the guide wire, the sutures, the steering cables, the needles, and any other components. FIG. 30D is a perspective view of the assembly steps illustrated in FIGS. 30A-30C.

Figure 30E:
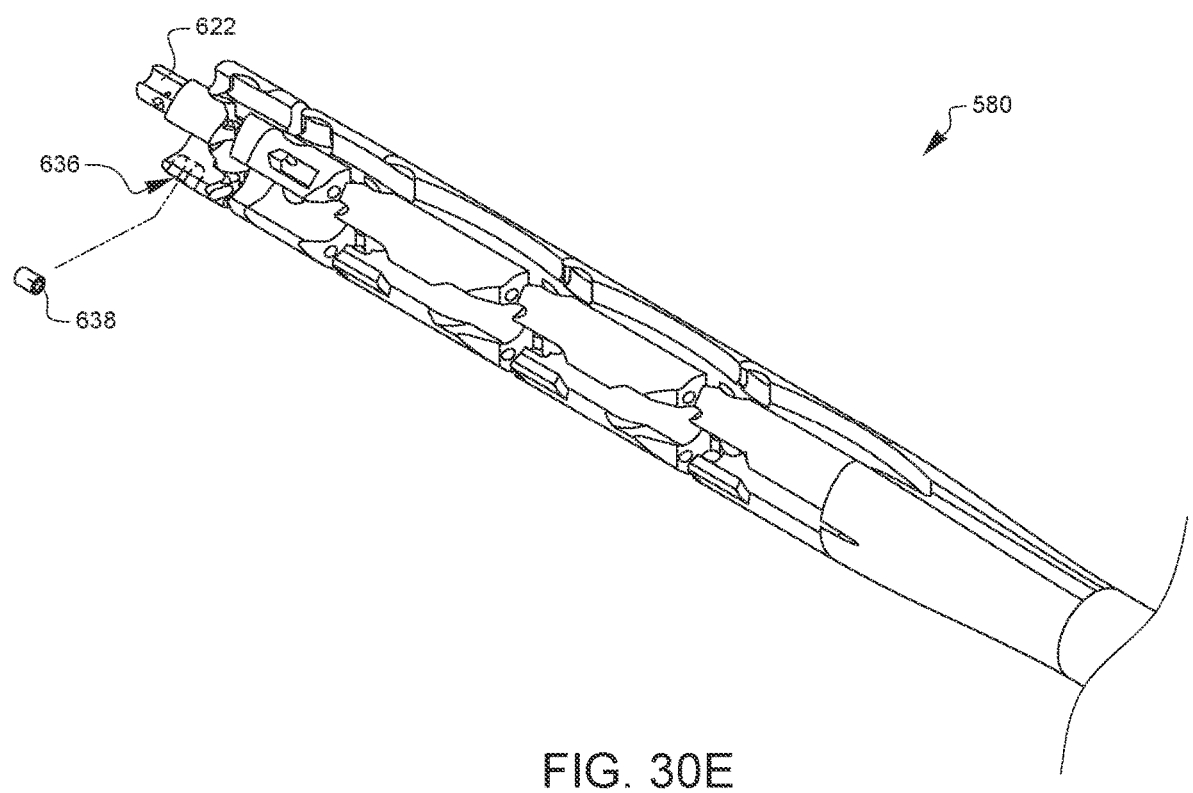
Figure 30F:
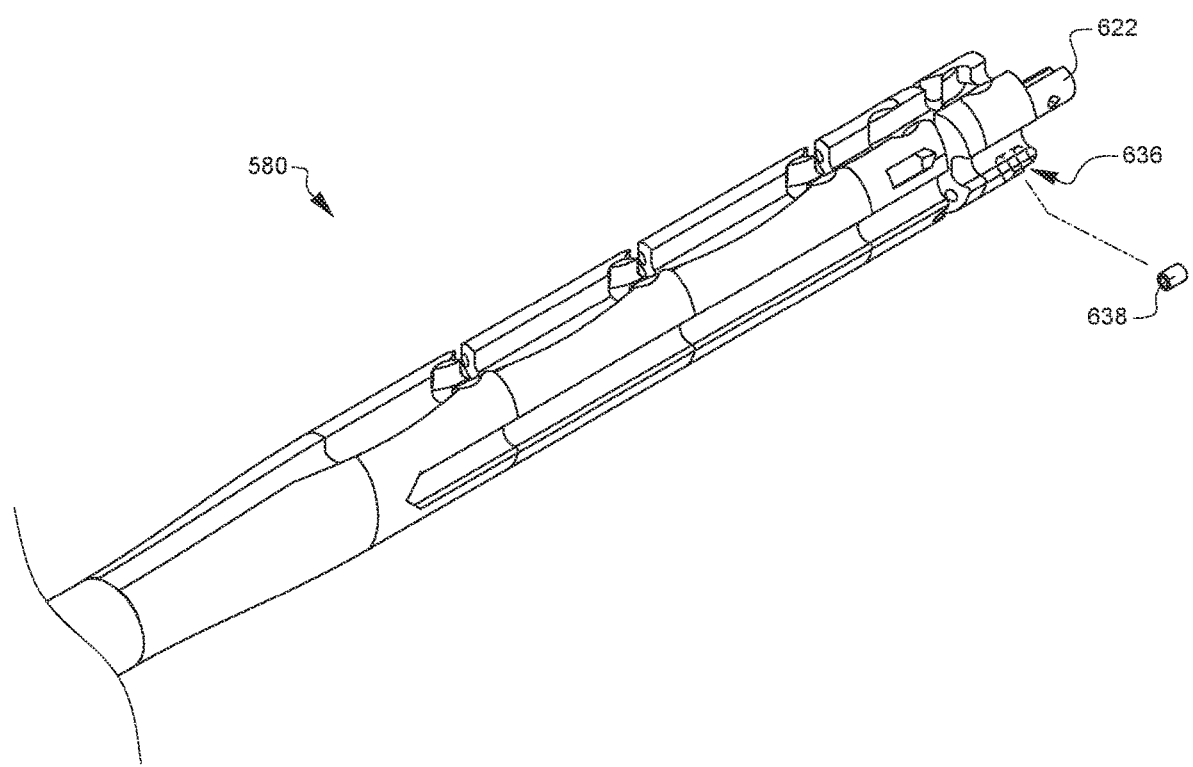
Figure 30G:
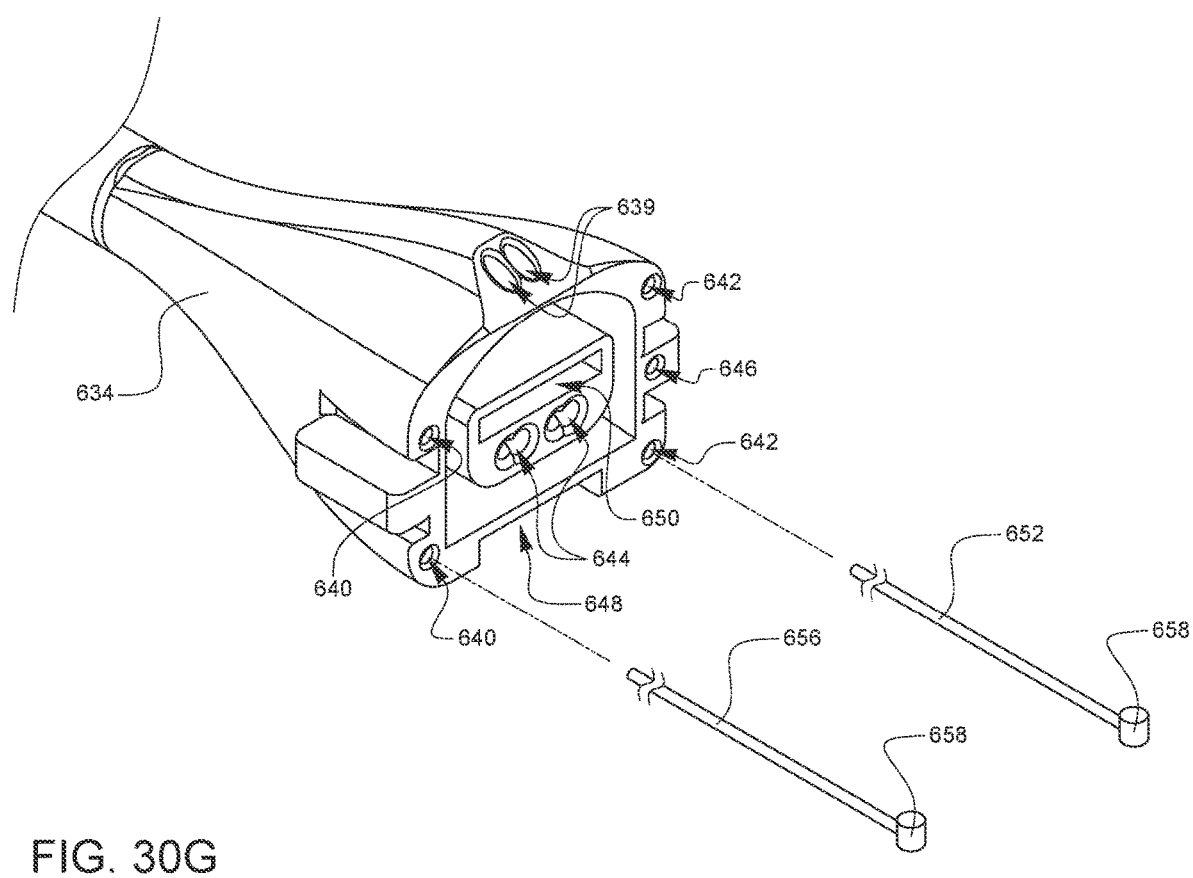

FIGS. 30E and 30F are exploded views illustrating another series of assembly steps of the surgical suturing device 544 of FIG. 29. In FIG. 30G, two lower steering cables 652 are inserted into steering cable channels 642 as defined by the shaft mount 634 from the previous assembly steps. The shaft mount 634 also defines a guide wire channel 646. The shaft mount 634 also defines two suture passages through which sutures can freely pass during the operation of the surgical suturing device 544. The shaft mount 634 further defines several steering cables channels 642 that continue throughout the rigid shaft 628 and flexible shaft portion 580. Upon insertion to the end of the flexible shaft portion 580, the ends of each of the upper and lower steering cables 652, 656 are each fixedly attached to a coupler 638 to hold the steering cable captive at the distal end of the flexible shaft 580 illustrated in FIGS. 30E and 30F. The shaft mount 634 also defines an upper mount slot 650 and a lower mount recess 648.

Figure 30H:
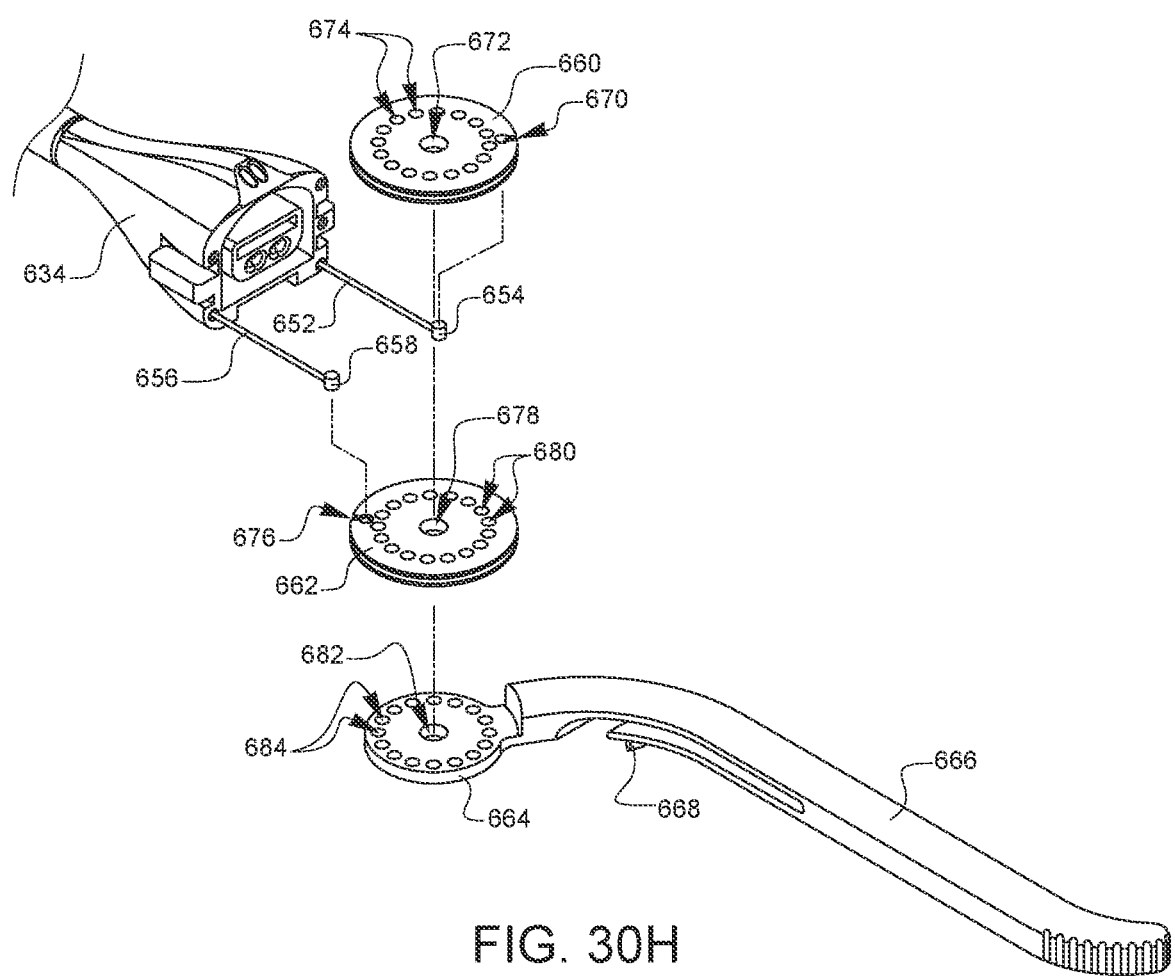
Figure 30J:
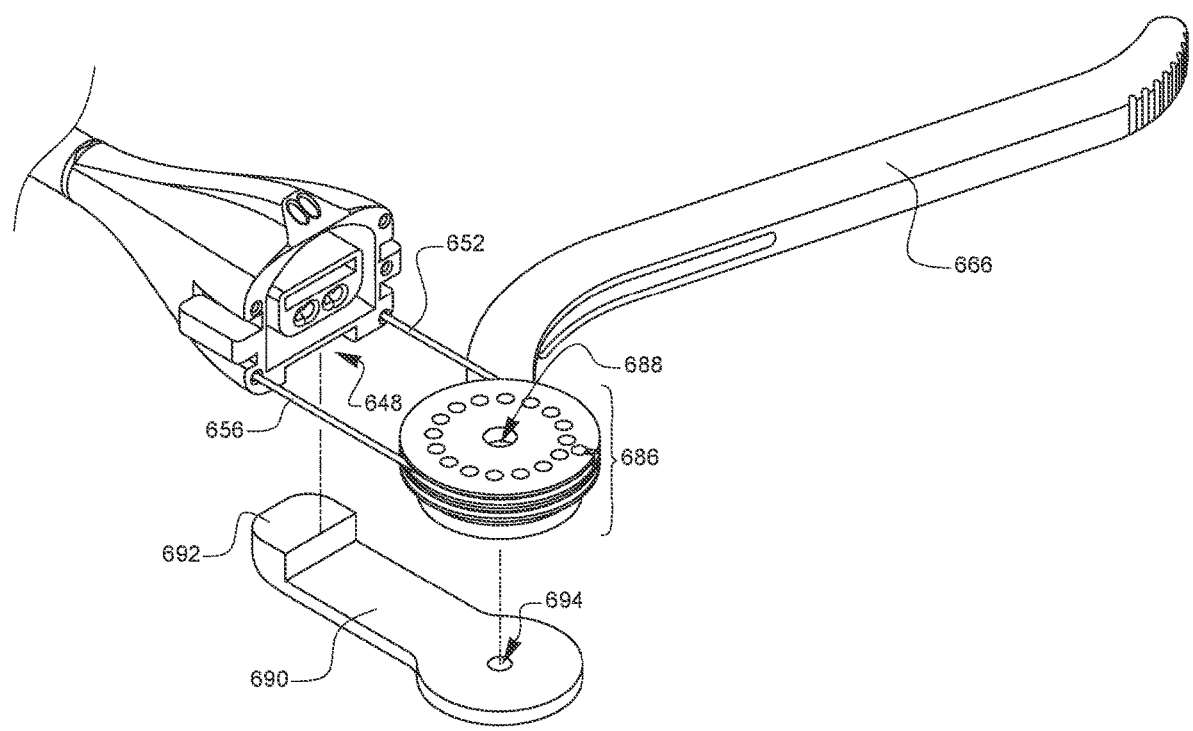
Figure 30K:
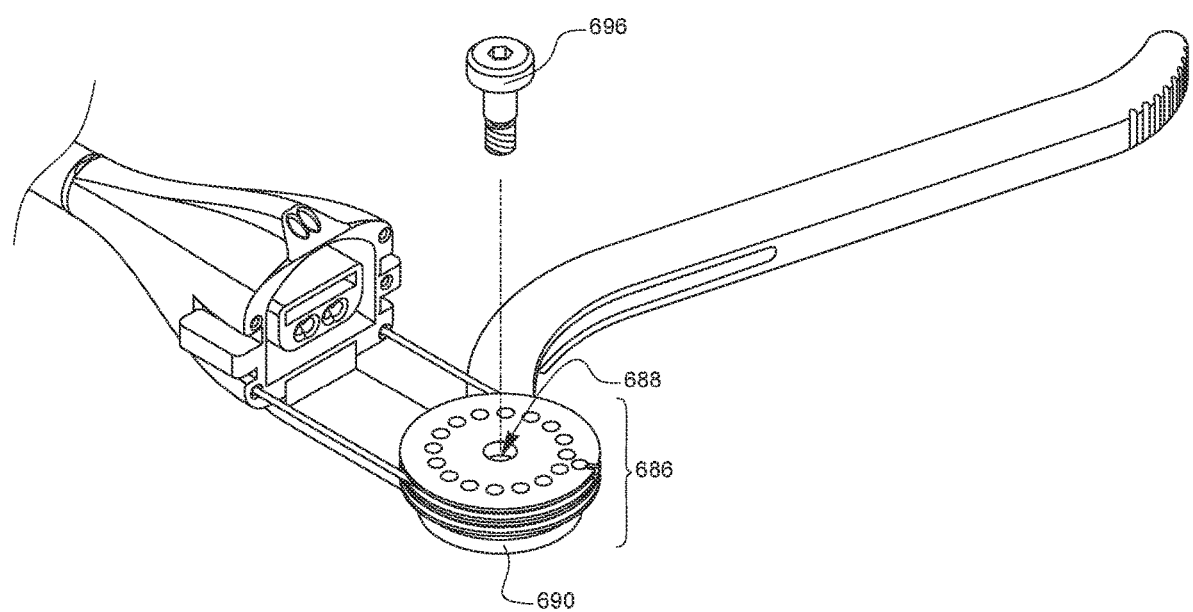

FIG. 30H is an exploded view illustrating an assembly step of the surgical suturing device of FIG. 29, depicting the assembly of the second or lower articulation lever sub-assembly. FIG. 30H shows the two lower steering cables 656, 652 from the previous assembly steps terminating in their respective couplers 658 extending from the shaft mount 634. The coupler 658 of the left lower steering cable 652 is inserted into a recess 636 defined by a lower pulley 662. The lower pulley 662 further defines a central hole 678 and several alignment holes 674, 680. The coupler 654, 658 of the right lower steering cable 652 is inserted into a recess 636 defined by an upper pulley 660. The upper pulley 660 also further defines a central hole 672 and several alignment holes 674. A second lower articulation lever 666 defines a stop tab 668 and a pulley section 664 with a center hole 682 and multiple alignment holes 684. The central holes 678, 672 of the second lower articulation lever 666, the lower pulley 662 and the upper pulley 660 are then stacked with their respective central holes aligned. This temporarily captures the couplers of the two steering cables in the recesses of their respective pulleys and in the second lower articulation lever 666 subassembly. FIG. 30J is a perspective view illustrating the result of the assembly step of FIG. 30H. FIG. 30I is not used or shown because the letter I may be mistaken for the numeral 1. FIG. 30J shows the alignment of the hole in the pulley section 664 as assembled in FIG. 30H with a lower pulley mount 690 having a central hole and a pulley mount tab 692. The pulley mount tab 692 is also inserted and fixedly attached to the mount recess 648 on the shaft mount 634. FIG. 30H also shows the second lower articulation lever 666, stop tab 668, pulley section 664, center hole, and attached steering cables 656, 652 in their sub assembly orientation. FIG. 30K illustrates the second lower articulation lever 666 subassembly step as completed in FIG. 30J, adding a screw to fixedly attach the pulley system 686 to the lower pulley mount 690.

Figure 30L:
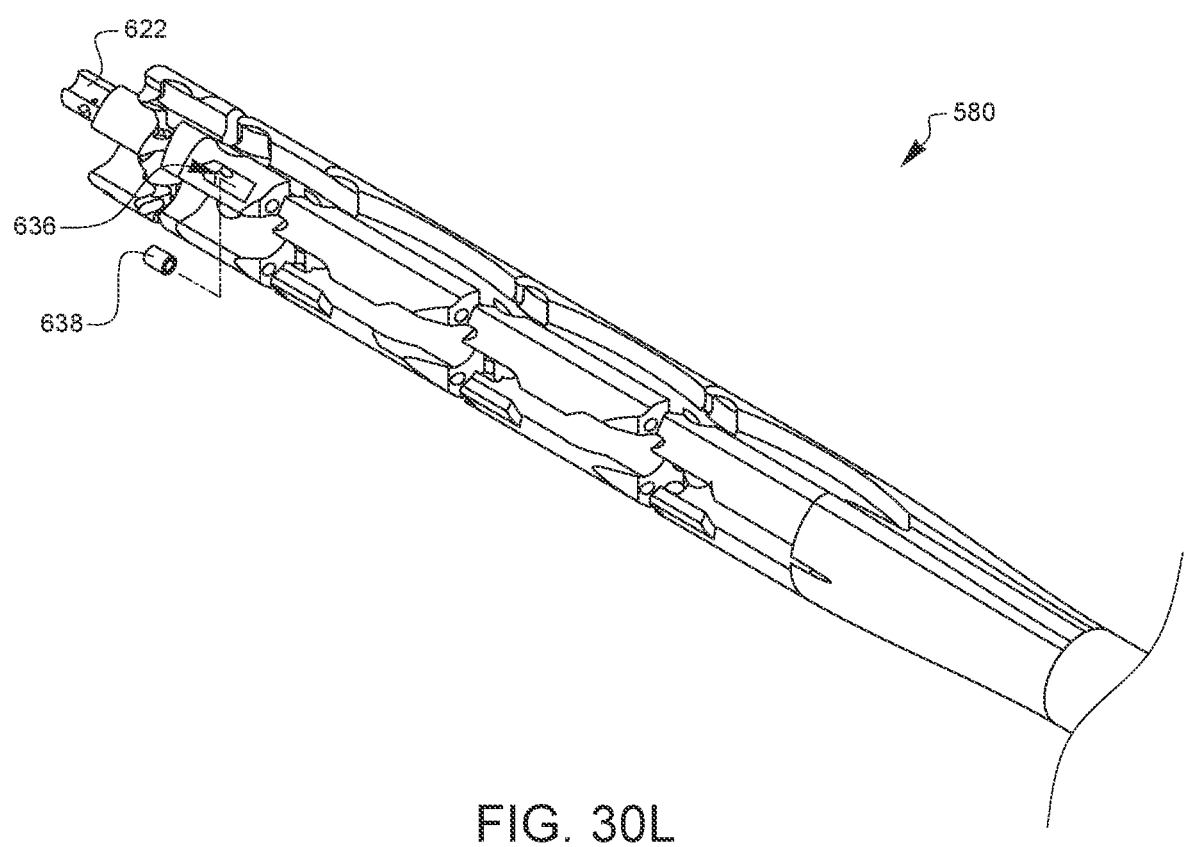
Figure 30M:
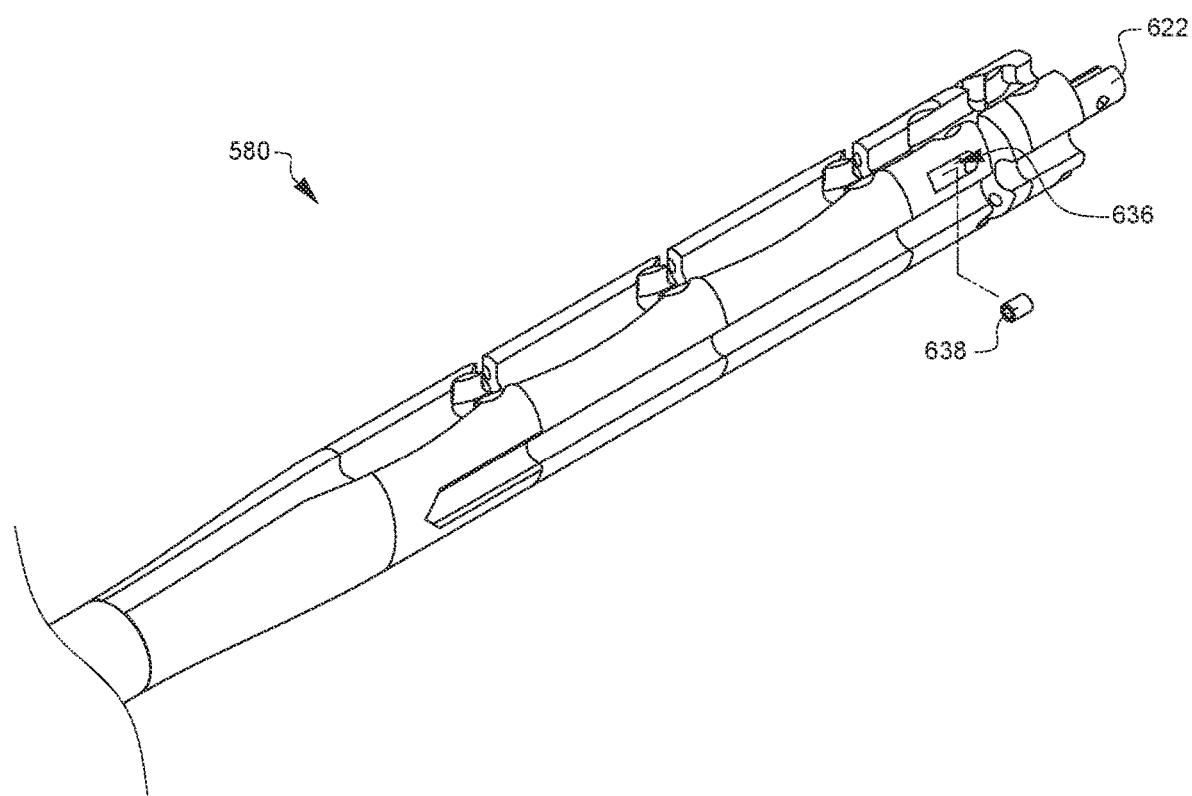
Figure 30N:
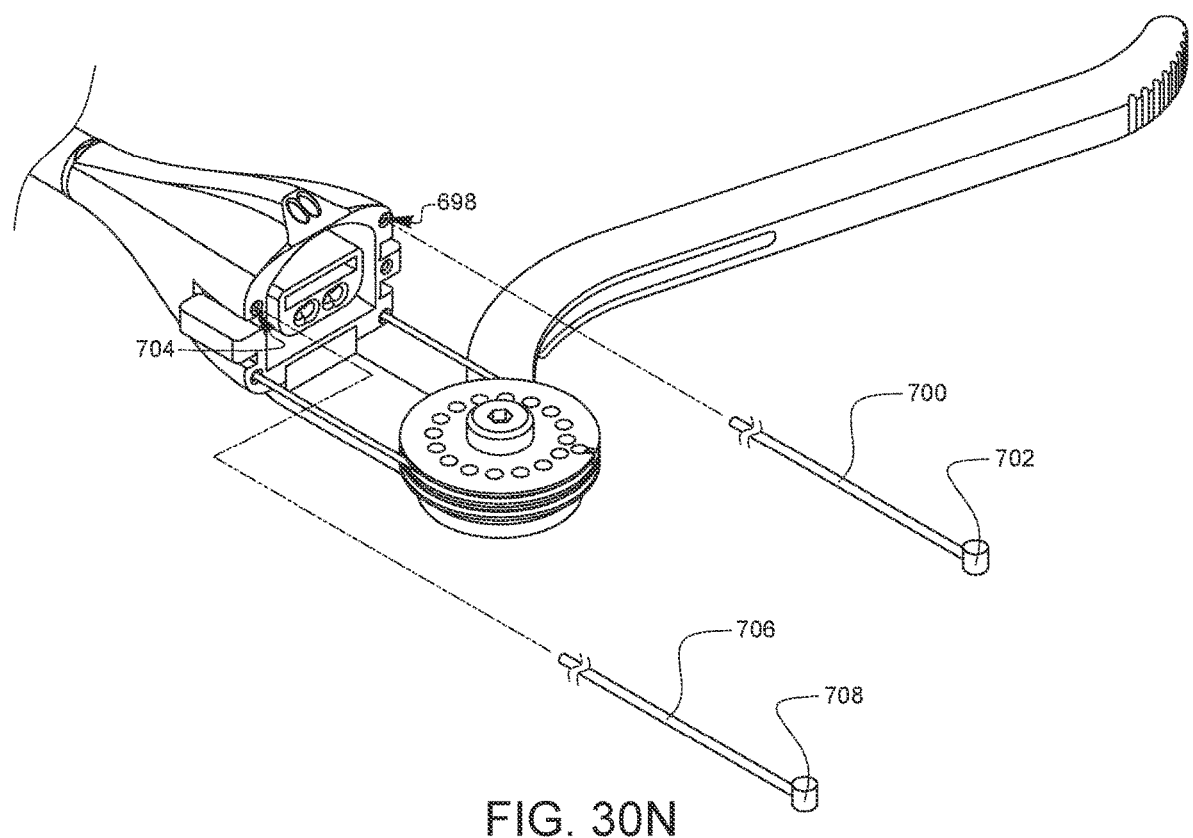
Figure 30P:
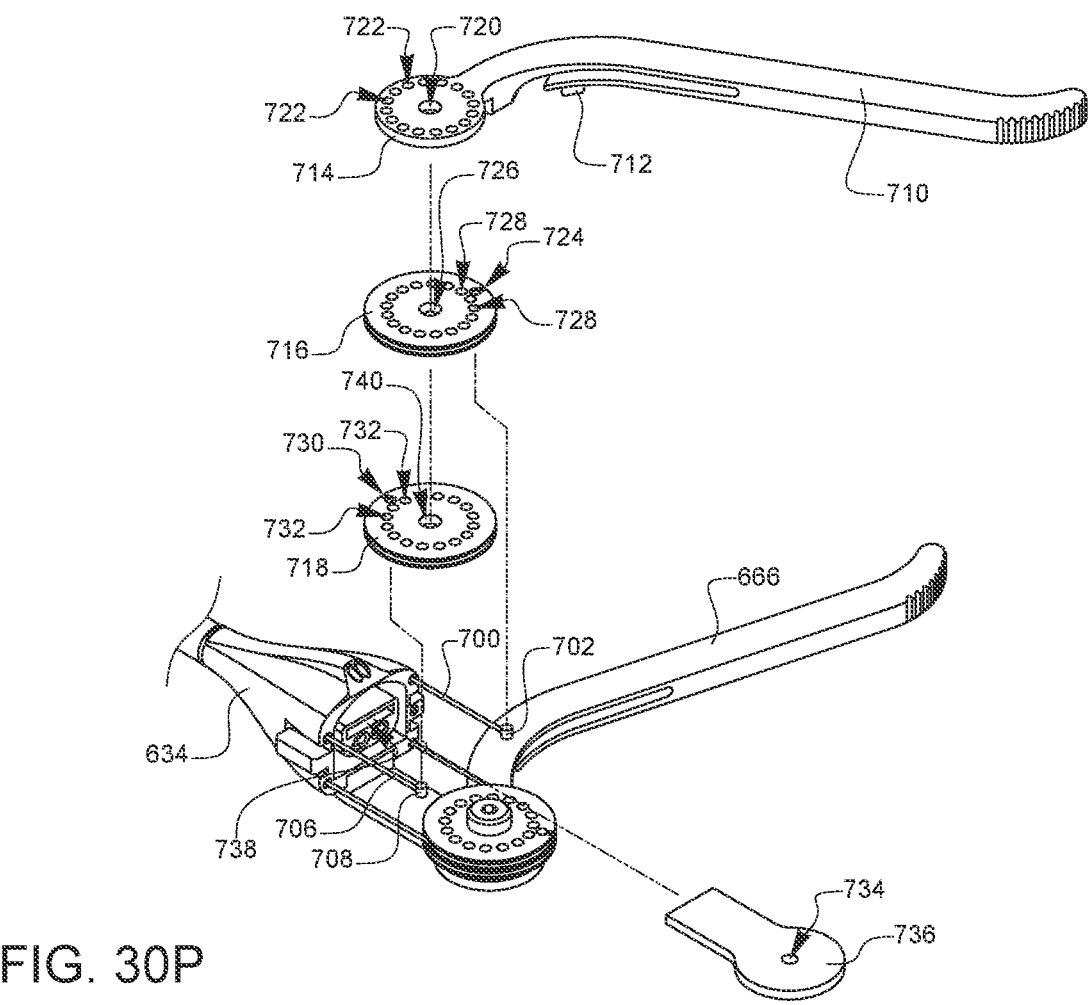
Figure 30Q:
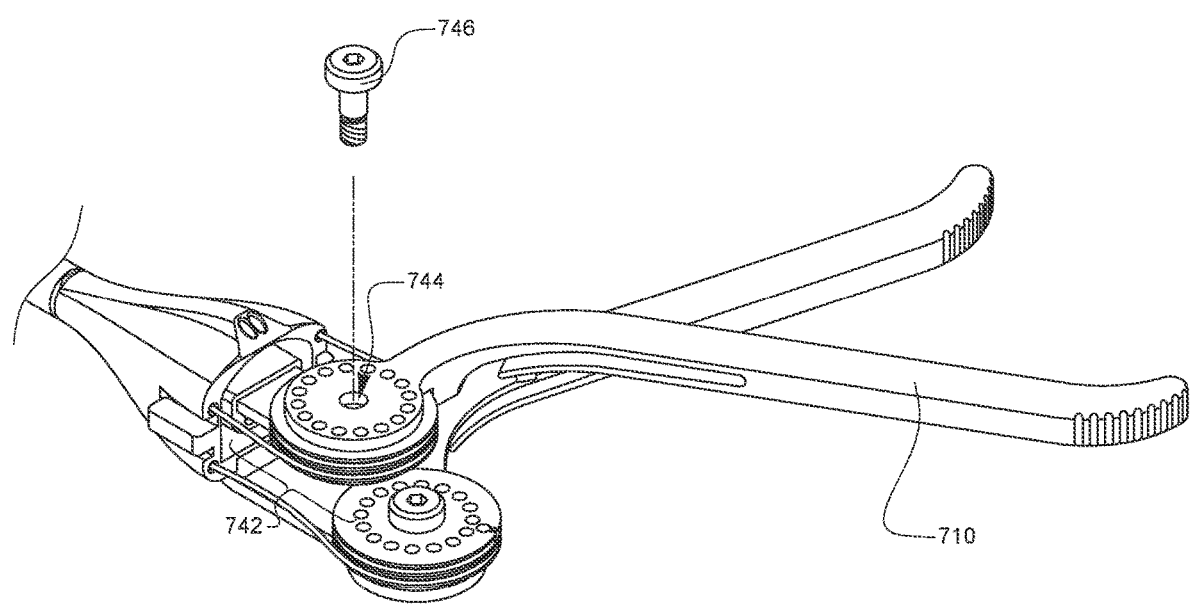
Figure 30R:
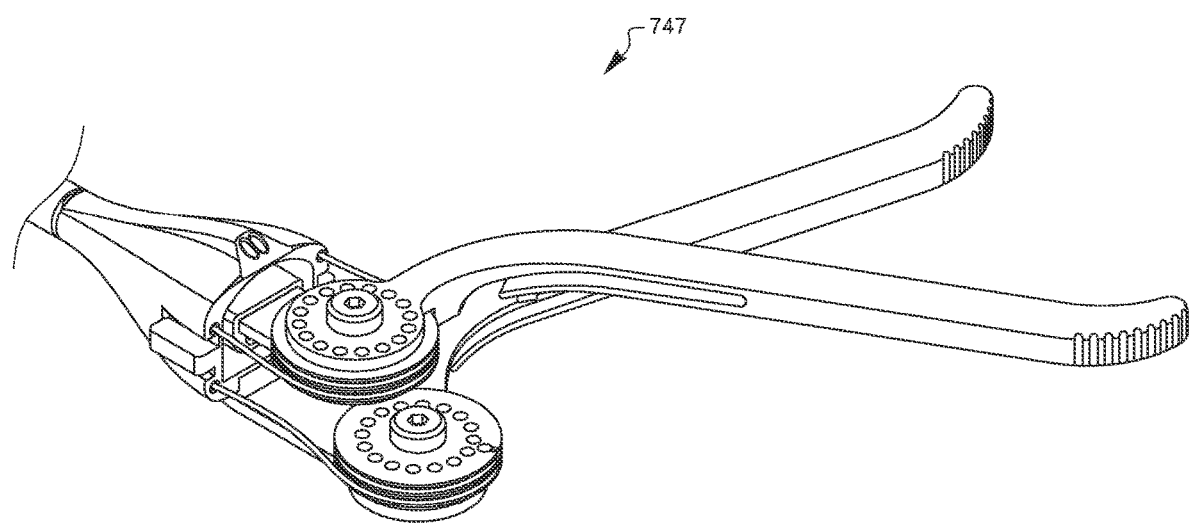

FIG. 30L-30M are a series of exploded views illustrating another series of assembly steps of the surgical suturing device 544 of FIG. 29. As shown in FIGS. 30L and 30M, two couplers 638, only one of which is shown here, are inserted into several corresponding recesses 636 in the distal end of the flexible shaft 580. In FIG. 30N, two upper steering cables 700, 706 are inserted into the upper steering cable channels 698 as defined by the shaft mount 634 shown in the previous assembly steps. FIG. 30O is not used to avoid confusion with the number 300. FIG. 30P is an exploded view illustrating an assembly step of the surgical suturing device of FIG. 29, depicting the assembly of the first or upper articulation lever 710 sub-assembly. FIG. 30L shows the two upper steering cables 700, 706 from the previous assembly steps terminating in their respective couplers 708, 702 extending from the shaft mount 634. The coupler 708 of the left upper steering cable 706 is inserted into a recess 724 defined by a lower pulley 718. The lower pulley 718 further defines a central hole 740 and several alignment holes 732. The coupler 708 of the right upper steering cable 706, 700 is inserted into a recess 730 defined by an upper pulley 716. The upper pulley 716 also further defines a central hole 720 and several alignment holes 722. A first upper articulation lever 710 defines a stop tab 712 and a pulley section 714 with a center hole 720 and multiple alignment holes 722. The central holes 720, 726, 740 of the first upper articulation lever 710, the upper pulley 716 and the lower pulley 718 are then stacked with their respective central holes 726, 740 aligned. This temporarily captures the couplers 708, 702 of the two steering cables 700, 706 in the recesses 724, 730 of their respective pulleys and in the first upper articulation lever 710 subassembly. FIG. 30Q illustrates the first upper articulation lever 710 subassembly step as completed in FIG. 30P, adding a screw to fixedly attach the pulley system 742 to the lower pulley mount 690. FIG. 30R is a perspective view of the result of the assembly steps of FIGS. 30G-30P.

Figure 30S:
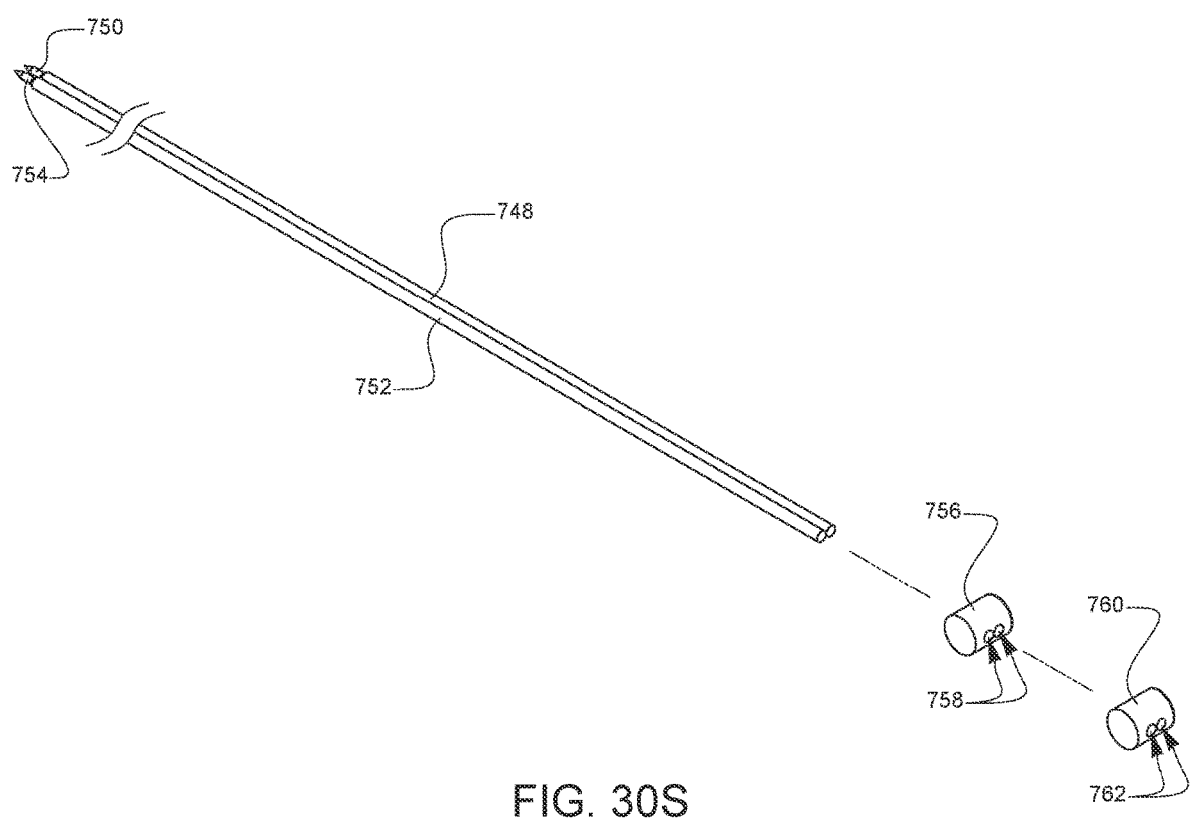

FIG. 30S is an exploded view illustrating an assembly step of the surgical suturing device of FIG. 29, depicting the assembly of the upper needle pair. Two flexible needles 748, each having ferrule engaging tips 750, 754, are inserted into two holes 758, 762 defined by a distal needle barrel 756, and subsequently into two holes 758, 762 defined by a proximal needle barrel 760. The distal needle barrel 756 and the proximal needle barrel 760 are fixedly attached to the needle pair 764, with the needle assembly terminating in the proximal needle barrel 760. FIG. 30J is a perspective view of the upper needle pair 764 assembly of FIG. 30S.

Figure 30T:
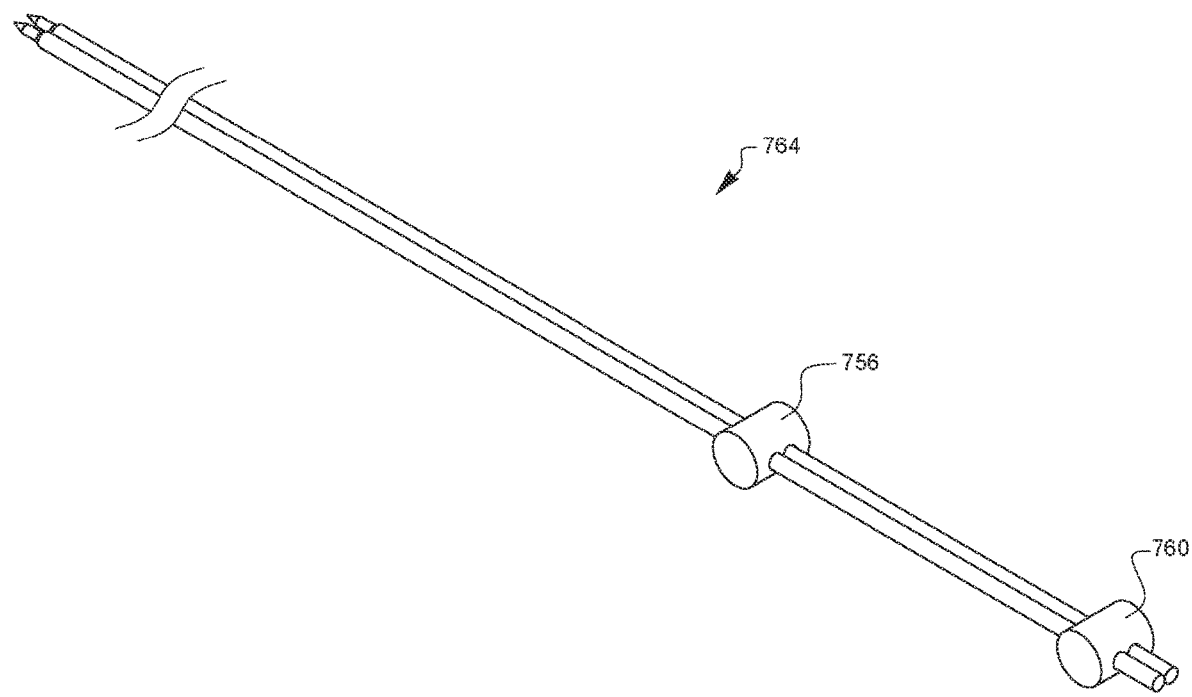
Figure 30U:
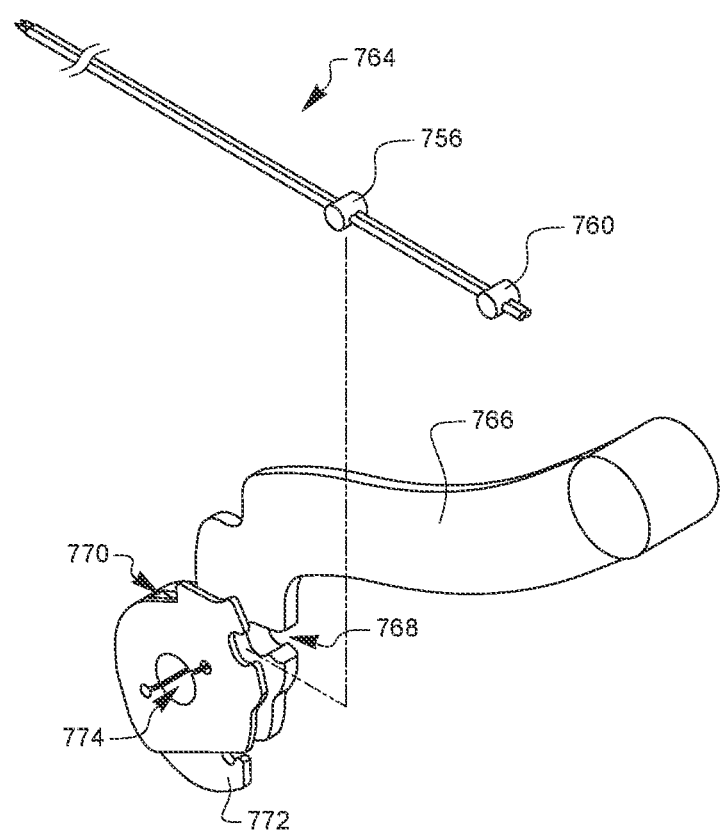
Figure 30V:
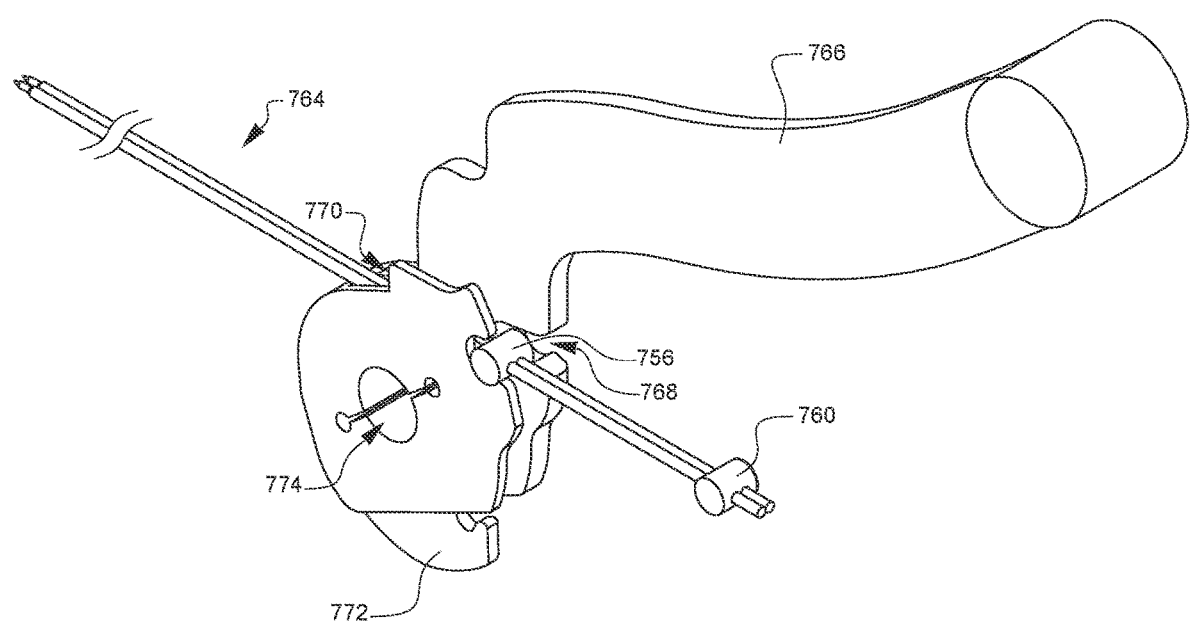

FIG. 30U is an exploded view illustrating an assembly step of the surgical suturing device of FIG. 29, depicting the assembly of the second upper needle pair 764 and the second needle drive lever 766. A second needle drive lever 766 defining a recess 770, a pivot hole 774, a barrel catch 768, and a spring catch 772 accepts the second upper lower needle pair 764 assembly of FIG. 30T into the recess 770, and releasably holds the distal barrel 756 of the second upper needle pair 764 assembly in the barrel catch 768 defined by the second needle drive lever 766. The needle pair 764 are allowed to travel freely within the recess 770 during operation of the surgical suturing device 544. The spring catch 772 is configured to connect a spring from the first needle drive lever to the housing of the surgical suturing device 544 and the pivot hole 774 is configured to constrain the rotation and allow pivotal movement of the second needle drive lever 766 around a captive pin in the housing of the surgical suturing device 544. These will be discussed in further detail later. FIG. 30V is a perspective view illustrating the result of the assembly step of FIG. 30U, showing the assembled configuration of the second upper lower needle drive subassembly, and the distal barrel 756 of the needle pair held within the barrel catch 768 of the second upper needle drive. Needle drive levers as described herein may also be referred to as needle actuators.

Figure 30W:
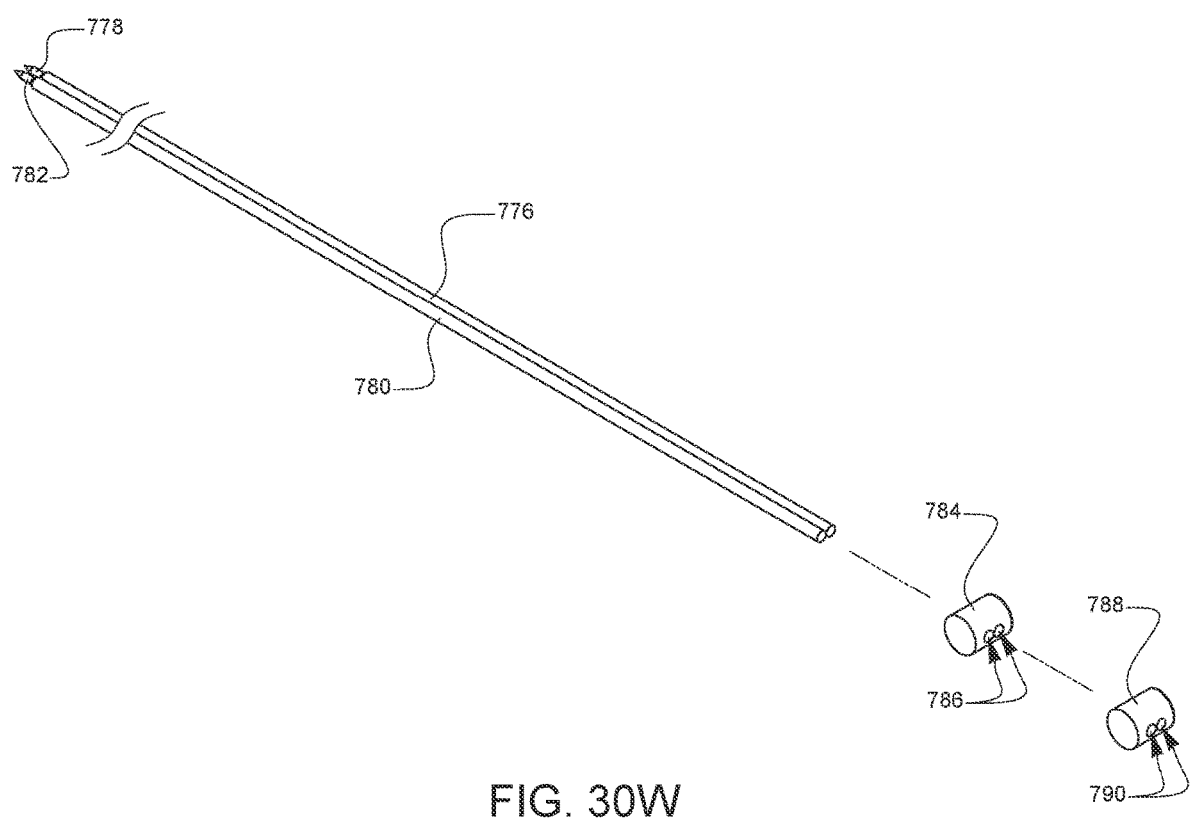
Figure 30X:
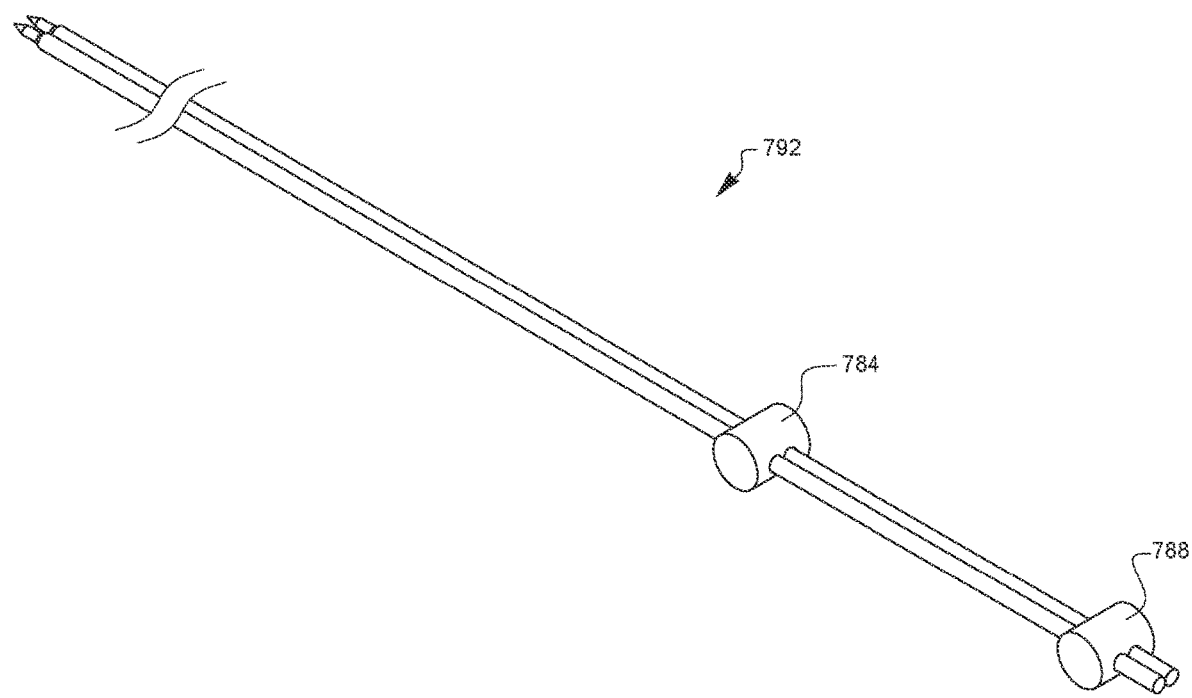

FIG. 30W is an exploded view illustrating an assembly step of the surgical suturing device of FIG. 29, depicting the assembly of the lower needle pair. Two flexible needles 780, each having ferrule engaging tips 778, 782, are inserted into two holes 786, 790 defined by a distal needle barrel 784, and subsequently into two holes 786, 790 defined by a proximal needle barrel 788. The distal needle barrel 784 and the proximal needle barrel 788 are fixedly attached to the needle pair 792, with the needle assembly terminating in the proximal needle barrel 788. FIG. 30X is a perspective view of the lower needle pair 792 assembly of FIG. 30W.

Figure 30Y:
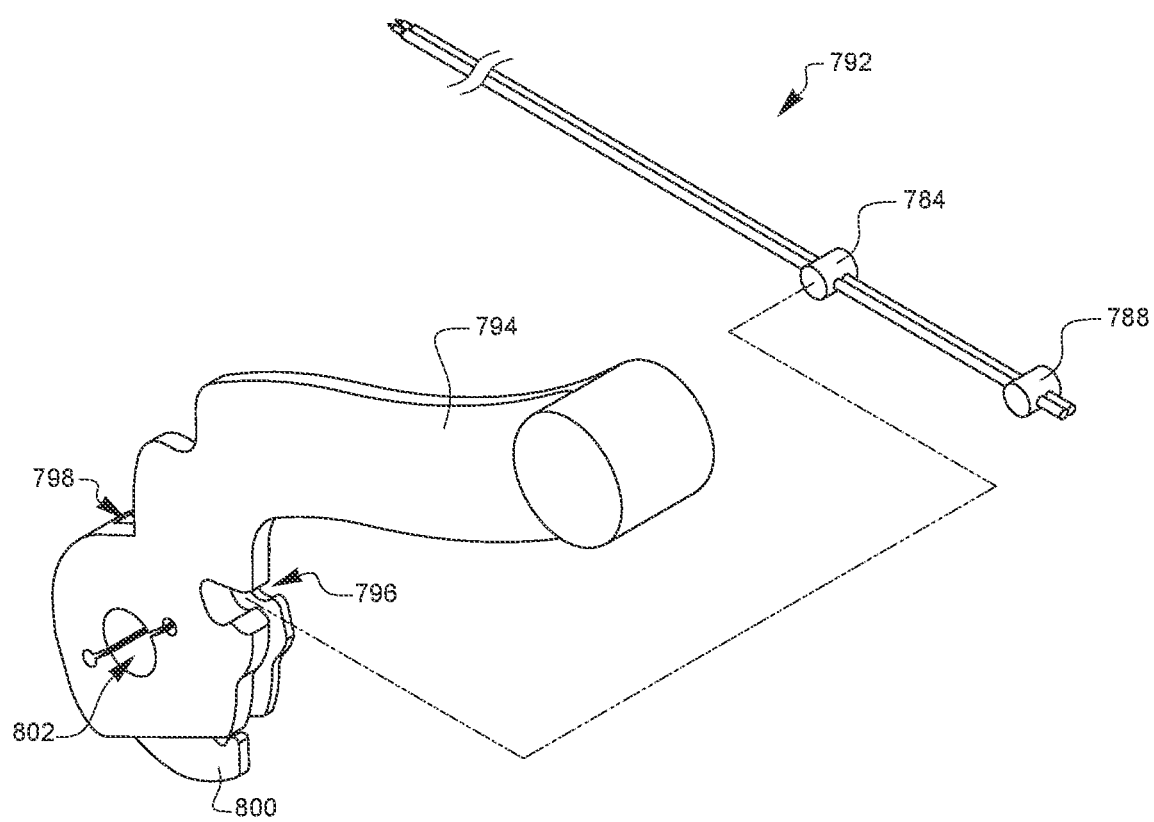
Figure 30Z:
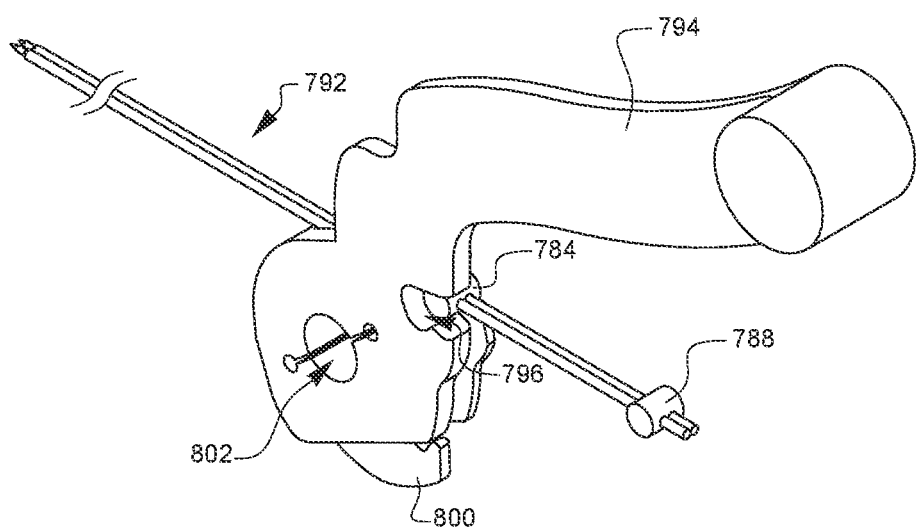
Figure 30A:
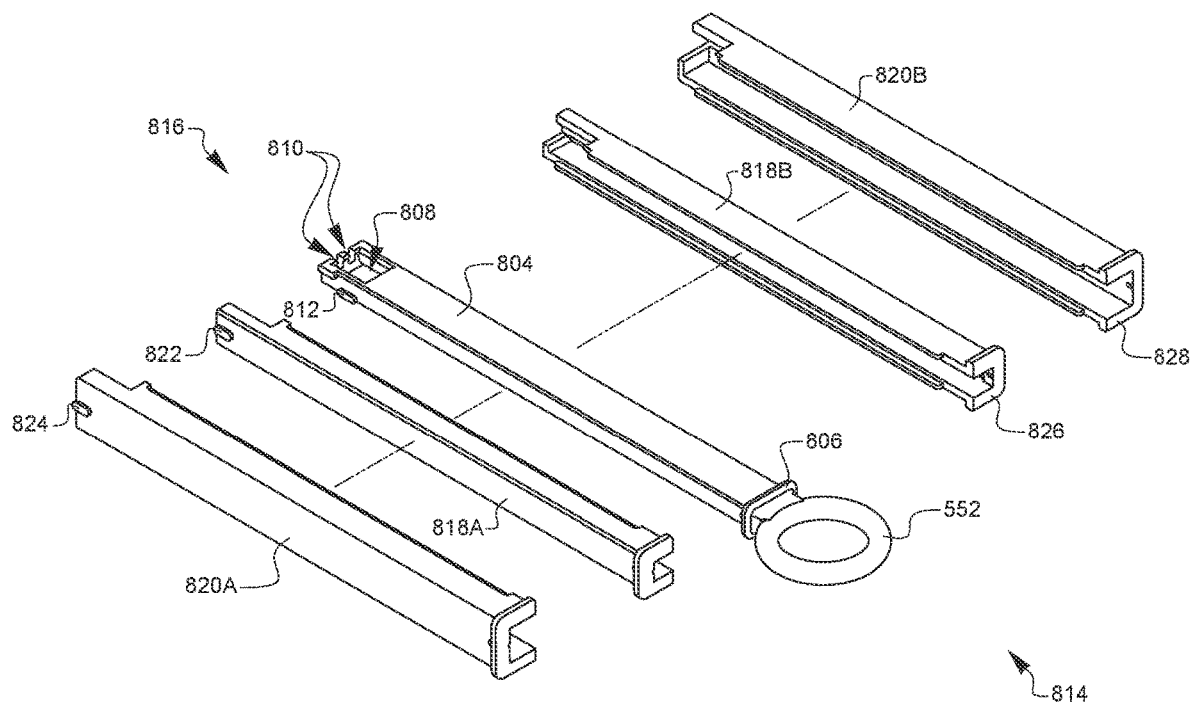
Figure 30A:
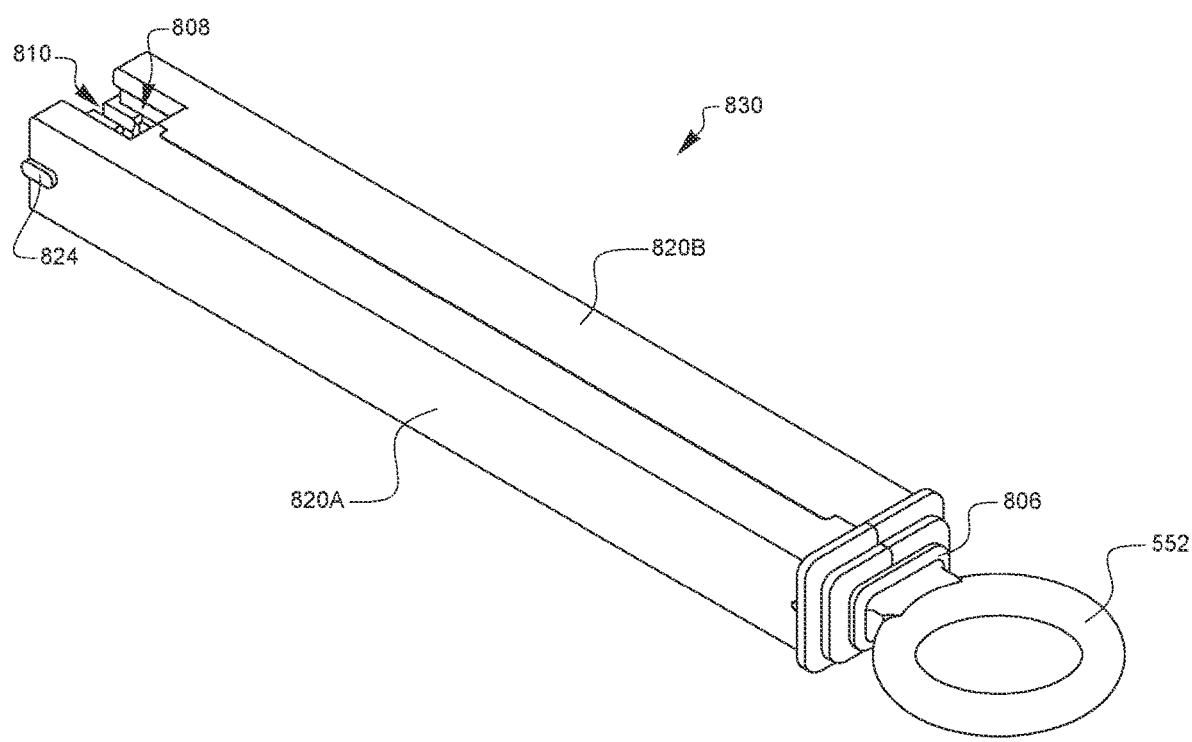
Figure 30A:
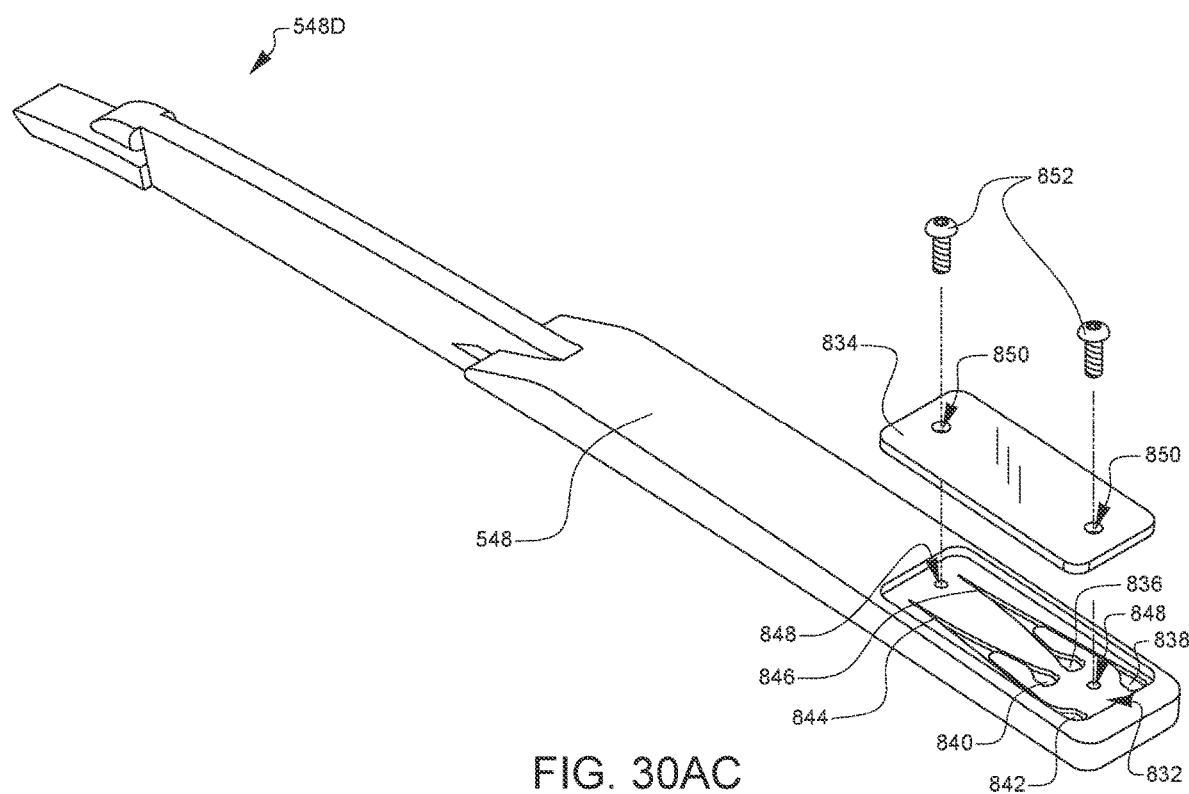
Figure 30A:
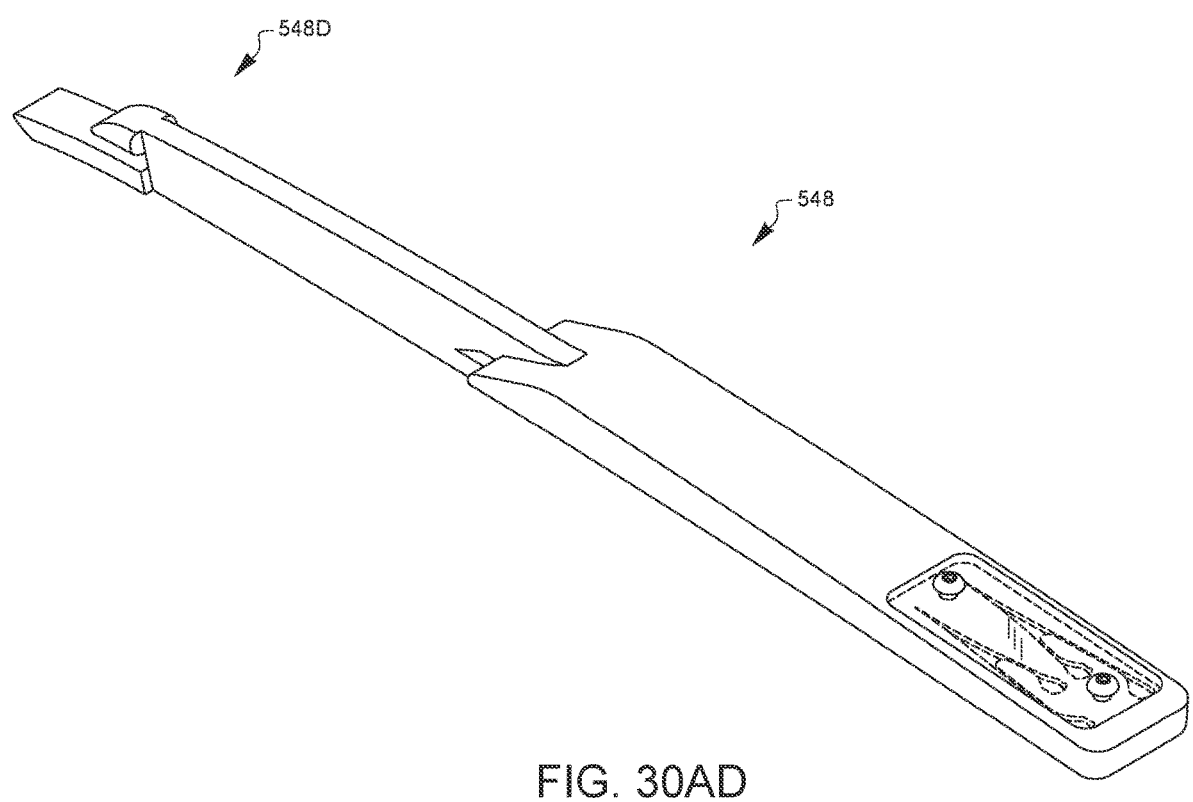
Figure 30A:
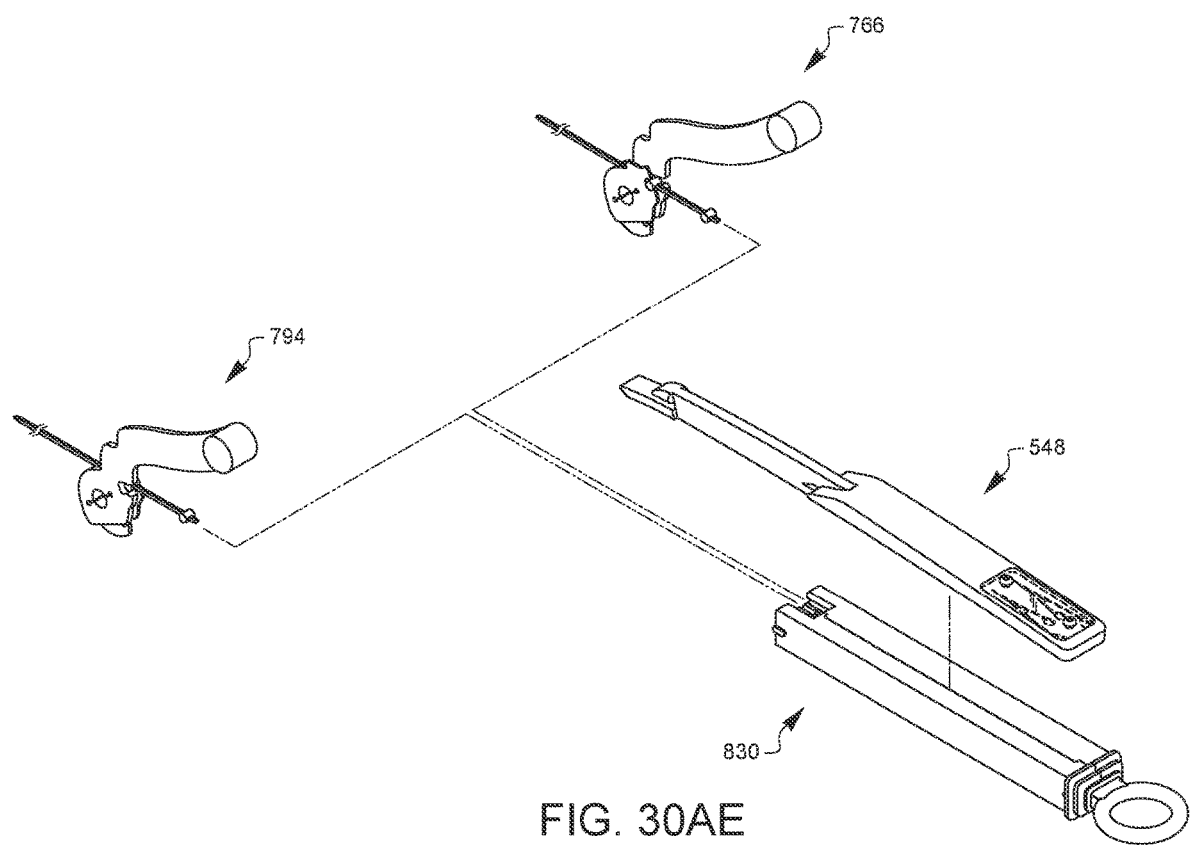
Figure 30A:
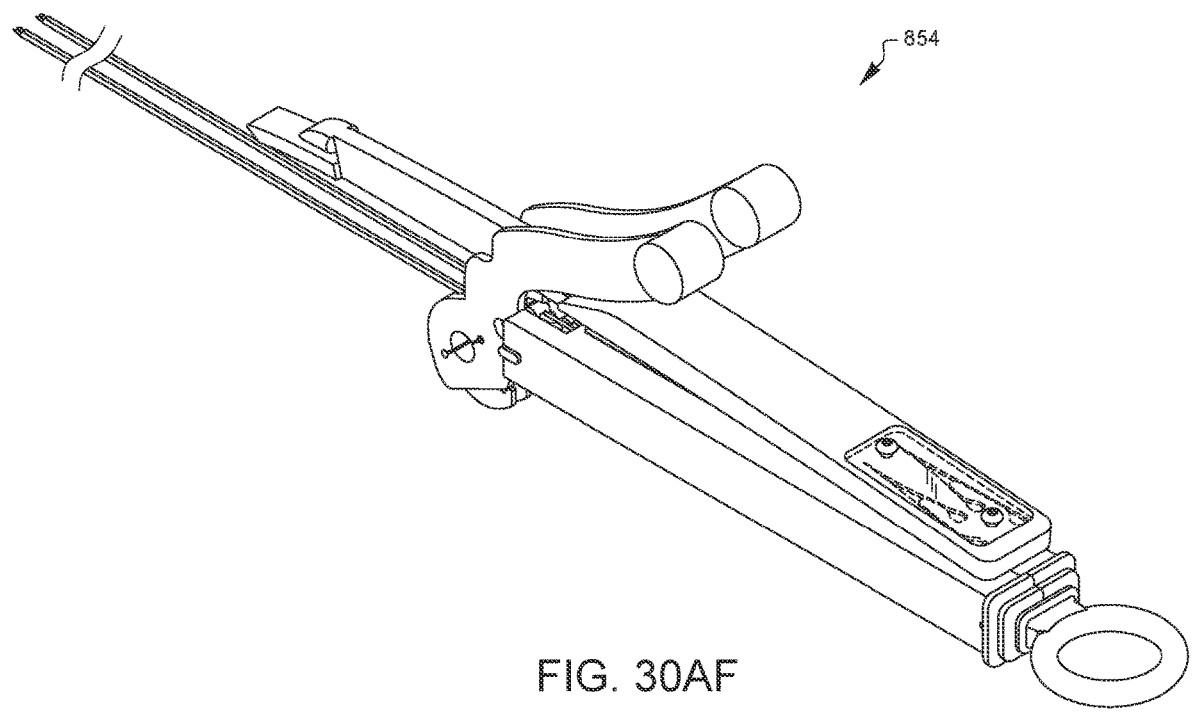
Figure 30A:
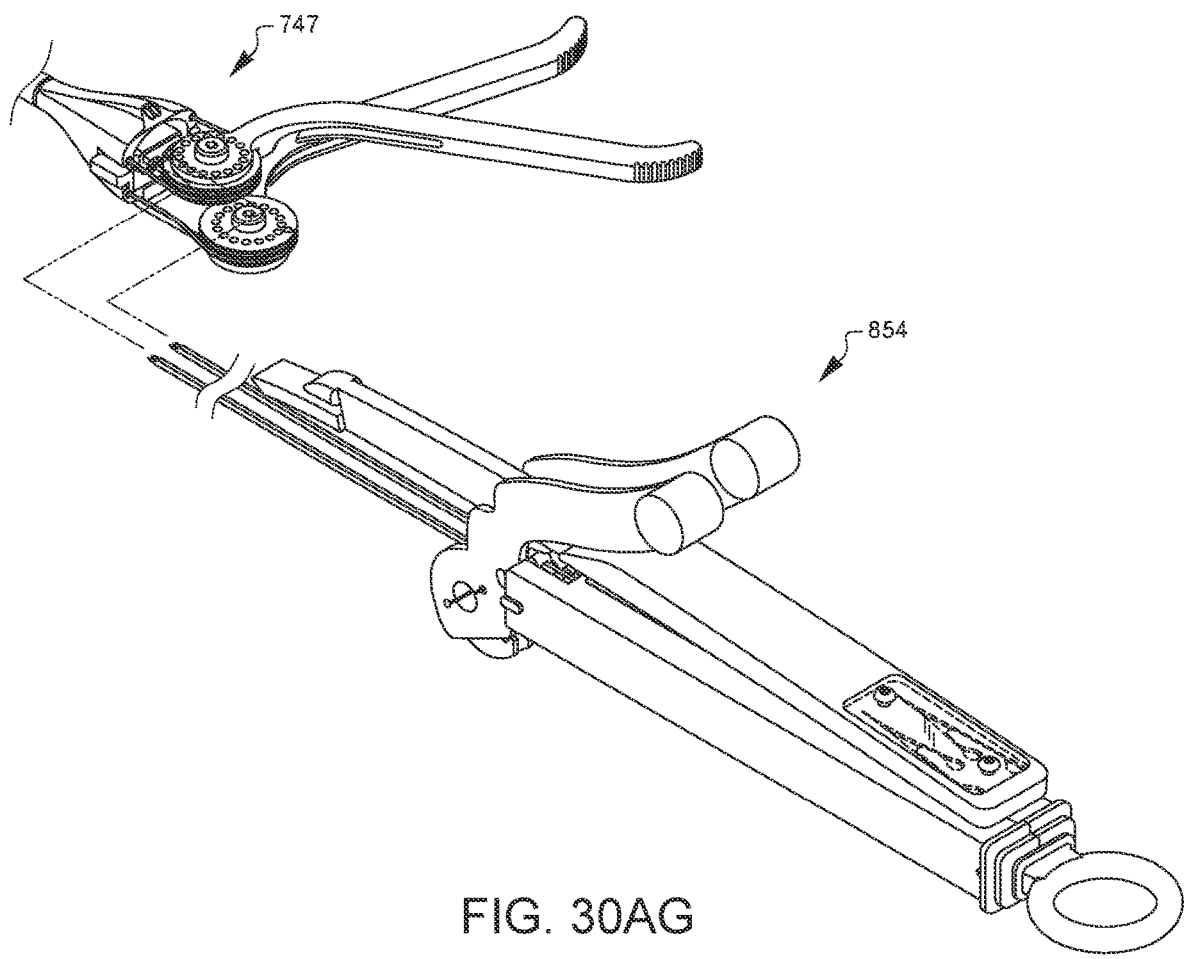
Figure 30A:
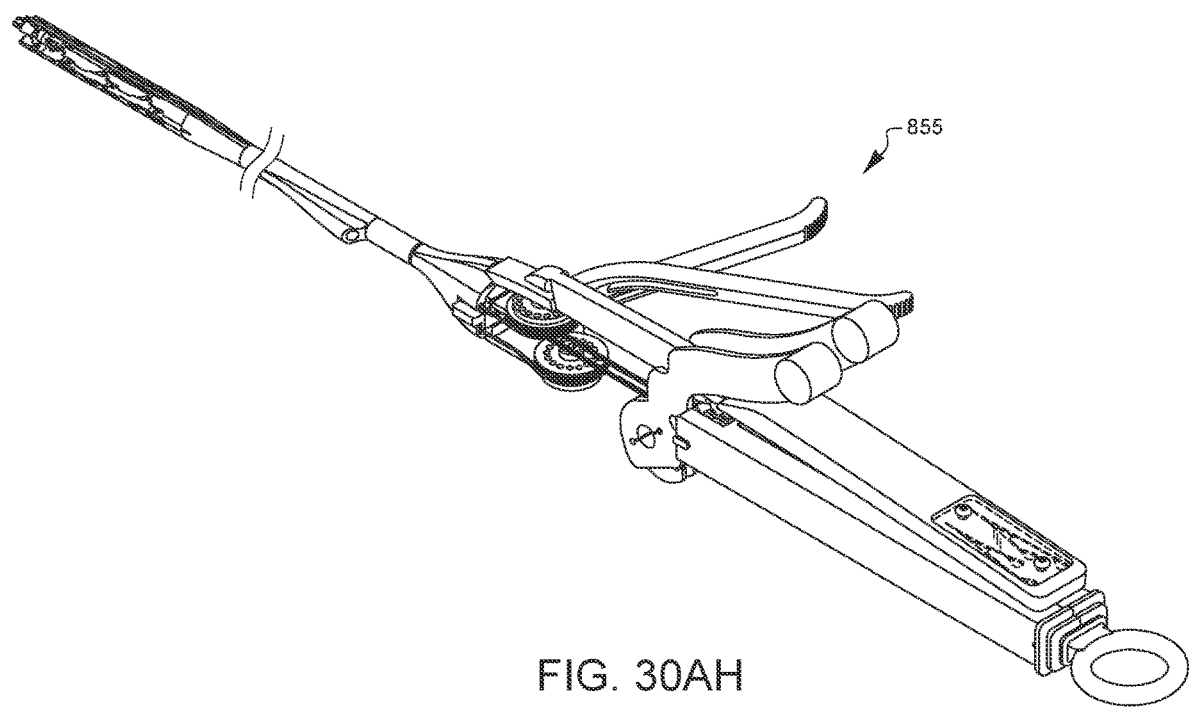
Figure 30A:
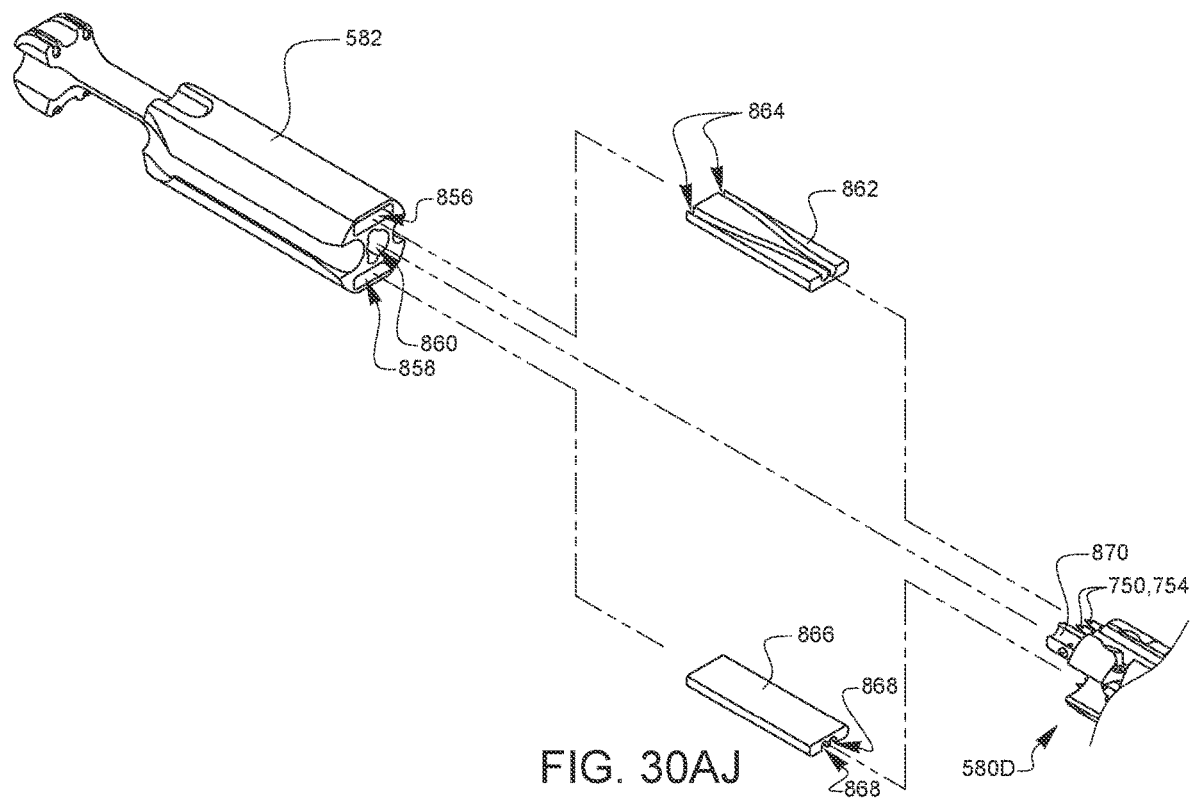
Figure 30A:
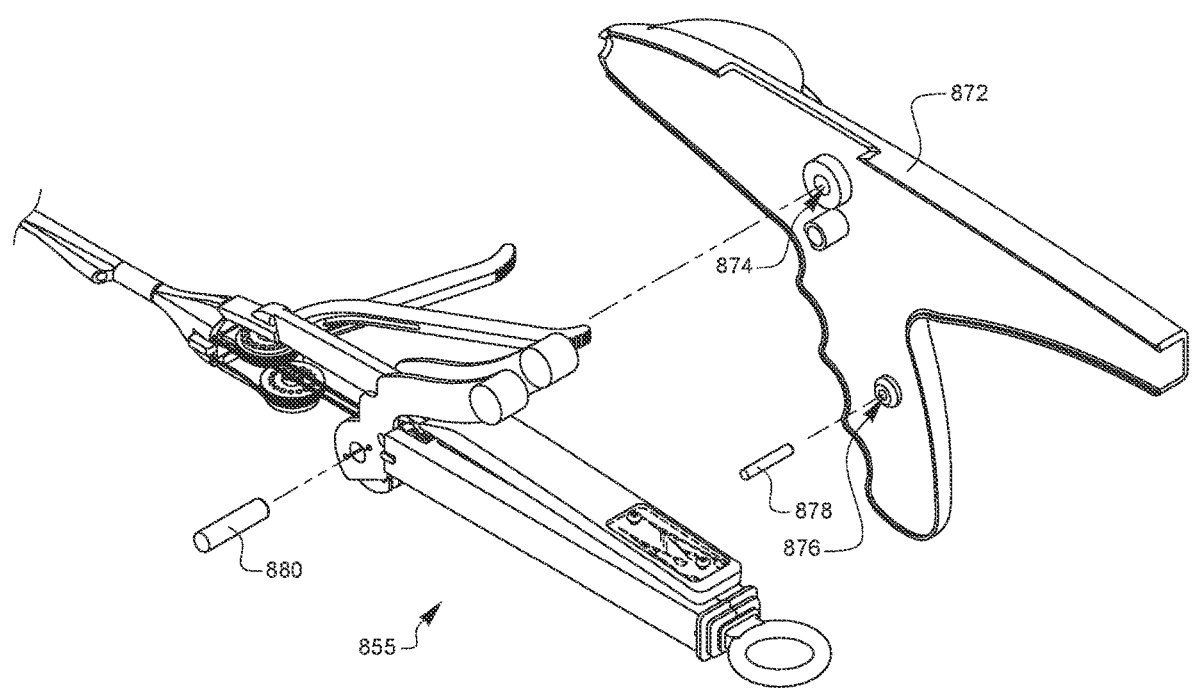
Figure 30A:
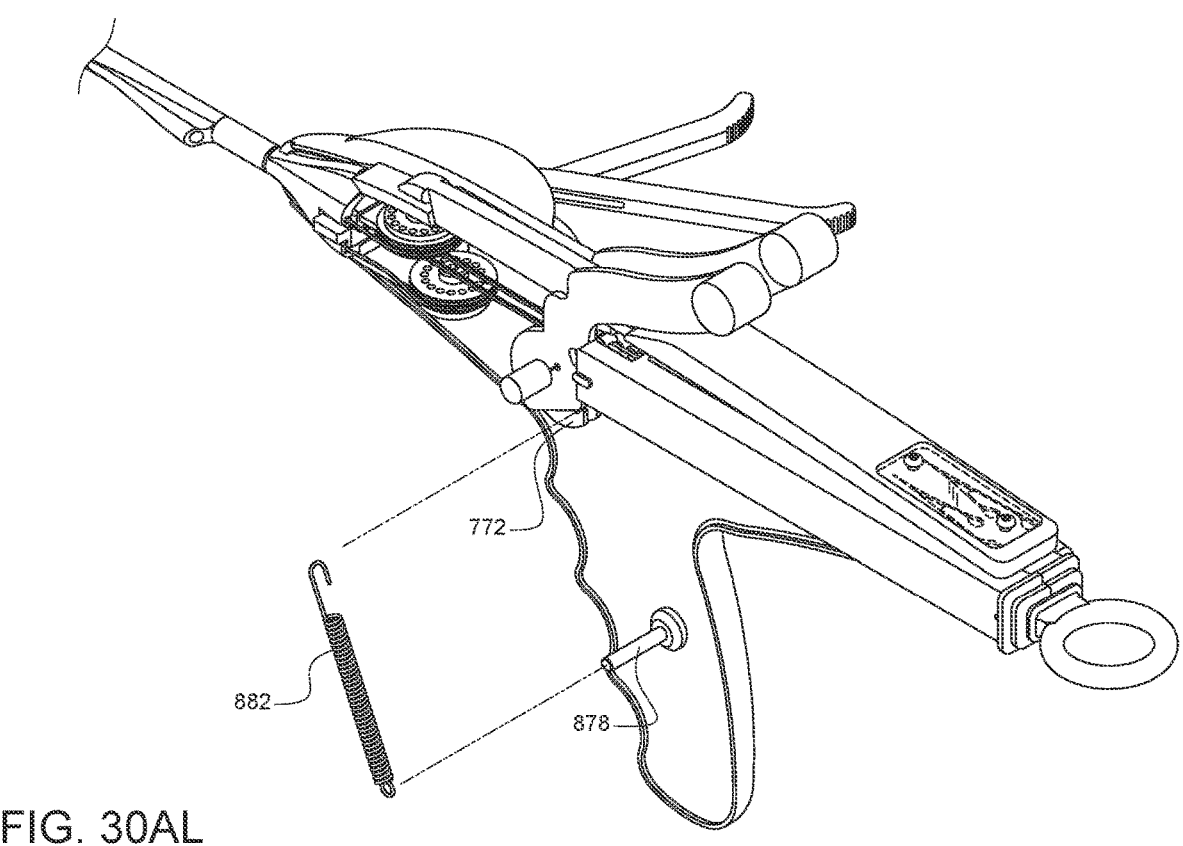
Figure 30A:
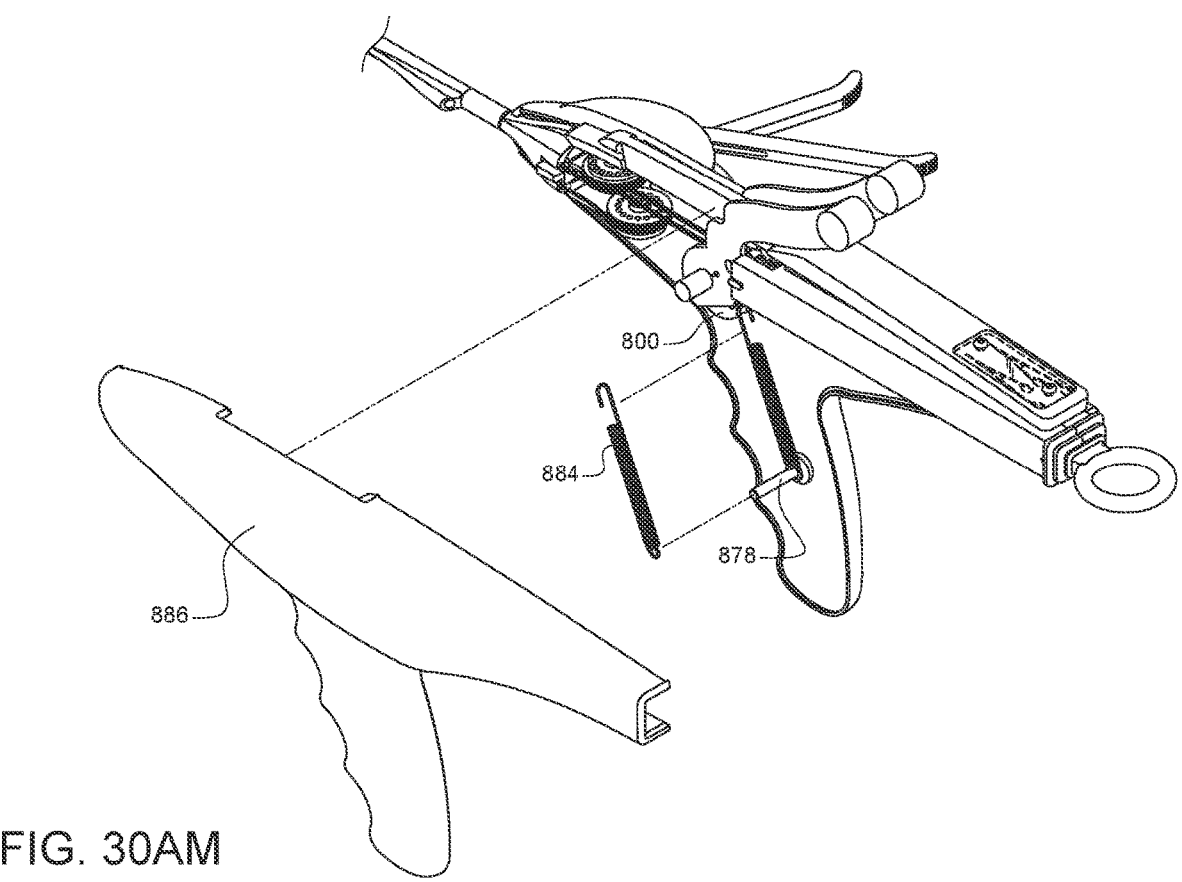
Figure 30A:
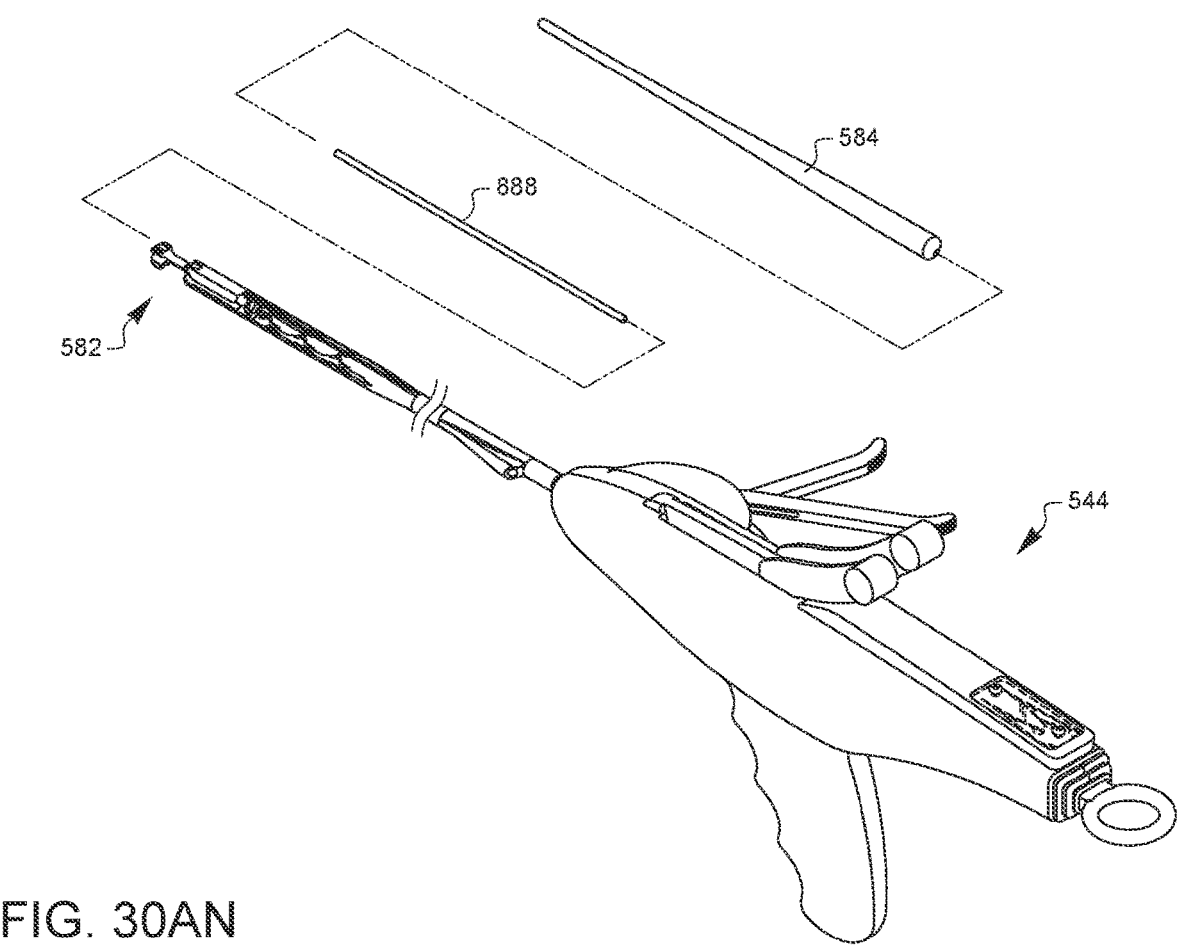
Figure 30A:
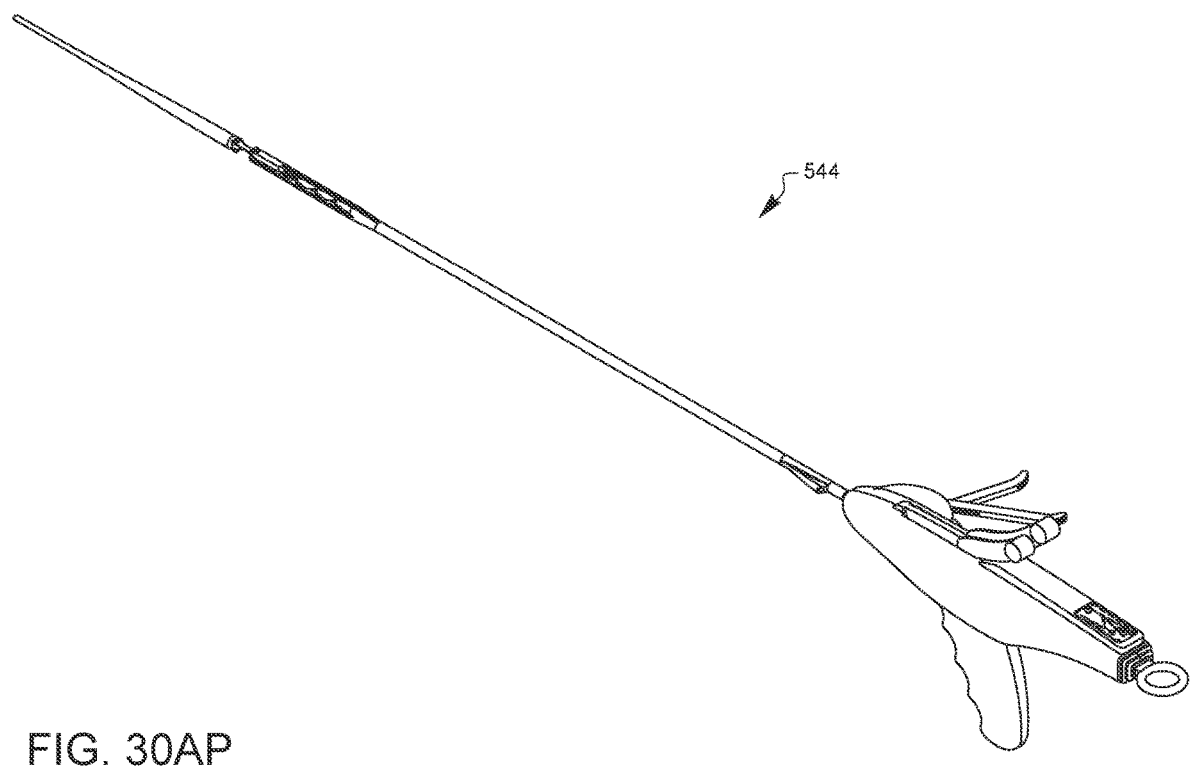

FIG. 30Y is an exploded view illustrating an assembly step of the surgical suturing device of FIG. 29, depicting the assembly of the first lower needle pair and the first needle drive lever. A first needle drive lever 794 defining a recess 798, a pivot hole 802, a barrel catch 796, and a spring catch 800 accepts the first lower needle pair 792 assembly of FIG. 30X into the recess 798, and releasably holds the distal barrel 784 of the first lower needle pair 792 assembly in the barrel catch 796 defined by the first needle drive lever 794. The needle pair 792 are allowed to travel freely within the recess 798 during operation of the surgical suturing device 544. The spring catch 800 is configured to connect a spring from the first needle drive lever 794 to the housing of the surgical suturing device 544 and the pivot hole 802 is configured to constrain the rotation and allow pivotal movement of the first needle drive lever 794 around a captive pin in the housing of the surgical suturing device 544. These will be discussed in further detail later. FIG. 30Z is a perspective view illustrating the result of the assembly step of FIG. 30Y, showing the assembled configuration of the first lower needle drive subassembly, and the distal barrel 784 of the needle pair 792 held within the barrel catch 796 of the first lower needle drive.

FIG. 30AA is an exploded view illustrating an assembly step of the surgical suturing device of FIG. 29, depicting the assembly of the retracting telescope. An inner telescope segment 804 defines a stop, two distal stops 822, 824 (one on either side) and a handle towards the proximal end 814 of the inner telescope segment 804. At the distal end 816 of the inner telescope segment 804, the inner telescope segment 804 defines two needle slots 810 and a barrel recess 808. Two middle telescope segment halves 818A, 818B are assembled over the inner telescope segment 804, these middle telescope segments 818A, 818B configured to enclose the inner telescope segment 804, yet allow slidable nesting such that the inner telescope segment 804 may be pulled towards the proximal end 814 and slide the inner telescope segment 804 outward. The stop defined by the inner telescope segment 804 is configured to prevent the inner telescope segment 804 from being inserted too far into the middle telescope segment 818A, 818B. The distal stops 812, 822, 824, on the inner telescope segment 804 prevent the inner telescope from sliding too far proximal and out of the middle telescope segment 818A, 818B once assembled, thus holding it captive. The middle telescope segments 818A, 818B also define two distal stops 822, 824 and combine to form a proximal stop 826. Two outer telescope segment halves 820A, 820B are assembled over the middle telescope segment 818A, 818B, these outer telescope segments 820A, 820B configured to enclose the middle telescope segment 818A, 818B, yet allow slidable nesting such that the middle telescope segment 818A, 818B may be pulled towards the proximal end 814 and slide the middle telescope segment 818A, 818B outward. The stop defined by the middle telescope segment 818A, 818B is configured to prevent the middle telescope segment 818A, 818B from being inserted too far into the outer telescope segment 820A, 820B. The distal stops 822, 824 on the middle telescope segment 818A, 818B prevent the middle telescope from sliding too far proximal and out of the outer telescope segment 820A, 820B once assembled, thus holding it captive. The outer telescope segments 820A, 820B also define two distal stops 822, 824 and combine to form a proximal stop 828. The stop defined by the outer telescope segment 820A, 820B is configured to prevent the outer telescope segment 820A, 820B from being inserted too far into the instrument housing. The distal stops 822, 824 on the outer telescope segment 820A, 820B prevent the outer telescope from sliding too far proximal and out of the instrument housing once assembled. The telescoping segment is configured to allow a proximal extension of each retracting telescope segment, which allows a stationary location of the surgical suturing device 544 within a patient during a minimally invasive surgical procedure, while also allowing the retraction of one or more needle pair from the surgical site. While this embodiment of a surgical suturing device 544 shows this particular retracting telescope and its telescoping function for the removal of one or more pair of needles from a surgical site, it could be configured or employed in alternate embodiments to allow for the retraction and removal from a surgical site of additional pair of needles or other instrumentation or implements used in minimally invasive surgical 544 procedures. FIG. 30AB is a perspective view illustrating the result of the assembly step of FIG. 30AA, showing the retracting telescope subassembly, and the assembled location of the barrel recess 808 and needle slots.

FIG. 30AC is an exploded view illustrating an assembly step of the surgical suturing device of FIG. 29, depicting the assembly of the suture storage housing. A suture storage housing 548 defines a suture recess 832 having two suture passages 844, 846 that communicate through the suture storage housing 548 and through to the suture passages 844, 846 on the shaft mount illustrated previously. The suture recess 832 of the suture storage housing 548 further defines a left outer suture loop recess 842, a left inner suture loop recess 840, a right outer suture loop recess 838, a right inner suture loop recess 836, and several holes 848, 850 for attaching screws 852 or other fasteners. A suture viewing window 834, which defines two holes 848, 850 and is transparent for visualizing the state of the suture during the procedure is configured to be inserted into the suture recess 832 and attached by the screws 852 into several threaded holes 848, 850 defined by the suture recess 832. FIG. 30AD is a perspective view illustrating the result of the assembly step of FIG. 30AC, showing the assembled suture storage housing 548.

FIG. 30AE is an exploded view illustrating an assembly step of the surgical suturing device of FIG. 29. The first proximal barrel of the first needle drive assembly 794 is inserted into the barrel recess 808 of the retracting telescope 830, with the needle pair being held in the needle slots of the retracting telescope. The second proximal barrel of the second needle drive assembly 766 is likewise inserted into the barrel recess 808 of the retracting telescope 830, with the needle pair being held in the needle slots of the retracting telescope 830. Finally, the suture storage housing 548 is placed on top of the retracting telescope 830 and held in place until a subsequent subassembly step. FIG. 30AF is a perspective view, illustrating the result of the previous subassembly steps.

FIG. 30AG is an exploded view illustrating an assembly step of the surgical suturing device of FIG. 29, depicting the assembly of the result of the assembly steps of FIG. 30R and FIG. 30AP. The two needle pair are inserted into the needle passages in the shaft mount (not shown here, but more clearly depicted in FIG. 30G) and further into the entire rigid and flexible shaft portions of the surgical suturing device. FIG. 30AH is a perspective view, illustrating the result of the subassembly step depicted in FIG. 30AG. FIG. 30AI is not used or shown because the letter I may be mistaken for the numeral 1.

FIG. 30AJ is an exploded view illustrating an assembly step of the surgical suturing device of FIG. 29, depicting the assembly of the distal tip 582 onto the end of the flexible shaft 580. Onto the distal end of the flexible shaft 580D, the protruding needles 748, 752 from previous subassembly steps are visible. The distal tip 582 defines an upper recess 856, a lower recess 858, and a central channel 860. An upper needle track 862 is inserted into the upper recess 856 defined by the distal tip 582 and a lower needle track 866 is inserted into the lower recess 858 defined by the distal tip 582. The upper and lower needle tracks 862, 866 define needle paths 864, 868 for further guiding the flexible needles 748, 752 through the distal tip 582 needle channels, which are not shown in this view, but are described later. It should be noted that while the needle paths from the flexible shaft 580 through to the distal tip 582 are defined by several components, this effect could also be accomplished with a single component or single distal tip 582 having the upper needle track 862 and lower track 866 as part of the distal tip 582.

FIG. 30AK is an exploded view illustrating an assembly step of the surgical suturing device of FIG. 29, depicting an assembly step of the surgical suturing device 544. The subassembly of FIG. 30AJ is shown. A first handle half 872 defines several holes 874, 876 for mounting a needle driver pin 880 and a spring pin 878. The needle driver pin 880 is inserted into the pivot hole of each needle drive lever as the subassembly of FIG. 30AJ is placed in the first handle half 872. FIG. 30AL shows the second needle drive spring being attached to the second needle drive spring catch 772 on the second needle drive lever and placed on the spring pin 878. FIG. 30AM shows the first needle drive spring 884 being attached to the first and needle drive levers. The opposite end of each spring is mounted over the spring pin 878. The second handle half 886 is placed over the other components, with the needle driver pin 880 and the spring pin 878 being inserted into corresponding holes (not shown) in the second handle half 886. The first and second handle halves 886 are then fixedly attached, completing the assembly of the instrument. The first and second handle half 886 can be attached by adhesives, ultrasonic welding, or other fastening means and methods known to those skilled in the art.

FIG. 30AN is an exploded view illustrating an assembly step of the surgical suturing device of FIG. 29, depicting the assembly of the IVC guide wire distal channel and the IVC monorail guide 584. IVC guide wire distal channel, IVC monorail guide 584. FIG. 30AP is an alternate perspective view of the completed surgical suturing instrument of FIG. 29.

Figure 31A:
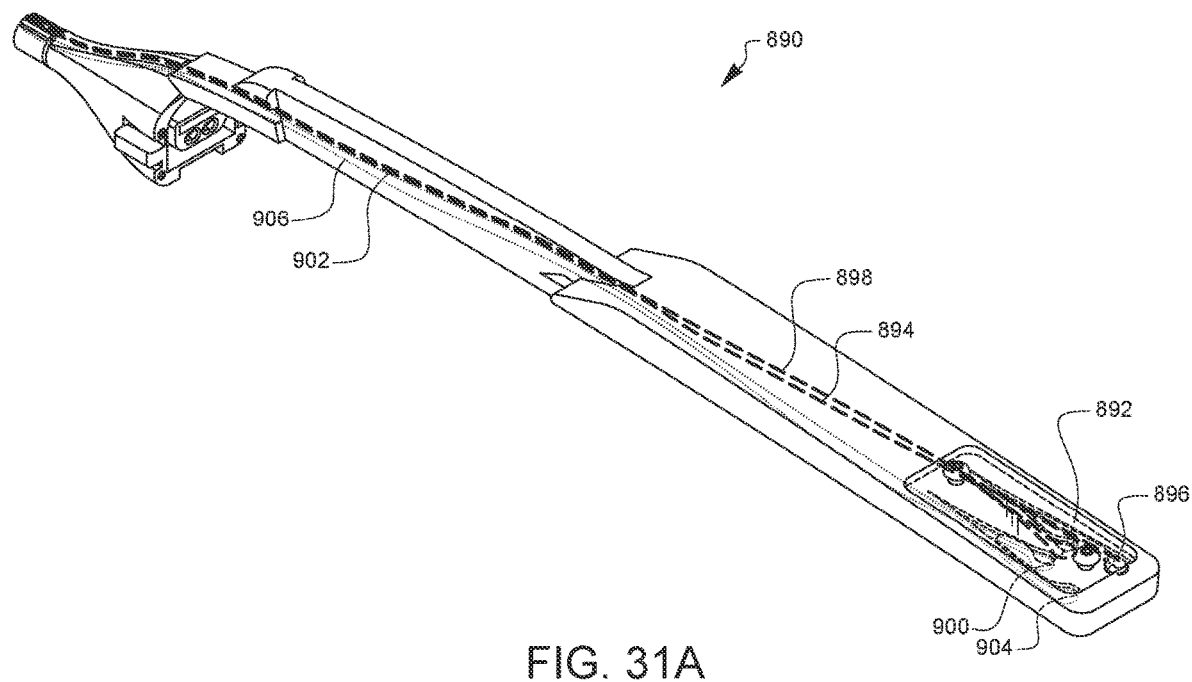
FIG. 31A is a top-left-rear perspective view of a portion of the surgical suturing device of FIG. 29.

FIG. 31A is a top-left-rear perspective view of a portion of the surgical suturing device 544 of FIG. 29 focusing on the top of the handle and the suture viewing window. The suture viewing window 834 is a transparent window used to view the state of the sutures within the device and to attain visual confirmation of tissue bites or stiches taking place when operating the device. The suture viewing window 834 allows the operator to view the state of the sutures 894,898, 902,906 and determine the completion of the operating steps during use. When the needle pairs are driven and the ferrules are engaged by the needles at their tips (not shown in this view), the suture loops 892, 896, 900, 904 pull forward towards the distal end of the device. The first lower needle bite pulls the more distal or inner suture loops distally (more forward) as a visual indication of ferrule or needle cap engagement onto the needle. The second upper needle bite pulls the more proximal or outer suture loops 896, 904 distally (more forward) as an indication of ferrule or needle cap engagement onto the needle. When the first bite of the lower needle set of the instrument is complete, one end of the blue or left inner suture 902 and one end of the white or right inner suture 894 will have advanced in a slightly distal direction within the suture viewing window 834. When the second bite of the upper needle set of the instrument is complete, one end of the blue or left outer suture 906 and one end of the white or right outer suture 898 will have advanced in a slightly distal direction within the suture viewing window 834.

Figure 31B:
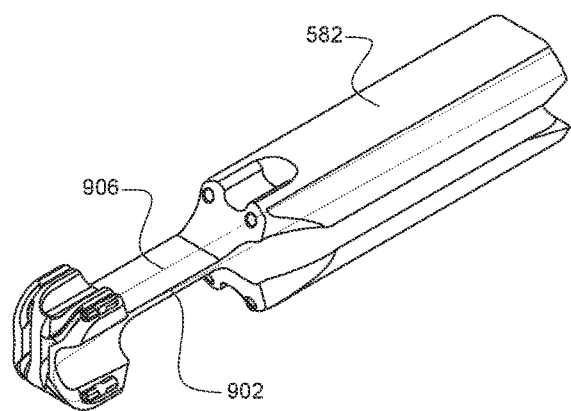
FIGS. 31B-31C are top-left-front perspective views of the distal tip of the surgical suturing instrument of FIG. 29.
Figure 31C:
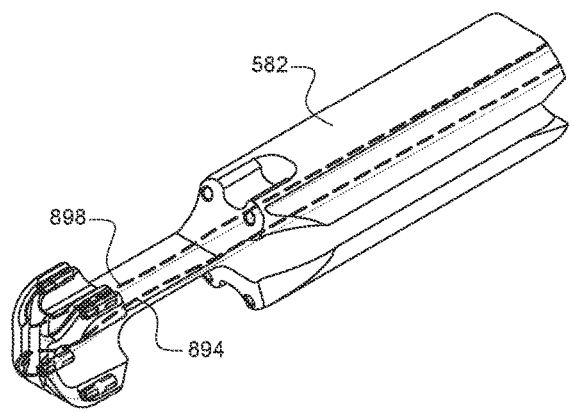

FIGS. 31B and 31C are top-left-front perspective views of the distal tip of the surgical suturing instrument 544 of FIG. 29. While the suture organization through shaft and at tip are similar to views shown in FIGS. 3A-3E, the suture ends 894, 898 corresponding to the suture loops shown in FIG. 31A are illustrated here.

Figure 32A:
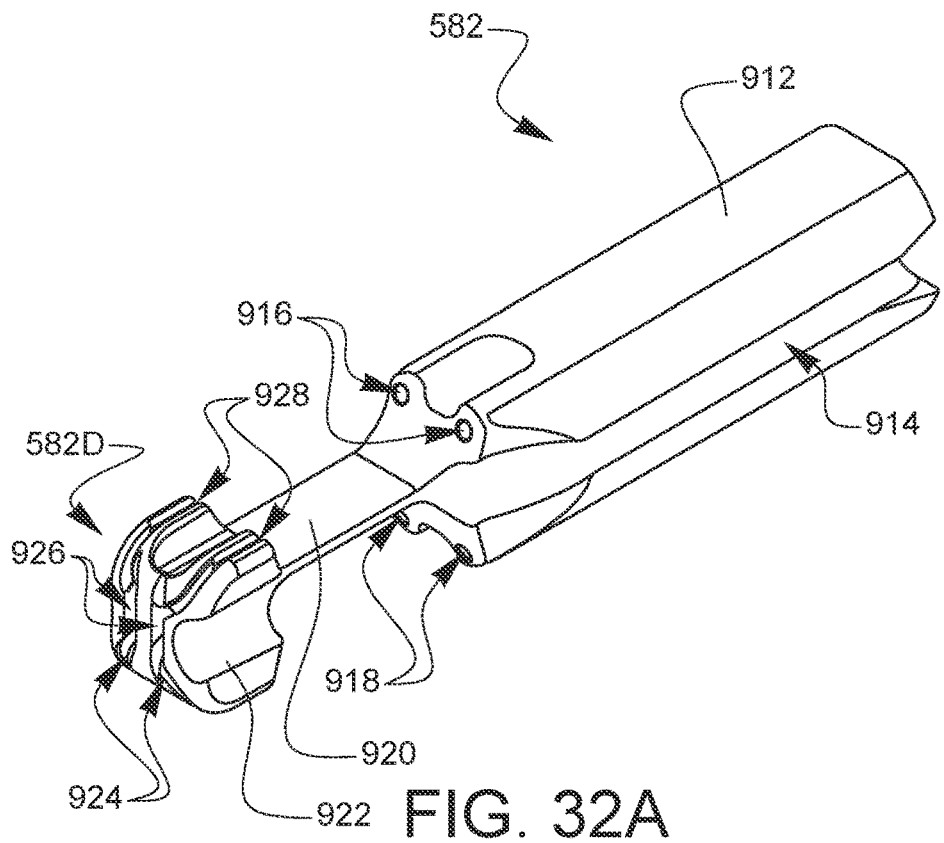
FIGS. 32A-32B are perspective views of the distal tip of the surgical suturing device of FIG. 29.
Figure 32B:
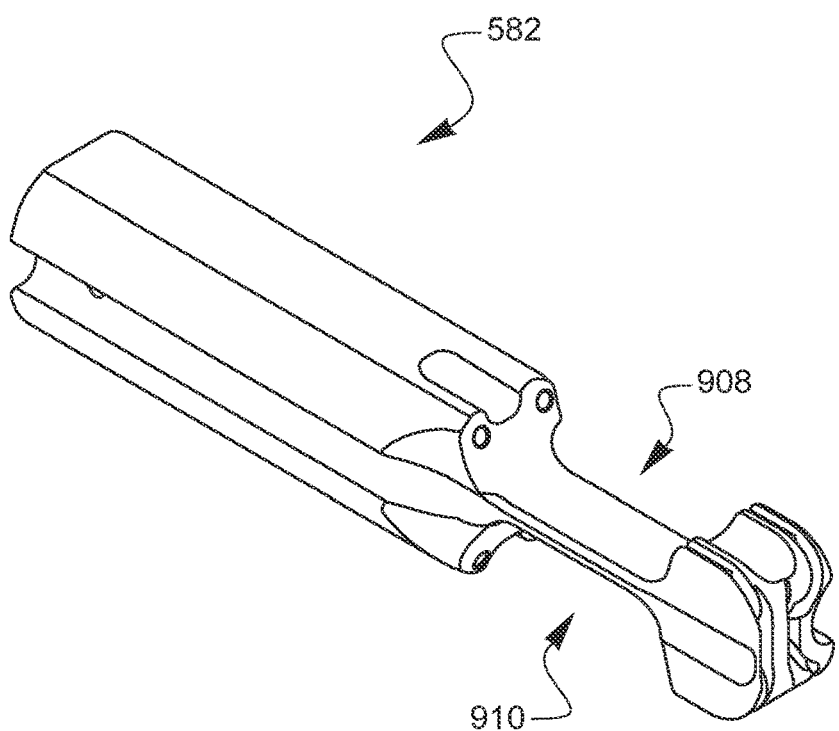
Figure 33E:
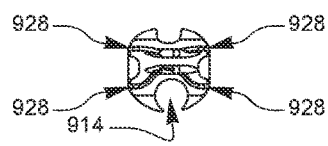
FIGS. 33A, 33B, 33C, 33D, 33E, and 33F are front, left side, right side, rear, top, and bottom elevational views, respectively of the distal tip of FIGS. 32A-32B.
Figure 33B:
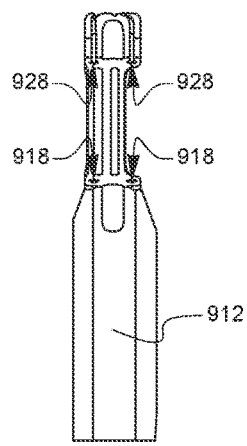
Figure 33A:
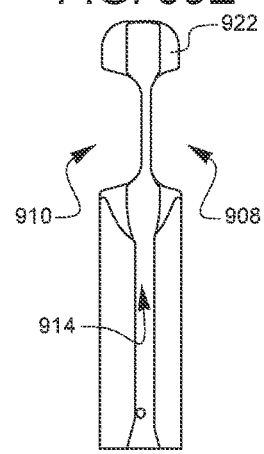
Figure 33C:
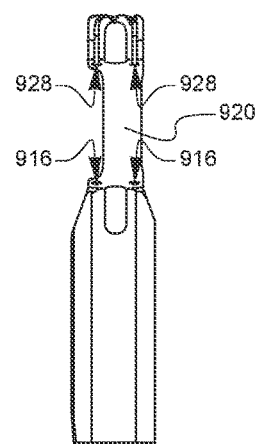
Figure 33D:
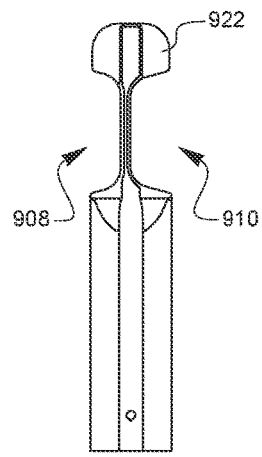
Figure 33F:
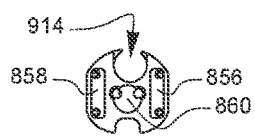
Figure 34A:
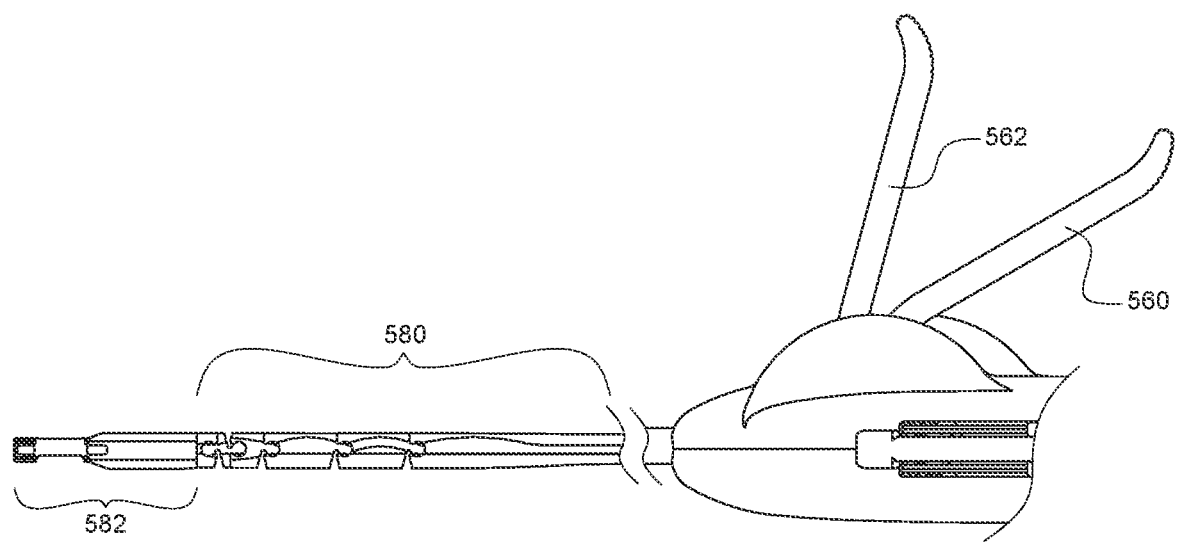
FIGS. 34A-34D are a series of partial top views of the surgical suturing device of FIG. 29 illustrating the operational principles of the distal tip articulation.

FIG. 32A and FIG. 32B are perspective views of the distal tip 582 of the surgical suturing device of FIG. 29. The distal tip 582 has a tip body 912 which defines an instrument channel 914 along one side of the tip body 912. This instrument channel 914 is configured to releasably hold various instrumentation used in a minimally invasive surgical procedure for treatment of tricuspid regurgitation. The instrument channel in the distal tip 582 is also in communication with the instrument channel 914 that is formed by the various segments or vertebrae of the flexible shaft portion. This channel continues back to the proximal end of the surgical suturing instrument 544. An example of an instrument used in this instance is an intracardiac echocardiography (ICE) probe which is useful in aiding visualization of various surgical procedure steps in the treatment of tricuspid regurgitation. Other instrumentation may also be configured for use within the instrument channel 914 for visualization, tissue grasping, or other uses within a minimally invasive surgical procedure. A flexible grasper may be useful in bringing tissue in closer proximity to either of the upper tissue bite area 908 or the lower tissue bite area 910 of the distal tip 582. The tip body 912 further defines two upper needle channels 916 and two lower needle channels 918 configured to guide the two pair of flexible needles across an upper tissue bite area 908 and a lower tissue bite area 910, respectively, to engage and pick up their corresponding ferrules and therefore the attached suture ends in the surgical suturing device 544. Towards the distal end 582D of the distal tip 582 is a tip support 920 or strut that defines an upper tissue bite area 908 and a lower tissue bite area 910. At the distal end 582D near the tip support 920, there is a tip head 922 that defines two suture passages, four suture guides 924, and four ferrule holders 928 for organizing and holding suture and ferrules in the distal tip 582 and along the shaft. The suture passages are in communication with and tunnel through from the distal tip head 922 to the tip support, further through the distal tip body 912 and through the shaft and back to the handle in the surgical suturing instrument 544. The suture may alternately follow an internal path through various channels within the distal tip 582 or be closely held in contact with the via suture holding features or guides along the distal tip 582. This distal tip 582 may have differing numbers of suture passages, suture guides, and ferrule holders depending on the requirements of a minimally invasive surgical procedure in which the instrument may be employed. FIGS. 33A, 33B, 33C, 33D, 33E, and 33F are front, left side, right side, rear, top, and bottom elevational views, respectively, of the distal tip shown in FIGS. 34A and 34B. The arrangement and pathways of the various sutures are arranged through the distal tip 582 suture passages and held within the suture guides in the tip head 922, traveling back through the entire distal tip 582 and through the shaft. This arrangement is similar to that described in regard to FIGS. 3A-3E.

Figure 34B:
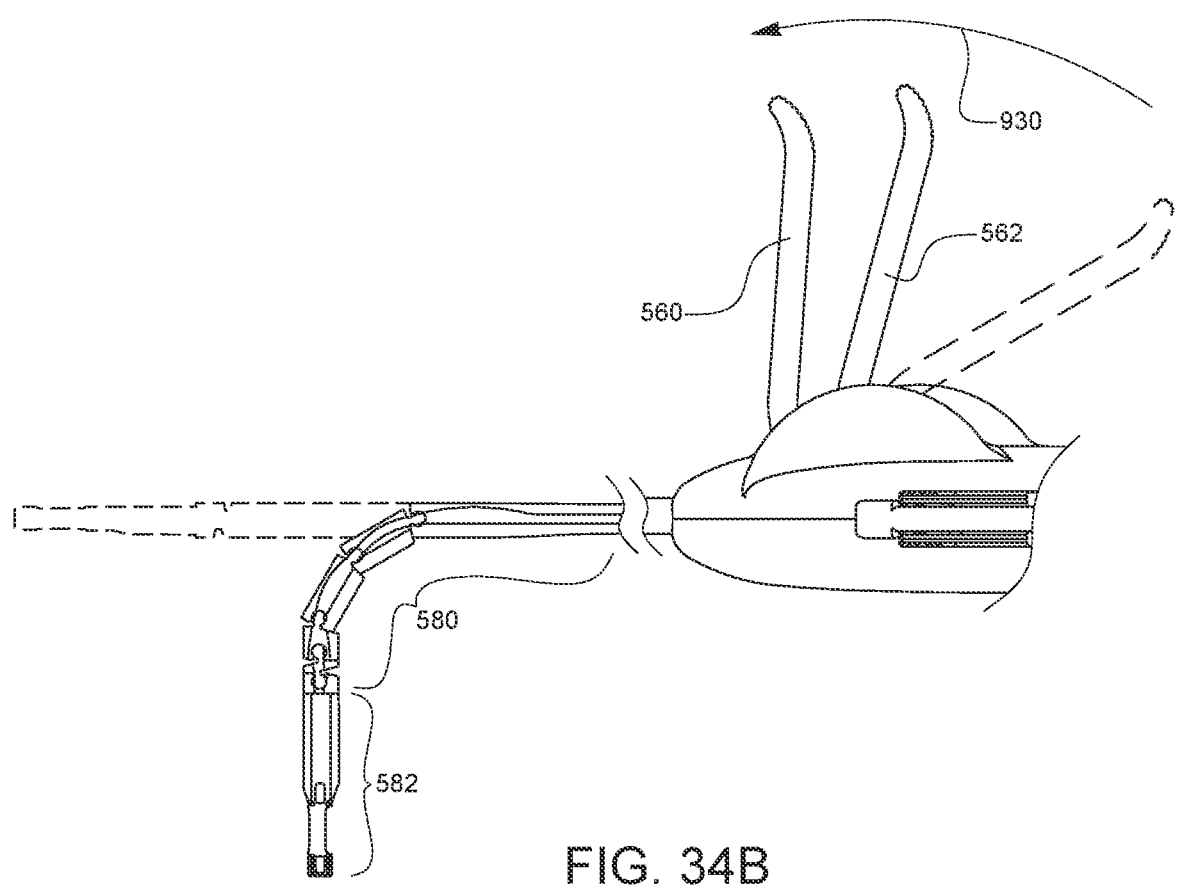
Figure 34C:
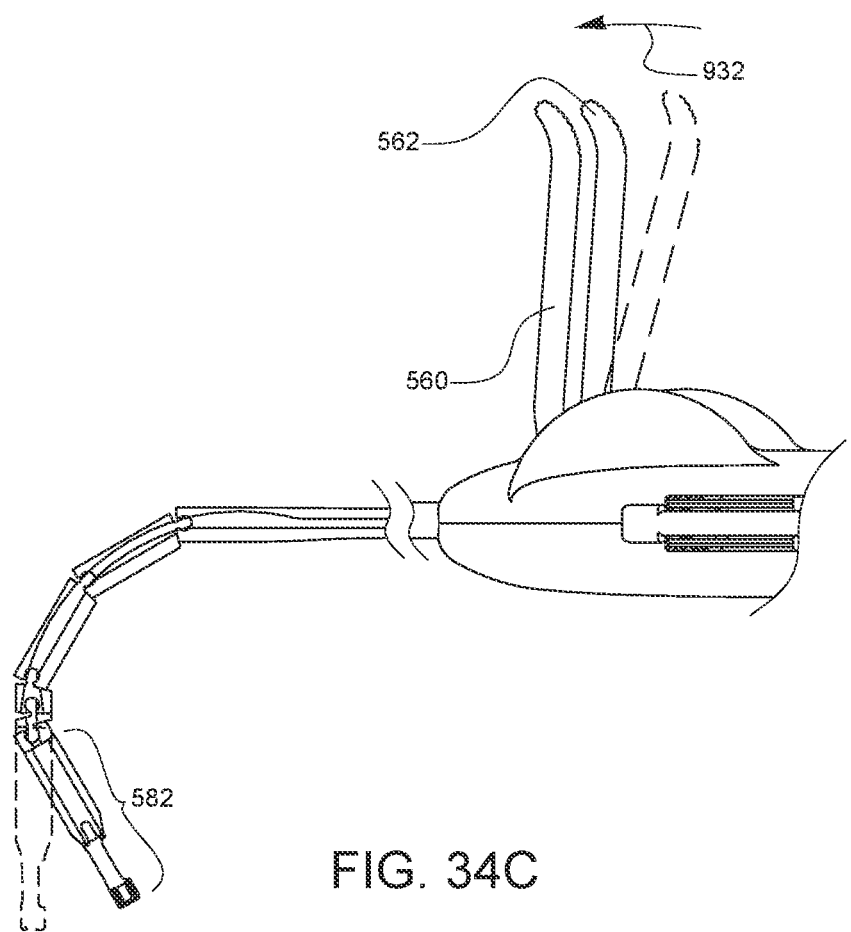
Figure 34D:
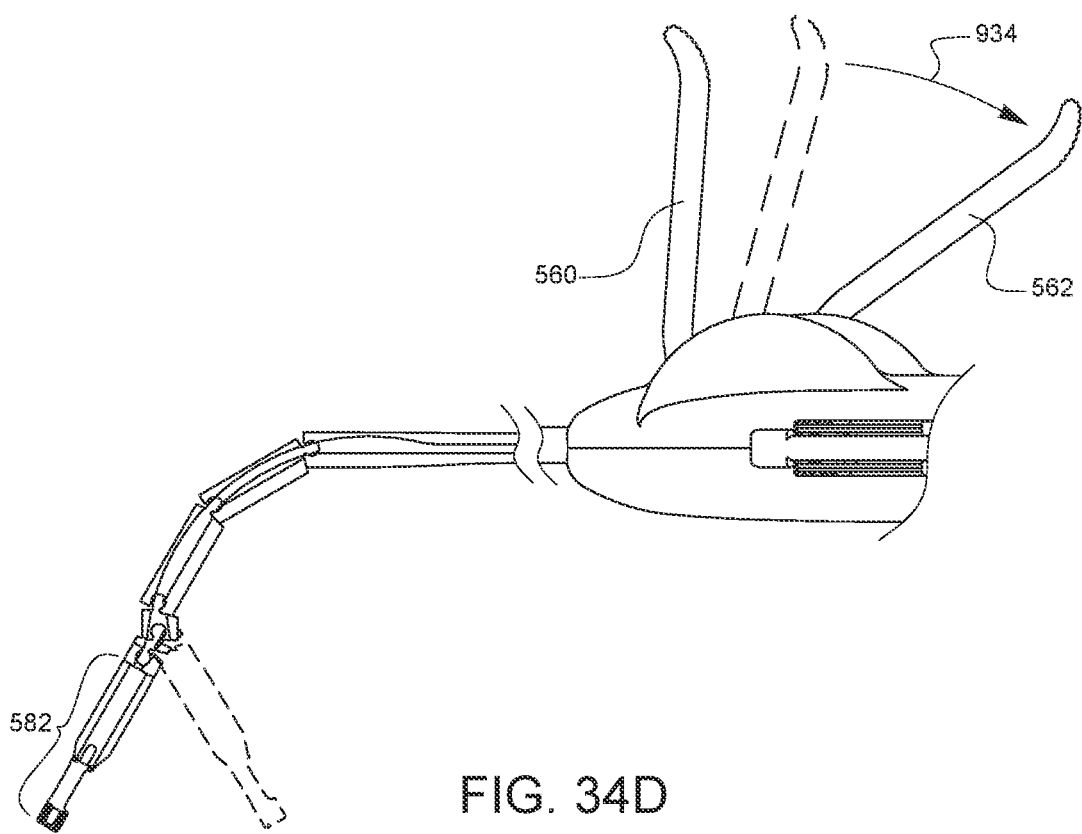
Figure 37A:
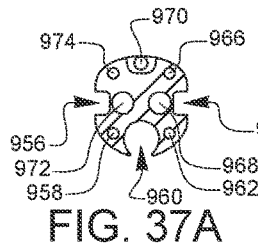
FIGS. 37A-37F are cross-sectional views of flexible shaft vertebra segments of FIG. 36.

FIGS. 34A-D are a series of top-views of the surgical suturing device of FIG. 29, illustrating the articulation of the flexible shaft and distal tip of the surgical suturing device. FIG. 37A is a top-view of the surgical suturing device 544 of FIG. 29 illustrating the articulation of the flexible shaft 580. The top or first articulation lever 560 is moved forward toward the distal end of the surgical suturing device 544. FIG. 34B is a top-view partial cross-sectional view of the surgical suturing device 544 of FIG. 29 demonstrating the state of the flexible shaft 580 portion when the first articulation lever 560 is fully articulated forward. A first articulation pulley system is rotated counter-clockwise, which in turn pulls a first left steering cable proximally. This movement articulates the flexible shaft 580 portion into an approximate ninety-degree angle to the left while leaving the distal tip 582 straight relative to the flexible shaft 580 portion. FIGS. 34C and 34D are top-view partial cross-sectional views of the surgical suturing device 544 of FIG. 29 demonstrating the state of the distal tip 582 portion when the lever is fully articulated forward and fully articulated backward, respectively. In FIG. 34C, the second articulation lever 562 is fully pushed forward, thereby placing a second articulation pulley system in a more counterclockwise position, pulling a second left steering cable proximally. The cables are not shown here, but have been described previously. This articulates the distal tip 582 into an approximate thirty-degree angle in the left direction relative to the flexible shaft 580. In FIG. 34D, the second articulation lever 562 is fully pushed backward, thereby placing the second articulation pulley system in a more clockwise position, pulling a second right steering cable proximally. This articulates the distal tip 582 into an approximate 30-degree angle in the right direction relative to the flexible shaft 580. These articulating controls, in addition to a simple rotation of the handle of the surgical suturing device 544, can be used in combination to allow for several degrees of freedom of movement for the purpose of placing stitches in desired positions within the annulus of the tricuspid valve, or in other surgical procedures as required. While these are the extreme positions of the flexible shaft 580 and distal tip 582 for this embodiment, other embodiments may travel further in their respective directions of in differing ranges of motion. Further, articulation in different directions or planes relative to a plane defined by the location of the rigid shaft may also be realized in alternate embodiments of the described surgical suturing device 544. While cable steering is used in this embodiment, other methods and materials for steering or articulation may be used, including the use of rigid rods, stranded or braided cable, strings, fiber or other thin flexible components.

Figures 35A, 35B:
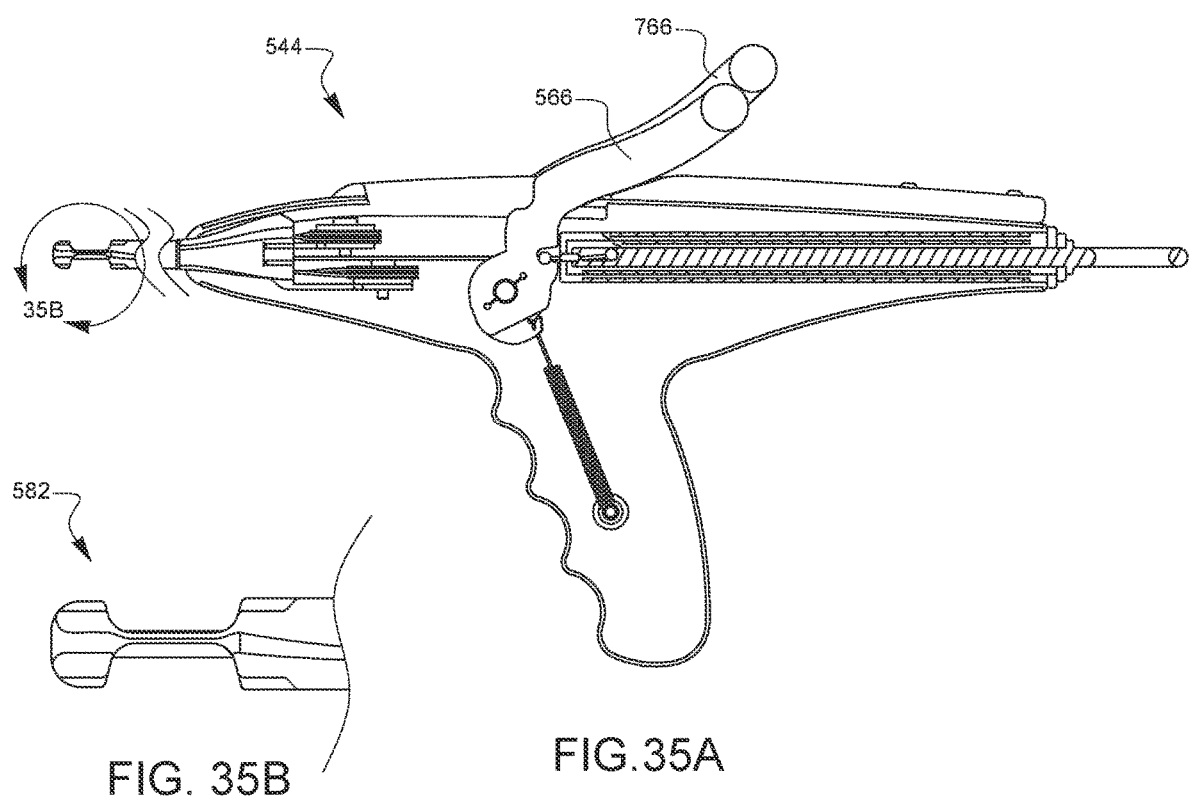

FIGS. 35A-35G are side partial cross-sectional views of the surgical suturing device of FIG. 29 illustrating the operation principles of the needle drivers and retracting telescope. FIG. 35A illustrates the state of the handle and needle drive levers prior to any needle driving operations. Both the first needle driver lever 566 and the second needle driver lever 766 are in a proximal position relative to the surgical suturing device 544. FIG. 35B is an enlarged view of the distal tip 582.

FIG. 35C is a side-view partial cross-sectional view illustrating the left or first needle driver lever 566 moved forward in a distal direction. This motion of the lever pivots the lever 566 around the lever pivot 802 and brings the barrel catch 796 towards a distal direction, which also brings the distal needle barrel 784 forward in a more distal direction. As the distal needle barrel 784 is attached to the lower flexible needle pair 792, this drives the lower needles forward into the lower tissue bite area 910 of the distal tip 582 of the surgical suturing instrument 544 and across to the ferrule holders, where the flexible needle tips of the lower needles engage the lower ferrules. During a minimally invasive surgical procedure such as tricuspid annular plication as described herein, the needles will first pierce the tissue of the annulus. In this position of the first needle driver lever 566, the first spring 884 is in a stretched configuration. This stretched configuration may assist in returning the first needle driver lever 566 to its starting position, which is shown in FIG. 35A. FIG. 35D is an enlarged side-view of the distal tip 582 area of the surgical suturing device 544 of FIG. 35C. In this enlarged side-view, the lower needle pair 792 is shown advanced distally through the lower tissue bite area 910, where it engages the lower pair of ferrules held in the ferrule holders of the tip head of the distal tip 582. Once the needle tips are engaged with the ferrules, they will pull the suture attached to the ferrules back through the tissue. The ferrules and ferrule holders are not indicated or visible in this view, but the function and use of ferrules and ferrule holders described elsewhere herein and is well-known in the art.

Figures 35E, 35F:
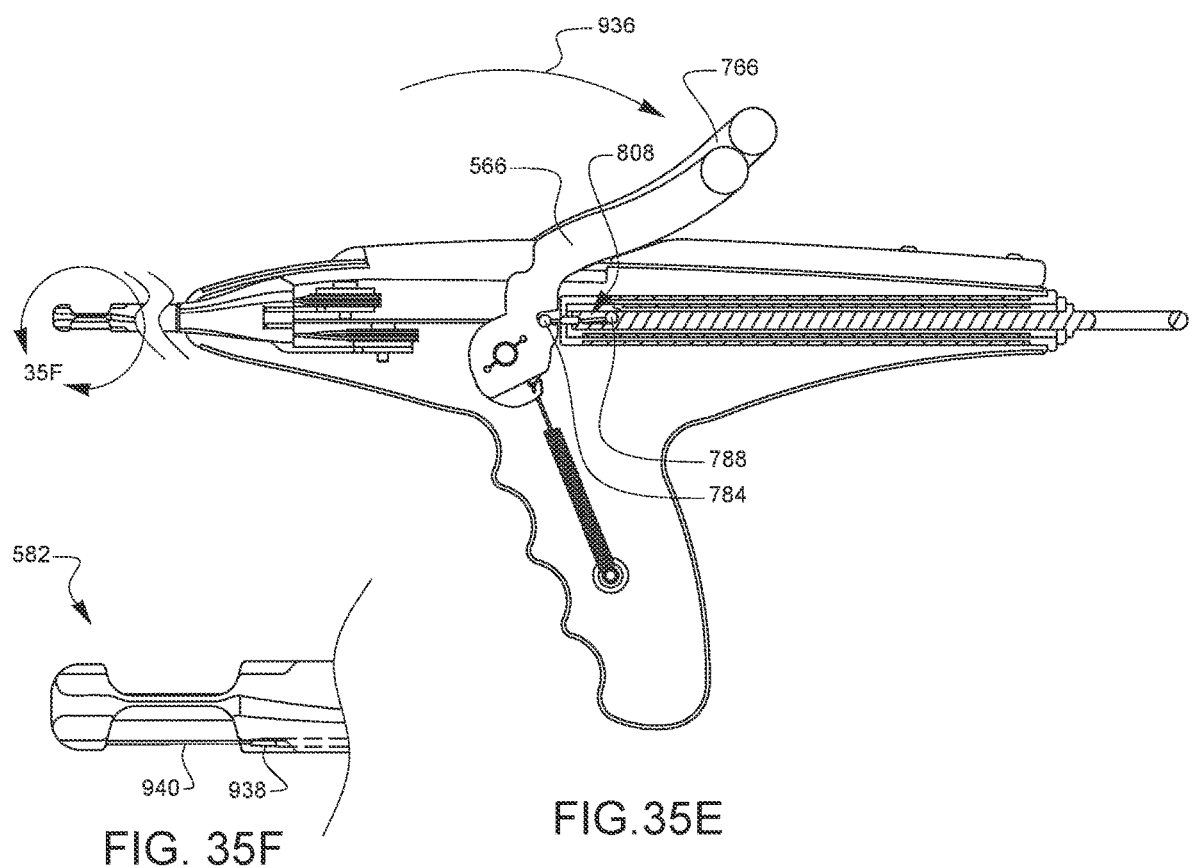

FIG. 35E is a side-view partial cross-sectional view illustrating the left or first needle driver lever 566 moved back to its initial position. This return stroke motion of the lever pivots 802 the lever around the lever pivot 802 and brings the barrel catch 796 back towards a proximal direction, which also brings the distal needle barrel 784 back in a more proximal direction. As the distal barrel 784 is attached to the lower flexible needle pair 792, this pulls the lower needles back into the tip body of the distal tip 582 of the surgical suturing instrument 544, bringing the engaged ferrules and attached suture back through the lower tissue bite area of the distal tip 582, and thus through the targeted tissue. While this position depicted in FIG. 35E is similar to the position of the surgical suturing device 544 illustrated in FIG. 35A, the enlarged side-view of the distal tip 582 area shown in FIG. 35F illustrates the position of the lower needles which would have engaged ferrules 938 now retracted and attached suture 940 now spanning the lower tissue bite area. In a surgical situation, these lower sutures 940 would be stitched through the tissue positioned within the lower tissue bite area of the distal tip 582 before the needles were deployed. Once the sutures are pulled back through the tissue bite area, the different position of the first needle bite sutures, or the left blue inner suture loop and the right white inner suture loop can also be viewed in the suture viewing window described in regard to FIG. 31A-31C. Once the flexible needle pairs 792 are in the retracted or proximal position, the proximal barrel 788 is handed off to the barrel recess 808, which is defined by the inner telescope portion 804. The arc traveled by the rounded portion of each needle drive levers or needle actuators allows the distal barrel 784 on each needle pair to freely move in a proximal direction. This actuation movement also moves the proximal barrel 788 attached to the needle pair 792 into the recess 808 of the inner telescope segment 804, and likewise moves each needle pair 792 into the needle slots in the inner telescope segment 804. At this point, the inner telescope portion 804 is moved back slightly by grasping the telescope handle and pulling in a proximal direction, which pulls out a small amount of suture through the shaft and around the head of the distal tip 582. This provides an amount of slack in the suture line, insuring the flexible shaft and distal tip can be articulated to the next location for placement of the upper tissue bite area where the second needle bite with the upper needles can take place. While not shown in this view, all described function and movement also happens with the right needle as well, even though only the left needle is shown in this series of side-view partial cross-sectional views. Once the return stroke depicted in FIG. 35E is completed, the handle, the flexible shaft, and the distal tip 582 are manipulated by the surgeon or operator to position the upper tissue bite area of the distal tip 582 of the surgical suturing device 544 to the desired location for the second needle bite, referring to the surgical procedure described in regard to FIGS. 4A-4R and 5.

Figure 35G:
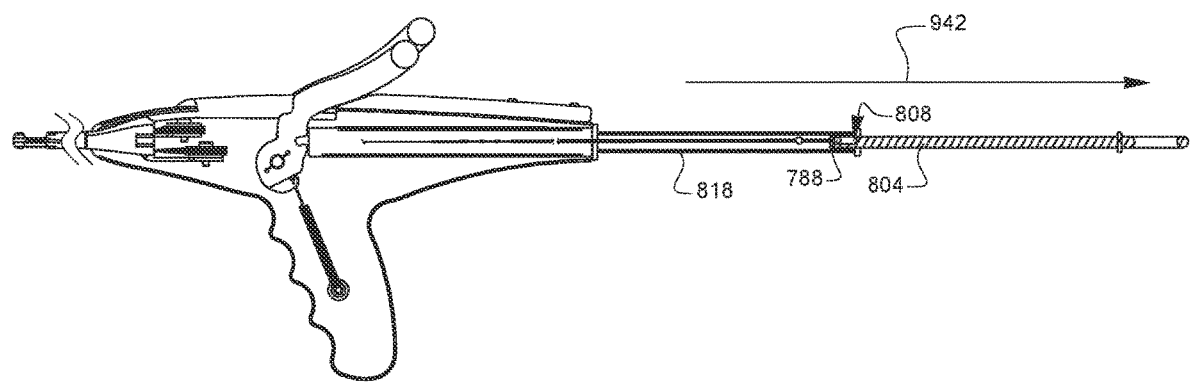

FIG. 35G is a side partial cross-sectional view of the surgical suturing device 544 of FIG. 29. Once both needle bites have been taken, placing both sutures in both locations of the tricuspid annulus during the procedure described herein, the proximal barrels 788 of both sets of flexible needles are held within the inner telescope portion 804 of the retracting telescope of the surgical suturing device 544. Once the desired sutures are made and all preliminary visual or conduction testing is complete and meets the satisfaction of the surgeon, the sutures 940 can be payed out from the patient. By grasping the telescope handle and pulling in a proximal direction while maintaining the position of the handle of the surgical suturing device 544, the proximal barrels 788 now handed off to the barrel recess 808 within the inner telescope segment 804 and therefore the flexible needles with the ferrules 938 and the respective sutures 940 attached at the needle tips by the ferrules 938 attached to the suture ends, can be pulled from the surgical site by pulling proximally 942 and retracting the telescope through each nested segment—the inner telescope segment 804, then the middle telescope segment 818, and finally the inner telescope segment 804. Once the suture 940 is pulled away from the surgical site and out of the patient, the handle can also be pulled in a proximal direction 942 and towards the extended, retracted telescope, thus removing the surgical suturing device from the patient completely, leaving the pledgeted sutures extending from the surgical site. It should be noted that throughout the operative steps described in the preceding figures needles and sutures 940 are held within plastic tubes or suture tubes to facilitate motion around bends and to reduce frictional forces. Alternate embodiments may be assembled without plastic tubes enclosing the flexible needles or sutures or may use other methods such as lubricants or alternate internal channel feature design to facilitate motion of the cables, needles and sutures along the pathway from the proximal end of the instrument towards the distal end of the surgical suturing instrument or vice versa.

Figure 36:
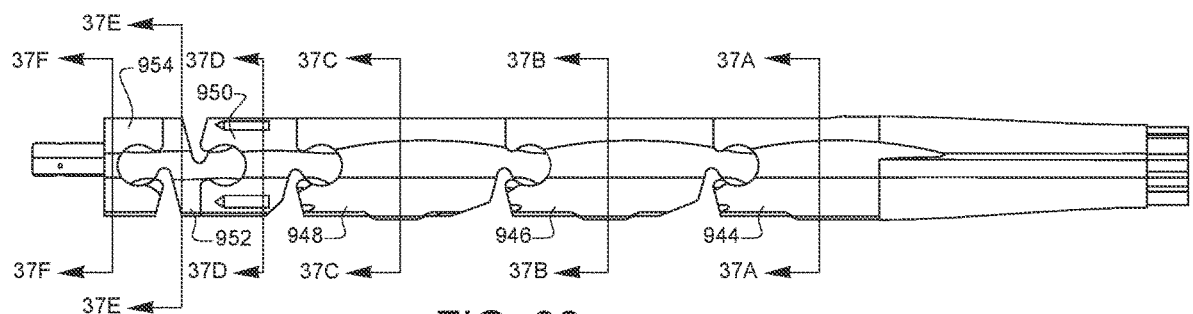
FIG. 36 is a top view of the flexible shaft portion of the surgical suturing device of FIG. 29.

FIG. 36 is a top view of the flexible shaft portion of the surgical suturing device of FIG. 29, detailing a number of unique vertebrae segments or links, the cross-sections of which are shown in greater detail in FIGS. 37A-F. These vertebrae segments, when connected, comprise the flexible shaft of the surgical suturing device of the present disclosure. Illustrated in FIG. 36 is a first vertebrae indicated by cross-sectional marker 37A, several vertebrae segments indicated by cross-sectional markers 37B, 37C, and 37D, a first middle link indicated by cross-sectional marker 37E, and a second middle link indicated by cross-sectional marker 37F. The first vertebrae, indicated by cross-sectional marker 37A, includes a linking end to fixedly attach the flexible shaft to the rigid shaft of the surgical suturing device. The cross-sectional features of these vertebrae are further discussed in regard to FIGS. 37A, 37B, 37C, 37D, 37E, and 37F. The cross-sectional features shown in this embodiment of the surgical suturing device are one arrangement, and it should be noted that other arrangements or configurations may be useful or effective in maintaining and articulating the various control and steering cables, sutures, guide wire, and needle pairs or sets along the internal path of a flexible shaft may be known to those skilled in the art.

FIG. 37A is a cross section of the vertebra segment of FIG. 36. The inner structure of the first vertebra 944 possesses several features related to pathway management throughout the length of the flexible shaft. The vertebra segment 944 defines an upper needle channel 964 and a lower needle channel 956 which are configured to guide the first needle pair along the flexible shaft. The vertebra segment 944 also defines a first suture pair passage 968 and a second suture pair passage 972, as well as channels for the upper (flexible shaft) steering cables 962, 966 and for the lower (distal tip) steering cables 958, 974. The vertebra segment or link of FIG. 37A also defines an instrument channel 960 and a guide wire channel 970. It should be noted that the internal path of the guidewire terminates at the link or vertebra segment of FIG. 37A, allowing the flexible shaft portion and distal tip to articulate while maintaining an instrument reference position within the IVC by the guidewire.

Figure 37B:
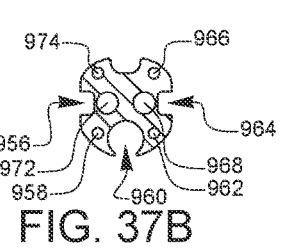
Figure 37C:
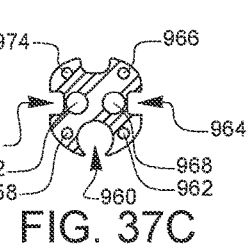

FIGS. 37B and 37C represent an identical link or vertebra segment, though they are located adjacent to one another. FIG. 37B is a cross section of the vertebra segment 946 indicated in FIG. 36. The inner structure of this vertebra possesses several features related to cable pathway management throughout the length of the flexible shaft. The inner structure is similar to the inner structure of the vertebra 944 illustrated in FIG. 37A, however, the vertebra segment 946 of FIG. 37B does not have a guidewire channel as in the vertebra segment of FIG. 37A. The vertebra segment 946 of FIG. 37B is identical to that of the vertebra segment 948 of FIG. 37C. The inner structure of the vertebra segments of FIGS. 37B and 37C have instrument channels 960, as well as channels for the upper needle pair 964, lower needle pair 956, the upper suture passage 968, lower suture passage 972, the upper steering cables 962, 966 for the flexible shaft, and the lower steering cables 958, 974 for the distal tip.

Figure 37D:
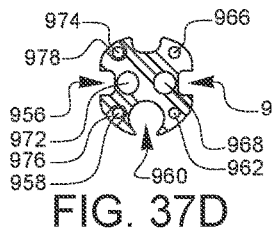

FIG. 37D is a cross section of the indicated vertebra segment of FIG. 36. The inner structure of this vertebra possesses several features related to cable pathway management throughout the length of the flexible shaft. The inner structure is similar to the vertebrae illustrated in FIGS. 37A-37C, but the vertebra segment 950 illustrated in FIG. 37D has two recesses 976, 978 that terminate and are configured to hold the lower flexible shaft steering cable couplers. The inner structure of the vertebra segment of FIG. 37D also defines channels for the upper needle pair 964, lower needle pair 956, the upper suture passage 968, lower suture passage 972, the upper steering cables 962, 966 and lower steering cables 958, 974 for the distal tip.

Figure 37E:
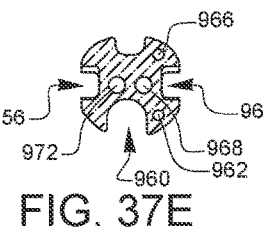

FIG. 37E is a cross-section of the indicated vertebra segment of FIG. 36. The inner structure of this vertebra 952 possesses several features related to cable pathway management throughout the length of the flexible shaft. The inner structure is similar to the vertebra segment 950 of FIG. 37D, but the vertebra segment 952 illustrated in FIG. 37E, contains no inner structure or features related to the flexible shaft steering cables, as they terminated in the vertebra link 950 described in regard to FIG. 37D. The inner structure of the vertebra segment 952 of FIG. 37E has an instrument channel 960, as well as channels for the upper needle pair 964, lower needle pair 956, the upper suture passage 968, lower suture passage 972, and the upper steering cables 962, 966 for the distal tip.

Figure 37F:
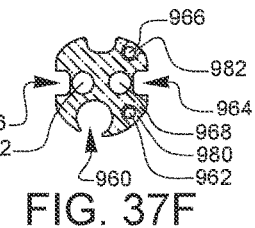

FIG. 37F is a cross-section of the vertebra link segment of FIG. 36. The inner structure is similar to the vertebra segment of 952 FIG. 37E, but the vertebra segment 954 illustrated in FIG. 37F has two recesses 980, 982 that terminate and are configured to hold the lower distal tip steering cable couplers. The inner structure of the vertebra segment 954 of FIG. 37F has an instrument channel 960, as well as channels for the upper needle pair 964, lower needle pair 956, the upper suture passage 968, the lower suture passage 972, and upper steering cables 962, 966.

Figure 38A:
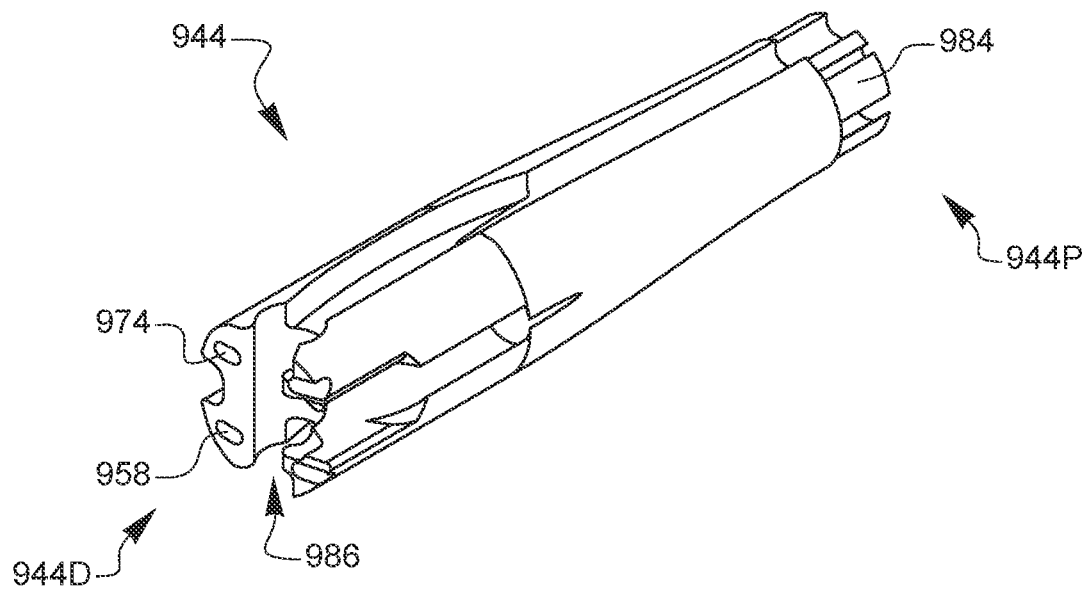
FIGS. 38A-38B are perspective views of the unique vertebra segment of FIG. 37A.
Figure 38B:
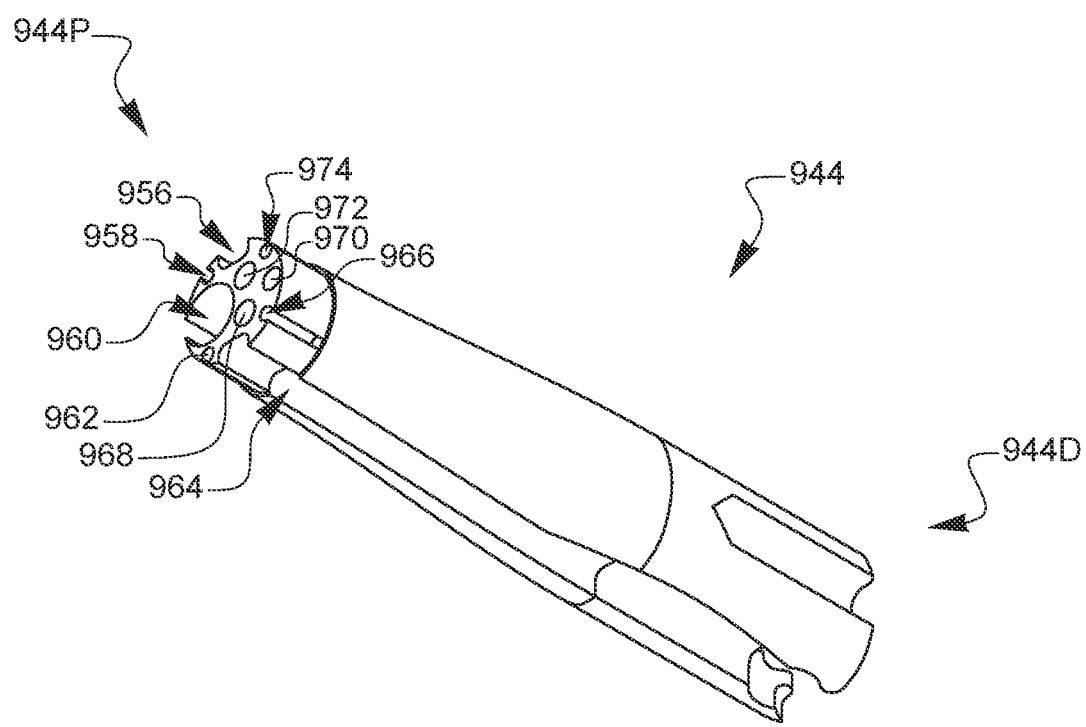

FIGS. 38A and 38B are perspective views of the unique vertebra segment of FIG. 37A. The features regarding the internal structure of this vertebra segment 944 have been described in detail with regard to FIG. 37A. The vertebra segment illustrated in FIGS. 38A and 38B further defines a vertebra recess 986 configured to link similar or distinct vertebra segments as described herein, depending the desired length of chain or inner channel configuration of a particular embodiment. The vertebra segment 944 also defines a recessed portion 984 about its circumference on the proximal end 944P such that the vertebra segment end can be inserted into the hollow end of the rigid shaft component during assembly of this embodiment. FIGS. 39A-39F are front, left side, right side, rear, top, and bottom elevational views, respectively of the unique vertebra segment of FIGS. 38A-38B.

Figure 40A:
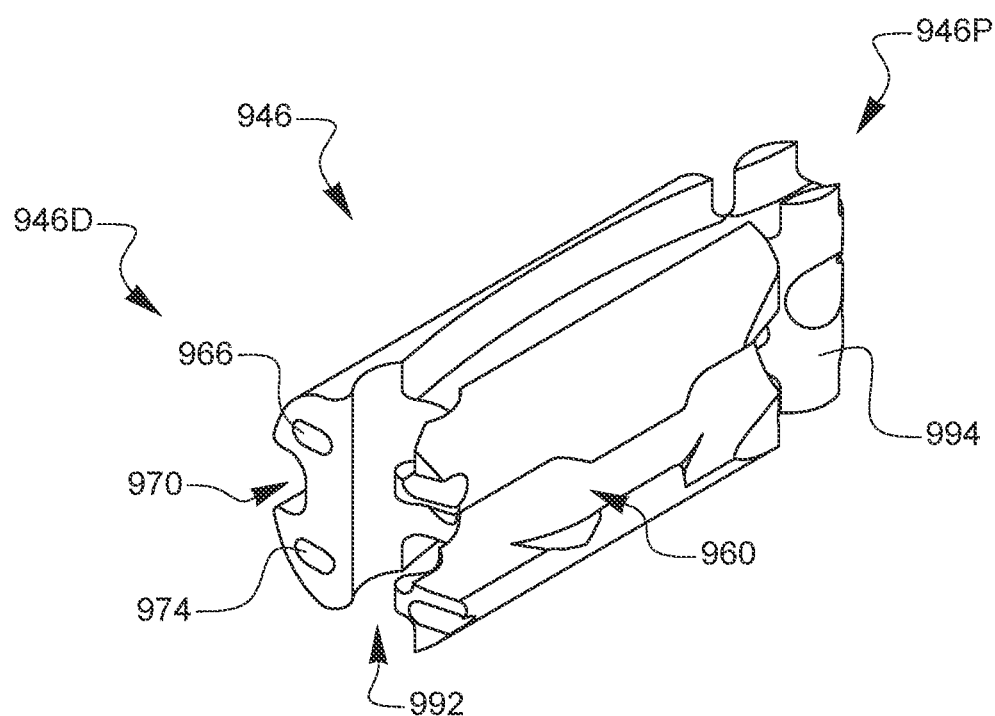
FIGS. 40A-40B are perspective views of the unique vertebra segment of FIG. 37B.
Figure 40B:
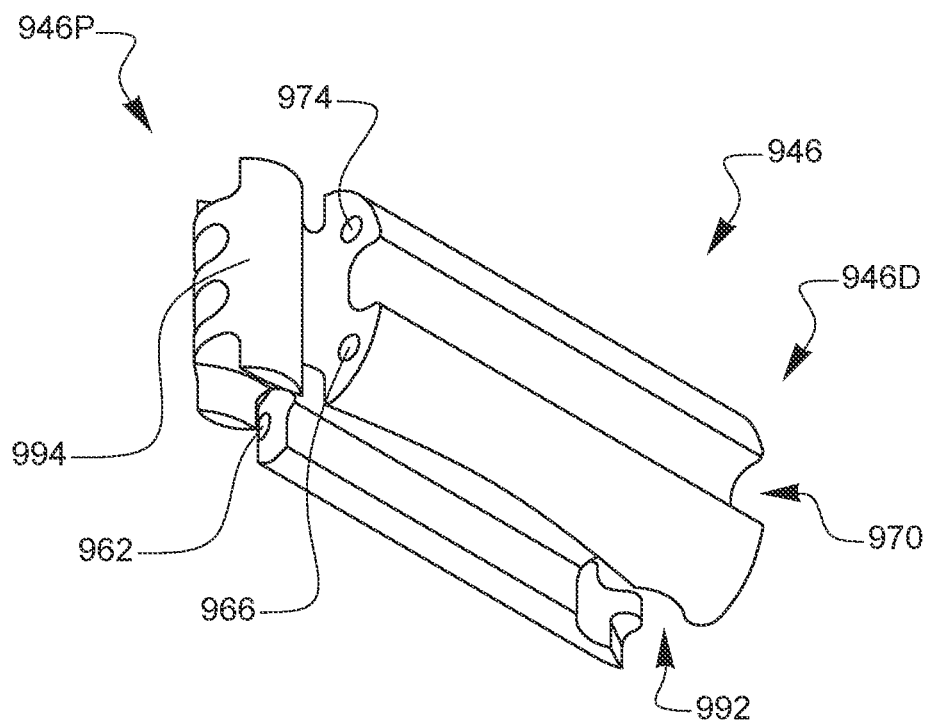
Figure 41E:
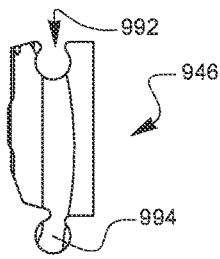
FIGS. 41A, 41B, 41C, 41D, 41E, and 41F are front, left side, right side, rear, top, and bottom elevational views, respectively of the unique vertebra segment of FIGS. 40A-40B.
Figure 41B:
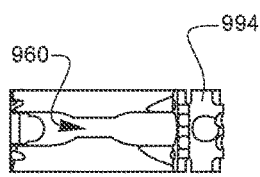
Figure 41A:
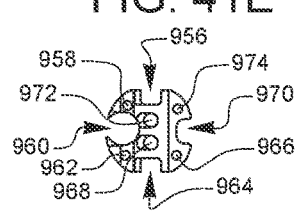
Figure 41C:
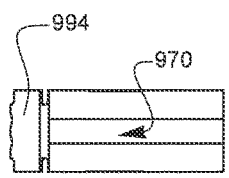
Figure 41D:
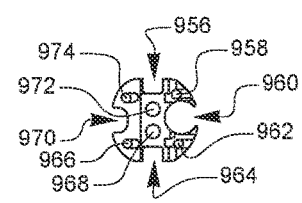
Figure 41F:
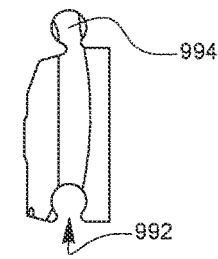

FIGS. 40A and 40B are perspective views of the unique vertebra segment of FIG. 37B. The features regarding the internal structure of this vertebra segment 946 have been described in detail with regard to FIG. 37B. The vertebra segment 946 also defines a link 994 on the proximal end 946P and a recess 992 on the distal end 946D that are configured to interlock with a corresponding recess or link of a subsequent vertebra segment in the flexible shaft. FIGS. 41A-41F are front, left side, right side, rear, top, and bottom elevational views, respectively of the unique vertebra segment of FIGS. 40A-40B.

Figure 42A:
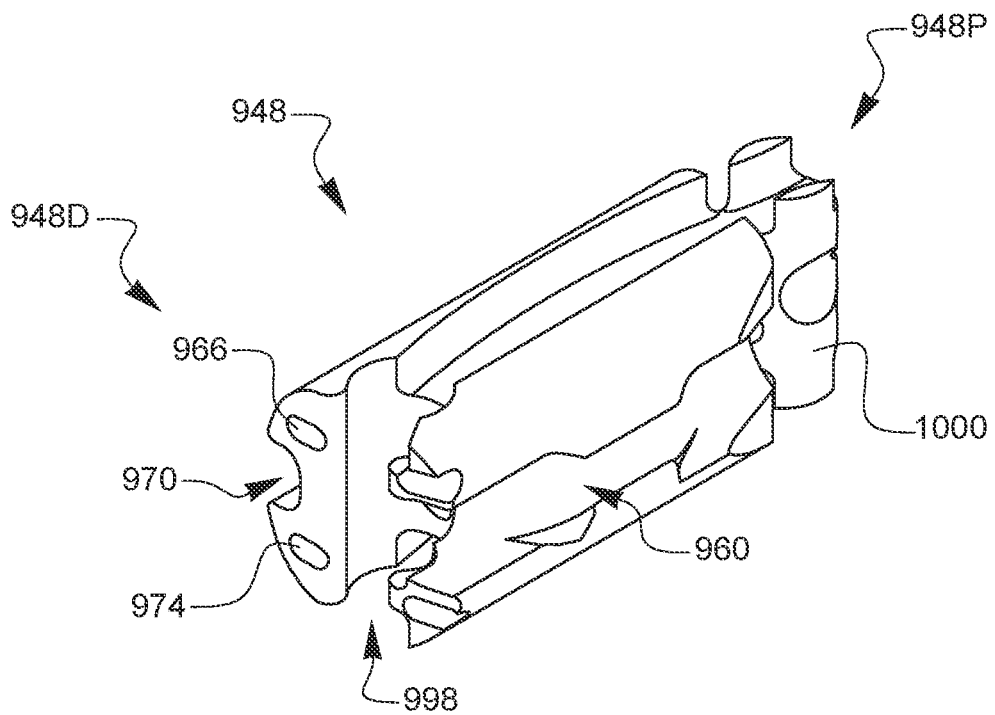
FIGS. 42A-42B are perspective views of the unique vertebra segment of FIG. 37C.
Figure 42B:
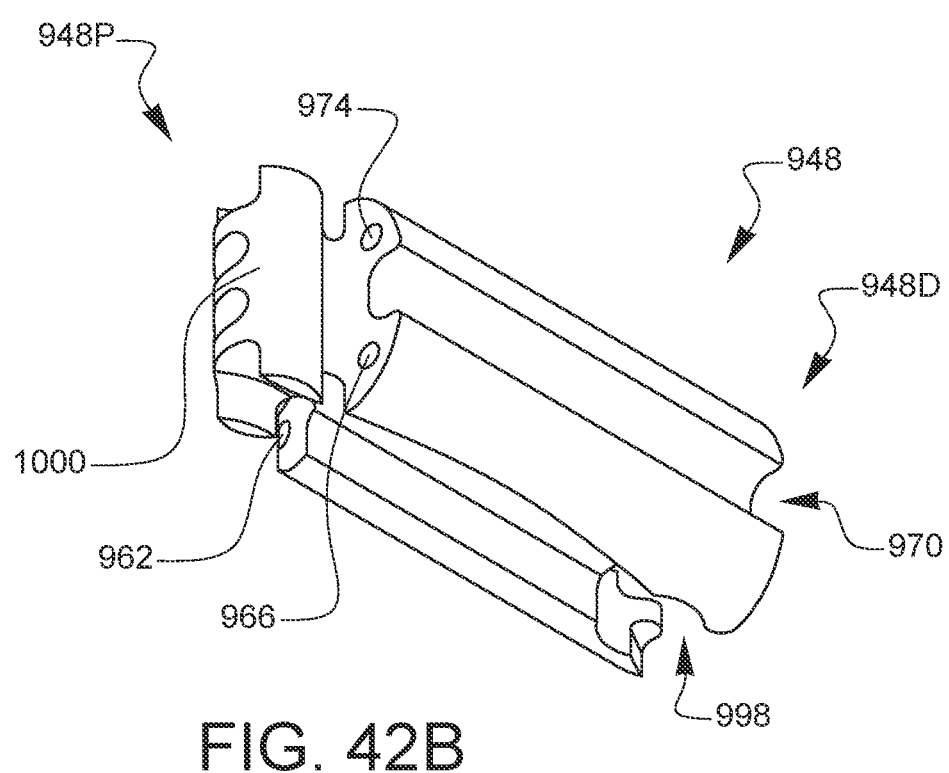
Figure 43E:
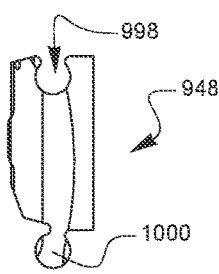
FIGS. 43A, 43B, 43C, 43D, 43E, and 43F are front, left side, right side, rear, top, and bottom elevational views, respectively of the unique vertebra segment of FIGS. 42A-42B.
Figure 43B:
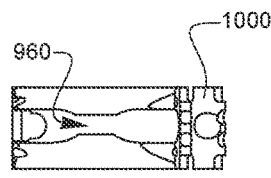
Figure 43A:
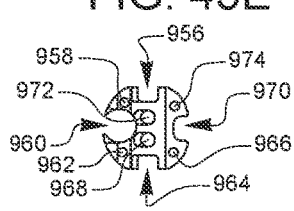
Figure 43C:
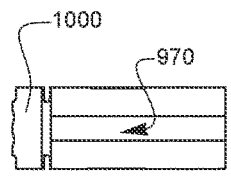
Figure 43D:
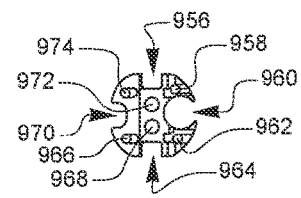
Figure 43F:
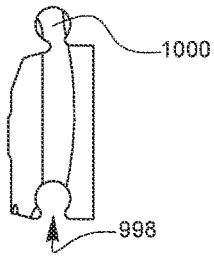

FIGS. 42A and 42B are perspective views of the unique vertebra segment of FIG. 37C. The features regarding the internal structure of this vertebra segment 948 have been described in detail with regard to FIG. 37C. The vertebra segment also defines a link 1000 on the proximal end 948P and a recess 998 on the distal end 948P that are configured to interlock with a corresponding recess or link of a subsequent vertebra segment in the flexible shaft. FIGS. 43A-43F are front, left side, right side, rear, top, and bottom elevational views, respectively of the unique vertebra segment of FIGS. 42A-42B.

Figure 44A:
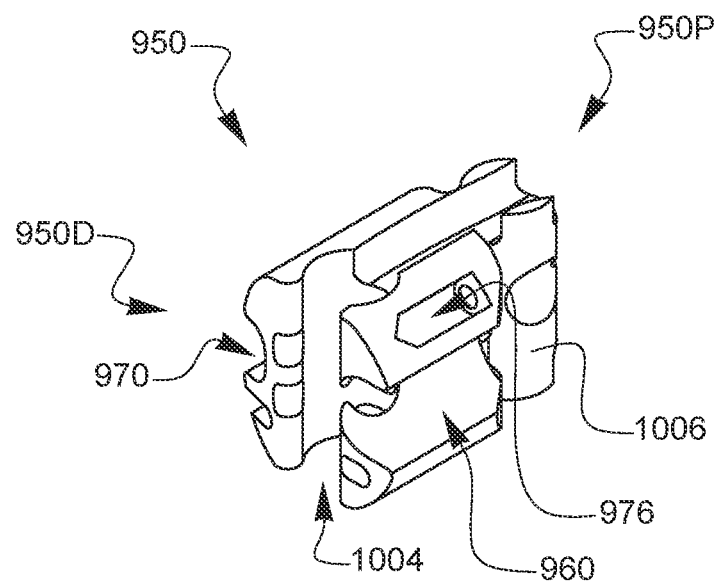
FIGS. 44A-44B are perspective views of the unique vertebra segment of FIG. 37D.
Figure 44B:
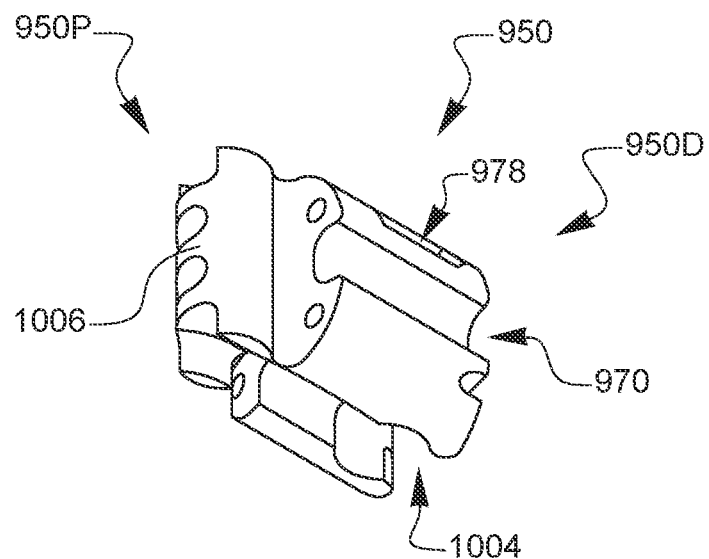
Figure 45E:
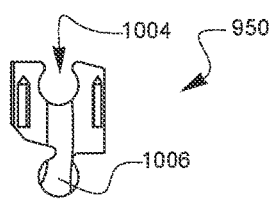
FIGS. 45A, 45B, 45C, 45D, 45E, and 45F are front, left side, right side, rear, top, and bottom elevational views, respectively of the unique vertebra segment of FIGS. 44A and 44B.
Figure 45B:
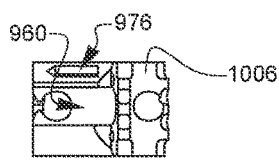
Figure 45A:
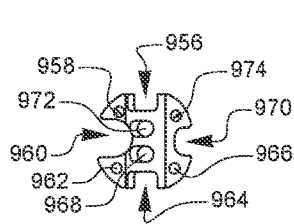
Figure 45C:
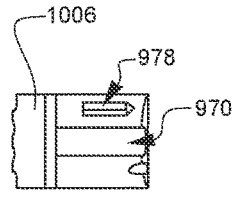
Figure 45D:
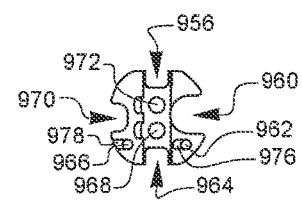
Figure 45F:
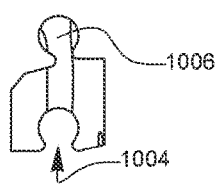

FIGS. 44A and 44B are perspective views of the unique vertebra segment of FIG. 37D. The features regarding the internal structure of this vertebra segment 950 have been described in detail with regard to FIG. 37D. The vertebra segment also defines a link 1000 on the proximal end 950P and a recess 1004 on the distal end 950D that are configured to interlock with a corresponding recess or link of a subsequent vertebra segment in the flexible shaft. A recess 976 for a lower flexible shaft steering coupler is also visible in this view. FIGS. 45A-45F are front, left side, right side, rear, top, and bottom elevational views, respectively of the unique vertebra segment of FIGS. 44A and 44B.

Figure 46A:
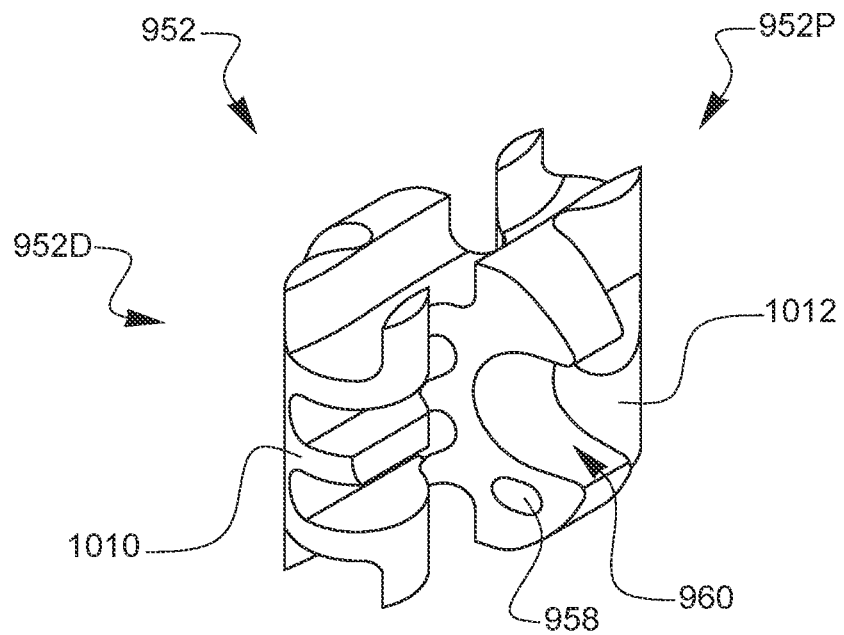
FIGS. 46A-46B are perspective views of the unique vertebra segment of FIG. 37E.
Figure 46B:
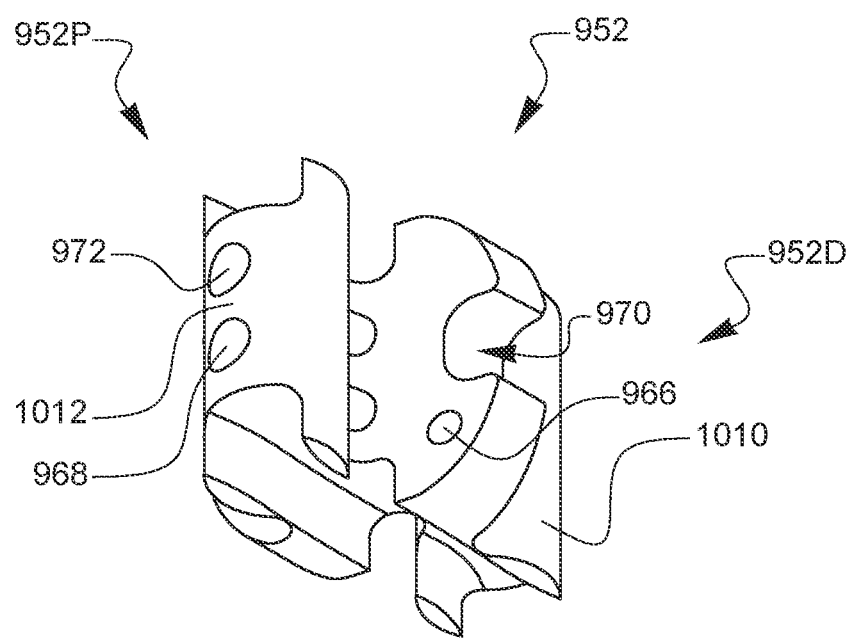
Figure 47E:
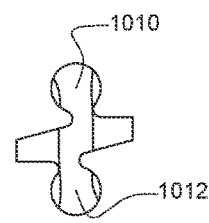
FIGS. 47A, 47B, 47C, 47D, 47E, and 47F are front, left side, right side, rear, top, and bottom elevational views, respectively of the unique vertebra segment of FIGS. 46A and 46B.
Figure 47B:
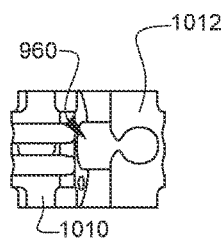
Figure 47A:
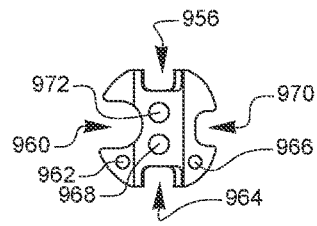
Figures 47C, 47D:
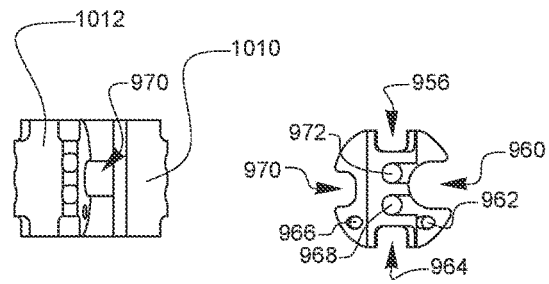
Figure 47F:
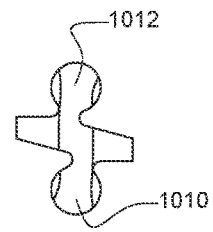

FIGS. 46A and 46B are perspective views of the unique vertebra segment of FIG. 37E. The features regarding the internal structure of this vertebra segment 952 have been described in detail with regard to FIG. 37E. The vertebra segment 952 defines a link 1012 on the proximal end 952P and a link 1010 on the distal end 952D that are configured to interlock with a corresponding recess of a previous or subsequent vertebra segment in the flexible shaft. FIGS. 47A-47F are front, left side, right side, rear, top, and bottom elevational views, respectively of the unique vertebra segment of FIGS. 46A and 46B.

Figure 48A:
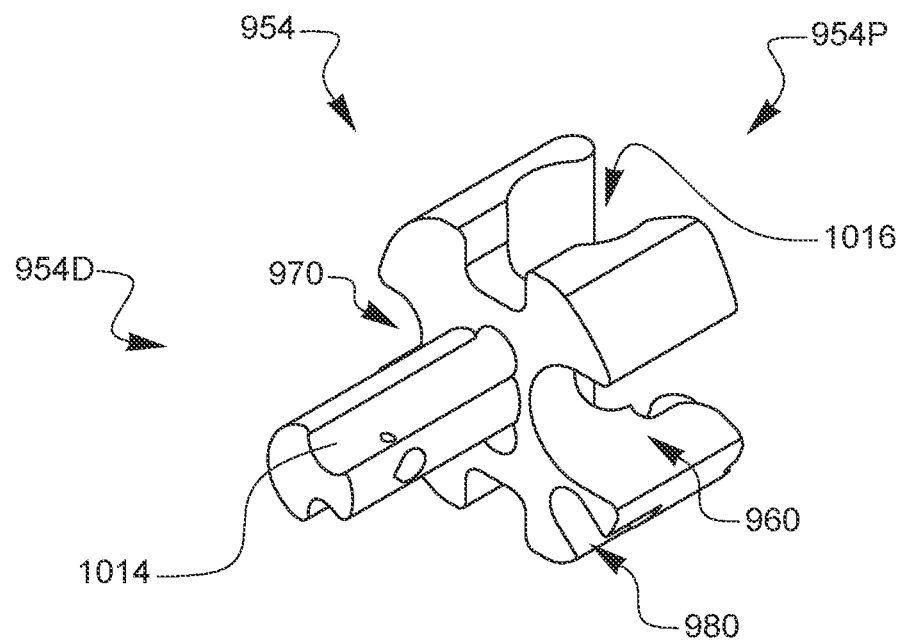
FIGS. 48A-48B are perspective views of the unique vertebra segment of FIG. 37F.
Figure 48B:
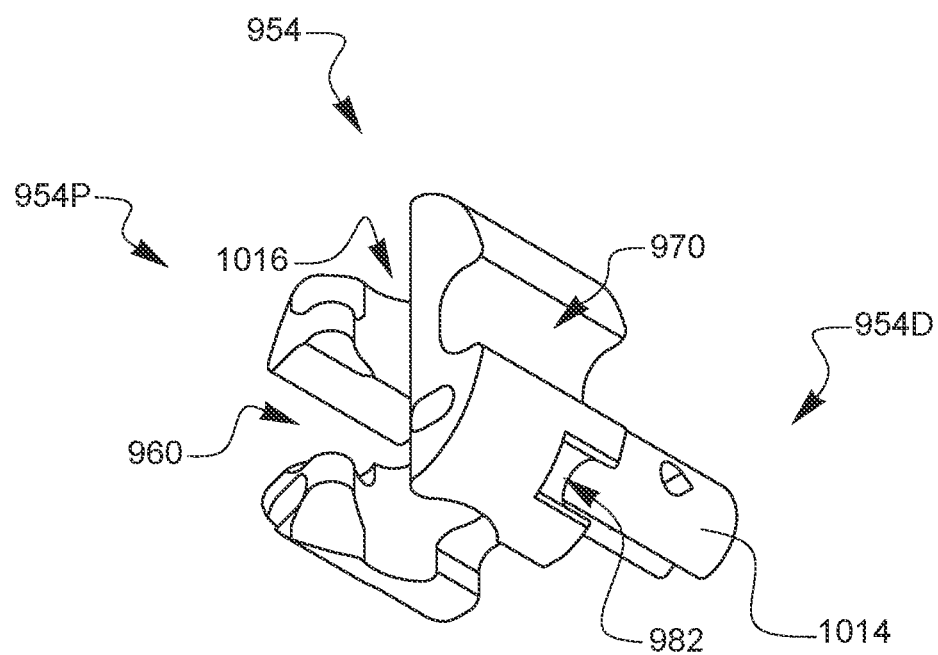
Figure 49E:
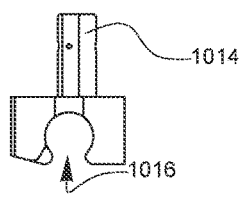
FIGS. 49A, 49B, 49C, 49D, 49E, and 49F are front, left side, right side, rear, top, and bottom elevational views, respectively of the unique vertebra segment of FIGS. 48A and 48B.
Figure 49B:
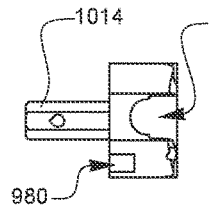
Figure 49A:
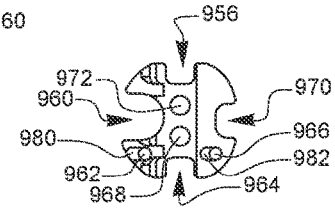
Figure 49C:
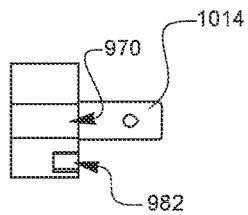
Figure 49D:
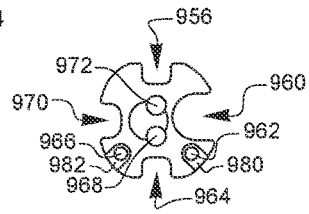
Figure 49F:
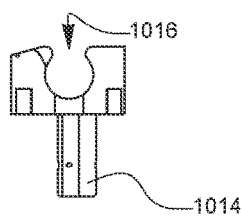

FIGS. 48A and 48B are perspective views of the unique vertebra segment of FIG. 37F. The features regarding the internal structure of this vertebra segment 954 have been described in detail with regard to FIG. 37F. The vertebra segment 954 defines a recess 1016 on the proximal end 954P and a post 1014 on the distal end 954D. The recess 1016 is configured to interlock with a corresponding link of a previous vertebra segment in the flexible shaft. The post 1014 is configured to be inserted into the central channel of the distal tip. FIGS. 49A-49F are front, left side, right side, rear, top, and bottom elevational views, respectively of the unique vertebra segment of FIGS. 48A and 48B.

Figure 50:
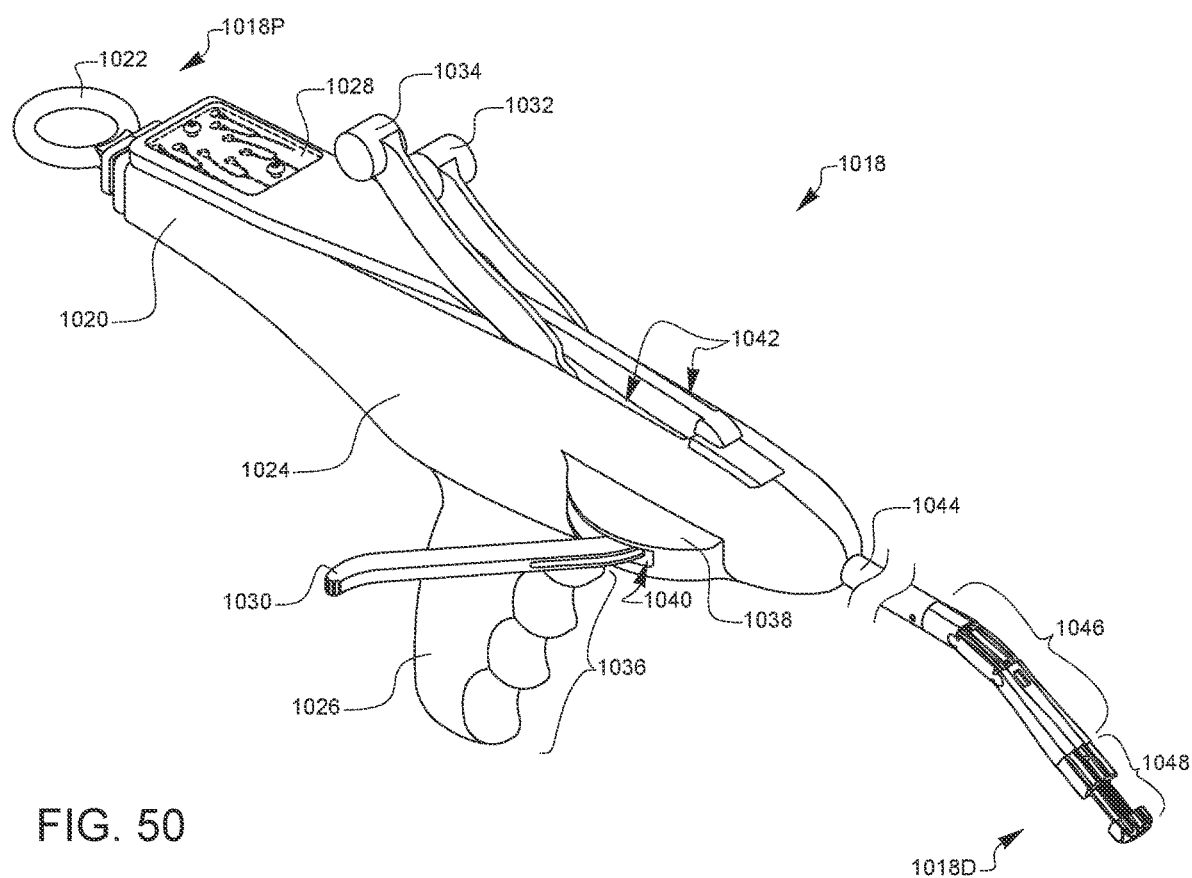
FIG. 50 is a top-right-front perspective view of another embodiment of a surgical suturing device.

FIG. 50 is a perspective view of another embodiment of a surgical suturing device as described herein. This embodiment of a surgical suturing device 1018 has a housing 1024 which defines a handle 1026, a lever stop 1038, a grip 1036, a telescope housing 1020, and a slot 1042 on the top surface of the housing 1024. The top of the lever stop 1038 may have internal gear stops (not shown in this view) to engage a corresponding tab on a distal tip articulation lever 1030. The housing 1024 further defines a slot 1040 within the lever stop that allows movement of the distal tip articulation lever 1030 towards a distal end 1018D or a proximal end 1018P of the surgical suturing device 1018. The distal tip articulation lever 1030 also is configured such that it can flex in a direction away from the gear stops and can be moved to a desired position and released, where the lever 1030 is biased such that a key on the articulation lever 1030 engages with the appropriate gear stop, preventing undesired movement of the articulation lever 1030. This described mechanism may also include positional keyways as described in regard to previous embodiments. The distal tip articulation lever 1030 adjusts the position of the flexible portion 1046 of the shaft and therefore the position of the distal tip 1048. This distal tip articulation lever 1030 may also be referred to as a distal tip steering actuator. The top of the housing 1024 further defines two slots 1042 that allows movement of a first needle driver 1032 or needle actuator and a second needle driver 1034 or needle actuator towards either the distal end 1018D or the proximal end 1018P of the surgical suturing device 1018. Towards the proximal end 1018P of the surgical suturing device 1018, a rigid shaft portion 1044 is attached to a mount held captive in the housing 1024. Further towards the proximal end 1018P of the surgical suturing device 1018, a flexible shaft portion 1046 is attached to the rigid shaft 1044, terminating in a distal tip 1048. The distal tip 1048 defines a first tissue gap and a second tissue gap, which in this embodiment are symmetrical and facing opposite directions. This distal tip 1048 embodiment is further described later. While discussed later with regard to the linkage exploded views, the needle passages in the middle link in the flexible shaft portion 1046 are not enclosed and configured such that the needle tubes can flex approximately 30 degrees. In this embodiment, the needles and the sutures are passed through plastic or suture tubes held within the suture passages and needle channels. Other embodiments may not utilize suture tubes, but may have alternate path or channel materials for the various cables, sutures, and needles to pass through the various elements of the instrument shaft, including the rigid shaft section and the flexible shaft section.

Figure 51A:
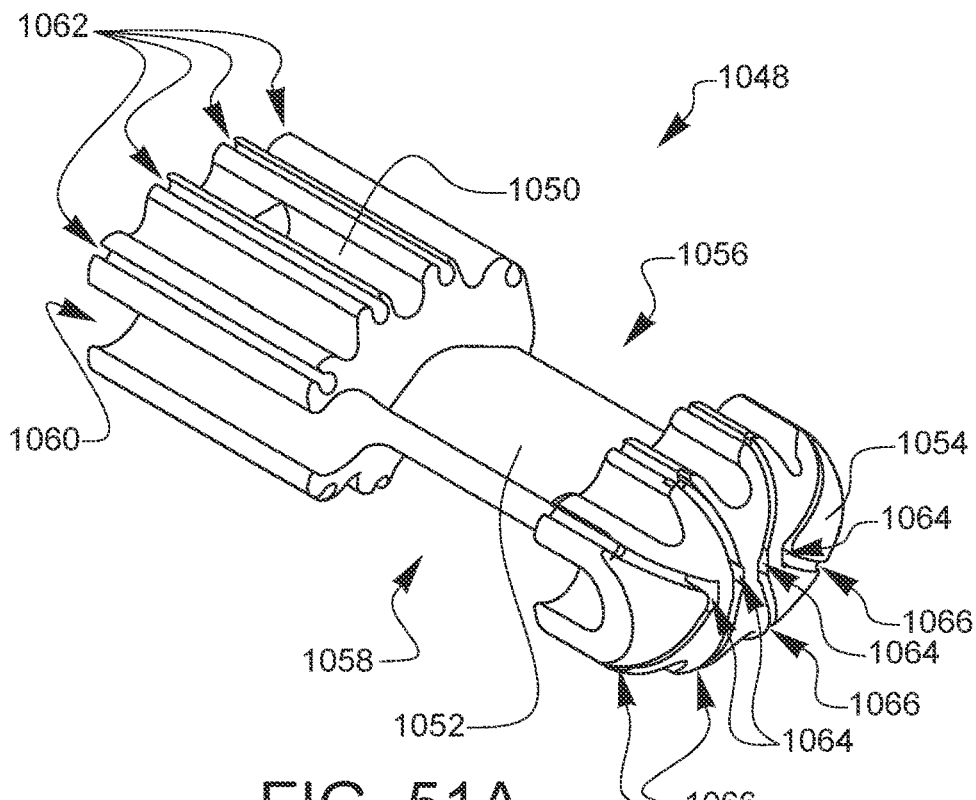
FIGS. 51A-51B are perspective views of a distal tip of the surgical suturing device of FIG. 50.
Figure 51B:
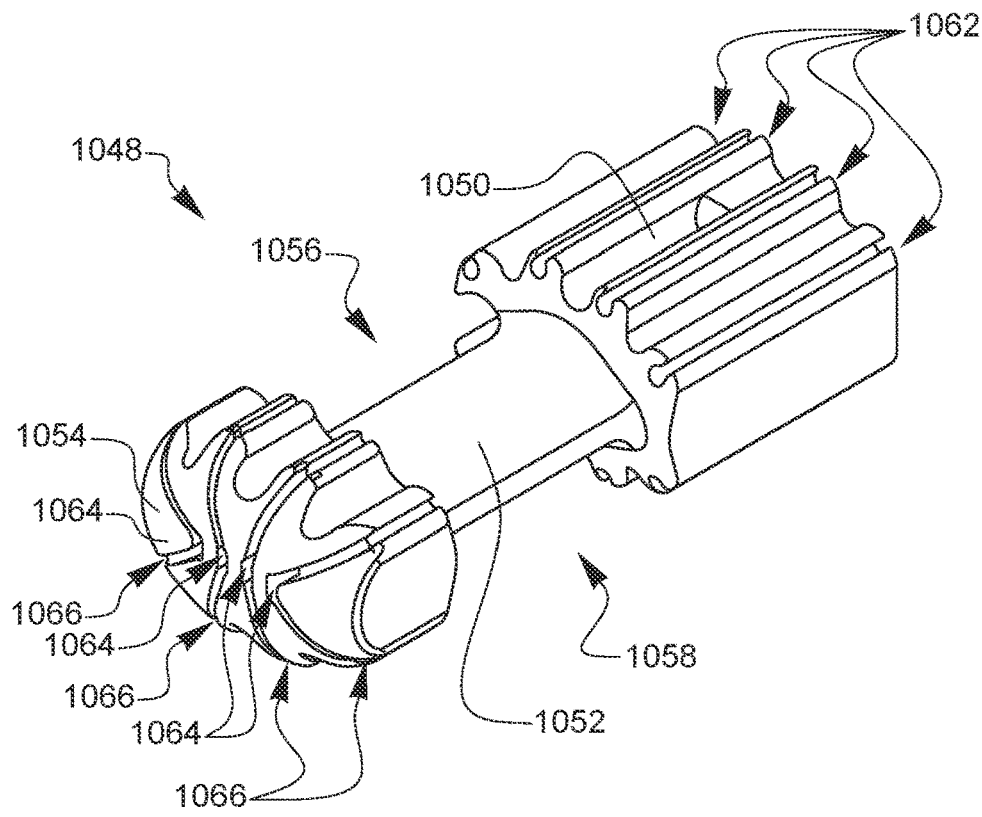
Figure 53:
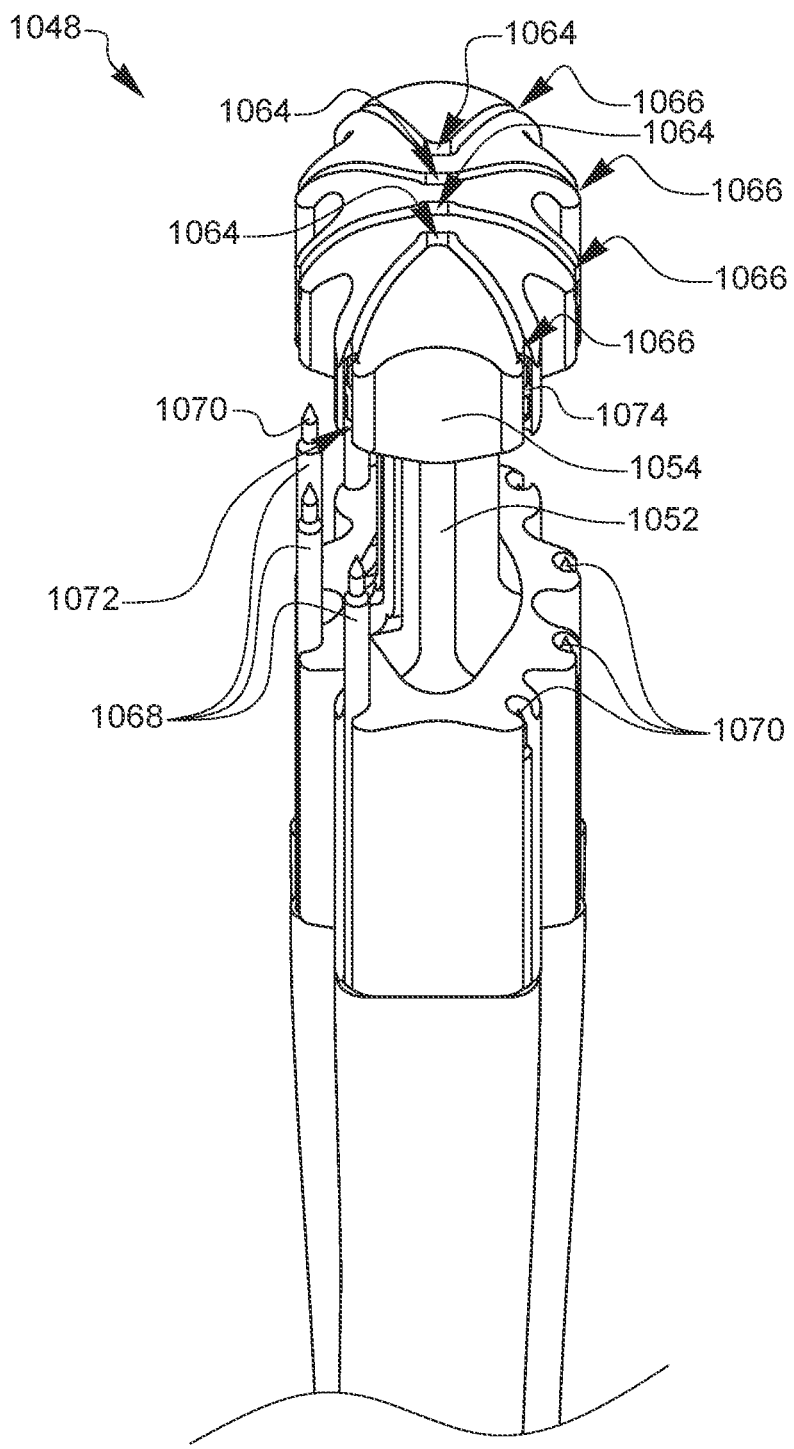
FIG. 53 is a left-front perspective view of the distal tip of FIG. 51A-51B.

FIG. 51A and FIG. 51B are perspective views of the distal tip of the surgical suturing device of FIG. 50. The distal tip 1048 has a tip body 1050 which defines an instrument channel 1060 along one side of the tip body. This instrument channel 1060 is configured to releasably hold various instrumentation used in a minimally invasive surgical procedure for treatment of tricuspid regurgitation. The instrument channel 1060 in the distal tip 1048 is also in communication with the instrument channel that is formed by the various segments of the flexible shaft portion, as previously described. This channel continues back to the proximal end of the surgical suturing instrument. An example of an instrument used in this instance is an intracardiac echocardiography (ICE) probe which is useful in aiding visualization of various surgical procedure steps in the treatment of tricuspid regurgitation. Other instrumentation may also be configured for use within the instrument channel for visualization, tissue grasping, or other uses within a minimally invasive surgical procedure. A flexible grasper may be useful in bringing tissue in closer proximity to either of an upper tissue bite area 1056 or a lower tissue bite area 1058 of the distal tip. The tip body 1050 further defines four upper needle channels 1062 and four lower needle channels 1062 configured to guide two sets of flexible needles across the upper tissue bite area 1056 and across the lower tissue bite area 1058 to engage and pick up their corresponding ferrules and therefore the attached suture ends in the surgical suturing device. Towards the distal end of the distal tip 1048 is a tip support 1052 or strut that defines an upper tissue bite area 1056 and a lower tissue bite area 1058. At the distal end of the tip support 1052, there is a tip head 1054 that defines four suture passages 1064, eight suture guides 1066, and eight ferrule holders 1072 for organizing and holding suture and ferrules in the distal tip and along the shaft. The suture passages 1064 are in communication and tunnel through from the distal tip head 1054 to the tip support 1052, further through the distal tip body 1050 and through the shaft and back to the handle in the surgical suturing instrument. The suture may alternately follow an internal path through various channels within the distal tip 1048 or be closely held in contact with the via suture holding features or guides along the distal tip 1048. This distal tip 1048 may have differing numbers of suture passages 1064, suture guides 1066, and ferrule holders 1072 depending on the details of the minimally invasive surgical procedure in which the instrument may be employed. FIGS. 52A, 52B, 52C, 52D, 52E, and 52F are front, left side, right side, rear, top, and bottom elevational views, respectively, of the distal tip shown in FIGS. 51A and 51B. FIG. 53 illustrates a left-front perspective view of the distal tip shown in FIGS. 51A and 51B in the context of the instrument, with multiple needles beginning to span the tissue bite area.

Figure 54:
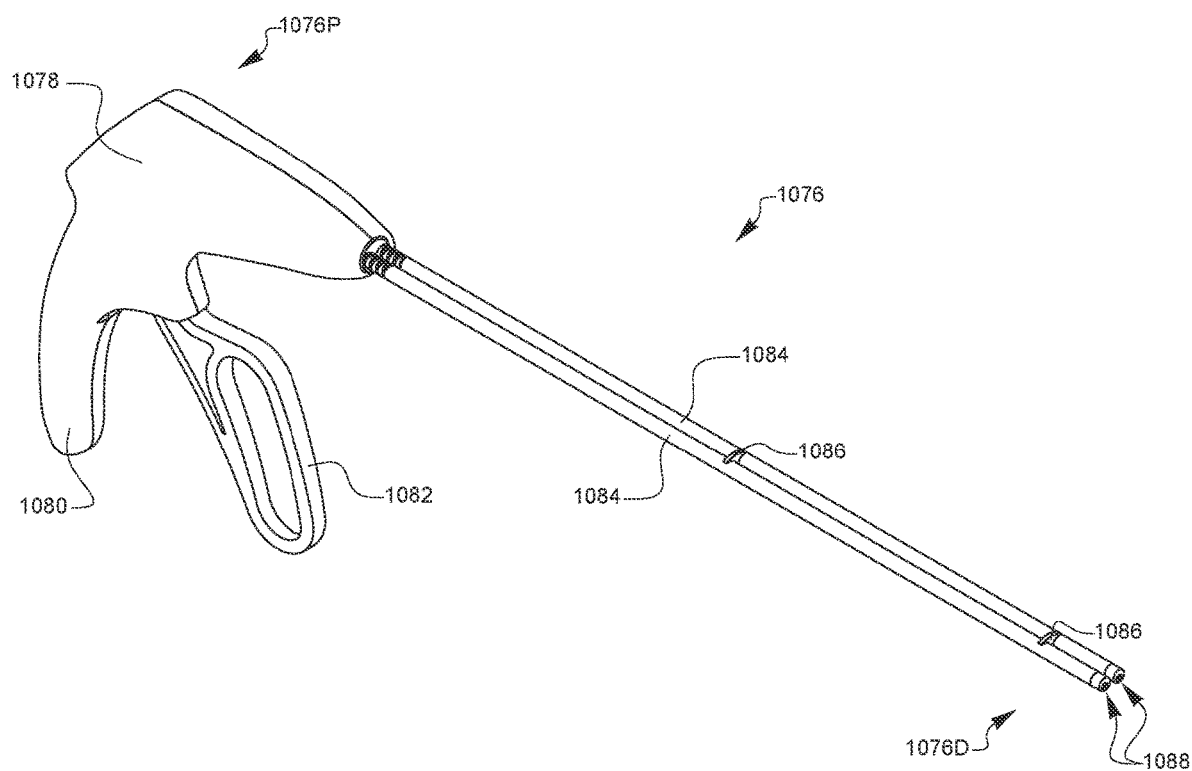
FIG. 54 is a top-right-front perspective view of an embodiment of a mechanical fastener knotting device having two shafts or barrels.

FIG. 54 is a perspective view of a mechanical fastener knotting device having two shafts or barrels. The mechanical fastener knotting device 1076 has a housing 1078 which defines a handle 1080. The mechanical fastener knotting device 1076 also has an actuation lever 1082. Connected to a distal end 1076D of the housing are two shafts 1084, each having several support rings 1086 and each terminating in a knotting tip 1088. When the lever 1082 is squeezed in a direction towards the handle 1080, both knotting tips 1088 are simultaneously triggered, which will crimp a mechanical fastener loaded into each knotting tip 1088 and trim or cut any sutures or threads passed through the mechanical fasteners. Suitable mechanical fastening devices, such as, but not limited to, the COR-KNOT® fastening device from LSI Solutions, Inc. (Victor, NY, www.lsisolutions.com) are intended for use in such a mechanical fastener knotting device. An advantage of a double-barrel mechanical fastener knotting device 1076 such as the one illustrated in FIG. 54 could be to reduce procedure time for a minimally invasive surgical procedure such as the tricuspid annular plication procedures described herein, by reducing the time required to fasten or stitch sutures in separate procedural steps. For example, one actuation of this device could effectively apply mechanical fasteners to four suture ends at once, which could be advantageous for the procedure described herein, as well as others requiring multiple fasteners.

Figures 55A, 55B:
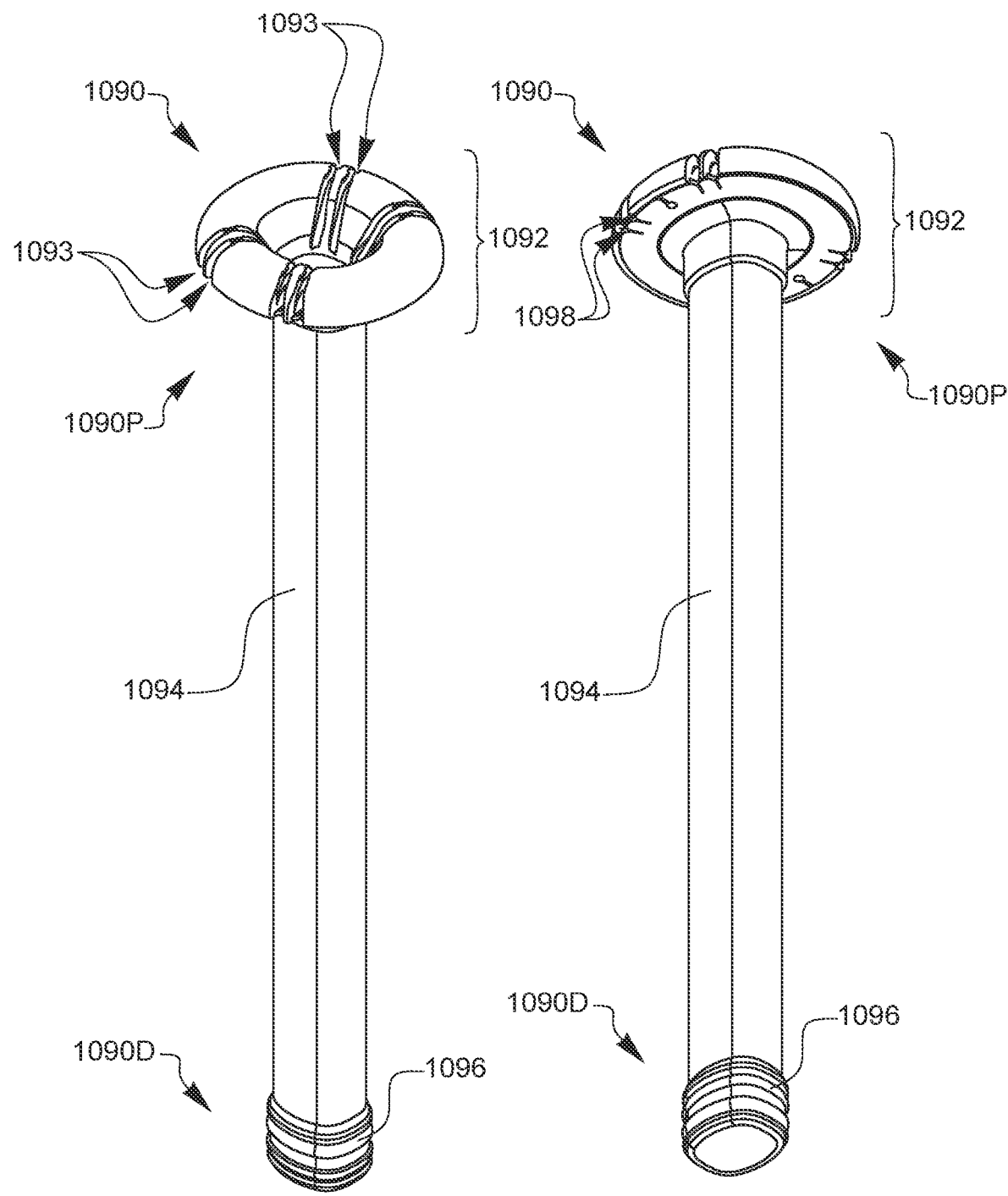
FIGS. 55A and 55B are top and bottom perspective views, respectively, of a cannula for use in combination with the surgical suturing device of FIG. 50.

FIGS. 55A and 55B are top and bottom perspective views, respectively, of a cannula for use in combination with the surgical suturing device of FIG. 50. The cannula 1090 may be provided for intercostal access to the right atrium of the heart while the heart is beating, such as in the procedure described previously in regard to FIGS. 4A-4R. On a proximal end 1090P, the cannula 1090 has an organization template 1092 around the circumference of the cannula. The organization template 1092 has tube management grooves 1093 around a portion of the circumference in which one or more tubes from a suture placement device may be mounted. A section of the organization template 1092 is devoid of tube management grooves 1093, and this corresponds to a portion of the tricuspid valve which should not be sutured, so that needles do not pierce vital segments of the heart's conduction path. This visual reminder on the organization template 1092 is a helpful reminder for surgeons. The cannula 1090 has a riser tube 1094 which is sized to allow the cannula 1090 to reach an incision in the right atrium, but is long enough so that the slightly pressurized blood passing through the right atrium during this beating heart procedure does not rise above and out of the cannula 1090. The distal end 1090D of the cannula 1090 has a groove 1096 to which a pursestring suture placed into the heart at the incision point may be tied to secure the heart tissue to the cannula 1090. Looking at the underside of the proximal end 1090P of the cannula 1090, it can be seen that there are suture pinching slots 1098 for holding various sutures if desired. The cannula can have an optional adapter, not shown here, for coupling to a stabilization arm or surgical equipment holder.

Figure 56:
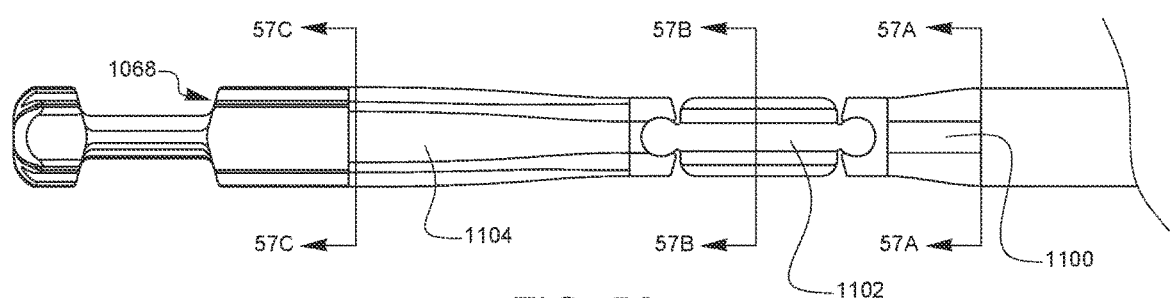
FIG. 56 is a top view of the flexible shaft portion of the surgical suturing device of FIG. 50, detailing a number of unique vertebrae segments or links.
Figure 57A:
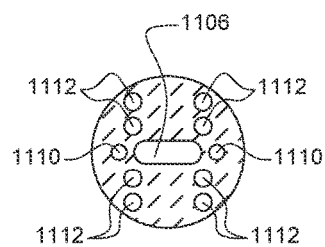
FIGS. 57A-57C are cross-sectional views of flexible shaft vertebra segments of FIG. 56.
Figures 57B, 57C:
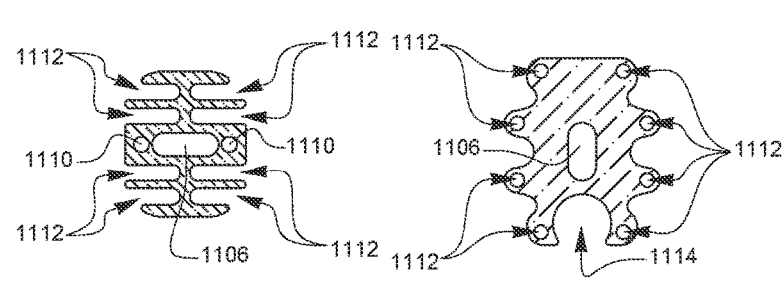

FIG. 56 is a top view of the flexible shaft portion of the surgical suturing device of FIG. 50, detailing a number of unique vertebrae segments or links, the cross-sections of which are shown in greater detail in FIGS. 57A-57C. These vertebrae segments 1100, 1102, 1104, when connected, comprise the flexible shaft 1046 of the surgical suturing device of FIG. 50. Illustrated in FIG. 56 is a first vertebrae 1100 indicated by cross-sectional marker 57A, an articulating vertebrae segment 1102 indicated by cross-sectional marker 57B, and a distal vertebra segment 1104 indicated by cross-sectional marker 57C. The first vertebrae 1100, indicated by cross-sectional marker 57A, includes a linking end to fixedly attach the flexible shaft to the rigid shaft of the surgical suturing device. The cross-sectional features of these vertebrae are further discussed in regard to FIGS. 57A, 57B, and 57C. The cross-sectional features shown in this embodiment of the surgical suturing device are one arrangement, and it should be noted that other arrangements or configurations may be useful or effective in maintaining and articulating the various control and steering cables, sutures, guide wire, and flexible needle pairs or sets along the internal path of a flexible shaft may be known to those skilled in the art.

FIG. 57A is a cross-section of the indicated vertebra segment of FIG. 56. The inner structure of the first vertebra 1100 possesses several features related to pathway management throughout the length of the flexible shaft. The vertebra segment 1100 defines four upper needle channels 1112 and four lower needle channels 1112 which are configured to guide the first needle set and second needle set, respectively, along the flexible shaft. The vertebra segment also defines a central suture passage 1106, as well as channels 1110 for the distal tip steering cables.

FIG. 57B represents a link or vertebra segment. FIG. 57B is a cross-section of the vertebra segment indicated in FIG. 56. The inner structure of this vertebra 1102 possesses several features related to cable pathway management throughout the length of the flexible shaft. The inner structure is similar to the inner structure of the vertebra illustrated in FIG. 57A, however, the needle passages 1112 in the vertebra segment of FIG. 57B are deeper, allowing some flexure of the needles or the tubes within which the needles travel through the surgical suturing device. The inner structure of the vertebra segment of FIG. 57B also has a suture passage 1106, configured to hold sutures enclosed within plastic tubes, as well as channels 1110 for the distal tip steering cables for the flexible shaft.

FIG. 57C is a cross section of the indicated vertebra segment of FIG. 57C. The inner structure of this vertebra possesses several features related to cable pathway management throughout the length of the flexible shaft. The inner structure is similar to the vertebrae 1100, 1102 illustrated in FIGS. 57A-57B, but the vertebra segment 1104 illustrated in FIG. 57C has an instrument channel 1114 configured to hold an instrument such as an ICE probe near the distal tip of the surgical suturing device for improved visualization during a minimally invasive surgical procedure such as a tricuspid annular plication. The inner structure of the vertebra segment 1104 of FIG. 57C also defines channels for the upper needle set 1112, lower needle set 1112, and suture passage 1106.

Figure 58A:
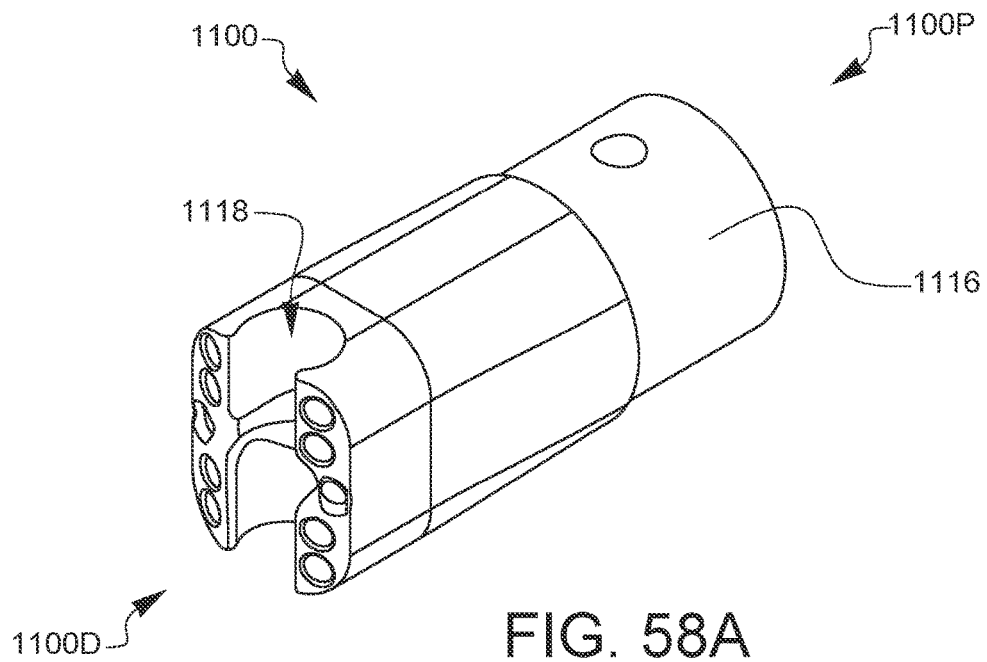
FIGS. 58A-58B are perspective views of the unique vertebra segment of FIG. 57A.
Figure 58B:
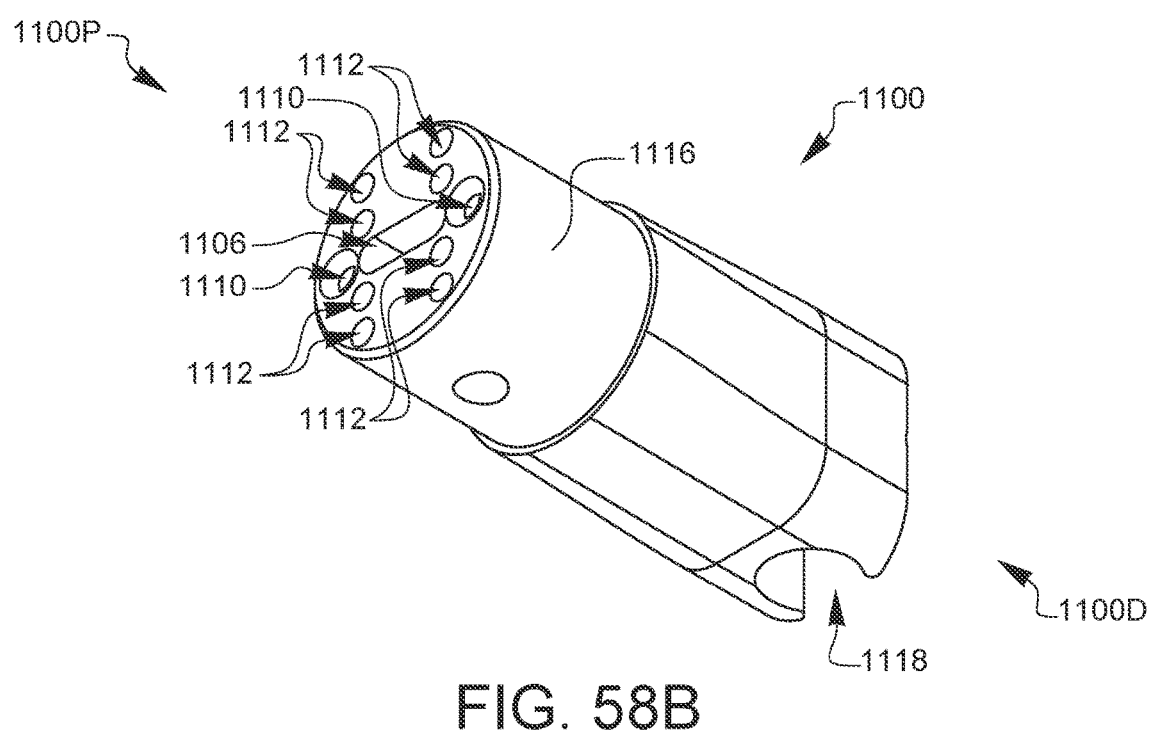
Figure 59E:
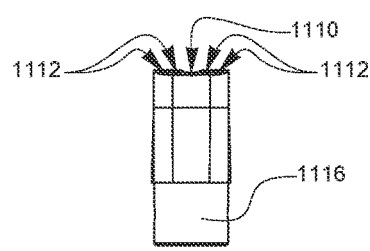
FIGS. 59A, 59B, 59C, 59D, 59E, and 59F are front, left side, right side, rear, top, and bottom elevational views, respectively of the unique vertebra segment of FIGS. 58A-58B.
Figure 59B:
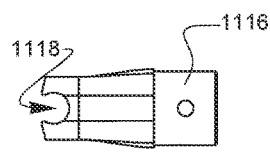
Figure 59A:
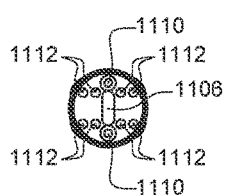
Figure 59C:
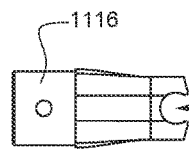
Figure 59D:
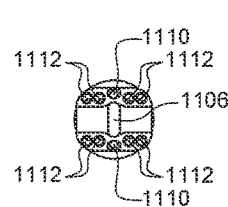
Figure 59F:
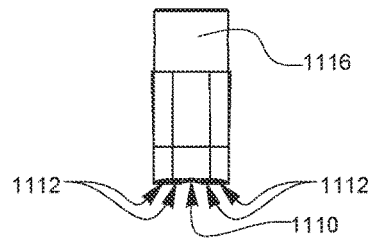

FIGS. 58A and 58B are perspective views of the unique vertebra segment of FIG. 57A. The features regarding the internal structure of this vertebra segment have been described in detail with regard to FIG. 57A. The vertebra segment also defines a recessed portion 1116 about its circumference on the proximal end 1100P such that the vertebra segment end can be inserted into the hollow end of the rigid shaft component during assembly of this embodiment. The vertebra segment 1100 also defines a recess 1118 on the distal end 1100D that is configured to interlock with a link of a subsequent vertebra segment in the flexible shaft. FIGS. 59A-59F are front, left side, right side, rear, top, and bottom elevational views, respectively of the unique vertebra segment of FIGS. 58A-58B.

Figure 60A:
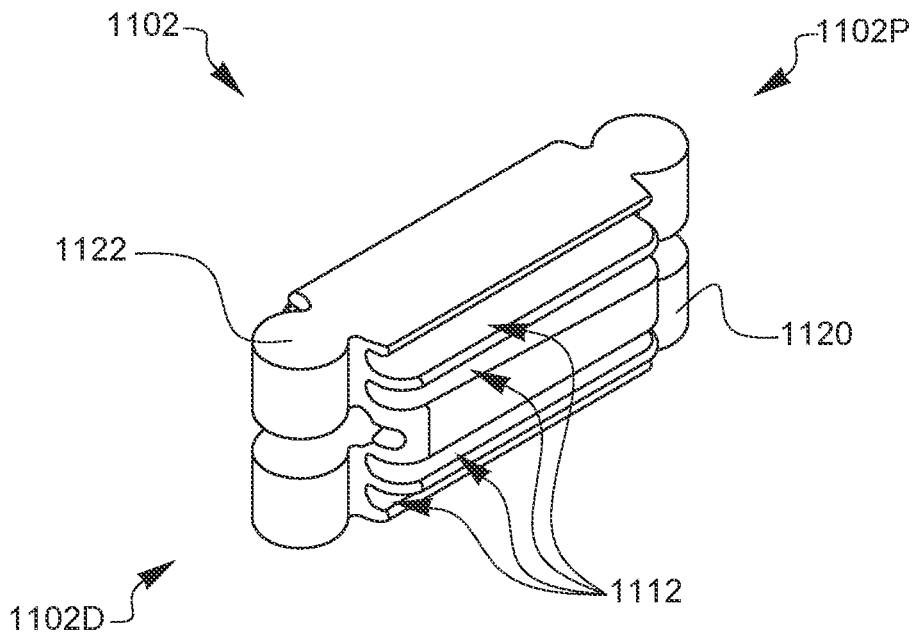
FIGS. 60A-60B are perspective views of the unique vertebra segment of FIG. 58B.
Figure 60B:
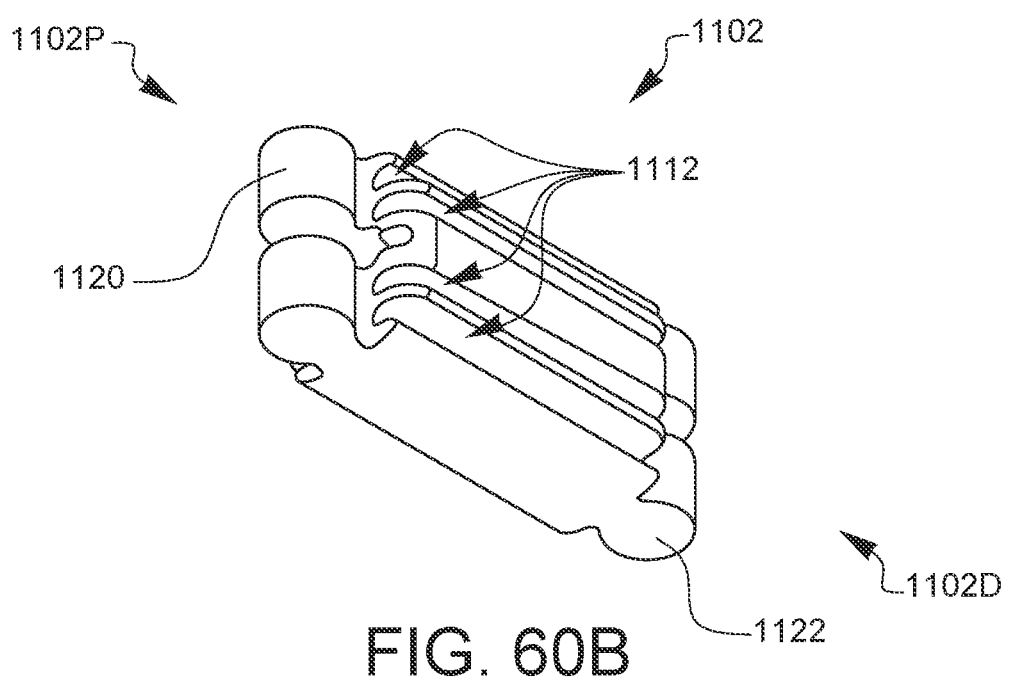

FIGS. 60A and 60B are perspective views of the unique vertebra segment 1102 of FIG. 58B. The features regarding the internal structure of this proximal link vertebra segment have been described in detail with regard to FIG. 58B. The vertebra segment 1102 defines a link 1120 on the proximal end 1102P and a link 1122 on the distal end 1102D that are configured to interlock with a corresponding recess of a previous or subsequent vertebra segment in the flexible shaft. FIGS. 61A-61F are front, left side, right side, rear, top, and bottom elevational views, respectively of the unique vertebra segment of FIGS. 60A and 60B.

Figure 62A:
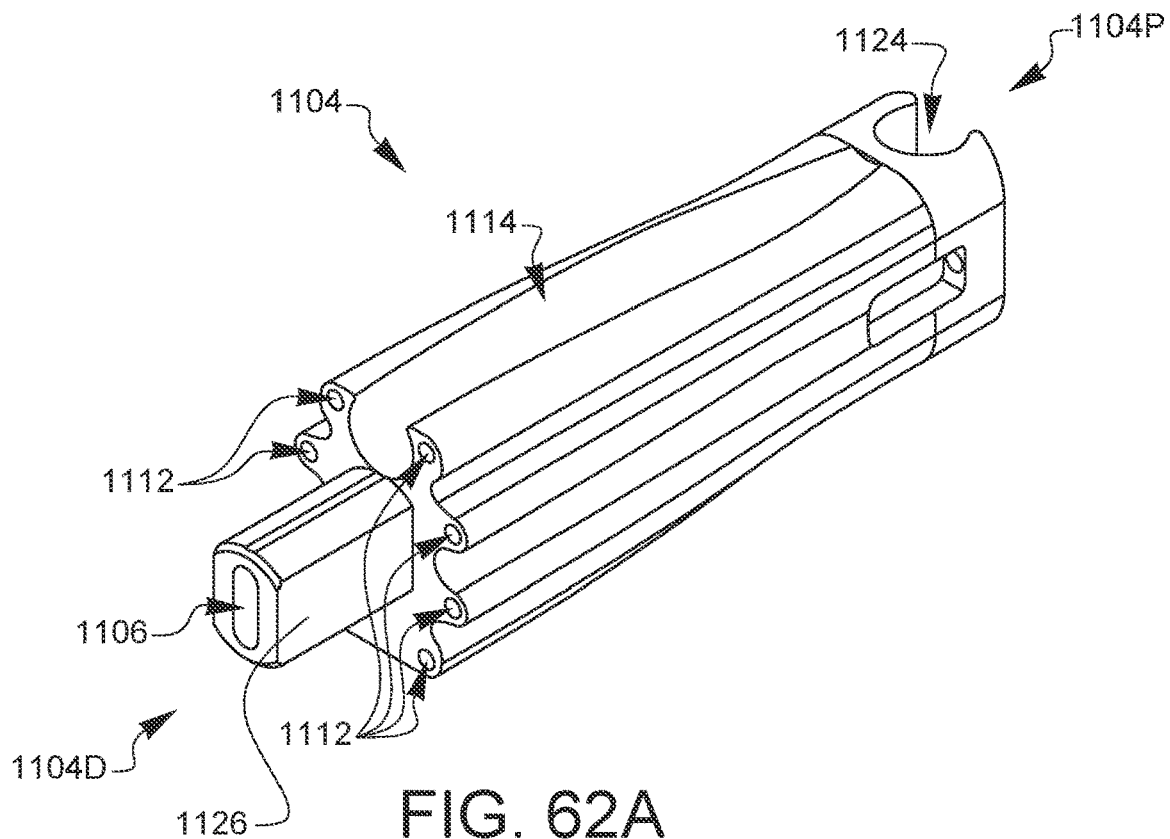
FIGS. 62A-62B are perspective views of the unique vertebra segment of FIG. 58C.
Figure 62B:
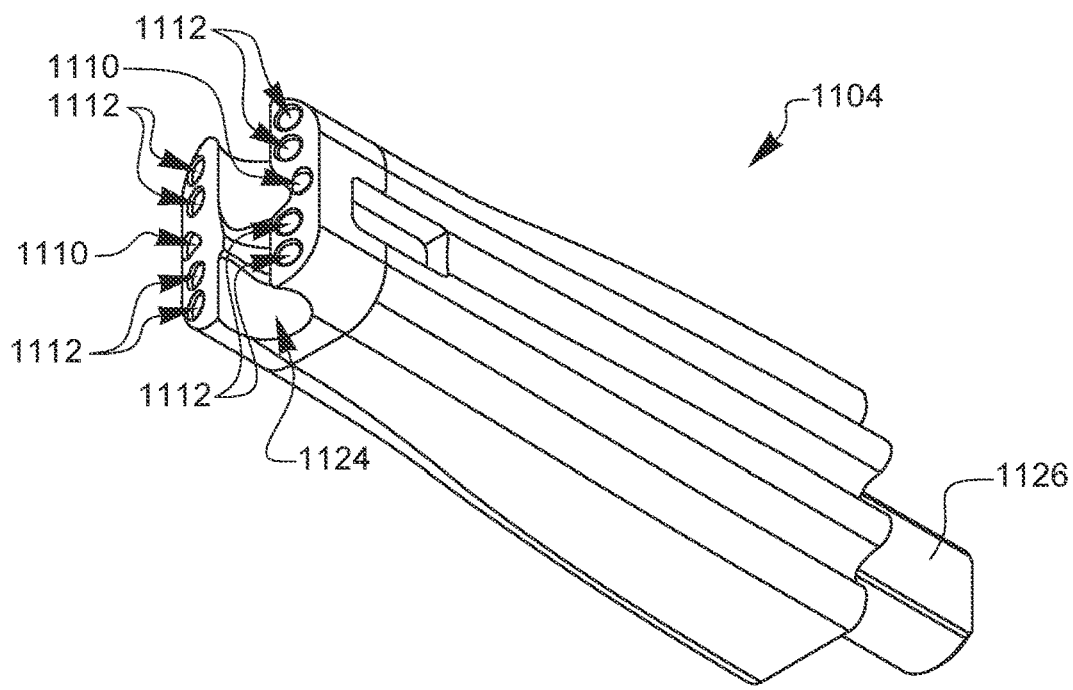

FIGS. 62A and 62B are perspective views of the unique vertebra segment of FIG. 58C. The features regarding the internal structure of this link vertebra segment have been described in detail with regard to FIG. 58C. The vertebra segment 1104 defines a recess 1124 on the proximal end 1104P and a post 1126 on the distal end 1104D. The recess 1124 is configured to interlock with a corresponding link of a previous vertebra segment in the flexible shaft. The post 1126 is configured to be inserted into the distal tip 1048 illustrated in FIGS. 51A-51B. FIGS. 63A-63F are front, left side, right side, rear, top, and bottom elevational views, respectively of the unique vertebra segment of FIGS. 62A and 62B.

Figure 64:
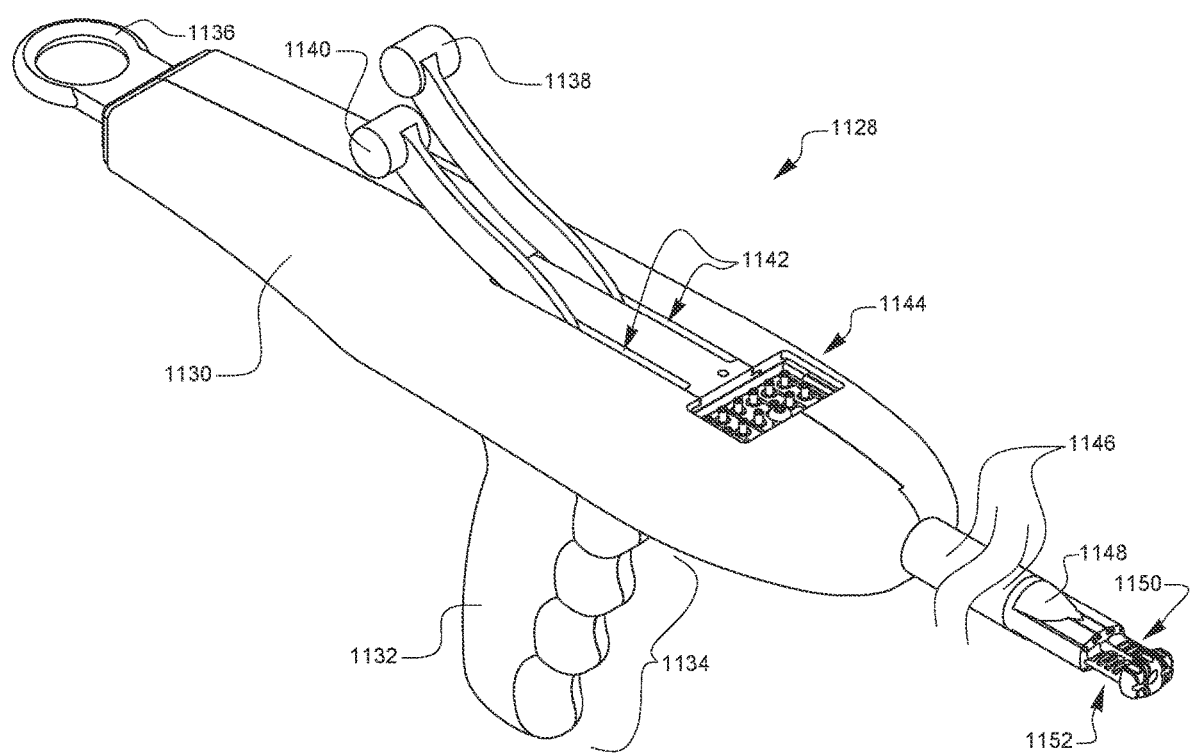
FIG. 64 is a top-right-front perspective view of another embodiment of a surgical suturing device.

FIG. 64 is a perspective view of another embodiment of a surgical suturing device as described herein. This embodiment of a surgical suturing device 1128 has a housing 1130 which defines a handle 1132 further defining a grip 1134, a telescope handle 1136, and several slots 1142 on the top surface of the housing 1130. The slots 1142 in the housing 1130 accommodate a first needle drive lever 1138 and a second needle drive lever 1140. The housing 1130 of the surgical suturing device 1128 also defines a suture storage and viewing window 1144. Connected to the housing 1130 is a shaft 1146 which terminates in a distal tip 1148 which further defines a first upper tissue bite area 1150 and a second lower tissue bite area 1152. The purpose and function of most of the salient features of this embodiment of a surgical suturing device 1128 have been described previously, and those which have not will be further discussed.

Figure 65:
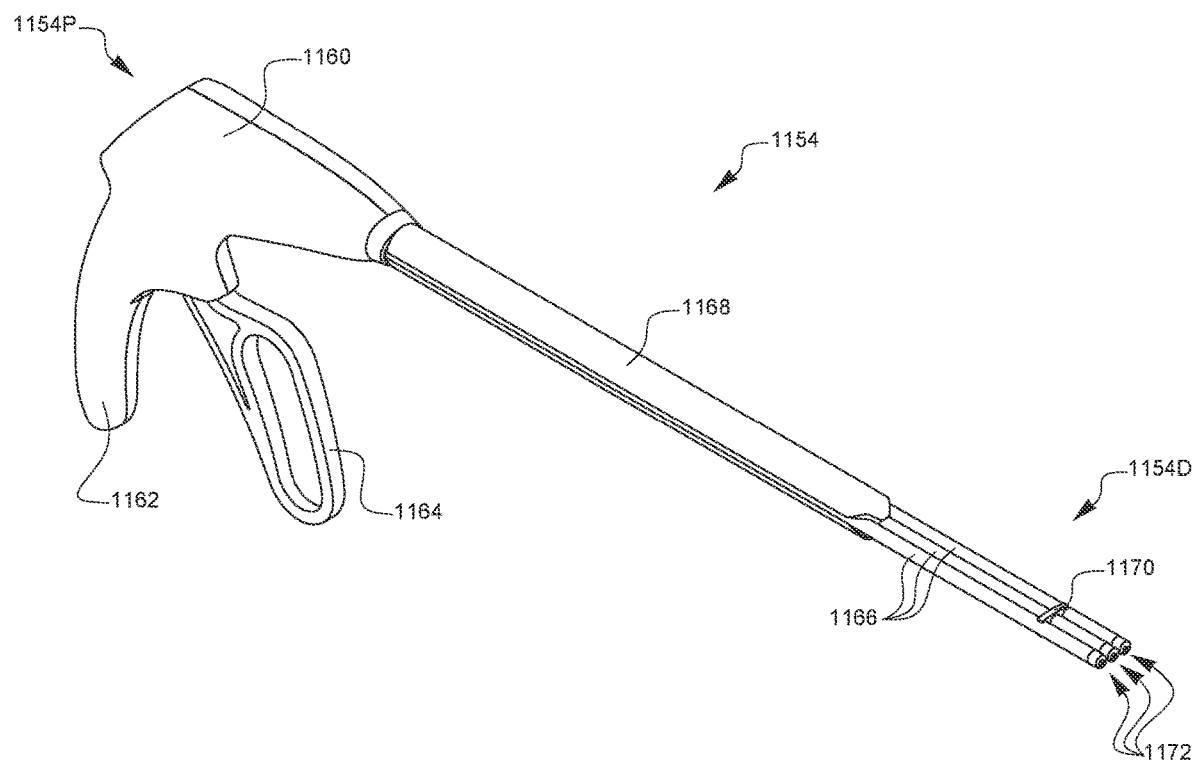
FIG. 65 is a top-right-front perspective view of an embodiment of a mechanical fastener knotting device having three shafts or barrels.

FIG. 65 is a perspective view of an embodiment of a mechanical fastener knotting device having three shafts or barrels. The mechanical fastener knotting device 1154 has a housing 1160 which defines a handle 1162. The mechanical fastener knotting device 1154 also has an actuation lever 1164. Connected to a distal end 1154D of the housing are three shafts 1166, with at least one support ring 1170 and with each shaft terminating in a knotting tip 1172. When the lever 1164 is squeezed in a direction towards the handle 1162, all three knotting tips 1172 are simultaneously triggered, which will crimp a mechanical fastener loaded into each knotting tip 1172 and trim or cut any sutures or threads passed through the mechanical fasteners. One actuation of the lever will effectively fasten three mechanical fasteners. Similar suitable mechanical fastening devices, such as, but not limited to, the COR-KNOT® fastening device from LSI Solutions, Inc. (Victor, NY, www.lsisolutions.com) are intended for use in such a mechanical fastener knotting device. An advantage of a triple-barrel mechanical fastener knotting device 1154 such as the one illustrated in FIG. 66 is to reduce procedure time for a minimally invasive surgical procedure such as the tricuspid annular plication procedures described herein, by reducing the time required to fasten or stitch sutures as compared to fastening using separate procedural steps or instruments for each fastener. For example, one actuation of this device could effectively apply mechanical fasteners to six suture ends at once, which could be advantageous for the procedure described herein as well as other procedures requiring multiple sutures or fasteners. This knotting device 1154 also has a sealing collar 1168 to maintain a seal within cannula when inserting the knotting device into a minimally invasive surgical site. This sealing collar 1168 may be constructed of a plastic, metal, or elastomeric material depending on the maneuverability required for the knotting device 1154 when inserted into a cannula or port when reaching a surgical site.

Figure 66A:
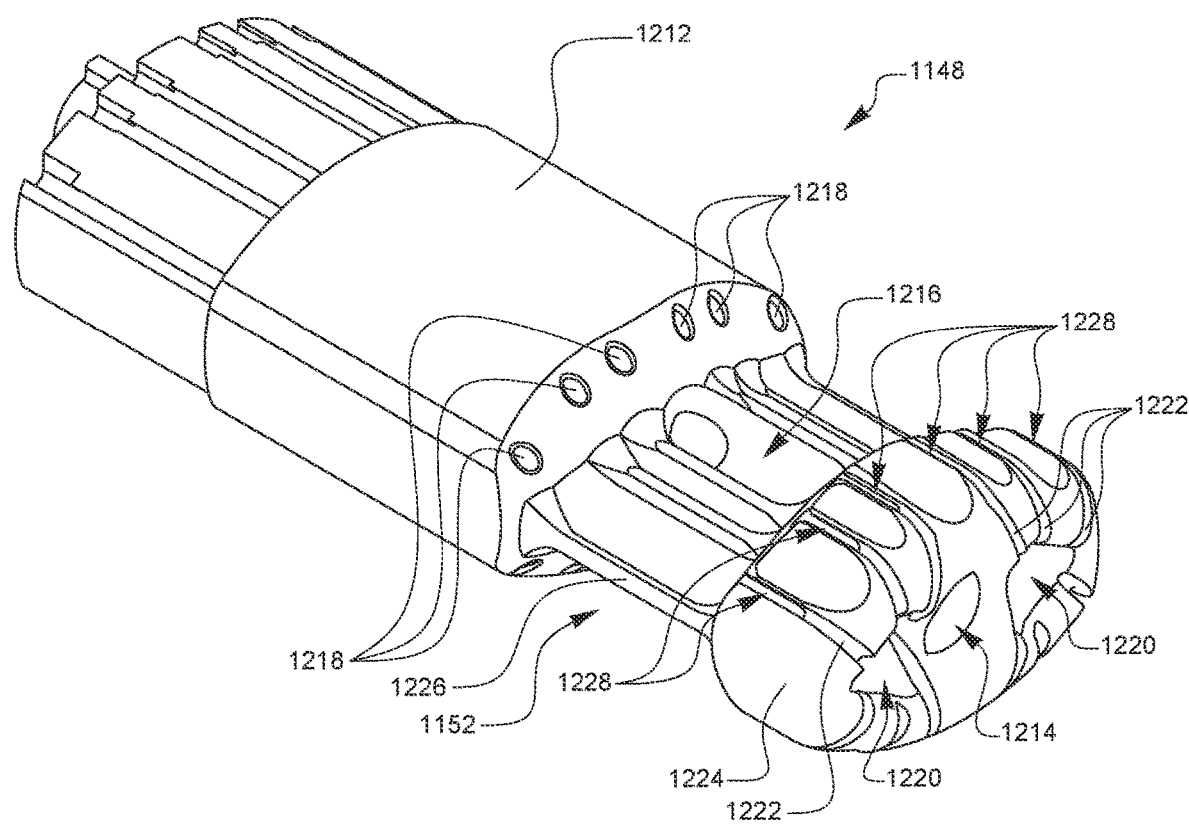
FIG. 66A is a top-right-front perspective view of a distal tip of the surgical suturing device of FIG. 64.

FIG. 66A is a perspective view of an alternate embodiment of a distal tip for the surgical suturing device of FIG. 64. The distal tip for this embodiment would accommodate twelve needles in two pairs of six, along with six suture pairs for use in a minimally invasive surgical procedure similar to the one described in regard to FIGS. 4A-4R, but with six suture pains other than two. The distal tip 1148 has a tip body 1212 which defines an internal instrument channel 1214 via the center of the tip body 1212. This instrument channel 1214 is configured to releasably hold various instrumentation used in a minimally invasive surgical procedure for treatment of tricuspid regurgitation. The distal tip 1148 also accommodates instrumentation in the instrument channel 1214 without compromising the depth of the tissue bite. The instrument channel 1214 in the distal tip 1148 is also in communication with the instrument channel that is formed by the various segments of the shaft. This channel continues back to the proximal end of the surgical suturing instrument where an instrument such as an intracardiac echocardiography (ICE) probe, which is not shown in this view, may be inserted. Other instrumentation may also be configured for use within the instrument channel for visualization, tissue grasping, or other uses within a minimally invasive surgical procedure. A flexible grasper may be useful in bringing tissue in closer proximity to either of the upper tissue bite area or the lower tissue bite area of the distal tip. The tip body 1212 further defines six upper needle channels 1218 and six lower needle channels (not visible here) configured to guide the two sets of flexible needles across an upper tissue bite area 1150 and across a lower tissue bite area 1152, that are both defined by the distal tip 1148, to engage and pick up their corresponding ferrules and therefore the attached suture ends in the surgical suturing device. Towards the distal end of the distal tip is a tip support 1226 or strut that defines the upper tissue bite area 1150 and lower tissue bite area 1152. The tip support 1226 also defines a viewing port 1216, which allows visibility into both the upper tissue bite area 1150 and the lower tissue bite area 1152 via the instrument channel 1214. At the distal end of the tip support 1226, there is a tip head 1224 that defines six suture passages 1220, twelve suture guides 1222, and twelve ferrule holders 1228 for organizing and holding suture and ferrules in the distal tip and along the shaft. The ferrule holders 1228 are aligned with the needle channels 1218. The suture passages 1220 are in communication with and tunnel through from the distal tip head 1224 to the tip support 1226, further through the distal tip body 1212, through the shaft, and back to the handle of the surgical suturing instrument. The suture may alternately follow an internal path through various channels within the distal tip or be closely held in contact with suture holding features or guides along the distal tip. Alternate embodiments of this distal tip may have differing numbers of suture passages, suture guides, and ferrule holders depending on the number of needles or on the details of the minimally invasive surgical procedure in which the instrument may be employed. For example, this tip is arranged to have six lower needles and six upper needles that are driven in pairs by needle drive actuators similar to those described in regard to previous embodiments. It should be noted that the needles in any of the embodiments described herein could be articulated individually, or in alternatively arranged pairs or coordinated sets or pluralities. Increasing the number of needle pairs or sets from two to four and subsequently to six or more provides the advantage for the operator of having the ability to introduce more sutures per bite, thus reducing the operating procedural time and improving the efficiency and efficacy of the operational procedure. Different orientations and spacing between each needle on either the top or bottom of the distal tip may also be used to improve accuracy of suturing or to avoid anatomical features during a minimally invasive surgical procedure. An embodiment employing such a distal tip as described in FIG. 66A may also necessitate enlarged or greater numbers of features of the surgical suturing device described herein, including but not limited to barrels configured to hold more needles, a wider retracting telescope, and a larger or greater numbers of needle alignment blocks.

Figure 66B:
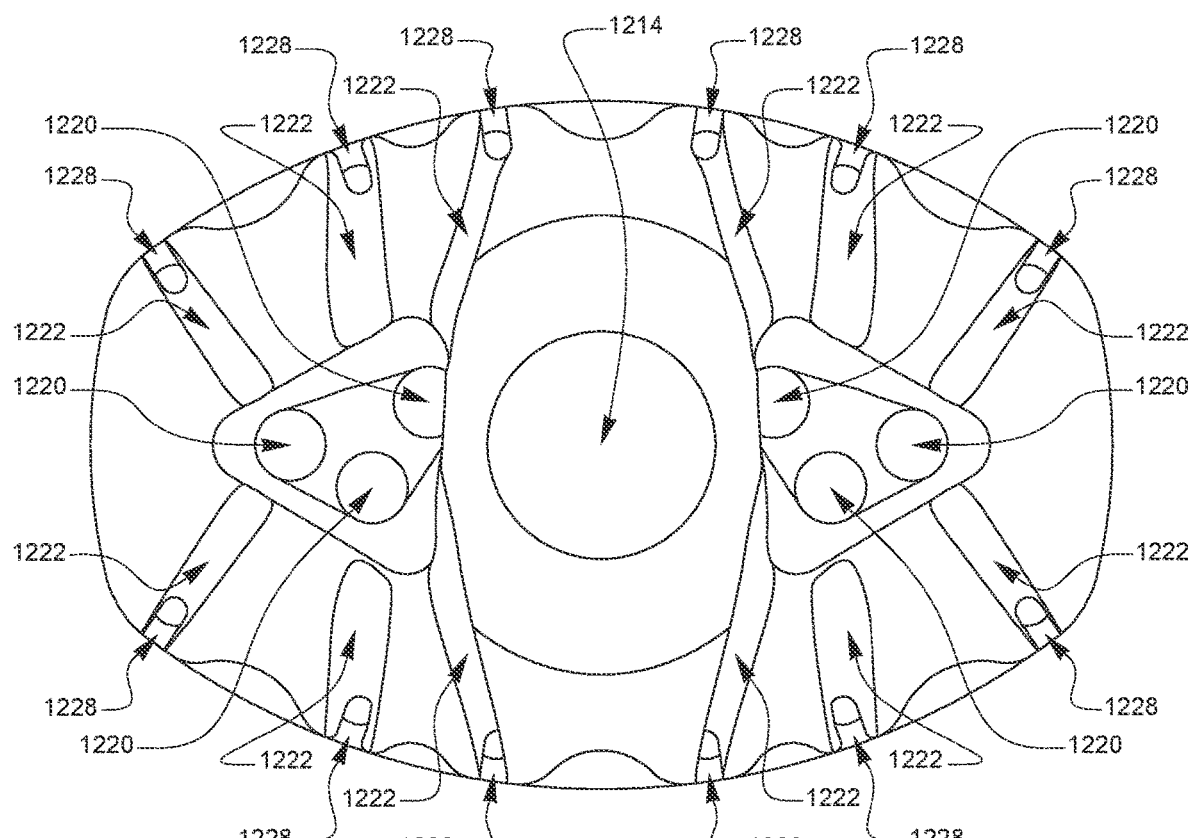
FIG. 66B is a front view of the distal tip of FIG. 66A.

FIG. 66B is a front-view of the distal tip for a surgical suturing device of FIG. 66A. As the surgical suturing device distal tip shown in FIG. 66A is introduced into the surgical site, the suturing and needle bites to be performed must be located in the intended position. As illustrated in FIG. 66B, the positions of the needles as indicated by the location of the ferrule holders 1228 and suture guides 1222 shown are slightly asymmetrical as compared to the spacing and positions of the needles and suture guides of previous embodiments. One purpose of this positioning is to avoid the bundle of HIS, a collection of heart muscle cells integral to electrical conduction in the heart, when making the required suture bites during a minimally invasive surgical procedure such as the one described herein. Other needle arrangements, spacings, or positioning may be used to either avoid or intentionally target particular anatomical features during a given minimally invasive surgical procedure, and other procedures aside from the one described herein may be accomplished with embodiments of the disclosed device. In addition to lateral needle spacing, needle bite depth may also be individually configured for each needle within the distal tip by modifying the shape and contour profile of the tip support or strut in the distal tip, depending on the intended suturing result or the particulars of the anatomical location of a minimally invasive surgical procedure for which the surgical suturing device may be used.

Figure 67A:
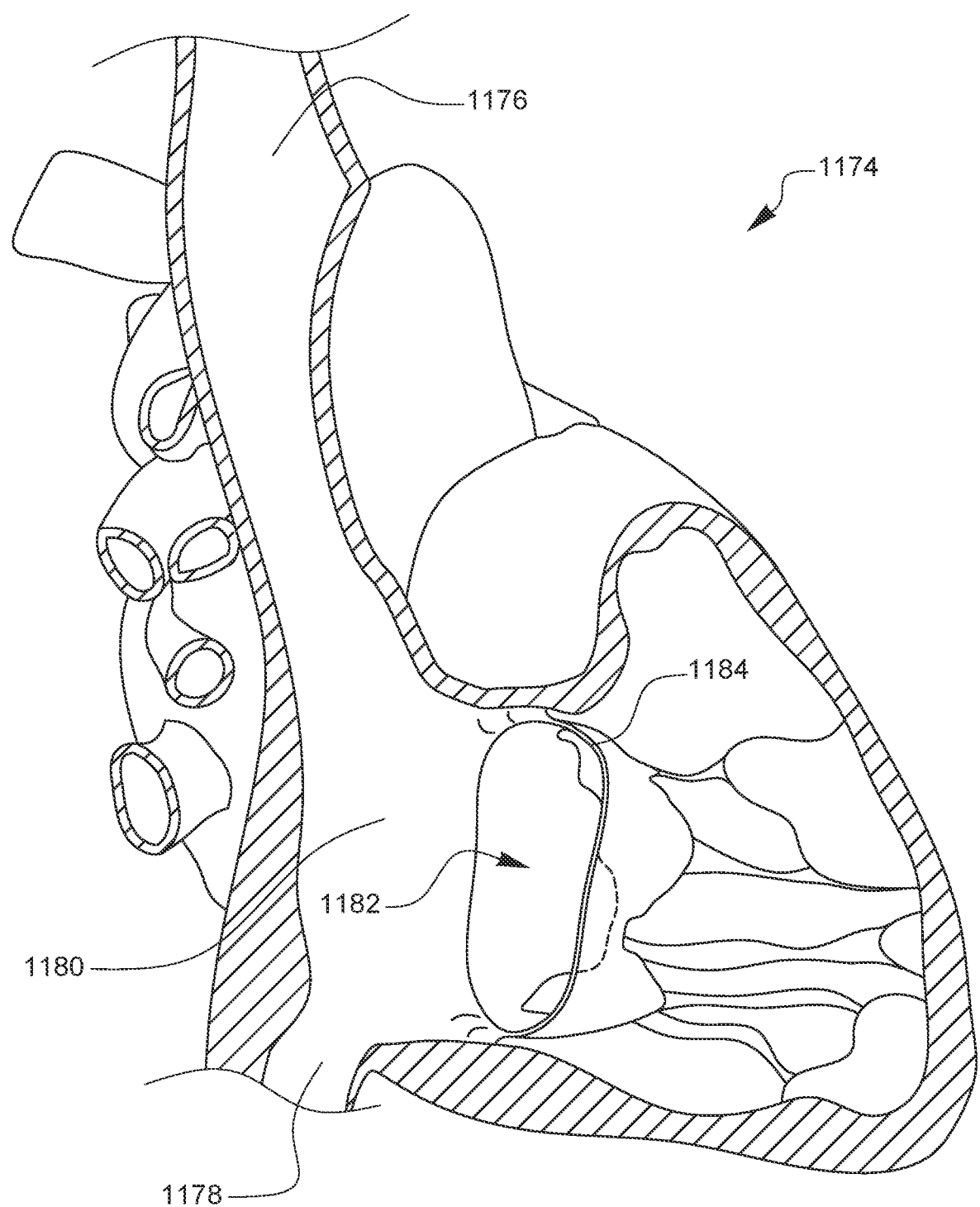
FIGS. 67A-67H, and 67J-67L are a series of schematic illustrations of a surgical method for repair of tricuspid regurgitation using the surgical suturing device of FIG. 64.
Figure 67B:
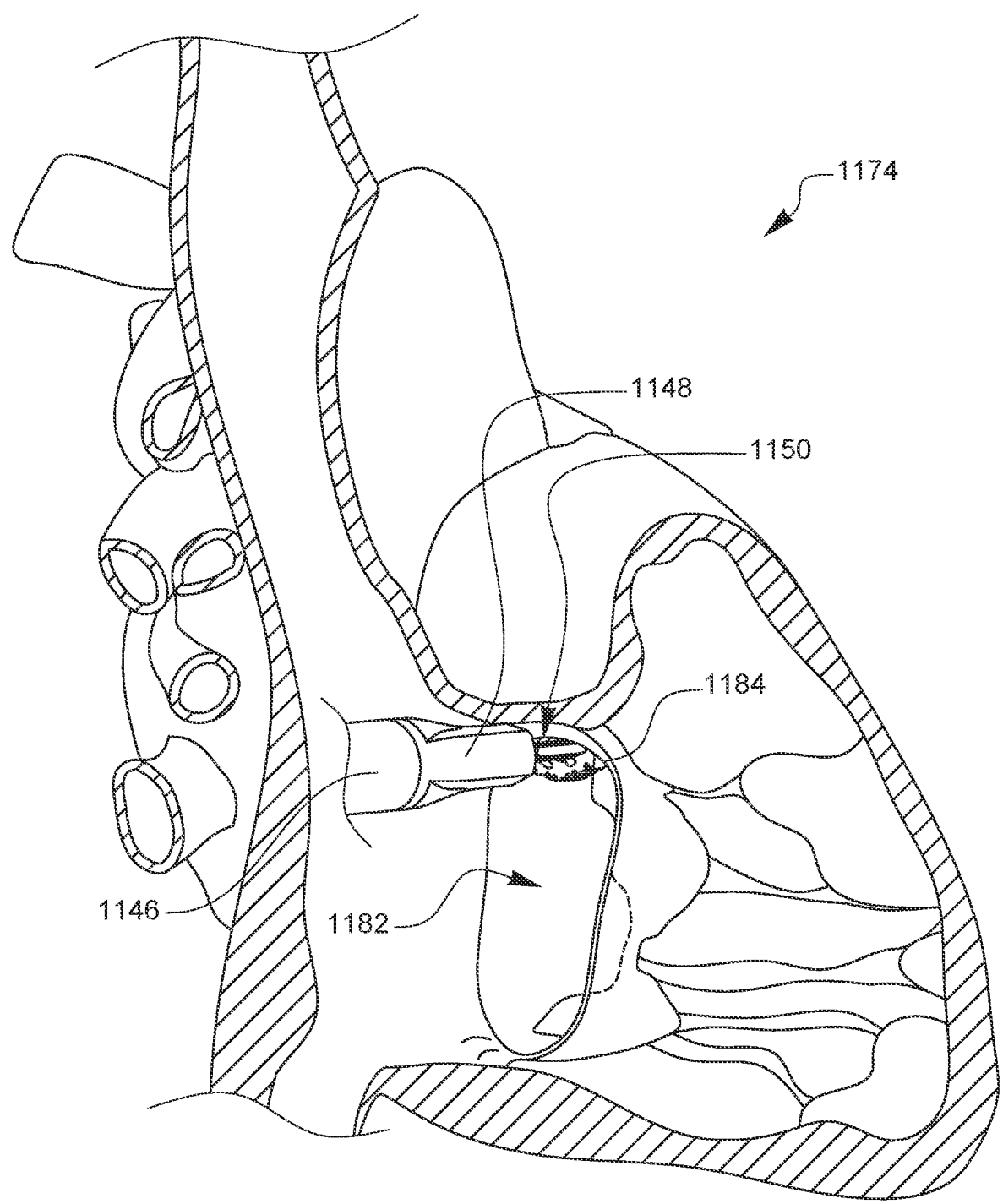

FIGS. 67A-67H, and 67J-67L are a series of schematic illustrations of a surgical method for repair of tricuspid regurgitation using the surgical suturing device of FIG. 64. Considering the surgical situation illustrated in FIGS. 4A-4R, and particularly the steps illustrated in FIGS. 4A-4L, it may be desirable for a surgeon to perform a minimally invasive tricuspid annular plication similar to the one described in regard to FIGS. 4A-4R by introduction of a surgical suturing device via an intercostal pathway rather than via the inner jugular vein. The introduction of a surgical suturing instrument such as the one shown in FIG. 64 through a cannula such as the one described later in regard to FIGS. 55A-55B, would not necessarily require the same degrees of freedom of movement or geometrical arrangement of the rigid shaft, flexible shaft, distal tip and needle arrangement as some of the previously described embodiments of the surgical suturing device embodiments described previously herein. An intercostal introduction of a surgical suturing device such as the one illustrated in FIG. 64 has a shorter shaft and does not have any distal tip articulation capability with respect to the position of the shaft and handle of the surgical suturing device. Such an instrument may also have a shorter retracting telescope given a shorter distance from the outside of the body to the right atrium as compared to the procedure illustrated in FIGS. 4A-4R, and 5. This type of minimally invasive surgical procedure may also be done under guidance of visualization methods such as TEE (transesophageal echocardiogram) or ICE (intracardiac echocardiography). FIG. 67A illustrates a side view of a heart 1174 with the general locations of the superior vena cava 1176, inferior vena cava 1178, right atrium 1180, tricuspid valve 1182, and tricuspid annulus 1184 indicated. FIG. 67B illustrates the introduction of a surgical suturing device into the right atrium 1180, with the first upper tissue bite area 1150 placed on the tricuspid annulus 1184, exerting pressure to obtain an appropriate bite depth. Only the shaft 1146 and the distal tip 1148 of the instrument are visible in this view.

Figure 67C:
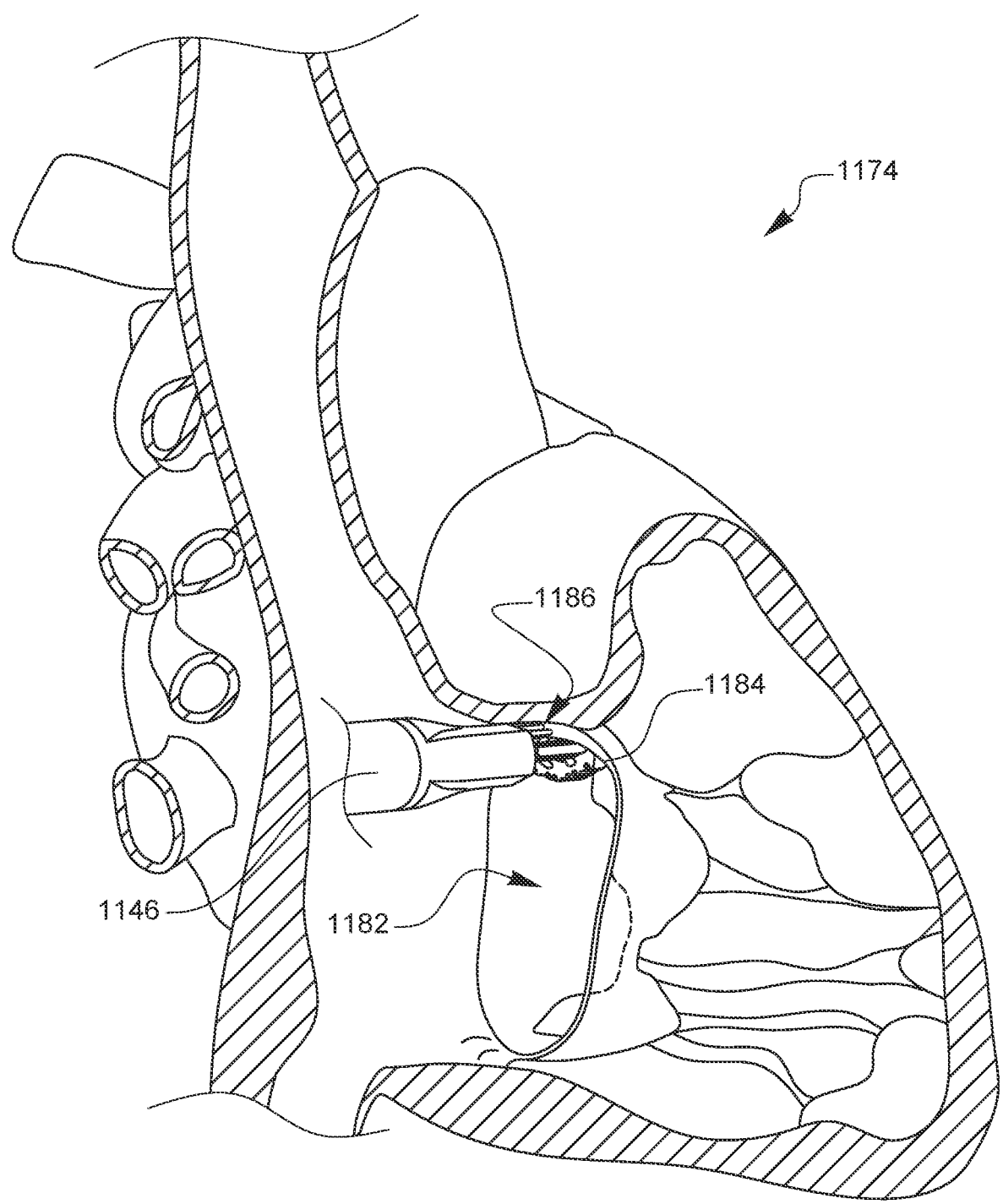
Figure 67D:
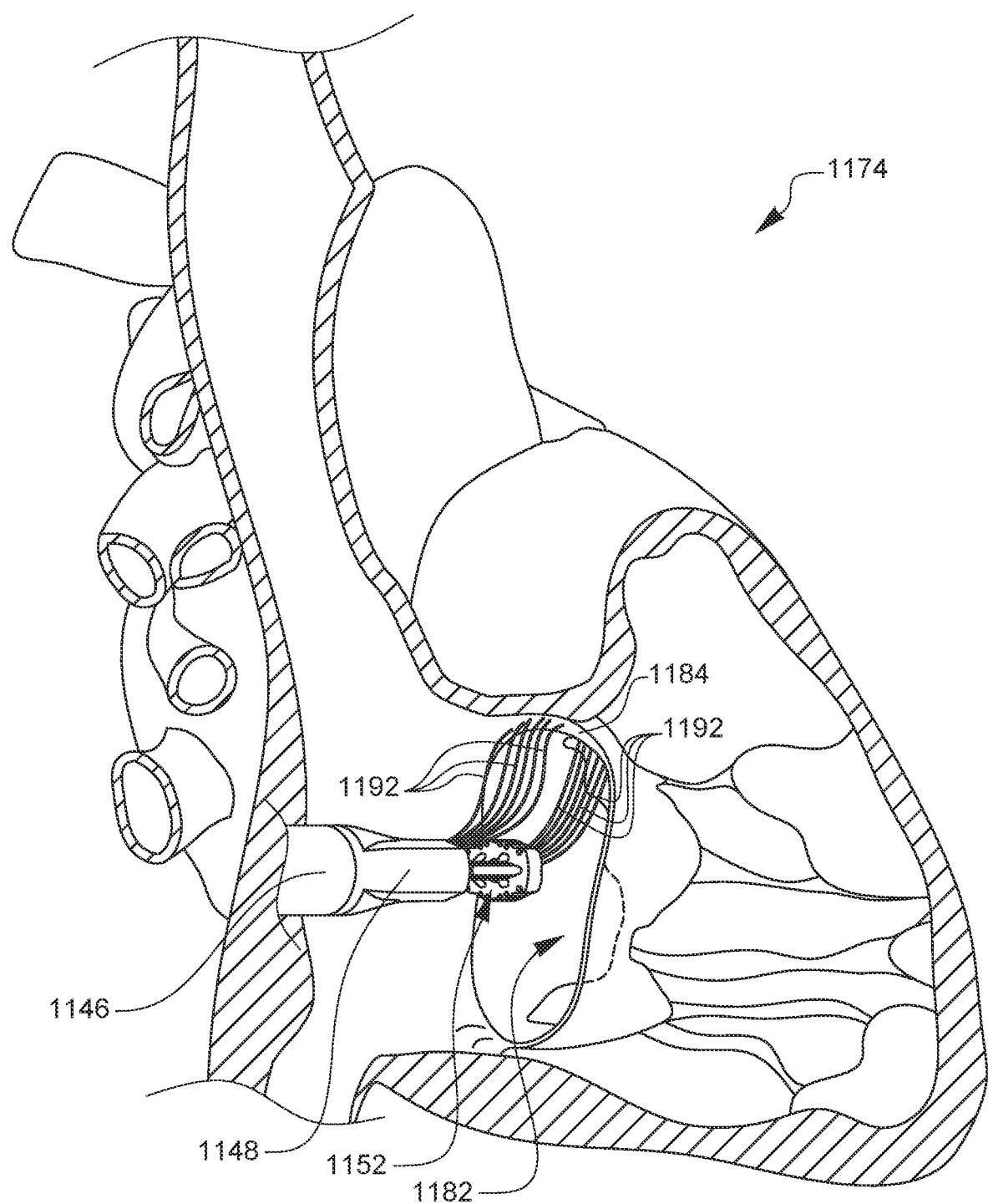
Figure 67E:
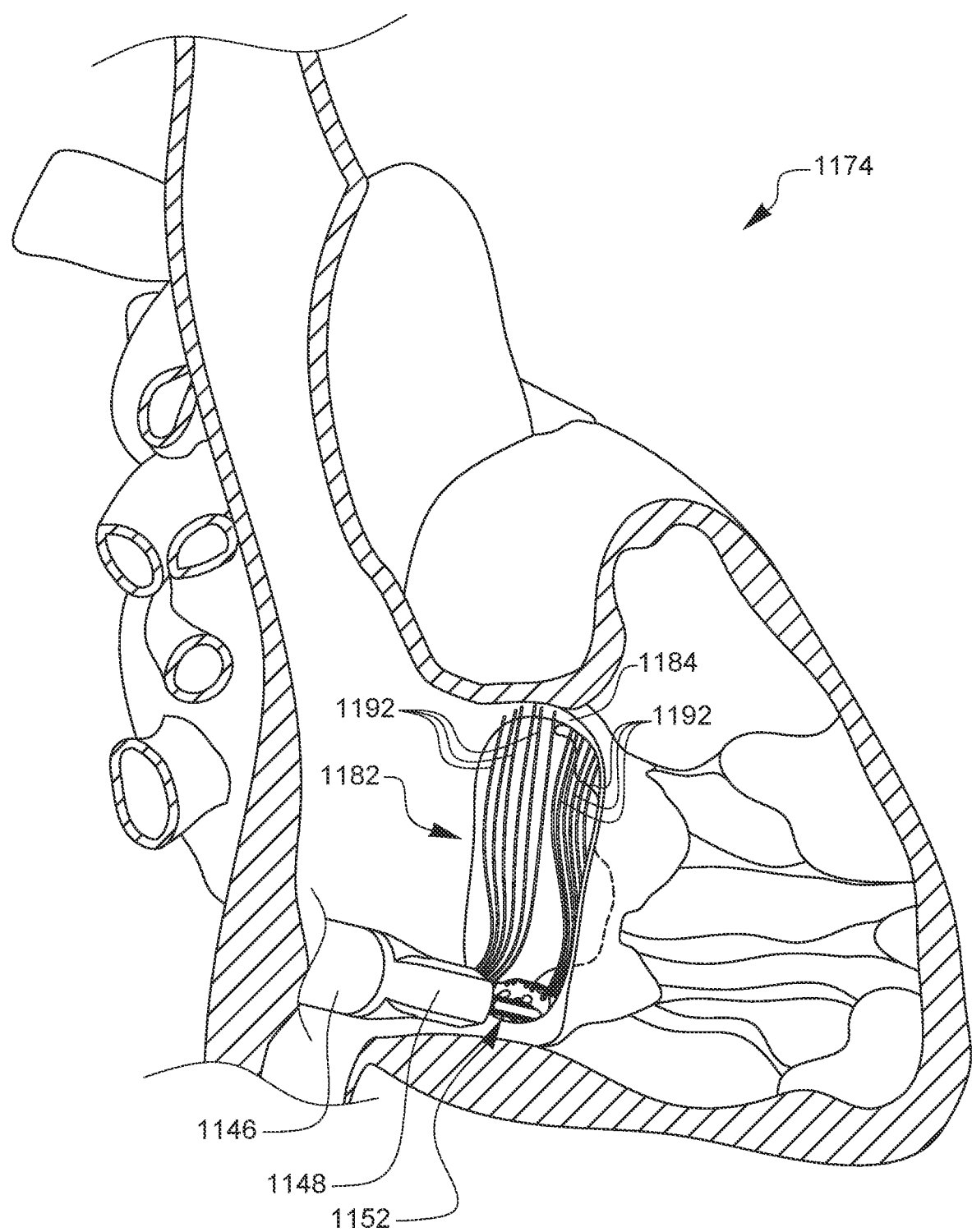

FIG. 67C illustrates a step in the surgical sequence wherein the first needle driver actuator is moved in a distal direction to advance the plurality of upper needles 1186 through the first upper tissue bite area 1150, through the tissue of the tricuspid annulus 1184 and into the ferrules. In FIG. 67D the first needle driver is pulled proximally to retract the plurality of upper needles 1186 attached to the ferrules, which are attached to their respective sutures 1192. This concept has been detailed previously herein. The retracting telescope of the surgical suturing device is pulled back partially in order to provide some slack on the sutures and allow for subsequent distal tip placement and placement of the second lower tissue bite area 1152 within the tricuspid valve 1182. FIG. 67E illustrates the placement of the second lower tissue bite area 1152 onto another location of the tricuspid annulus 1184, exerting pressure to obtain an appropriate bite depth. This step may be accomplished with the assistance of either direct visualization of with visualization guidance by instrumentation.

Figure 67F:
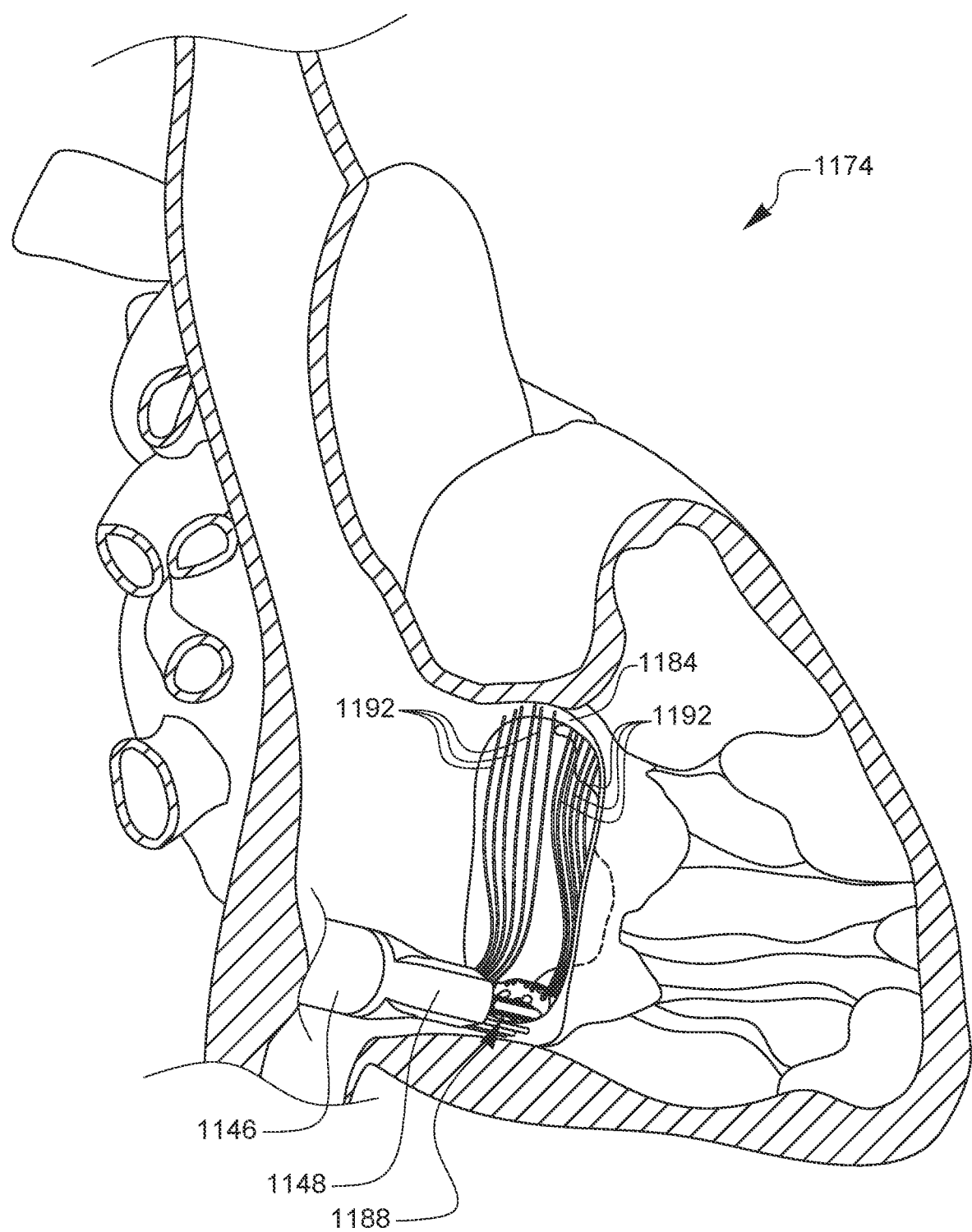

FIG. 67F The second needle driver actuator is moved in a distal direction to advance the four upper needles through the upper tissue bite area and through the tissue and into the ferrules. FIG. 67F illustrates a step in the surgical sequence wherein the second needle driver actuator is moved in a distal direction to advance the plurality of lower needles 1188 through the second lower tissue bite area 1152, through the tissue of the tricuspid annulus 1184 and into its respective ferrules. Subsequently, the second needle driver is pulled proximally to retract the plurality of lower needles 1188 attached to the ferrules which are attached to their respective sutures.

Figure 67G:
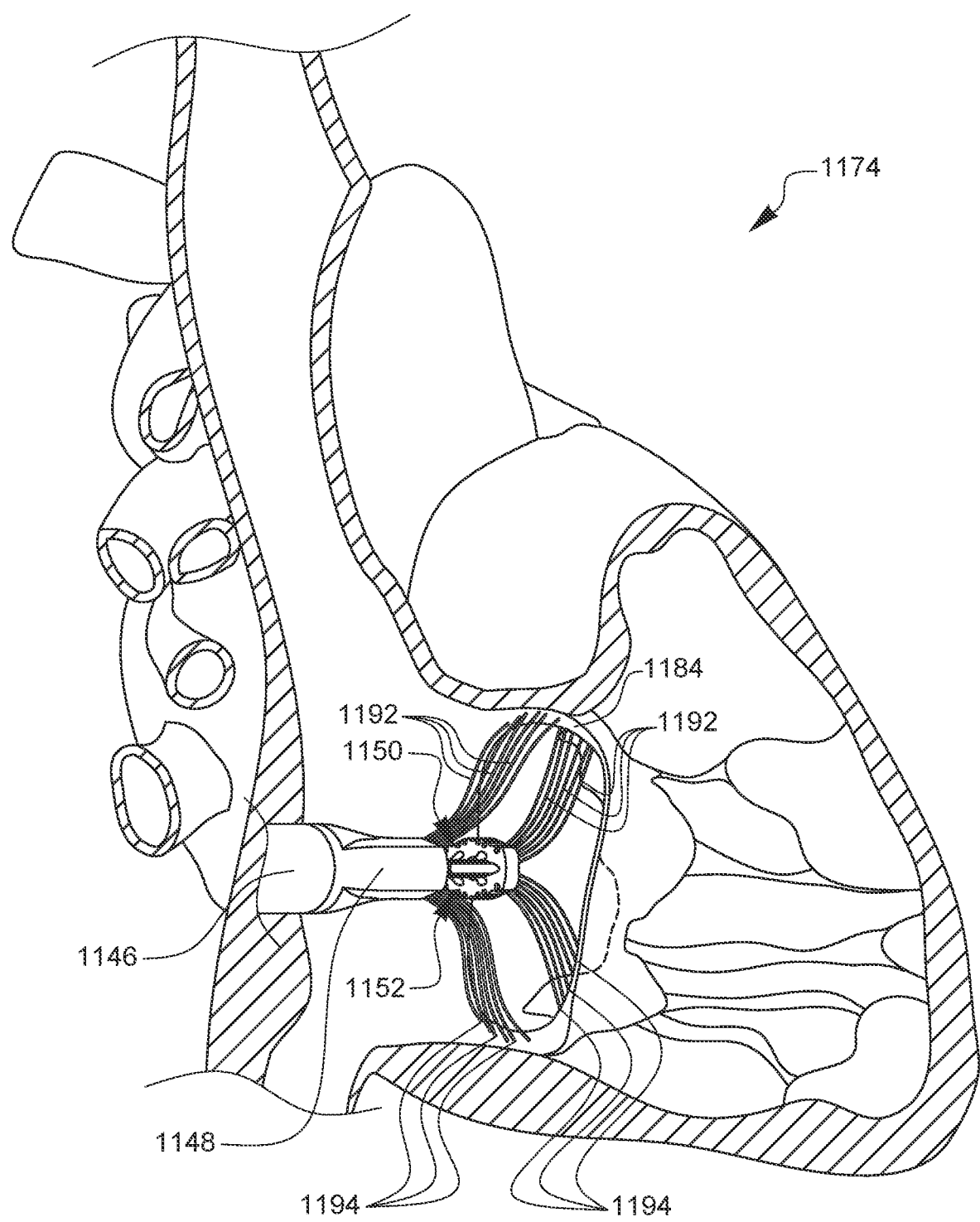
Figure 67H:
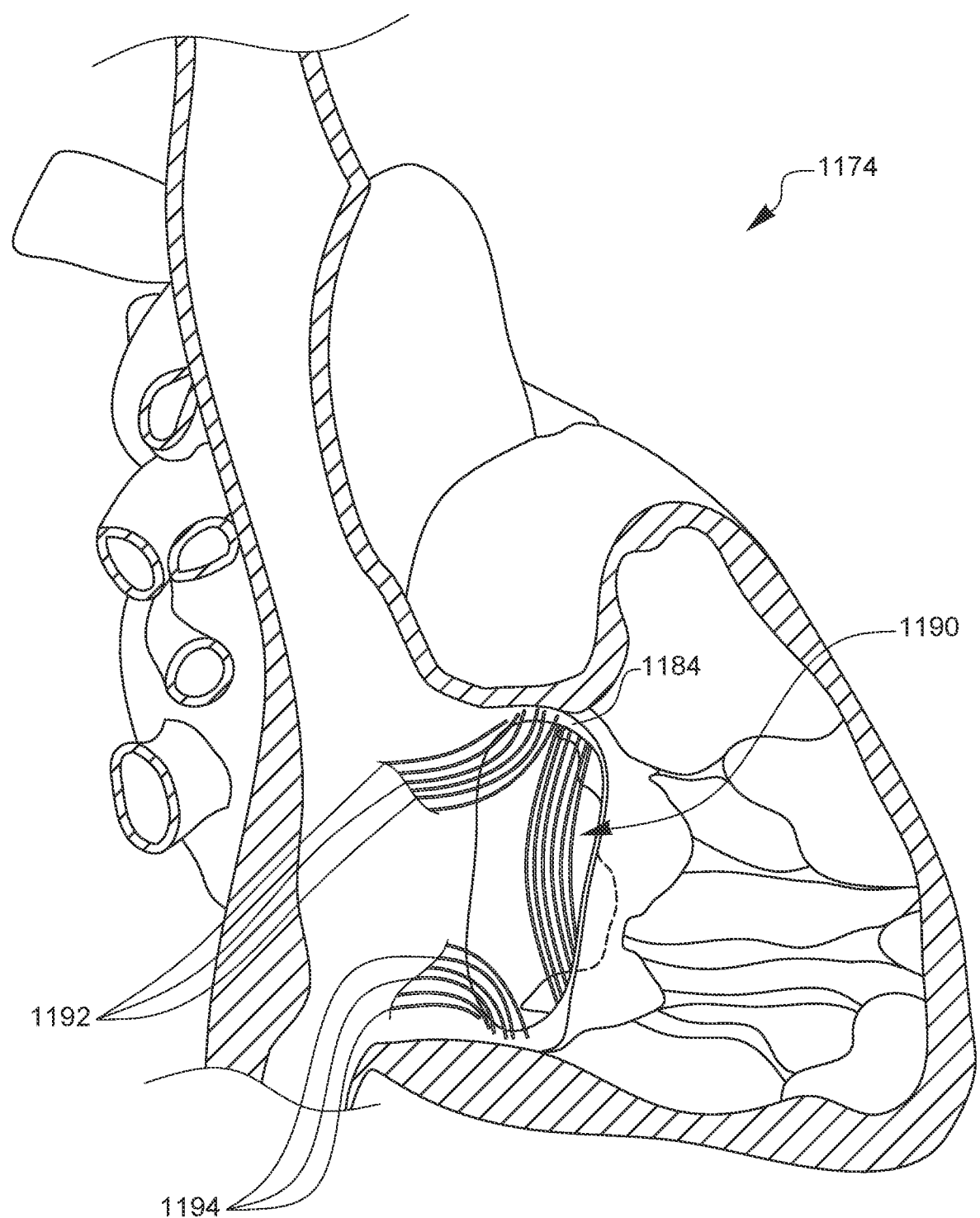

FIG. 67G illustrates the step in the surgical procedure where there is still slack in the sutures 1192 and the retracting telescope handle has been slowly and fully pulled away from the heart to payout sutures through the tissue and back through the body of the surgical suturing device. FIG. 67H shows a step in the surgical procedure where the operator, while holding the retracting telescope stationary, removes the handle and remaining portion of the surgical suturing device of FIG. 64. This leaves twelve suture ends exiting the surgical site, possibly at a cannula such as the one further described in regard to FIG. 55A-55B.

Figure 67J:
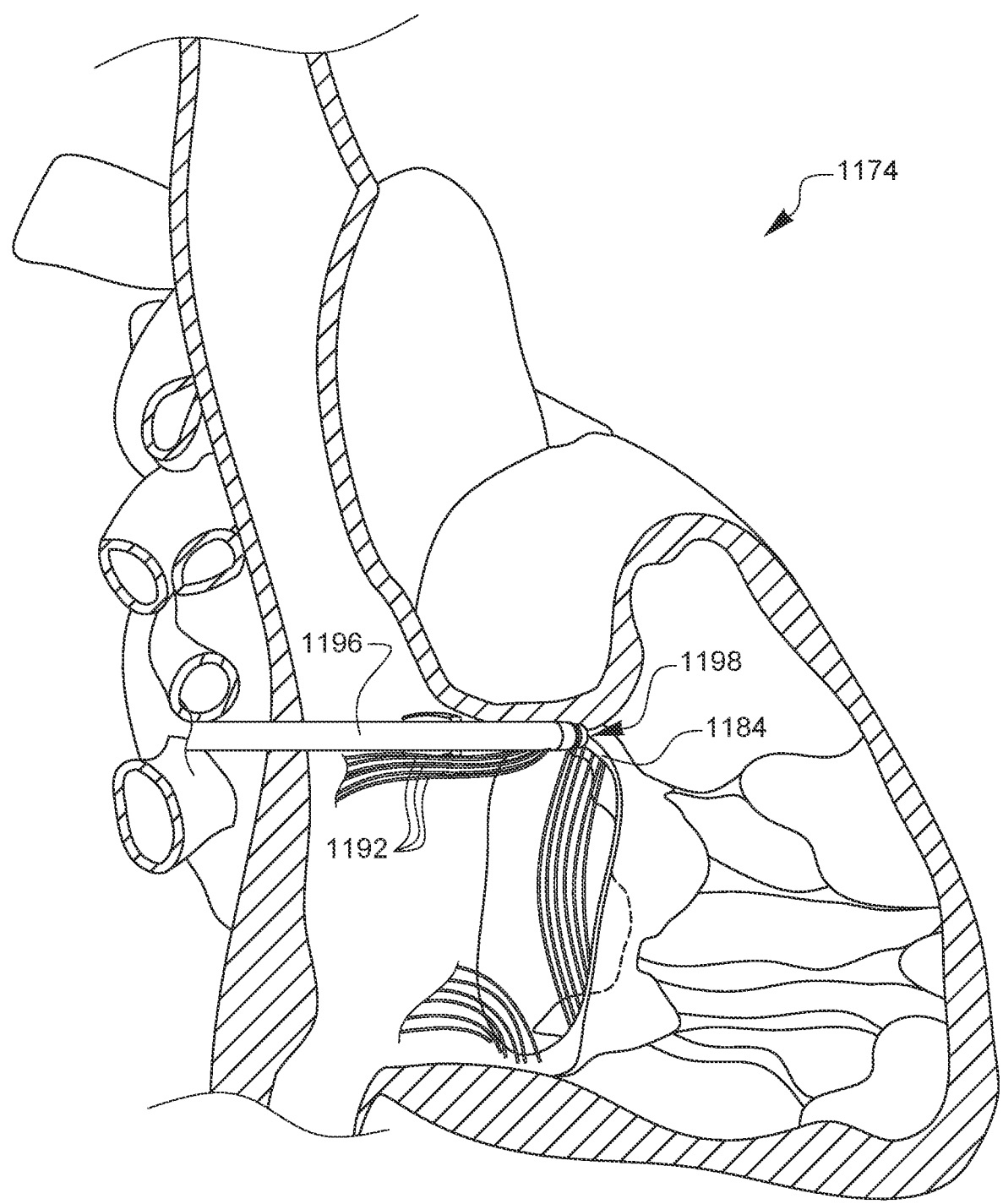
Figure 67K:
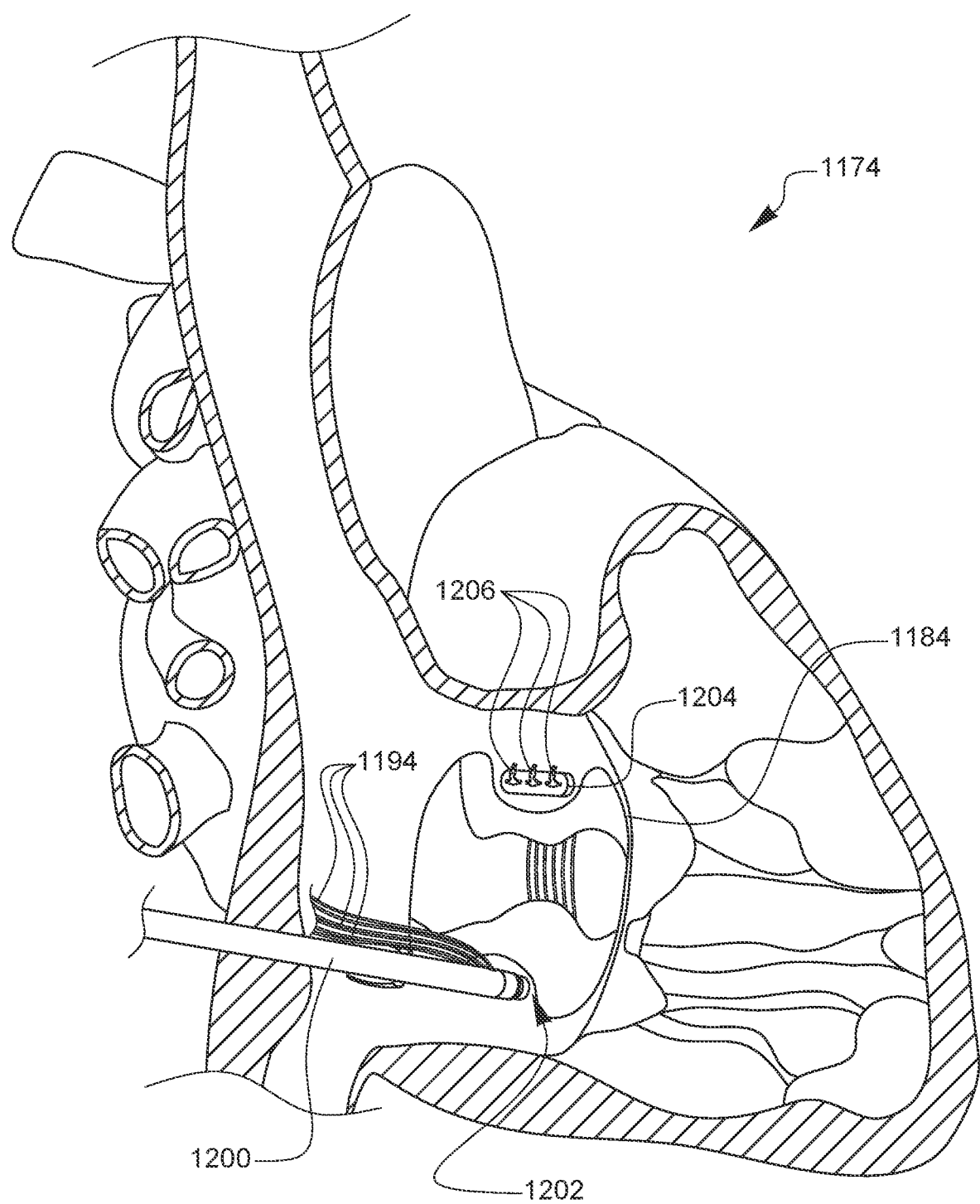
Figure 67L:
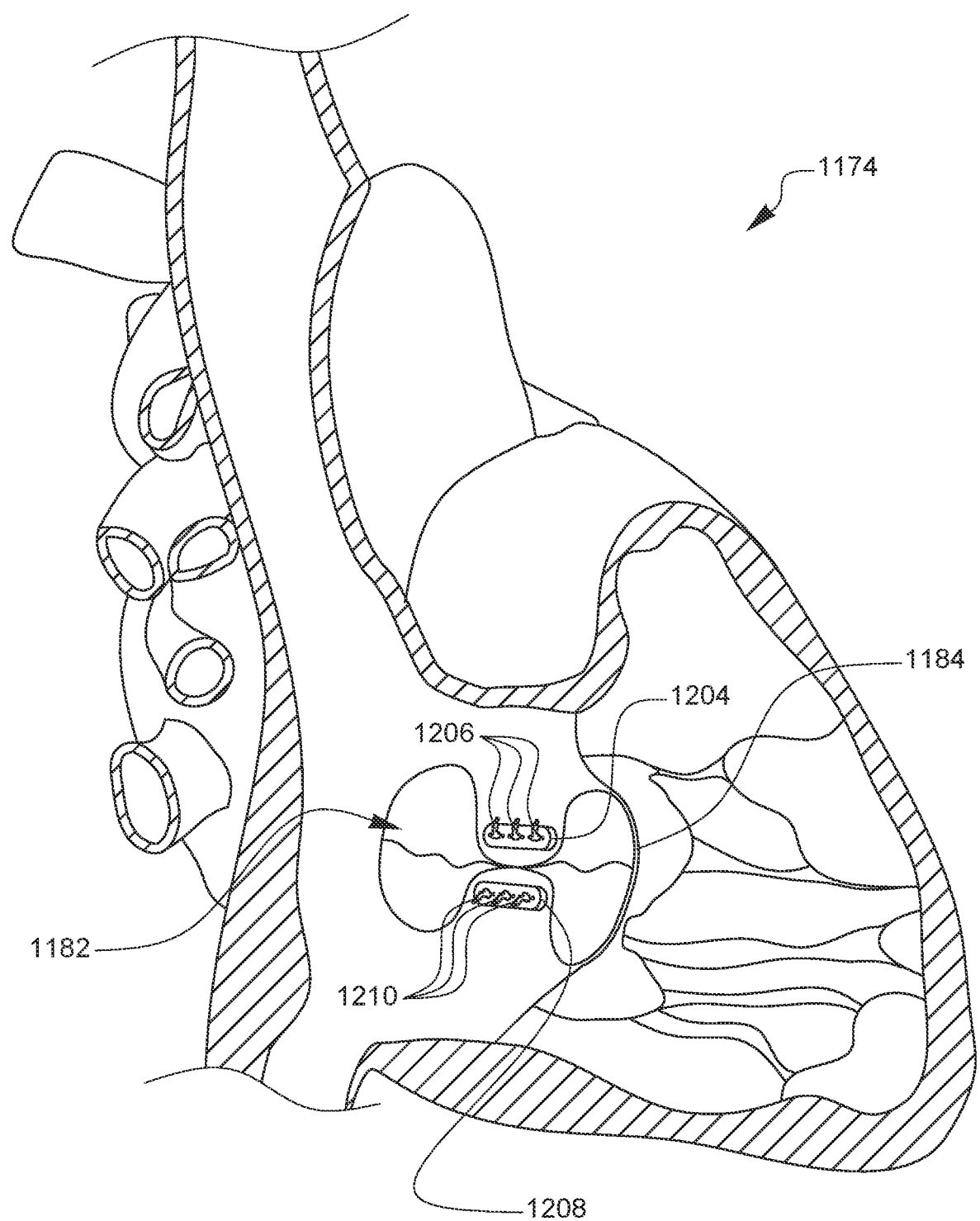

FIG. 67J illustrates the use of a mechanical fastener knotting device having three shafts or barrels as previously shown in and described in regard to FIG. 65 to secure the portion of the sutures 1190 attached at the first suture site described in regard to FIG. 67C. The knotting tips 1198 of a first triple knotting device 1196 are placed in proximity to the suture sites, and the device is actuated, simultaneously applying three mechanical fasteners and trimming the ends of the sutures 1190. FIG. 67K illustrates the suture site having a first pledget 1204 fastened to the first suturing site described in regard to FIG. 67C using a first set of three mechanical fasteners 1206. Also shown is the introduction of a second triple knotting device 1200 having three shafts or barrels as previously shown in and described in regard to FIG. 65 to secure the portion of the sutures 1190 attached at the second suture site described in regard to FIG. 67F. The sutures 1190 are shown in a partially loose state, yet once they are fully tightened and the tricuspid annular plication is in a state that is satisfactory to the surgeon, the knotting tips 1202 of the second triple knotting device 1200 are placed in proximity to the suture sites, the sutures are fully tightened and the device is actuated, simultaneously applying three mechanical fasteners and trimming the ends of the sutures 1190. FIG. 67L shows the completed plication, with the mechanical fasteners 1210 fully securing the second suturing site with a second pledget 1208 in the tricuspid annulus 1184.

Figure 68A:
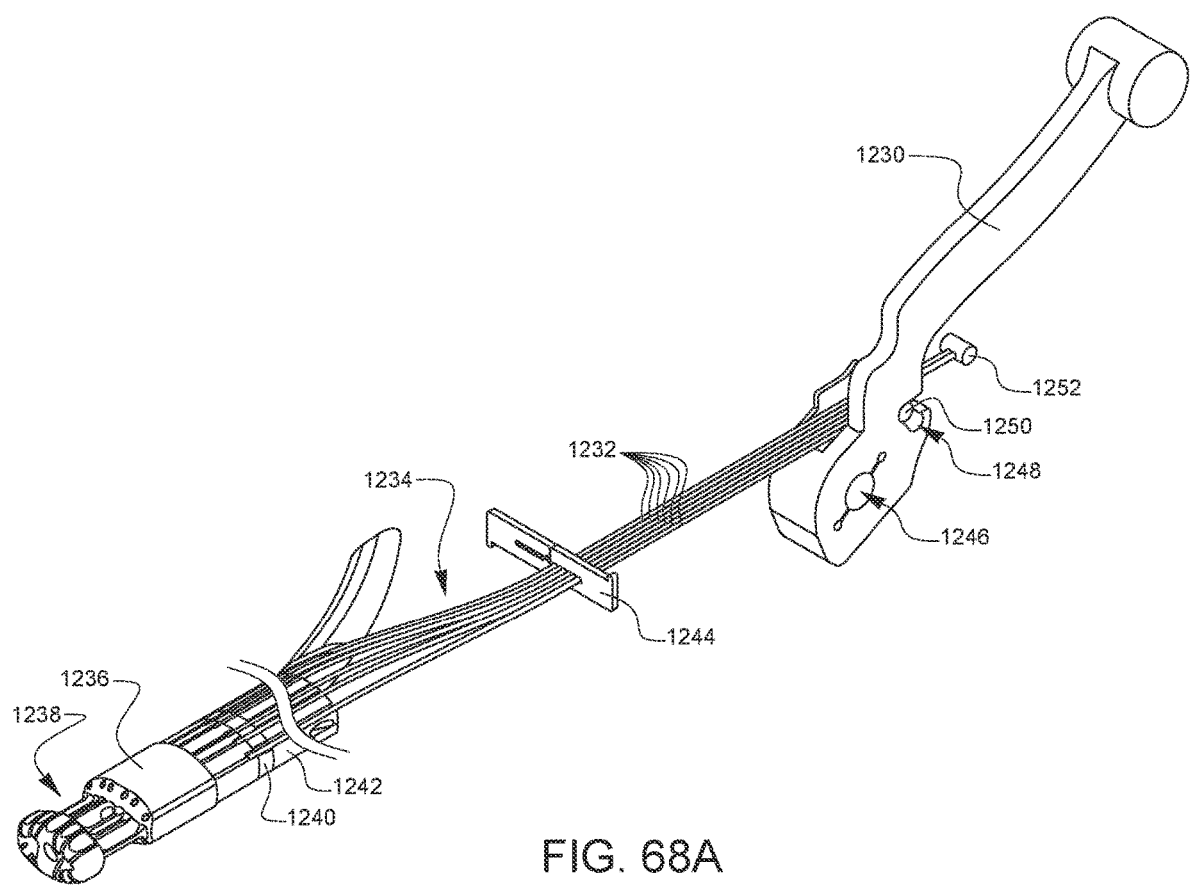
FIGS. 68A-68B are top-left-front perspective views of internal portions of an embodiment of a surgical suturing device highlighting the arrangement of a set of needles.
Figure 68B:
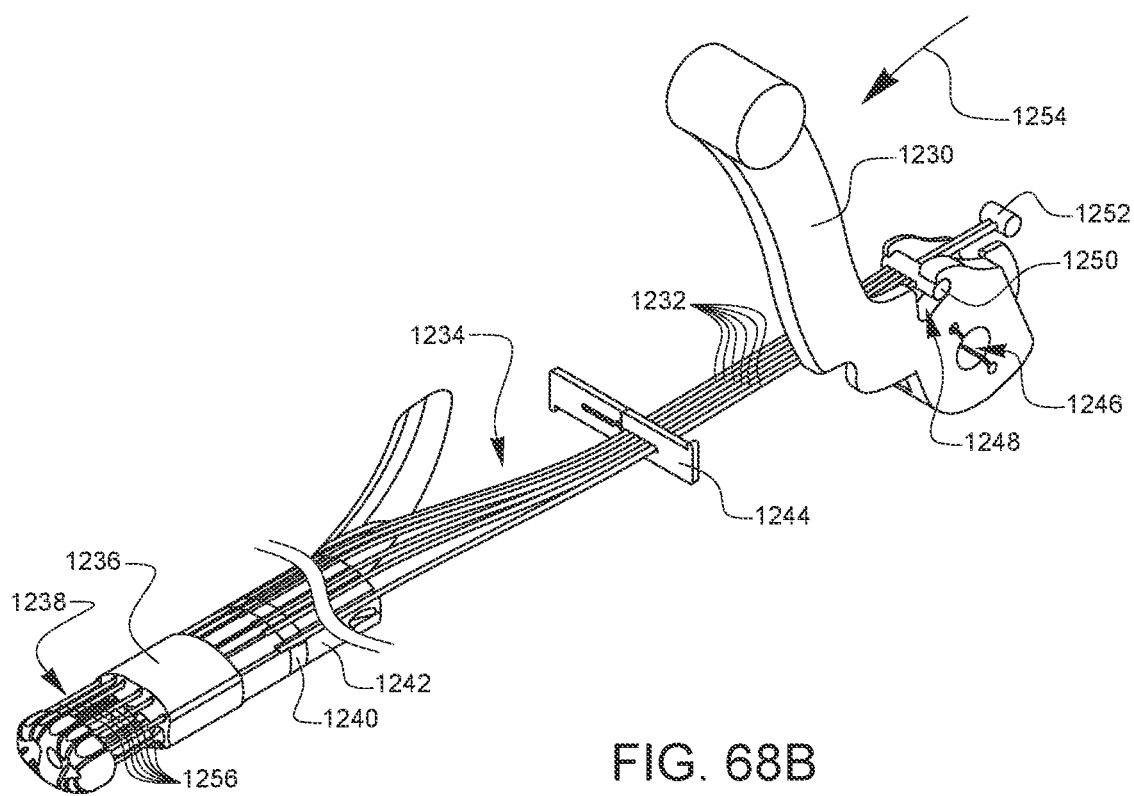

FIGS. 68A and 68B are top-left-front perspective views of internal portions of an embodiment of a surgical suturing device highlighting the arrangement of a set of needles. FIG. 68A illustrates an internal portion of a surgical suturing device, showing a second needle drive lever similar to those previously described herein. The second needle drive lever 1230 defines a barrel catch 1248 configured to hold a distal barrel 1250 for a group of needles and a pivot hole 1246 about which the second needle drive lever 1230 pivots. Extending from the distal barrel 1250 is a group of six needle tubes 1232, which are configured to slidably and coaxially enclose a needle within each of the needle tubes 1232. The needle tubes 1232 pass through a proximal needle tube lock plate 1244 towards and through the shaft (not shown here) of a surgical suturing instrument through a divergent path 1234 for the tubes and needles, through an inner shaft, to terminate in a distal needle tube locking plate 1240. The needles (not shown in this view) exit the needle tubes 1232 and are configured to be driven through the tissue bite area 1238 of the distal tip 1236 when the second needle drive lever 1230 is actuated. Each tube 1232 has a notch at either end that sits within and is locked into a protrusion, with a corresponding notch and protrusion pair at the opposite end to fixedly seat the tube in the stationary block end. This set of features, which will be described in more detail, sets the length of tube held fixed at a constant length from the distal needle tube lock plate 1240 to the proximal needle tube lock plate 1240. The needle tubes 1232 carrying the needles may follow different paths within the surgical suturing device from the distal end to the proximal end. While the paths differ, the distance of needle travel will be the same independent of the path they take through the instrument as a result of this notch protrusion pair feature at either end. This set of features guarantees the needles will be the same length and be driven the same distance when actuated. If no notch and protrusion feature set or method of setting length via tube was utilized, it could require 6 different lengths of needles and/or tubes in a set to insure consistent needle lengths and needle drive distances. Other means of achieving a consistent length needle may be known in the art and may be used in alternate embodiments. In addition to these needle tube lock plates, alternate needle supports may also be used to guide needle tube and needle pathways from the distal end to the proximal end of the surgical suturing device.

FIG. 68B is a top-left-front perspective view of the internal portion of the surgical suturing device of FIG. 68A, showing the second needle drive lever similar to those previously described herein being actuated to drive the upper needle set forward. As the second needle drive lever 1230 is actuated in a forward direction 1254, the needles slide within the needle tubes 1232 and advance forward to traverse the tissue bite area 1238 in the distal tip 1236. All needles travel the same distance forward to pick up their respective ferrules (not shown here), and the needle tubes 1232 remain stationary.

Figure 69:
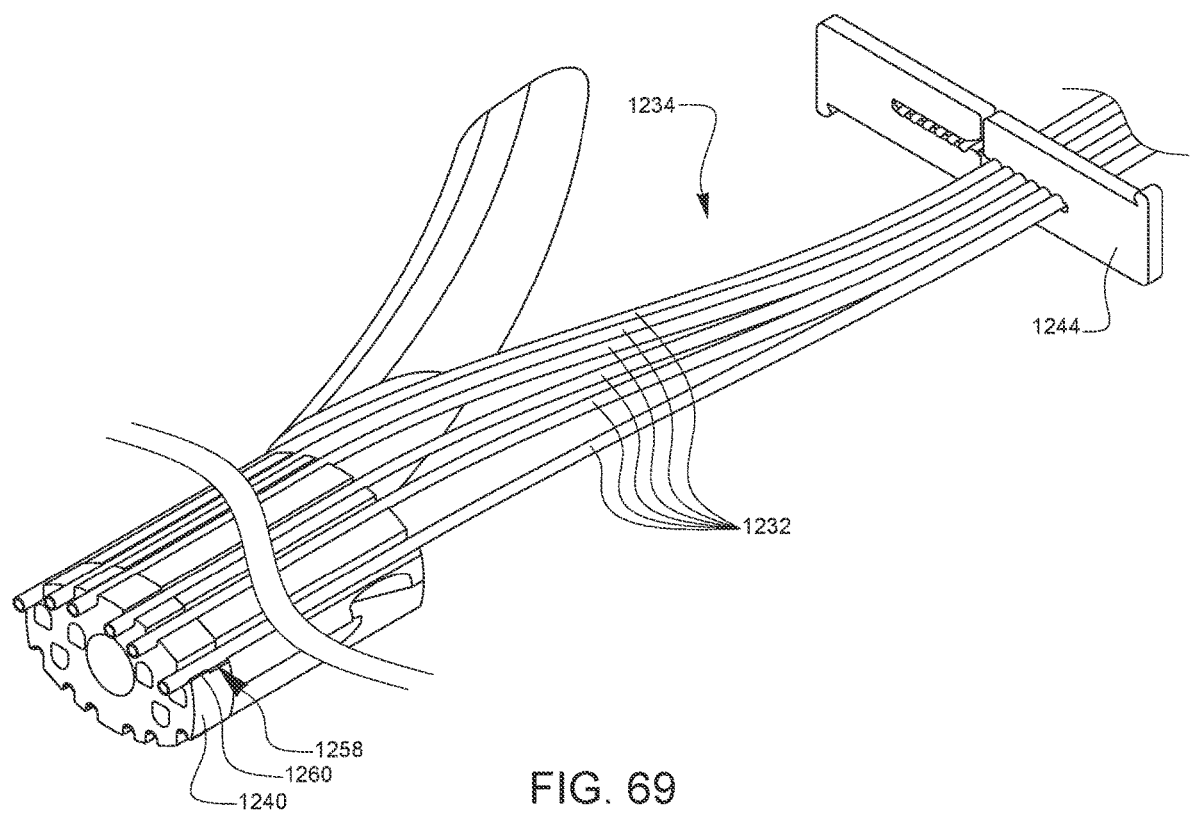
FIG. 69 is a top-left-front perspective view of internal portions of the embodiment of the surgical suturing device of FIGS. 68A and 68B further highlighting the arrangement of a set of needles.

FIG. 69 is a top-left-front perspective view of internal portions of the embodiment of the surgical suturing device of FIGS. 68A and 68B further highlighting the arrangement of a set of needles. FIG. 69 illustrates the details of how an embodiment of a surgical suturing device holds the needle tubes within the distal tip in the distal needle lock plate. The distal needle lock plate 1240 defines several protrusions 1260 that are each configured to mate with a corresponding tube notch 1258 in each needle tube 1232. The size and depth of the notch 1258 in the needle tube 1232 does not prohibit or restrict the needle from traveling within the tube but is substantial enough to restrict movement of the needle tube once it is placed in the distal needle tube lock plate.

Figure 70:
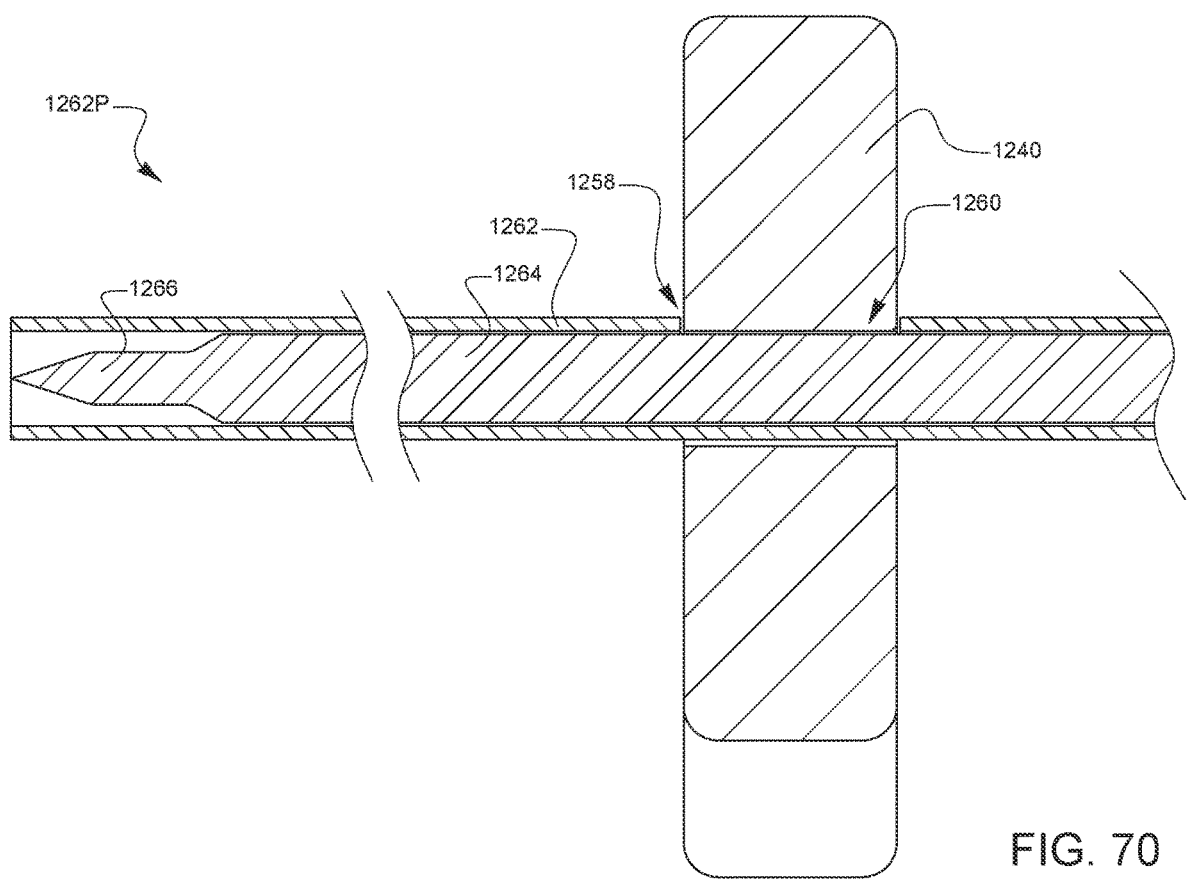
FIG. 70 is an enlarged cross-sectional side view of a segment of the internal portions of a surgical suturing device shown in FIG. 69.

FIG. 70 is a cross-sectional side view of a segment of the internal portions of a surgical suturing device shown in FIG. 69. FIG. 70 illustrates the details of how an embodiment of a surgical suturing device holds the needle tubes 1262 in the housing within the proximal needle lock plate 1240. The proximal needle lock plate 1240 defines a protrusion 1260 for each needle tube 1262 configured to mate with a corresponding tube notch 1258 in each needle tube 1262 at the proximal end 1262P of the needle tube 1262. The size and depth of the notch 1258 in the needle tube 1262 does not prohibit or restrict the needle 1264 from traveling within the tube 1262 but is substantial enough to restrict movement of the needle tube 1262 once it is placed in the proximal needle tube lock plate 1240. Alternate embodiments for restricting the length and holding in place needle tubes may be employed such as clamps, screws, or other means of mechanical restriction. Other means of restricting the needle tubes to a fixed distance between the proximal and distal end of a surgical suturing device may be known to those skilled in the art, provided the needles may still pass freely within the needle tube once the needle tube is held in place. In addition to tubes, alternate embodiments may have additional structural support inside the device housing or within other components for the needles or tubes which may be used in order to better facilitate, guide or direct the management of needle pathways throughout the surgical suturing device. Such needle tube guides or supports may be arranged with alternate spacing or orientation in a manner intended to facilitate efficient operation and movement of the needles within the needle tubes. Alternatively, the shape and orientation of one of the needle lock plates may be configured or oriented in other patterns or arrangements to control the position of the needle tubes.

Figure 71:
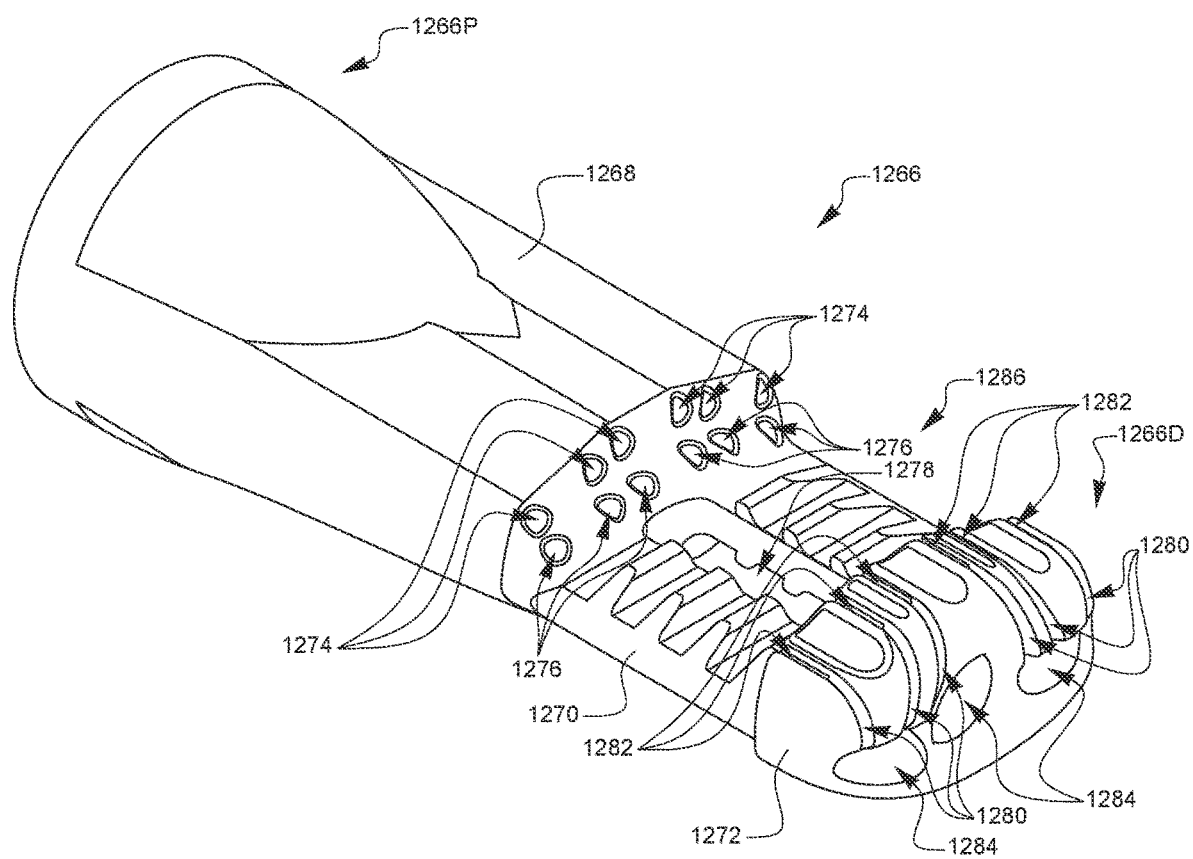
FIG. 71 is a top-right-front perspective view of another embodiment of a distal tip for a surgical suturing device.

FIG. 71 is a top-right-front perspective view of another embodiment of a distal tip for a surgical suturing device. The distal tip 1266 shown in FIG. 71 is similar to other embodiments shown herein, but has a single tissue gap 1286, rather than two tissue gaps on opposing sides of the distal tip. Most of the features of this embodiment of a distal tip 1266 share a common purpose to corresponding features in other embodiments described previously. The distal tip 1266 is characterized by a tip body 1268, a tip support 1270 connected to the tip body 1268, and a tip head 1272 towards the distal end 1266D of the distal tip 1266 connected to the tip support 1270. The distal tip 1266 also defines a set of upper needle channels 1274 and a set of lower needle channels 1276. The tip support 1270 defines a viewing port 1278 configured such that an instrument held within an instrument channel, which is included in this embodiment but is not visible, could have visual access to a suturing site during a minimally invasive surgical procedure. The tip head 1272 also defines several features previously discussed herein, several suture guides 1280, suture channels 1284, and ferrule holders 1282.

Various advantages of a surgical suturing device for repair of tricuspid regurgitation, a loading and retrieval apparatus, and methods thereof have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:
1. A surgical suturing device, comprising:
a first tissue gap;
a second tissue gap;
a first pair of needles configured to be movable across the first tissue gap, each of the first pair of needles having a tip portion;
a second pair of needles configured to be movable across the second tissue gap, each of the second pair of needles having a tip portion;
a flexible shaft, wherein the flexible shaft is at least partially steerable and comprises one or more articulating links;
a guidewire tip, wherein the one or more articulating links are positioned within the guidewire tip in a retracted position, and the one or more articulating links are articulated outside of the guidewire tip in an advanced position;
a distal tip having a first portion defining the first tissue gap and a second portion defining the second tissue gap, the distal tip further defining:
a first ferrule holder configured to releasably retain a first ferrule coupled to a first portion of a first suture;
a second ferrule holder configured to releasably retain a second ferrule coupled to a second portion of the first suture;
a third ferrule holder configured to releasably retain a third ferrule coupled to a third portion of a second suture;
a fourth ferrule holder configured to releasably retain a fourth ferrule coupled to a fourth portion of the second suture; and a needle actuator operable between a first configuration and a second configuration, wherein in the first configuration, the tip portion of each of the first pair of needles is configured to displace across the first tissue gap and into communication with the first ferrule and the third ferrule, respectively; and wherein in the second configuration, the tip portion of each of the second pair of needles is configured to displace across the second tissue gap and into communication with the second ferrule and the fourth ferrule, respectively.

2. The surgical suturing device of claim 1, wherein the needle actuator comprises:

a lever; and a selection switch configured to selectively couple the lever to either the first pair of needles or the second pair of needles.

3. The surgical suturing device of claim 1, wherein the flexible shaft comprises one or more vertebrae.

* * * * *